US007951823B2

(12) United States Patent
Tully et al.

(10) Patent No.: US 7,951,823 B2
(45) Date of Patent: *May 31, 2011

(54) COMPOUNDS AND COMPOSITIONS AS CHANNEL ACTIVATING PROTEASE INHIBITORS

(75) Inventors: David C. Tully, San Diego, CA (US); Arnab K. Chatterjee, Encinitas, CA (US); Agnes Vidal, San Diego, CA (US); Hank Michael James Petrassi, Cardiff, CA (US); Zhiwei Wang, Carlsbad, CA (US); Badry Bursulaya, San Diego, CA (US); Glen Spraggon, San Diego, CA (US)

(73) Assignee: IRM LLC, Hamilton (BM)

( * ) Notice: Subject to any disclaimer, the term of this patent is extended or adjusted under 35 U.S.C. 154(b) by 547 days.

This patent is subject to a terminal disclaimer.

(21) Appl. No.: 11/749,430

(22) Filed: May 16, 2007

(65) Prior Publication Data

US 2007/0275906 A1    Nov. 29, 2007

Related U.S. Application Data

(60) Provisional application No. 60/802,983, filed on May 23, 2006, provisional application No. 60/860,604, filed on Nov. 22, 2006.

(51) Int. Cl.
*A61K 31/445* (2006.01)
*C07D 413/14* (2006.01)

(52) U.S. Cl. ........ 514/321; 546/184; 546/192; 546/195; 546/196; 546/198; 514/315; 514/317; 514/319

(58) Field of Classification Search .................. 546/184, 546/192, 195, 196, 198; 514/315, 317, 319, 514/321

See application file for complete search history.

(56) References Cited

U.S. PATENT DOCUMENTS

| | | | |
|---|---|---|---|
| 5,523,308 A | 6/1996 | Costanzo et al. |
| 5,705,487 A | 1/1998 | Schacht et al. |
| 5,707,966 A | 1/1998 | Schacht et al. |
| 5,710,130 A | 1/1998 | Schacht et al. |
| 5,726,159 A | 3/1998 | Schacht et al. |
| 5,874,585 A | 2/1999 | Gyorkos et al. |
| 5,914,319 A | 6/1999 | Schacht et al. |
| 6,022,861 A | 2/2000 | Scarborough et al. |
| 6,211,154 B1 | 4/2001 | Scarborough et al. |
| 6,323,219 B1 | 11/2001 | Costanzo |
| 6,469,036 B1 | 10/2002 | Costanzo et al. |
| 2003/0216325 A1 | 11/2003 | Saksena et al. |
| 2004/0167201 A1 | 8/2004 | Sharma et al. |
| 2004/0186060 A1 | 9/2004 | Duncan et al. |
| 2006/0275366 A1 | 12/2006 | Malcolm et al. |
| 2007/0032433 A1 | 2/2007 | Saksena et al. |
| 2007/0276002 A1 | 11/2007 | Tully et al. |
| 2008/0176901 A1 | 7/2008 | Tully et al. |

FOREIGN PATENT DOCUMENTS

| | | |
|---|---|---|
| EP | 0291234 | 3/1994 |
| EP | 0 672 658 B1 | 9/1995 |
| EP | 0 743 320 | 11/1996 |
| EP | 1 114 822 A2 | 7/2001 |
| EP | 1 157 998 A1 | 11/2001 |
| JP | 08-020597 | 1/1996 |
| WO | 95/23608 A1 | 9/1995 |
| WO | 95/33763 A1 | 12/1995 |
| WO | WO 96/11697 | 4/1996 |
| WO | 96/16080 A1 | 5/1996 |
| WO | WO 96/40741 | 12/1996 |
| WO | WO 96/40742 | 12/1996 |
| WO | WO 96/40744 | 12/1996 |
| WO | WO 96/40748 | 12/1996 |
| WO | 97/17363 A1 | 5/1997 |
| WO | WO 97/31939 | 9/1997 |
| WO | WO 97/48687 | 12/1997 |
| WO | WO 98/07308 | 2/1998 |
| WO | 98/17679 A1 | 4/1998 |
| WO | 98/24806 | 6/1998 |
| WO | 98/50420 A1 | 11/1998 |
| WO | WO 98/49190 | 11/1998 |
| WO | 99/07734 | 2/1999 |
| WO | 00/09543 | 2/2000 |
| WO | 00/09558 A1 | 2/2000 |
| WO | WO 00/23421 | 4/2000 |
| WO | WO 00/39124 | 7/2000 |
| WO | WO 00/44733 | 8/2000 |
| WO | 01/02424 | 1/2001 |
| WO | WO 01/27096 | 4/2001 |
| WO | 01/40262 A1 | 6/2001 |
| WO | WO 01/44226 | 6/2001 |
| WO | WO 02/08244 | 1/2002 |
| WO | 02/018369 | 3/2002 |
| WO | 02/079146 | 10/2002 |
| WO | 03/006490 A1 | 1/2003 |
| WO | 03/013571 A1 | 2/2003 |
| WO | WO 03/062265 | 7/2003 |
| WO | 03/072528 A2 | 9/2003 |
| WO | WO 2005/023804 | 3/2005 |

(Continued)

OTHER PUBLICATIONS

Costanzo, et al., "Potent, Small-Molecule Inhibitors of Human Mast cell Tryptase. Antiasthmatic Action of a Dipeptide-Based Transition-State Analogue Containing a Benzothiazole Ketone", *J. Med. Chem.*, vol. 46, pp. 3865-3876, 2003.

(Continued)

*Primary Examiner* — Golam M Shameem
(74) *Attorney, Agent, or Firm* — Emily Tongco Wu; Genomics Institute of the Novartis Research Foundation

(57) ABSTRACT

The invention provides compounds and pharmaceutical compositions thereof, which are useful for modulating channel activating proteases, and methods for, using such compounds to treat, ameliorate or prevent a condition associated with a channel activating protease, including but not limited to prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, or neutrophil elastase.

15 Claims, No Drawings

FOREIGN PATENT DOCUMENTS

| WO | 2005/035525 A1 | 4/2005 |
|---|---|---|
| WO | 2005/037860 | 4/2005 |
| WO | 2005/058821 A1 | 6/2005 |
| WO | WO 2005/076886 | 8/2005 |
| WO | 2005/087721 | 9/2005 |
| WO | 2005/090329 A1 | 9/2005 |
| WO | 2005/113581 A1 | 12/2005 |
| WO | WO 2006/006644 | 1/2006 |
| WO | 2006/108643 A2 | 10/2006 |
| WO | 2007/140117 A1 | 12/2007 |
| WO | 2008/085608 A1 | 7/2008 |
| WO | 2008/097673 A1 | 8/2008 |
| WO | 2008/097676 A1 | 8/2008 |

OTHER PUBLICATIONS

Donnelly, et al., "Therapy for chronic Obstructive Pulmonary Disease in the 21st Century", *Drugs*, vol. 63, No. 19, 2003, pp. 1973-1998.

Edwards, et al., "Discovery and Biological Activity of Orally Active Petidyl Trifluoromethyl Ketone Inhibitors of Human Neutrophil Elastase", *J. Med. Chem.* 1997 vol. 40, pp. 1876-1885.

Costanzo, et al., "In-Depth Study of Tripeptide-Based α-Ketoheterocycles as Inhibitors of Thrombin. Effective Utilization of the $S_1$' Subsite and Its Implications to Structure-Based Drug Design", *J. Med. Chem.*, vol. 48, pp. 1984-2008, 2005.

U.S. Appl. No. 11/749,001, filed May 15, 2007 in the name of David C. Tully, et al.

Planes et al.; "Regulation of the Epithelial Na+ Channel by Peptidases", Current Topics in Developmental Biology; 2007; vol. 78:23-46; pp. 1-19, NIH Public Access.

English translation of JP8020597 (JP1996020597A); Meiji Seika Kaisha Ltd.; published Jan. 23, 1996.

U.S. Appl. No. 12/525,991, filed Jan. 4, 2008 in the name of David C. Tully et al. (P1272).

U.S. Appl. No. 12/526,029, filed Jan. 7, 2008 in the name of David C. Tully et al. (P1284).

Schweinitz et al., "New Substrate Analogue Inhibitors of Factor Xa Containing 4-Amidinobenzylamide as P1 Residue: Part 1"; Medicinal Chemistry, vol. 2, No. 4, pp. 349-361, 2006.

COMPOUNDS AND COMPOSITIONS AS CHANNEL ACTIVATING PROTEASE INHIBITORS

CROSS REFERENCE TO RELATED APPLICATIONS

This application claims the benefit of U.S. provisional applications Ser. No. 60/802,983, filed 23 May 2006; and Ser. No. 60/860,604, filed 22 Nov. 2006. Each of these applications is incorporated herein by reference in its entirety.

TECHNICAL FIELD

The invention generally relates to channel activating protease (CAP) inhibitors.

BACKGROUND ART

Prostasin is a trypsin-like serine protease that is present in a variety of mammalian tissues. It is a membrane anchored protease that is expressed on the extra-cellular membrane of cells, but may also be secreted into body fluids such as semen, urine and airway surface liquid. Prostasin (PRSS8), together with proteases such as matriptase, CAP2, CAP3, trypsin, PRSS22, TMPRSS11, cathepsin A, and neutrophil elastase, may stimulate the activity of the amiloride-sensitive epithelial sodium channel (ENaC). Inhibiting these enzymes may induce changes in epithelial ion transport and therefore fluid homeostasis across epithelial membranes. For example, CAP inhibition in the kidney is thought to promote diuresis, whilst CAP inhibition in the airways promotes the clearance of mucus and sputum in lung. CAP inhibition in the kidney may therefore be used therapeutically to treat hypertension. CAP inhibition in the airways prevents the stagnation of respiratory secretions that otherwise tends to make sufferers vulnerable to secondary bacterial infections.

DISCLOSURE OF THE INVENTION

The invention provides compounds, pharmaceutical compositions and methods of using such compounds for modulating channel activating proteases (CAP). For example, the compounds and compositions of the invention may be used for modulating prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, and neutrophil elastase.

In one aspect, the present invention provides compounds of Formula (1):

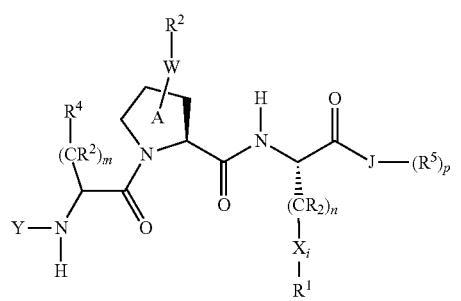

and pharmaceutically acceptable salts, hydrates, solvates and stereoisomers thereof, wherein:

J is a 5-12 membered monocyclic or fused carbocyclic ring, aryl, heteroaryl or heterocyclic ring containing N, O and/or S;

$R^1$ is $-(CR_2)_l-NR_2$, $-(CR_2)_l-NRC(=NR)-NR_2$, $-(CR_2)_l-C(=NR)-NR_2$ or a 5-7 membered nitrogen-containing non-aromatic heterocyclic ring;

W—$R^2$ is a substituent at any position on ring A;

W is $-O(CR_2)_k-$, $-S(CR_2)_k-$, $-S(O)(CR_2)_k-$, $-SO_2(CR_2)_k-$ or $-OC(O)(CR_2)_k-$;

$R^2$ is $C_{1-6}$ alkyl, $C_{2-6}$ alkenyl, $C_{2-6}$ alkynyl, $R^8$, $-CR^{10}=CR^{10}-R^8$, or

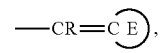

wherein ring E is an optionally substituted 5-7 membered monocyclic or fused carbocyclic or heterocyclic ring; or W—$R^2$ together form $C_{1-6}$ alkyl, a 5-7 membered aryl or $-OC(O)NR^6R^7$;

Y is $SO_2R^3$, $-(CO)-NR-R^3$, $-(CO)-O-R^3$, $SO_2NR^6R^7$ or $C_{1-6}$ alkyl;

$R^3$ is $C_{1-6}$ alkyl, $C_{2-6}$ alkenyl, $C_{2-6}$ alkynyl, $-(CR_2)_l-C_{3-7}$ cycloalkyl or $-(CR_2)_l-R^8$;

$R^4$ is H, $C_{1-6}$ alkyl, $C_{2-6}$ alkenyl, $-CR^{10}=CR^{10}-R^8$, $-CR[(CR_2)_l-R^8]_2$, $C_{2-6}$ alkynyl, $-O-(CR_2)_l-R^9$, $NR^6R^7$,

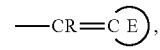

or an optionally substituted 5-7 membered carbocyclic ring, heterocyclic ring, aryl or heteroaryl; or $R^4$ together with Y form an optionally substituted 5-12 membered non-aromatic heterocyclic ring;

$R^5$ is halo, $C_{1-6}$ alkyl, $C_{1-6}$ alkoxy, $OR^9$ or $R^9$;

$R^6$ and $R^7$ are independently H, $C_{1-6}$ alkyl, $C_{2-6}$ alkenyl, $C_{2-6}$ alkynyl or $-(CR_2)_l-R^8$; or $R^6$ and $R^7$ together with N may form an optionally substituted 5-7 membered monocyclic or fused heterocyclic ring;

X, $R^8$ and $R^9$ are independently an optionally substituted 5-7 membered carbocyclic ring, heterocyclic ring, aryl or heteroaryl; or $R^9$ may be H or $C_{1-6}$ alkyl;

$R^{10}$ is H or $C_{1-6}$ alkyl;

each R is H, $C_{1-6}$ alkyl, $C_{2-6}$ alkenyl, or $C_{2-6}$ alkynyl, wherein a carbon may optionally be substituted or replaced with NR, O or S;

i is 0-1;
k, l and m are independently 0-6;
n is 1-6; and
p is 0-3.

In compounds of Formula (1), $R^2$ may be an optionally substituted phenyl, thienyl, $C_{5-7}$ cycloalkyl (e.g., cyclohexyl or cyclopentyl), furanyl, piperidinyl, methylenecyclohexyl,

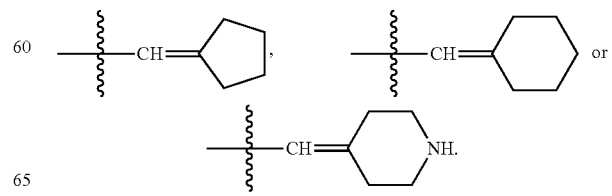

For example, $R^2$ substituents may be optionally substituted with halo, $CF_3$, $C_{1-6}$ alkyl, $C_{2-6}$ alkenyl, $O-(CH_2)_{0-4}-R^9$.

In one embodiment, the invention provides compounds of Formula (2A) or (2B):

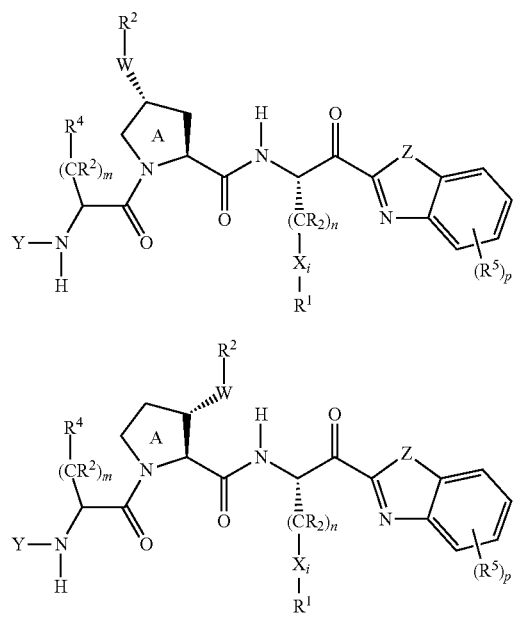

(2A)

(2B)

wherein Z is O or S;
$R^1$ is $NH_2$, $-NHC(=NH)-NH_2$ or $-C(=NH)-NH_2$;
W is $-O(CH_2)_k-$ or $-S(O)(CH_2)_k-$;
$R^2$ is an optionally substituted phenyl, or $W-R^2$ together form $C_{1-6}$ alkyl or an optionally substituted phenyl;
Y is $SO_2R^3$ or $-(CO)-O-R^3$;
$R^3$ is $C_{1-6}$ alkyl, $-(CH_2)_l$-cyclopropyl or $-(CH_2)_l-R^8$ wherein $R^8$ is an optionally substituted phenyl;
$R^4$ is an optionally substituted, phenyl, piperidinyl, $C_{5-7}$ cycloalkyl, cyclohexanol, imidazolyl, thienyl,

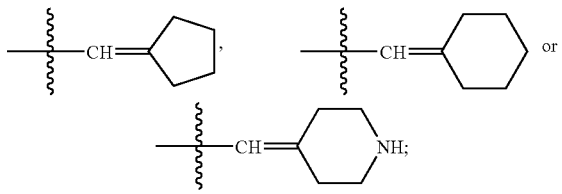

i and p are 0;
k is 1;
l is 0-1; and
m and n are independently 1-4.

In some examples, the compounds are of Formula (2A) or (2B) and $R^4$ is piperidinyl. In other examples, Z is O.

In compounds of Formula (2A) or (2B) where $R^2$ is phenyl or $W-R^2$ together form phenyl, each phenyl may optionally be substituted with halo.

In compounds of Formula (1), (2A) and (2B), W may be $-O(CR_2)_k-$, $-S(CR_2)_k-$, $-S(O)(CR_2)_k-$, $-SO_2(CR_2)_k-$ or $-OC(O)(CR_2)_k-$; and k is 1.

In another embodiment, the invention provides compounds of Formula (3A) or (3B):

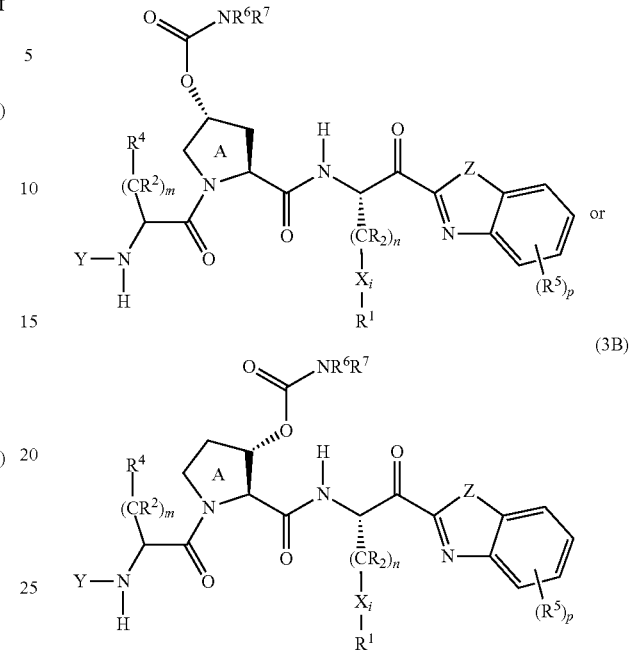

(3A)

(3B)

wherein $R^6$ and $R^7$ are independently H, $C_{1-6}$ alkyl or $-(CR_2)_l-R^8$; or $R^6$ and $R^7$ together with N form an optionally substituted pyrrolidinyl, piperidinyl, morpholino, piperazinyl or diazepanyl;
$R^8$ is an optionally substituted phenyl, furanyl, tetrahydrofuranyl, piperidinyl or thienyl; and
i and p are 0.

In some compounds of Formula (3A) or (3B), each optionally substituted substituent may be substituted with $NR^9_2$, halo, $C_{1-6}$ alkyl, $-(CR_2)_l-COR^9$, $-(CR_2)_l-R^9$, $-(CR_2)_l-SO_2R^9$ or $NRSO_2R^9$, wherein $R^9$ is H, $C_{1-6}$ alkyl, or an optionally substituted carbocyclic ring, heterocyclic ring, aryl or heteroaryl. For example, $R^9$ may be phenyl, furanyl, tetrahydrofuranyl or thienyl, each of which may be optionally substituted by substituents described above.

In the compounds of the invention, $R^1$ may be $-(CH_2)_l-NH_2$, $-(CH_2)_l-NHC(=NH)-NH_2$ or $-(CH_2)_l-C(=NH)-NH_2NH_2$, wherein each l is 0-1; or $R^1$ is piperidinyl. In some examples, each R group in $(CR_2)$ is H.

In the compounds of the invention, Y may be $SO_2R^3$, $-(CO)-NH-R^3$ or $-(CO)-O-R^3$; $R^3$ is $C_{1-6}$ alkyl, $-(CR_2)_l-C_{3-7}$ cycloalkyl (e.g., cyclopentyl, cyclohexyl and particularly cyclopropyl, each of which may be optionally substituted), or $-(CR_2)_l-R^8$ where $R^8$ is an optionally substituted phenyl. Optional substituents for $R^3$ and $R^8$ include but are not limited to halo, $CF_3$, $C_{1-6}$ alkyl, $C_{2-6}$ alkenyl or $O-(CH_2)_{0-4}-R^9$.

In the compounds of the invention, $R^4$ may be H, $C_{1-6}$ alkyl, $C_{2-6}$ alkenyl, $-NH_2$, or an optionally substituted phenyl, phenoxy, piperidinyl, cyclohexyl, cyclohexanol, imidazolyl, thienyl,

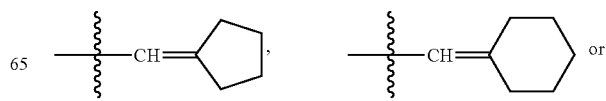

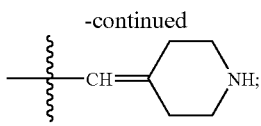

or $R^4$ together with Y form an optionally substituted pyrrolidinyl, pyrrolidinonyl, tetrahydroisoquinolinyl or tetrahydronapthalenyl. Each optionally substituted substituent may be substituted with halo, $CF_3$, $OCF_3$, $C_{1-6}$ alkyl, $C_{2-6}$ alkenyl, $R^8$, O—$(CH_2)_{0-4}$—$R^9$ or $CO_2R^9$, wherein $R^9$ may be H, C1-6 alkyl, or phenyl.

In the compounds of the invention, -J-$(R^5)_p$ together may be

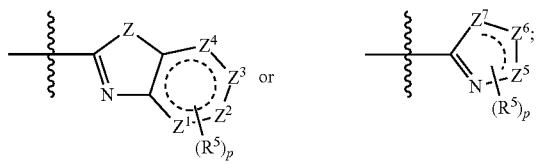

wherein Z is O or S;

$Z^1$, $Z^2$, $Z^3$ or $Z^4$ are independently N, CH, or C when attached to $R^5$;

$Z^5$, $Z^6$ or $Z^7$ are independently N, O, S, CH, or C when attached to $R^5$;

p is 0-1; and $R^5$ is halo or $C_{1-6}$ alkyl.

In the compounds of the invention, J may be benzothiazolyl, benzoxazolyl, thiazolyl, or oxadiazolyl. In particular examples, J is benzothiazolyl or benzoxazolyl.

In the compounds of the invention where $R^8$ is a substituent, $R^8$ may be an optionally substituted phenyl, $C_{5-7}$ cycloalkyl (e.g., cyclopentyl or cyclohexyl), piperidinyl, cyclohexanol, imidazolyl, thienyl, furanyl,

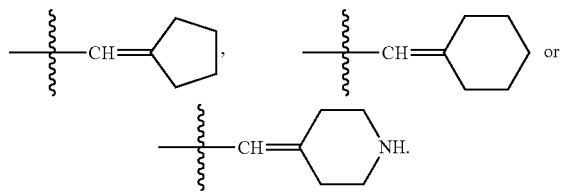

In the compounds of the invention, X may be cyclohexyl, phenyl or piperidinyl, each of which is optionally substituted with $C_{1-6}$ alkyl, $C_{1-6}$ alkoxy, halo, or a combination thereof.

In another aspect, the present invention provides pharmaceutical compositions comprising a compound having Formula (1), (2A), (2B), (3A) or (3B), and a pharmaceutically acceptable excipient.

The invention also provides methods for modulating a channel activating protease, comprising administering to a system or a subject in need thereof, a therapeutically effective amount of a compound having Formula (1), (2A), (2B), (3A) or (3B), or pharmaceutically acceptable salts or pharmaceutical compositions thereof, thereby modulating said channel activating protease.

In yet another aspect, the invention provides methods for ameliorating a condition mediated by a channel activating protease, comprising administering to a system or subject in need of such treatment an effective amount of a compound having Formula (1), (2A), (2B), (3A) or (3B), or pharmaceutically acceptable salts or pharmaceutical compositions thereof, and optionally in combination with a second therapeutic agent, thereby treating said condition. Examples of a second therapeutic agent which may be used with the compounds of the invention include but are not limited to an anti-inflammatory, bronchodilatory, antihistamine, anti-tussive, antibiotic or DNase.

Examples of channel activating protease which may be modulated using the compounds of the invention include but are not limited to prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, or neutrophil elastase. In particular examples, the invention provides methods for modulating prostasin, or methods for treating a condition mediated by prostasin.

In the above methods for using the compounds of the invention, a compound having Formula (1), (2A), (2B), (3A) or (3B) may be administered to a system comprising cells or tissues. For example, a compound having Formula (1), (2A), (2B), (3A) or (3B) may be contacted with bronchial epithelial cells, which may be human cells. In other embodiments, a compound having Formula (1), (2A), (2B), (3A) or (3B) may be administered to a human or animal subject.

In one embodiment, the invention provides methods for ameliorating a condition associated with the movement of fluid across ion transporting epithelia or the accumulation of mucus and sputum in respiratory tissues, or a combination thereof. For example, the condition may be cystic fibrosis, primary ciliary dyskinesia, lung carcinoma, chronic bronchitis, chronic obstructive pulmonary disease, asthma or a respiratory tract infection.

Furthermore, the present invention provides the use of a compound of Formula (1), (2A), (2B), (3A) or (3B), or pharmaceutically acceptable salts or pharmaceutical compositions thereof, and optionally in combination with a second therapeutic agent, for modulating a channel activating protease (e.g., for inhibiting prostasin). The present invention also provides the use of a compound having Formula (1), (2A), (2B), (3A) or (3B), or pharmaceutically acceptable salts or pharmaceutical compositions thereof, and optionally in combination with a second therapeutic agent, in the manufacture of a medicament for treating a condition mediated by a channel activating protease (e.g., a prostasin-mediated condition).

DEFINITIONS

"Alkyl" refers to a moiety and as a structural element of other groups, for example halo-substituted-alkyl and alkoxy, and may be straight-chained or branched. An optionally substituted alkyl, alkenyl or alkenyl as used herein may be optionally halogenated (e.g., $CF_3$), or may have one or more carbons that is substituted or replaced with a heteroatom, such as NR, O or S (e.g., —$OCH_2CH_2O$—, alkylthiols, thioalkoxy, alkylamines, etc).

"Aryl" refers to a monocyclic or fused bicyclic aromatic ring containing carbon atoms. For example, aryl may be phenyl or naphthyl. "Arylene" means a divalent radical derived from an aryl group.

"Heteroaryl" as used herein is as defined for aryl above, where one or more of the ring members is a heteroatom. Examples of heteroaryls include but are not limited to pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring may contain N, O, S, —N=, —S—, —S(O), —S(O)$_2$—, or —NR— wherein R may be hydrogen, $C_{1-4}$alkyl or a protecting group. Examples of heterocyclic rings include but are not limited to morpholino, pyrrolidinyl, pyrrolidinyl-2-one, piperazinyl, piperidinyl, piperidinylone, 1,4-dioxa-8-aza-spiro[4,5]dec-8-yl, etc.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1), (2A), (2B), (3A) or (3B) and a co-agent, are both administered to a patient simultaneously in the form of a single entity or dosage. The term "non-fixed combination" means that the active ingredients, e.g. a compound of Formula (1), (2A), (2B), (3A) or (3B) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" and or "administering" of the subject compound should be understood to mean as providing a compound of the invention and prodrugs thereof, to the individual in need of treatment.

As used herein, the terms "treat", "treating" and "treatment" refer to a method of alleviating or abating a disease and/or its attendant symptoms.

The term "prostasin" may also be referred to as: human channel-activating protease (hCAP); channel-activating protease-1; and PRSS8, MERPOPS ID S01.159.

MODES OF CARRYING OUT THE INVENTION

The invention provides compounds, pharmaceutical compositions and methods of using such compounds for modulating channel activating proteases (CAP).

In one aspect, the present invention provides compounds of Formula (1):

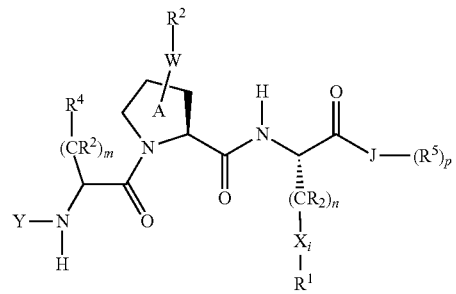

(1)

and pharmaceutically acceptable salts, hydrates, solvates and stereoisomers thereof, wherein:

J is a 5-12 membered monocyclic or fused carbocyclic ring, aryl, heteroaryl or heterocyclic ring containing N, O and/or S;

$R^1$ is —$(CR_2)_l$—$NR_2$, —$(CR_2)_l$—NRC(=NR)—$NR_2$, —$(CR_2)_l$—C(=NR)—$NR_2$ or a 5-7 membered nitrogen-containing non-aromatic heterocyclic ring;

W—$R^2$ is a substituent at any position on ring A;

W is —$O(CR_2)_k$—, —$S(CR_2)_k$—, —$S(O)(CR_2)_k$—, —$SO_2(CR_2)_k$— or —$OC(O)(CR_2)_k$—;

$R^2$ is $C_{1-6}$ alkyl, $C_{2-6}$ alkenyl, $C_{2-6}$ alkynyl, $R^8$, —$CR^{10}$=$CR^{10}$—$R^8$, or

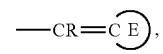

wherein ring E is an optionally substituted 5-7 membered monocyclic or fused carbocyclic or heterocyclic ring; or W—$R^2$ together form $C_{1-6}$ alkyl, a 5-7 membered aryl or —$OC(O)NR^6R^7$;

Y is $SO_2R^3$, —(CO)—NR—$R^3$, —(CO)—O—$R^3$, $SO_2NR^6R^7$ or $C_{1-6}$ alkyl;

$R^3$ is $C_{1-6}$ alkyl, $C_{2-6}$ alkenyl, $C_{2-6}$ alkynyl, —$(CR_2)_l$—$C_{3-7}$ cycloalkyl or —$(CR_2)_l$—$R^8$;

$R^4$ is H, $C_{1-6}$ alkyl, $C_{2-6}$ alkenyl, —$CR^{10}$=$CR^{10}$—$R^8$, —$CR[(CR_2)_l$—$R^8]_2$, $C_{2-6}$ alkynyl, —O—$(CR_2)_l$—$R^9$, $NR^6R^7$,

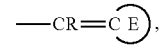

or an optionally substituted 5-7 membered carbocyclic ring, heterocyclic ring, aryl or heteroaryl; or $R^4$ together with Y form an optionally substituted 5-12 membered non-aromatic heterocyclic ring;

$R^5$ is halo, $C_{1-6}$ alkyl, $C_{1-6}$ alkoxy, $OR^9$ or $R^9$;

$R^6$ and $R^7$ are independently H, $C_{1-6}$ alkyl, $C_{2-6}$ alkenyl, $C_{2-6}$ alkynyl or —$(CR_2)_l$—$R^8$; or $R^6$ and $R^7$ together with N may form an optionally substituted 5-7 membered monocyclic or fused heterocyclic ring;

X, $R^8$ and $R^9$ are independently an optionally substituted 5-7 membered carbocyclic ring, heterocyclic ring, aryl or heteroaryl; or $R^9$ may be H or $C_{1-6}$ alkyl;

$R^{10}$ is H or $C_{1-6}$ alkyl;

each R is H, $C_{1-6}$ alkyl, $C_{2-6}$ alkenyl, or $C_{2-6}$ alkynyl, wherein a carbon may optionally be substituted or replaced with NR, O or S;

i is 0-1;

k, l and m are independently 0-6;

n is 1-6; and p is 0-3.

In one embodiment, the compounds of the invention have Formula (2A) or (2B):

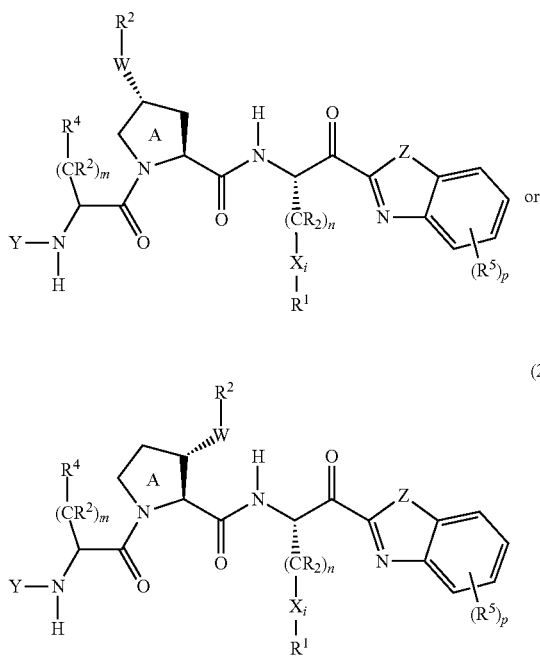

(2A)

(2B)

wherein Z is O or S;

R¹ is NH₂, —NHC(=NH)—NH₂ or —C(=NH)—NH₂;

W is —O(CH₂)$_k$— or —S(O)(CH₂)$_k$—;

R² is an optionally substituted phenyl, or W—R² together form C$_{1-6}$ alkyl or an optionally substituted phenyl;

Y is SO₂R³ or —(CO)—O—R³;

R³ is C$_{1-6}$ alkyl, —(CH₂)$_l$-cyclopropyl or —(CH₂)$_l$—R⁸ wherein R⁸ is an optionally substituted phenyl;

R⁴ is an optionally substituted, phenyl, piperidinyl, C$_{5-7}$ cycloalkyl, cyclohexanol, imidazolyl, thienyl,

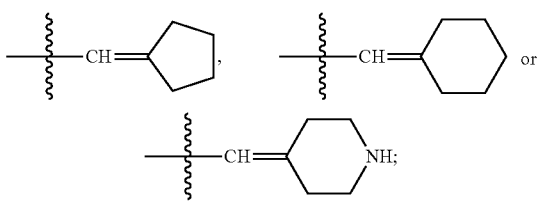

i and p are 0;

k is 1;

l is 0-1; and m and n are independently 1-4.

In another embodiment, the compounds of the invention have Formula (3A) or (3B):

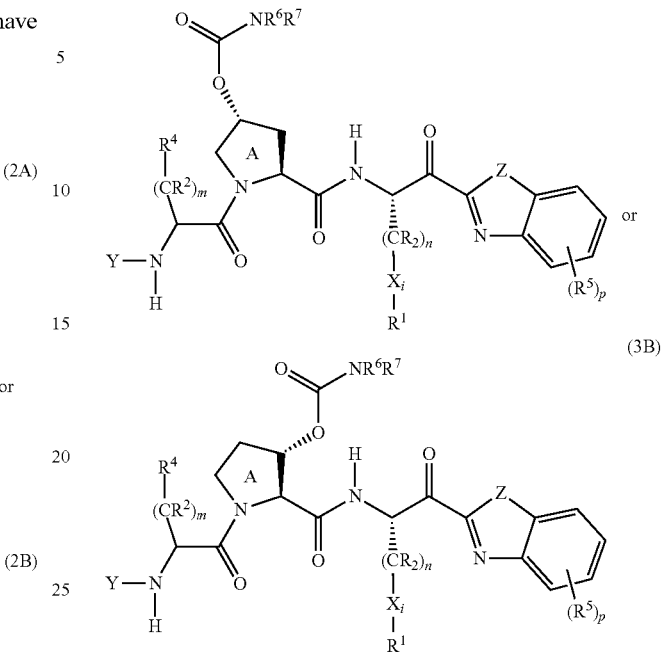

(3A)

(3B)

wherein R⁶ and R⁷ are independently H, C$_{1-6}$ alkyl or —(CR₂)$_l$—R⁸; or R⁶ and R⁷ together with N form an optionally substituted pyrrolidinyl, piperidinyl, morpholino, piperazinyl or diazepanyl;

R⁸ is an optionally substituted phenyl, furanyl, tetrahydrofuranyl, piperidinyl or thienyl; and i and p are 0.

In some embodiments, X, R⁸ and R⁹ may be an optionally substituted C$_{3-7}$ cycloalkyl.

In each of the above formula, R¹ may be NR'R", NH—C(NR'R")=NH, NH—C(NHR')=NR", NH—C(R')=NR", S—C(NR'R")—NH, S—C(NHR')—NR", C(NR'R")=NH, C(NHR')=NR" or CR=NR"; where R'R" are the same or different and are H, C$_{1-6}$ alkyl, C$_{1-3}$ arylalkyl, aryl or where R'R" forms a nitrogen-containing nonaromatic heterocyclic cyclic ring.

The compounds and compositions of the invention may be useful for modulating a channel activating protease. Examples of channel activating proteases which may be modulated using the compounds and compositions of the invention include but are not limited to prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, or neutrophil elastase. The novel compounds of this invention may also inhibit the activity of proteases that stimulate the activity of ion channels, such as the epithelial sodium channel, and may be useful in the treatment of CAP-associated diseases.

Pharmacology and Utility

Compounds of the invention modulate the activity of channel activating protease, for example, trypsin-like serine proteases such as prostasin, and as such, are useful for treating diseases or disorders in which prostasin contributes to the pathology and/or symptomology of the disease.

Diseases mediated by inhibition of a channel activating protease, for example, by a trypsin-like serine protease such as prostasin, include diseases associated with the regulation of fluid volumes across epithelial membranes. For example, the volume of airway surface liquid is a key regulator of mucociliary clearance and the maintenance of lung health. The inhibition of a channel activating protease will promote fluid accumulation on the mucosal side of the airway epithelium, thereby promoting mucus clearance and preventing the accumulation of mucus and sputum in respiratory tissues (including lung airways). Such diseases include respiratory diseases such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases mediated by inhibition of channel activating proteases also include diseases other than respiratory diseases that are associated with abnormal fluid regulation across an epithelium, perhaps involving abnormal physiology of the protective surface liquids on their surface, for example xerostomia (dry mouth) or keratoconjunctivitis sire (dry eye). Furthermore, CAP regulation of ENaC in the kidney could be used to promote diuresis and thereby induce a hypotensive effect.

Chronic obstructive pulmonary disease includes chronic bronchitis or dyspnoea associated therewith, emphysema, as well as exacerbation of airways hyper-reactivity consequent to other drug therapy, in particular other inhaled drug therapy. The invention is also applicable to the treatment of bronchitis of whatever type or genesis including, for example, acute, arachidic, catarrhal, croupus, chronic or phthinoid bronchitis.

The compounds of the invention may be used for the treatment of asthma, including but not limited to intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects of, for example, less than 4 or 5 years of age, exhibiting wheezing symptoms and diagnosed or diagnosable as "wheezy infants", an established patient category of major medical concern and now often identified as incipient or early-phase asthmatics, or as "wheezy-infant syndrome".

The suitability of a channel activating protease inhibitor such as a prostasin inhibitor for the treatment of a disease mediated by inhibition of a channel activating protease, may be tested by determining the inhibitory effect of the channel activating protease inhibitor according to the assays described below and following methods known in the art.

In accordance with the foregoing, the present invention further provides a method for preventing or treating any of the diseases or disorders described above in a subject in need of such treatment, which method comprises administering to said subject a therapeutically effective amount of a compound of Formula (1), (2A), (2B), (3A) or (3B), or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents.

Channel activating protease inhibitors of the invention are also useful as co-therapeutic agents for use in combination with other drug substances such as anti-inflammatory, bronchodilatory, antihistamine or anti-tussive drug substances, particularly in the treatment of cystic fibrosis or obstructive or inflammatory airways diseases such as those mentioned hereinbefore, for example as potentiators of therapeutic activity of such drugs or as a means of reducing required dosaging or potential side effects of such drugs.

The channel activating protease inhibitor may be mixed with the other drug substance in a fixed pharmaceutical composition or it may be administered separately, before, simultaneously with or after the other drug substance.

Accordingly, the invention may include a combination of channel activating protease inhibitor with an anti-inflammatory, bronchodilatory, antihistamine, anti-tussive, antibiotic or DNase drug substance, said channel activating protease inhibitor and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in international patent application WO 02/88167, WO 02/12266, WO 02/100879, WO 02/00679 (for example, Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists such as montelukast and zafirlukast; PDE4 inhibitors such cilomilast (ARIFLO® GlaxoSmithKline), ROFLUMILAST® (Byk Gulden), V-11294A (Napp), BAY19-8004 (Bayer), SCH-351591 (Schering-Plough), AROFYLLINE® (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; and adenosine $A_{2B}$ receptor antagonists such as those described in WO 02/42298, each of which is incorporated herein in its entirety.

Suitable bronchodilatory drugs include beta-2 adrenoceptor agonists such as albuterol (salbutamol), metaproterenol, terbutaline, salmeterol fenoterol, procaterol, formoterol, or carmoterol and pharmaceutically acceptable salts thereof, and compounds of Formula (1) as described in WO 00/75114 (in free or salt or solvate form), which is incorporated herein by reference in its entirety, such as a compound of formula:

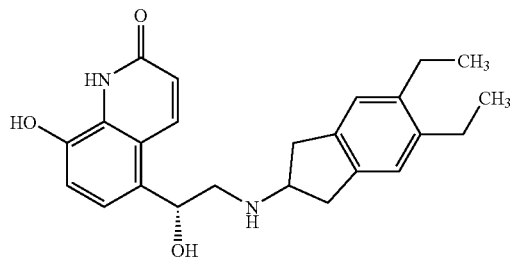

and pharmaceutically acceptable salts thereof; compounds of Formula (1) of WO 04/16601; as well as compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083 and WO 04/80964, each in free or salt or solvate form. Each of these publications is incorporated herein in its entirety.

Suitable bronchodilatory drugs also include anticholinergic or antimuscarinic agents, in particular ipratropium bromide, oxitropium bromide, tiotropium salts and CHF 4226 (Chiesi), glycopyrrolate, and also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285, each of which is incorporated herein in its entirety.

Suitable dual anti-inflammatory and bronchodilatory drugs include dual beta-2 adrenoceptor agonist/muscarinic antagonists such as those disclosed in US 2004/0167167, WO 04/74246 and WO 04/74812, each of which is incorporated herein in its entirety.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841, each of which is incorporated herein in its entirety.

Suitable antibiotics include macrolide antibiotics, for example tobramycin (TOBI™).

Suitable DNase drug substances include dornase alfa (PULMOZYME™), a highly purified solution of recombinant human deoxyribonuclease I (rhDNase), which selectively cleaves DNA. Dornase alfa is used to treat cystic fibrosis.

Other useful combinations of channel activating protease inhibitors with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methyl-phenyl)-5H-benzo-cyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037, WO 00/66558, WO 00/66559, WO 04/018425 and WO 04/026873, each of which is incorporated herein in its entirety.

In the treatment of a disease mediated by inhibition of prostasin in accordance with the invention, a channel activating protease inhibitor of the invention in free form or in pharmaceutically acceptable salt form, may be administered by any appropriate route, for example orally, e.g. in tablet, capsule or liquid form; parenterally, for example in the form of an injectable solution or suspension; intranasally, for example in the form of an aerosol or other atomisable formulation using an appropriate intranasal delivery device, e.g. a nasal spray such as those known in the art; or by inhalation, such as use with a nebulizer.

The channel activating protease inhibitor may be administered in a pharmaceutical composition together with a pharmaceutically acceptable diluent or carrier. Such compositions may be, for example dry powders, tablets, capsules and liquids, but also injection solutions, infusion solutions or inhalation suspensions, which may be prepared using other formulating ingredients and techniques known in the art.

The dosage of the channel activating protease inhibitor in free form or in pharmaceutically acceptable salt form may depend on various factors, such as the activity and duration of action of the active ingredient, the severity of the condition to be treated, the mode of administration, the species, sex, ethnic origin, age and weight of the subject and/or its individual condition. In a normal case, the daily dose for administration, for example oral administration to a warm-blooded animal, particularly a human being weighing about 75 kg, is estimated to be from approximately 0.7 mg to approximately 1400 mg; or in some examples, from approximately 5 mg to approximately 200 mg. That dose may be administered in a single dose or in several part doses, for example, from 5 to 200 mg.

When the composition comprises an aerosol formulation, it may contain a hydro-fluoro-alkane (HFA) propellant such as HFA134a or HFA227 or a mixture thereof; one or more co-solvents known in the art such as ethanol (up to 20% by weight); one or more surfactants such as oleic acid or sorbitan trioleate; and/or one or more bulking agents such as lactose. When the composition comprises a dry powder formulation, it may contain, for example, the channel activating protease inhibitor having a particle diameter up to 10 microns, optionally together with a diluent or carrier, such as lactose, of the desired particle size distribution and a compound that helps to protect against product performance deterioration due to moisture (e.g. magnesium stearate). When the composition comprises a nebulised formulation, it may contain, for example, the channel activating protease inhibitor either dissolved, or suspended, in a vehicle containing water, a co-solvent such as ethanol or propylene glycol and a stabiliser, which may be a surfactant.

The invention includes (A) a compound of the invention in inhalable form, e.g. in an aerosol or other atomisable composition or in an inhalable particulate, e.g. micronised form; (B) an inhalable medicament comprising a compound of the invention in inhalable form; (C) a pharmaceutical product comprising a compound of the invention in inhalable form in association with an inhalation device; and (D) an inhalation device containing a compound of the invention in inhalable form.

Processes for Making Compounds of the Invention

The present invention also includes processes for the preparation of compounds of the invention. In the reactions described, reactive functional groups, where desired in the final product (e.g., hydroxy, amino, imino, thio or carboxy groups), may be protected using protecting groups known in the art, to avoid their unwanted participation in the reactions. Conventional protecting groups may be used in accordance with standard practice, for example, see T. W. Greene and P. G. M. Wuts in "Protective Groups in Organic Chemistry", John Wiley and Sons, 1991.

In one embodiment, compounds of the invention may be prepared following the Reaction scheme I below:

Reaction Scheme I

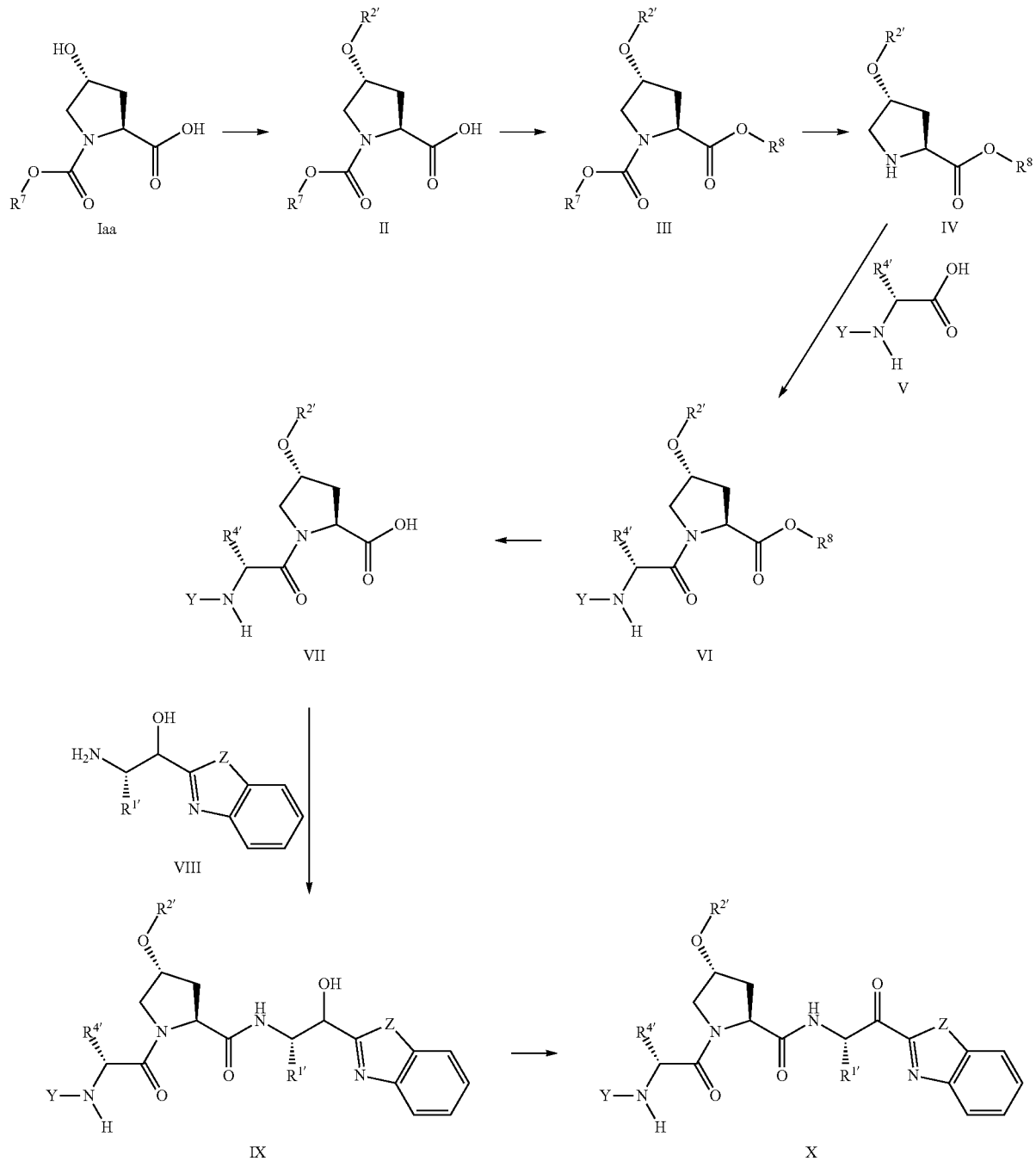

wherein R$^{1'}$ is (CR$_2$)$_n$—X$_i$—R$^1$;
R$^{2'}$ is (CR$_2$)$_k$R$^2$;
R$^{4'}$ is (CR$_2$)$_m$—R$^4$;
R$^1$, R$^2$, R$^4$, X, Y, Z, i, k, m and n are as defined in Formula (1);
R$^7$ and R$^8$ are alkyl protecting groups (for example, methyl, ethyl, t-butyl or benzyl and the like).

In the above Reaction Scheme I, the intermediate compound II may be synthesized by reacting intermediate compound Iaa with an alkyl reagent of the type R$^2$—X where X is a leaving group, in the presence of a suitable base and a suitable organic solvent. Examples of leaving groups in alkyl reagents R$^2$—X include but are not limited to halides such as chlorides and bromides, or a tosylate, mesylate, or besylate leaving groups, and the like. Intermediate compound III may be prepared by reacting intermediate compound II with diazomethane or (trimethylsilyl)diazomethane in the presence of a suitable organic solvent. These reactions may proceed in a temperature range of about 0° C. to about 60° C., and may take up to about 24 hours to complete.

Alternatively, intermediate compound III may be synthesized by reacting intermediate compound II with an alkyl reagent of the type $R^8$—X where X is a leaving group as previously described above, in the presence of a suitable base and a suitable organic solvent. The reaction may proceed in a temperature range of about 0° C. to about 80° C., and may take up to about 24 hours to complete.

Alternatively, intermediate compound III may be synthesized by reacting intermediate compound II with an alcohol of the type $R^8$—OH with a suitable peptide coupling reagent and a suitable base in the presence of a suitable solvent. Suitable bases for this reaction include but are not limited to triethylamine, DIEA, pyridine, 2,4,6-collidine, and other suitable bases within the knowledge of those skilled in the art. The reaction may proceed in a temperature range of about 0° C. to about 40° C., and may take up to about 24 hours to complete.

In the above Reaction Scheme I, intermediate compound IV may be synthesized by removing the carbamate protecting group (e.g., where $R^7$ is t-butyl) from intermediate compound III with a suitable acid, and optionally in the presence of a suitable organic solvent. Suitable acids include but are not limited to TFA, p-TsOH, TfOH, HCl, HBr, HF, $HBF_4$, and other suitable acids within the knowledge of those skilled in the art. The reaction may proceed in a temperature range of about −20° C. to about 40° C., and may take up to about 24 hours to complete.

Alternatively, intermediate IV may be synthesized by removing the carbamate protecting group from intermediate compound III (e.g., where $R^7$ is benzyl or any benzylic derivative) with hydrogen gas in the presence of a suitable catalyst and a suitable solvent or water. Examples of suitable catalysts include but are not limited to Pd/C, Pt, $PtO_2$, Pt/C, Rh/C, and other suitable catalysts within the knowledge of those skilled in the art. The reaction may proceed in a temperature range of about 0° C. to about 80° C., with hydrogen pressures of about 15 psi to about 80 psi, and may take up to about 48 hours to complete.

Intermediate compound VI may be synthesized by reacting intermediate compounds IV and V in the presence of a peptide coupling reagent and a suitable base ($Et_3N$, DIEA, pyridine, 2,4,6-collidine, and the like) in the presence of a suitable organic solvent. The reaction may proceed in a temperature range of about 0° C. to about 40° C., and may take up to about 24 hours to complete. Intermediate compound VII may be synthesized by reacting intermediate compound VI with a suitable base (for example LiOH, NaOH, KOH, $K_2CO_3$, $NaCO_3$, $CsCO_3$, and the like) in the presence of a suitable organic solvent or water. The reaction may proceed in a temperature range of about 0° C. to about 40° C., and may take up to about 24 hours to complete. Intermediate compound of IX may be synthesized by reacting intermediate compounds VII and VIII in the presence of a suitable peptide coupling reagent and a suitable base ($Et_3N$, DIEA, pyridine, 2,4,6-collidine, and the like) in the presence of a suitable organic solvent. The reaction may proceed in a temperature range of about 0° C. to about 40° C., and may take up to about 24 hours to complete.

The final compound X may be synthesized by reacting intermediate compound IX with a suitable oxidant in the presence of a suitable organic solvent or water. Suitable oxidants include but are not limited to for Dess-Martin periodinane, 2-iodobenzoic acid with oxone, TEMPO with trichlor-isocyanuric acid, TEMPO with NaOCl, DMSO with oxalyl chloride, pyridinium chlorochromate, $MnO_2$, $CrO_2$, and other suitable oxidants within the knowledge of those skilled in the art. The reaction may proceed in a temperature range of about 0° C. to about 40° C., and may take up to about 24 hours to complete.

In another embodiment, compounds of the invention may be prepared following the Reaction scheme II below, and following conditions for similar reactions as described in Reaction Scheme I:

Reaction Scheme II

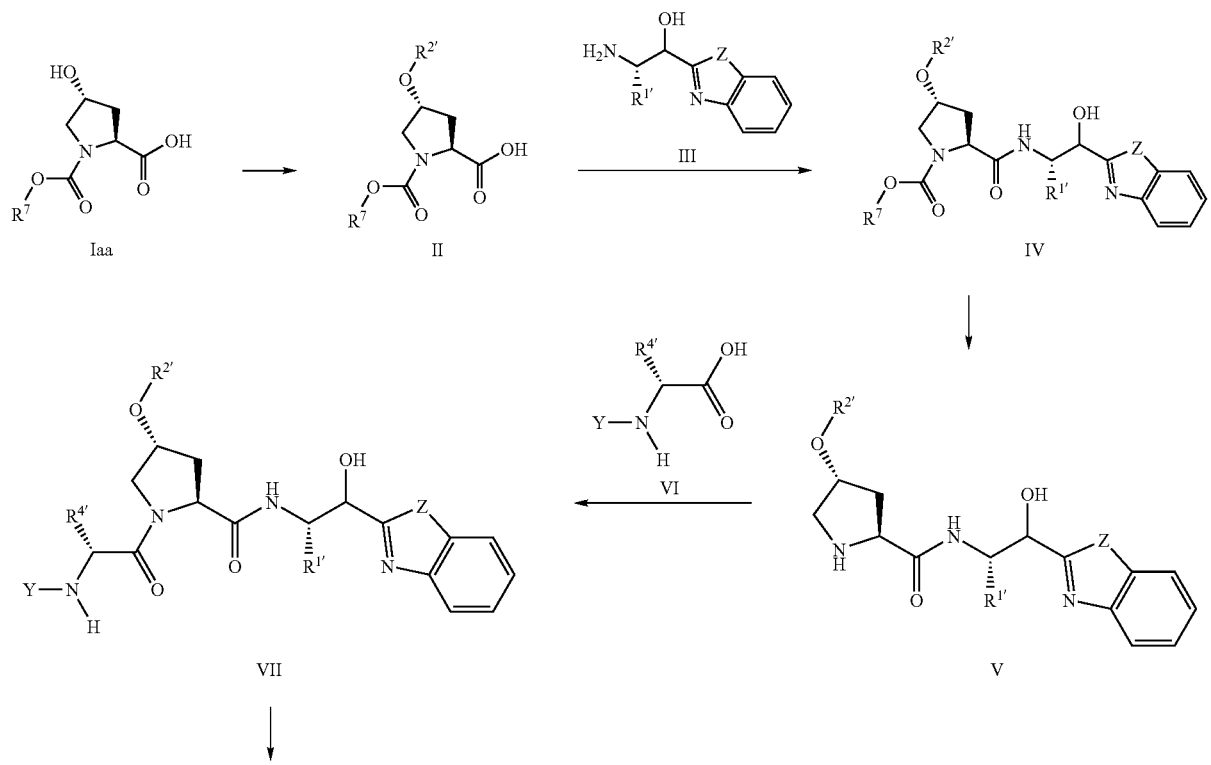

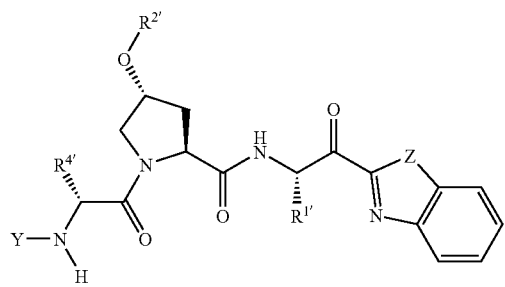

VIII wherein $R^{1'}$, $R^{2'}$, $R^{4'}$, Y and Z are as described in Reaction Scheme I.

In the above Reaction Scheme II, intermediate compound II may be synthesized by reacting intermediate compound Iaa with an alkyl reagent of the type $R_2$—X where X is a leaving group, in the presence of a base and solvent. Intermediate compound IV may be synthesized by reacting intermediate compounds II and III with a peptide coupling reagent and a base in a solvent. Intermediate compound V may be synthesized by removing the carbamate protecting group from intermediate compound IV (e.g., where $R^7$ is t-butyl), by reacting intermediate compound IV with an acid, and optionally in a solvent. Alternatively, intermediate compound V may be synthesized by removing the carbamate protecting group from intermediate compound IV (where $R^7$ is benzyl or any benzylic derivative), with hydrogen gas in the presence of a catalyst in an organic solvent or water. Intermediate compound VII may be synthesized by reacting intermediate compounds V and VI with a peptide coupling reagent and a base in solvent. The final compound VIII may be synthesized by reacting intermediate compound VII with an oxidant in an organic solvent or water.

In yet another embodiment, compounds of formula (2) may be prepared following the Reaction Scheme III below, and following conditions for similar reactions as described in Reaction Scheme I:

Reaction Scheme III

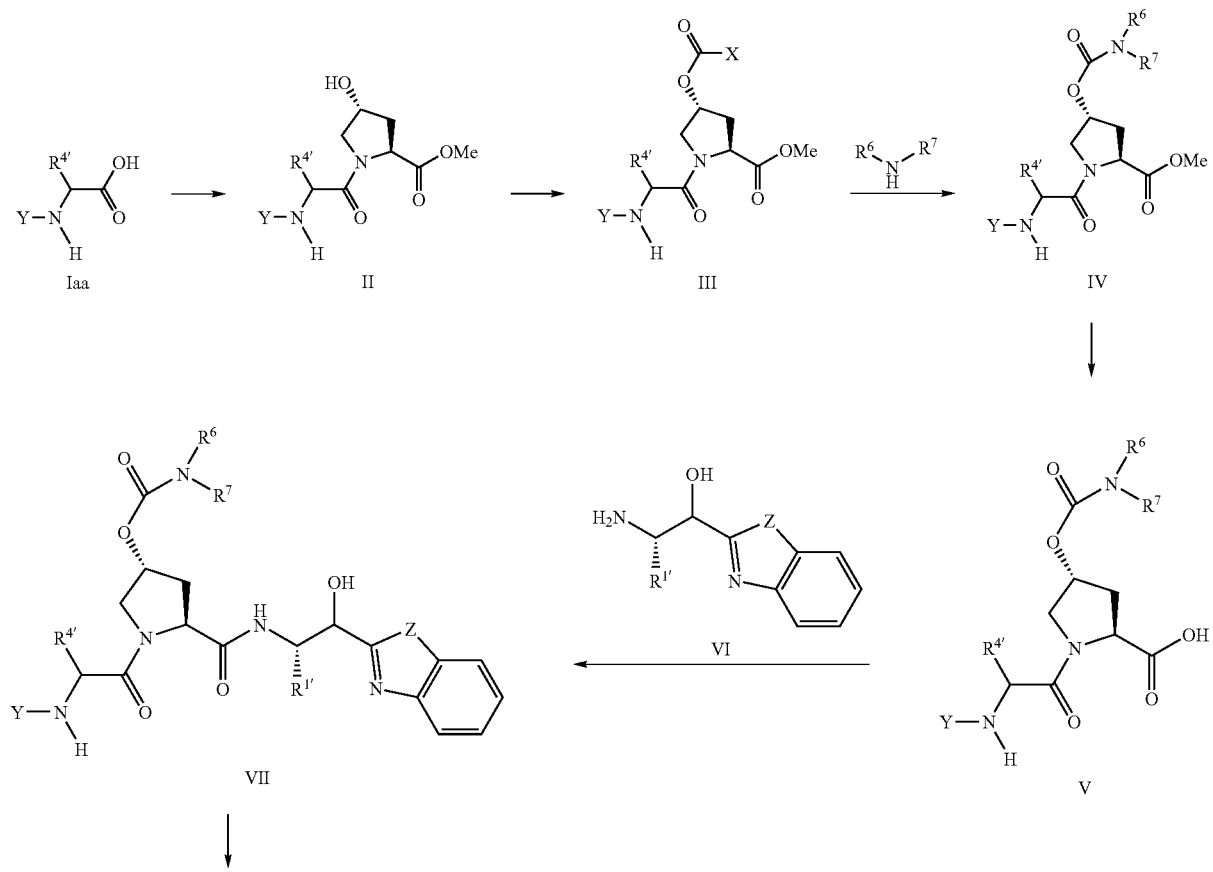

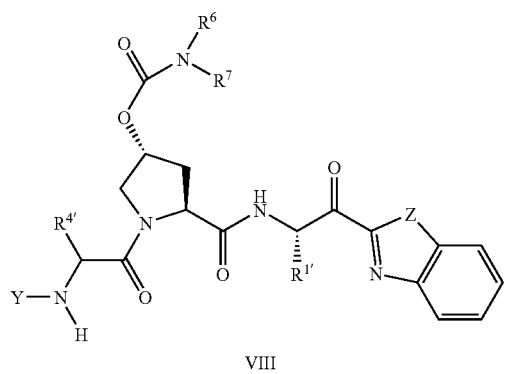

VIII wherein $R^{1'}$, $R^{4'}$, $R^6$, $R^7$, Y and Z are as defined in Formula (1), and X is an activated leaving group such as —OPhNO$_2$, or —Cl.

In the above Reaction Scheme III, intermediate compound II may be synthesized by reacting intermediate compound Iaa with trans-4-hydroxyproline methyl ester and a peptide coupling reagent in the presence of a solvent and base. The reaction may proceed at room temperature, and may take up to about 24 hours to complete.

Intermediate compound III may be synthesized by reacting intermediate compound II with a suitable reactive chemical intermediate (for example, phenyl chloroformate, 4-nitrophenyl chloroformate, pentafluorophenyl chloroformate and the like) and a suitable base in a suitable solvent. The reaction may proceed in a temperature range of about 0° C. to about 60° C., and may take up to about 24 hours to complete.

Intermediate compound IV may be synthesized by reacting intermediate compound III with a suitable primary or secondary amine in the presence of a suitable solvent. The reaction may proceed in a temperature range of about 0° C. to about 60° C., and may take up to about 24 hours to complete. Intermediate compound V may be synthesized by reacting intermediate compound IV with a suitable base (for example LiOH, NaOH, KOH and the like) in a suitable organic solvent with or without water. The reaction may proceed in a temperature range of about 0° C. to about 40° C., and may take up to about 24 hours to complete. Intermediate compound VII may be synthesized by reacting intermediate compound V with the intermediate amine VI in the presence of a peptide coupling reagent and a base in solvent. The final compound VIII may be synthesized by reacting intermediate compound VII with a suitable oxidant in a solvent.

Suitable peptide coupling reagents for use in the reactions described in Reaction schemes I, II and III include but are not limited to DCC, DIC, HATU, BOP, PyBOP, EDC, and other coupling reagents within the knowledge of those skilled in the art.

Suitable bases for use in the reactions described in Reaction schemes I, II and III include but are not limited to hydroxides such as NaOH, KOH, or LiOH; carbonates such as K$_2$CO$_3$ or CsCO$_3$; hydrides such as NaH or KH, and the like. Other suitable bases are amines, DIEA, pyridine, 2,4,6-collidine, and other suitable bases within the knowledge of those skilled in the art.

Suitable organic solvents for use in the reactions described in Reaction schemes I, II and III include but are not limited to DMSO, THF, DMF, DMAc, acetonitrile, acetone, 2-propanone, butanone, HMPA, NMP, dichloromethane, chloroform, 1,2-dichloroethane, diethyl ether, methanol, ethanol, t-butanol, isopropanol, propanol, n-butanol, cyclohexanol, acetonitrile, dioxane, MTBE, benzene, toluene, and mixtures thereof, and other suitable solvents within the knowledge of those skilled in the art.

Additional Processes for Making Compounds of the Invention

A compound of the invention may be prepared as a pharmaceutically acceptable acid addition salt by reacting the free base form of the compound with a pharmaceutically acceptable inorganic or organic acid. Alternatively, a pharmaceutically acceptable base addition salt of a compound of the invention may be prepared by reacting the free acid form of the compound with a pharmaceutically acceptable inorganic or organic base.

Alternatively, the salt forms of the compounds of the invention may be prepared using salts of the starting materials or intermediates.

The free acid or free base forms of the compounds of the invention may be prepared from the corresponding base addition salt or acid addition salt from, respectively. For example, a compound of the invention in an acid addition salt form may be converted to the corresponding free base by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details, see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal may be found in T. W. Greene, "Protecting Groups in Organic Chemistry", 3$^{rd}$ edition, John Wiley and Sons, Inc., 1999.

Compounds of the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubilities, reactivity, etc.), and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In summary, the compounds of Formula (1) may be made by a process, which involves:

(a) that of Reaction Scheme I, II or III;

(b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or may be prepared analogously to methods known in the art or as disclosed in the Examples hereinafter. One of skill in the art will appreciate that the above transformations are only representative of methods for preparation of the compounds of the present invention, and that other well known methods may similarly be used. The present invention is further exemplified, but not limited, by the following intermediates (Reference compounds) and Examples that illustrate the preparation of the compounds of the invention.

In the synthetic methodologies below, the following common abbreviations known in the art are used: DCM (dichloromethane); THF (tetrahydrofuran); and DIEA (diisopropylethylamine).

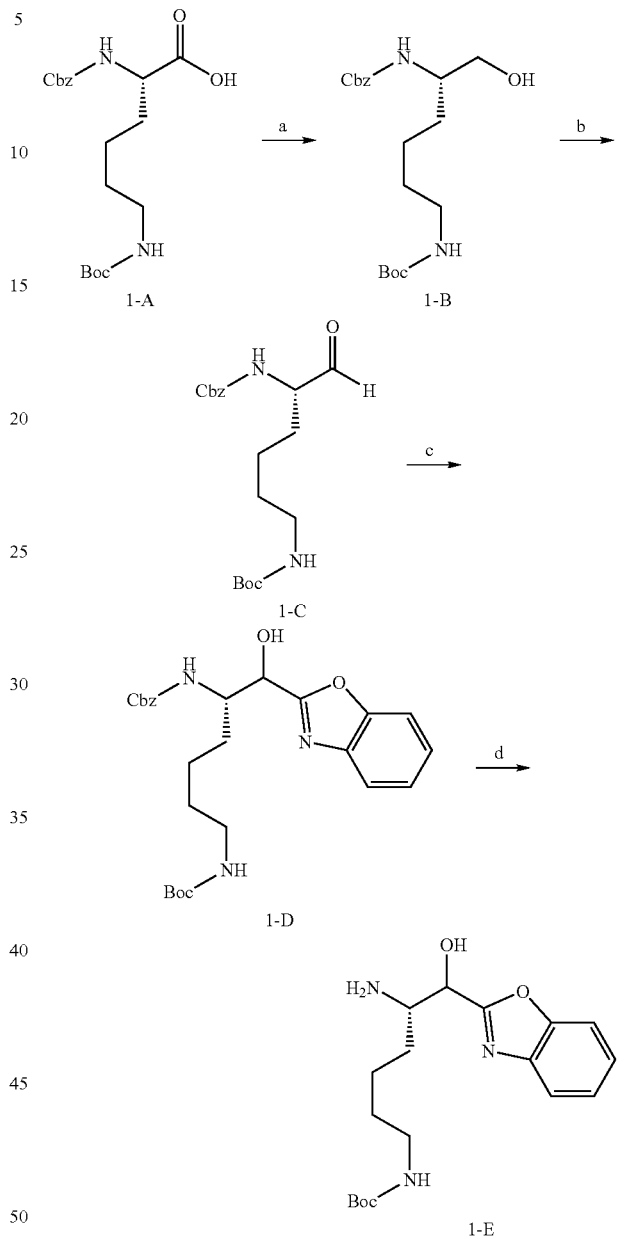

In the above Scheme 1, the reagents and conditions are: (a) iso-BuOCOCl, Et$_3$N, THF; NaBH$_4$, H$_2$O. (b) Dess-Martin periodinane, CH$_2$Cl$_2$; (c) iso-PrMgCl, benzoxazole, THF, −20° C., 30 min, then 1-C, −20° C. to rt. (d) H$_2$ (40 psi), EtOH, Pd/C 10%, rt, 18 h.

1-B: The crude starting material, Z-Lys(Boc)OH (320 g, 842 mmol) is dissolved in THF (2500 mL) and the solution is cooled to −10° C. followed by the addition of triethylamine (115.2 mL, 1.0 eq) and dropwise addition of iso-butylchloroformate (118.7 mL, 1.1 eq). The resulting suspension is stirred for 2 h at 0° C. The reaction mixture is filtered and cooled to −10° C. NaBH$_4$ (64.6 g, 2.1 eq) is dissolved in water (500 mL) at 0° C. and the solution is added portionwise to the THF solution (heavy CO$_2$ evolution). The reaction mixture is allowed to warm to room temperature and stirred for one hour.

The reaction mixture is acidified with 1N HCl solution, and the aqueous phase is extracted several times with EtOAc. The combined organic layers are washed with water, saturated aqueous NaHCO$_3$ solution and brine; dried on MgSO$_4$; and the solvent is removed in vacuo. The product is purified by flash column chromatography (hexanes/ethyl acetate) to afford the desired product as a white foam.

1-C: The alcohol (200 g, 545.8 mmol) is dissolved in DCM (2000 mL) and cooled to 0° C. A solution of the Dess-Martin reagent (231 g, 1.0 eq) in DCM (2000 mL) is added portionwise. The suspension is allowed to warm to room temperature and stirred until complete conversion (1-4 hours). A 1:1 mixture of saturated aqueous NaHCO$_3$ solution and a 1M Na$_2$S$_2$O$_3$ solution is added and the resulting biphasic system is stirred vigorously for 20 minutes. The organic layer is separated and the aqueous layer is extracted one time with DCM. The combined organic layers are distilled in vacuo and the resulting oil is taken up in EtOAc and washed six times with the NaHCO$_3$/Na$_2$S$_2$O$_3$ mixture, water and brine; dried on MgSO$_4$ and the solvent is removed in vacuo to give the crude aldehyde as a yellowish oil. The material is directly used in the next step without further purification.

1-D: To a solution of isopropyl-magnesium chloride (1.67 eq. vs aldehyde, 390 mL of a 2M-THF solution from Sigma-Aldrich) in THF (1500 mL) is added benzoxazole (92.8 g, 1.67 eq) in THF (1000 mL) at −20° C. The reaction mixture is stirred at −20° C. for 30 minutes (color change: deep red) and a solution of the aldehyde (170 g, 466 mmol) in THF (1500 mL) is added slowly under temperature control at −20° C. to −15° C. The reaction mixture is allowed to warm to room temperature and stirred until completion. The reaction mixture is quenched with saturated aqueous NH$_4$Cl solution and the solvent is removed in vacuo. The aqueous phase is extracted three times with EtOAc; the combined organic layers are excessively washed with 1N HCl solution, water, brine, dried on MgSO$_4$, and the solvent is removed in vacuo to give the crude benzoxazole as a deep red oil. Purification on silica with EtOAc/hexanes (1:5 to 1:1) gave the benzoxazole as a yellow solid.

1-E: A solution of Compound 5 (25.0 g, 51.7 mmol) is dissolved in ethanol (150 mL). Pd/C (10%, wet, Degussa type) is added, and the flask is placed on a Parr shaker overnight and subjected to hydrogen gas at 40 psi. The catalyst is filtered through Celite, and solvent is removed in vacuo. The crude material is purified by flash chromatography using first a gradient of hexanes/EtOAc to remove less polar and colored impurities, then followed by a gradient of DCM/MeOH to elute the desired compound 5. The solvent is removed in vacuo, and the compound is triturated several times in ether to afford the desired reference compound 1 as a white powder. $^1$H-NMR (DMSO-d6, 400 MHz) δ 7.73-7.70 (2H, m), 7.40-7.34 (2H, m), 6.78-6.73 (1H, m), 4.55-4.51 (1H, m), 3.05-3.01 (1H, m), 2.92-2.83 (2H, m), 1.48-1.18 (14H, m). LCMS: 350.5 (M+H)$^+$.

Scheme 2

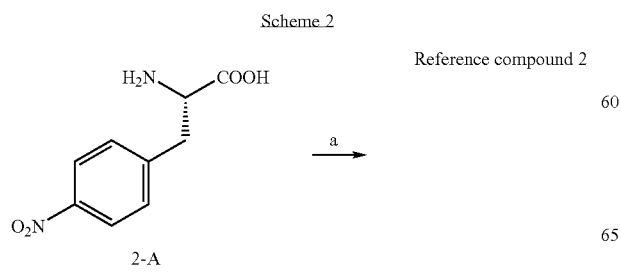

2-A

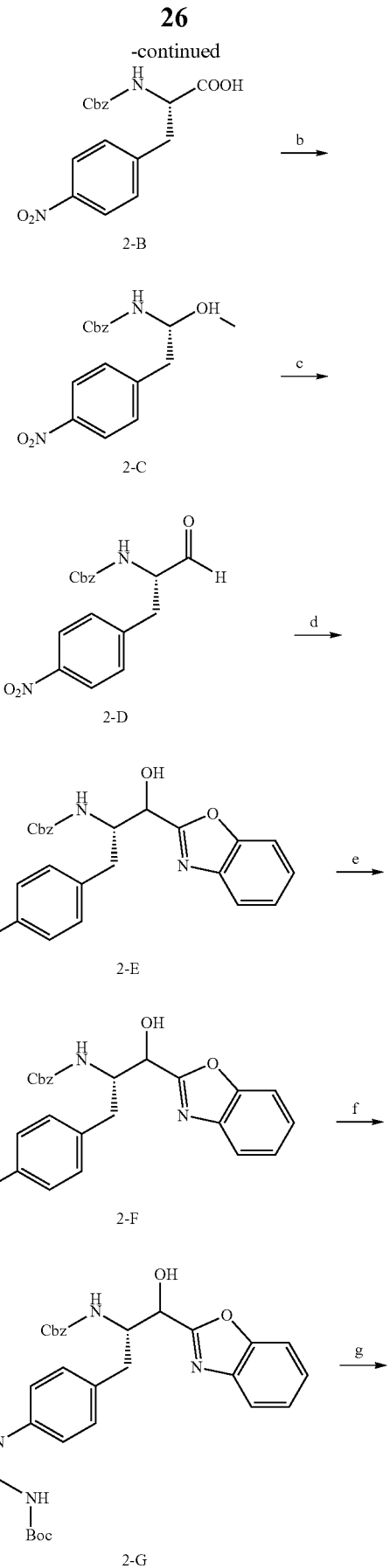

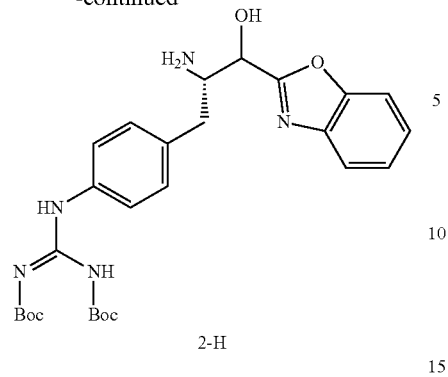

2-H

In the above Scheme 2, the reagents and conditions are: a) Cbz-OSu, Et$_3$N, THF, H$_2$O, rt, 18 h, (b) i. iso-BuOCOCl, Et$_3$N, THF; ii. NaBH$_4$, H$_2$O; (c) Dess-Martin periodinane, CH$_2$Cl$_2$; (d) iso-PrMgCl, benzoxazole, THF, −20° C., 30 min, then 2-D, −20° C. to rt; (e) Indium, NH$_4$CT, EtOH, reflux, 5 h; (f) N,N-Bis(tert-butoxycarbonyl)-1H-pyrazole-1-carboxamidine, DIEA, MeOH; (g) H$_2$, (40 psi), 10% Pd/C, EtOH.

2-B: L-Nitrophenylalanine hydrochloride (4.45 g, 18.0 mmol) and N-(Benzyloxycarbonyloxy)succinimide (Cbz-OSu) (4.49 g, 18.0 mmol) are added to a round bottomed flask containing THF (60 mL) and water (20 mL). The mixture is stirred at room temperature and Et$_3$N (10.1 mL, 72.0 mmol) is added, and the reaction is stirred overnight at room temperature. The clear solution is diluted with EtOAc (200 mL), and washed with 1N HCl (3×100 mL) and brine (1×100 mL) and dried with MgSO$_4$. Solvent is evaporated in vacuo to afford intermediate 2-B as a white solid.

2-C to 2-E: These intermediates are prepared following methods analogous to those described for preparing intermediates 1-B to 1-D of Reference compound 1, respectively.

2-F: The nitrophenyl analog 5-E (1.85 g, 4.15 mmol) is dissolved in EtOH (50 mL) and heated to reflux. Saturated aqueous NH$_4$Cl (5 mL) is added, followed by powdered indium (3.2 g, 27.9 mmol). The reaction mixture is stirred at reflux for 5 h, cooled to room temperature, and the solvent is removed in vacuo. The crude material is suspended in EtOAc (100 mL), washed with saturated NaHCO$_3$ (3×100), dried with MgSO$_4$, and filtered through Celite. The solvent is removed in vacuo to afford the aniline 2-F as an off-white waxy solid.

2-G: Aniline 2-F (1.52 g, 3.67 mmol) is dissolved in MeOH (10 mL). DIEA (0.7 mL, 4.4 mmol) and N,N-Bis(tert-butoxycarbonyl)-1H-pyrazole-1-carboxamidine (1.37 g, 4.4 mmol) are added, and the reaction mixture is stirred at room temperature. After 4 h, another 0.5 equiv of N,N-Bis(tert-butoxycarbonyl)-1H-pyrazole-1-carboxamidine (0.685 g, 2.2 mmol) is added and the reaction is then stirred overnight at room temperature. EtOAc (100 mL) is added, and the organic layer is washed with water, brine, dried on MgSO$_4$. The solvent is removed in vacuo, and the crude material is purified by silica gel chromatography with EtOAc/hexanes (0 to 100% gradient) to afford the desired product 2-G as an oil.

2-H: This compound is prepared from 2-G following methods analogous to those described for the preparation of intermediate 1-E for Reference compound 1.

Scheme 3

Reference compound 3

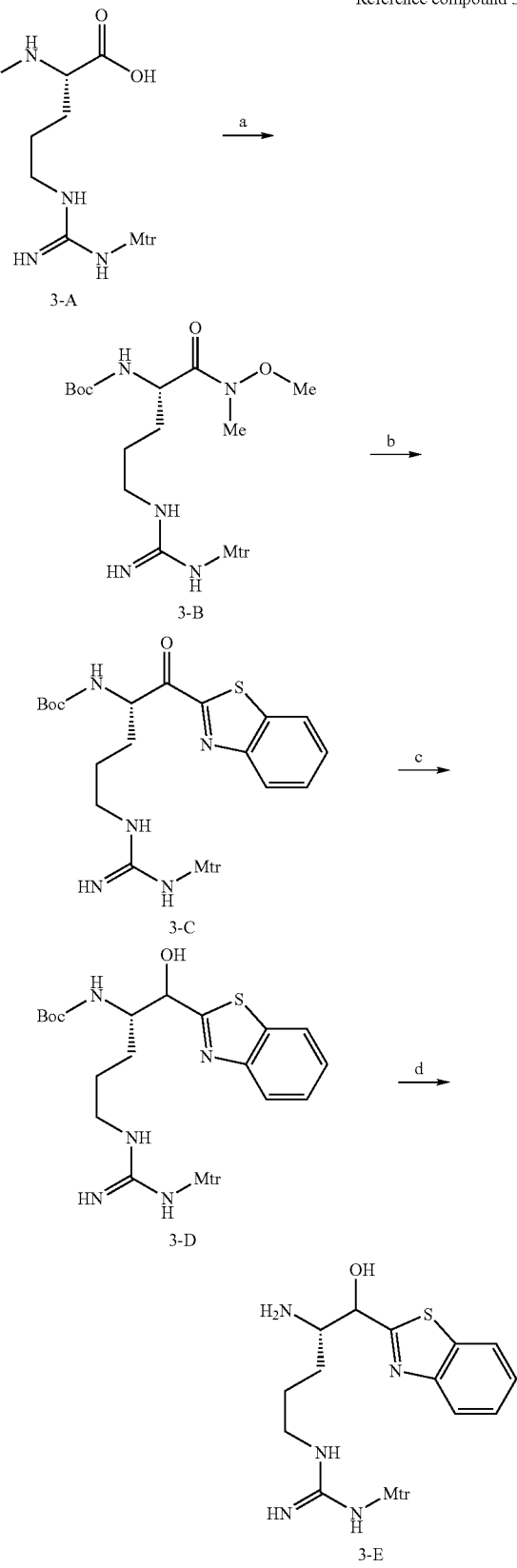

In the above Scheme 3, the reagents and conditions are: (a) HN(OMe)Me.HCl, BOP, Et₃N, DMF, 0° C. to rt; (b) n-BuLi (2.5 M in hexanes), benzothiazole, THF, −78° C., then 3-B, THF, −70° C. to rt; (c) NaBH₄, MeOH; (d) p-TsOH, CH₂Cl₂, 6 h.

3-B: BOP (50 g, 112 mmol) is added in one portion to a stirring solution of 3-A (49.92 g, 102.6 mmol), N,O-dimethylhydroxylamine hydrochloride (30.4 g, 224 mmol) and triethylamine (88 ml, 616 mmol) in dry DMF (200 mL) under argon at 0° C. The reaction mixture is allowed to slowly warm to room temperature over 2 h, filtered through diatomaceous earth, and concentrated in vacuo. The residue is dissolved in ethyl acetate; washed with H₂O, 1 M aqueous KHSO₄, saturated aqueous NaHCO₃, and brine; dried, and concentrated in vacuo. The residue is purified by silica gel column chromatography to give compound 3-B.

3-C: n-Butyllithium (2.5 M in hexanes, 272.2 ml, 681.4 mmol) is added dropwise at −78° C. under argon to a stirring solution of benzothiazole (115.72 g, 850.7 mmol) in dry THF (1660 mL) at a rate that kept the reaction temperature below −64° C. Upon completion of addition, the reaction mixture is stirred for 30 min at −70° C., and a solution of compound 3-B (45 g, 85.7 mmol) in dry THF (300 ml) is added at a rate that maintained the reaction temperature below −70° C. The reaction is stirred for 15 min, quenched with saturated aqueous NH₄Cl, and stirred for 16 h at room temperature. The resulting organic layer is separated; diluted with ethyl acetate; washed with water and brine; dried and concentrated in vacuo; and purified by silica gel chromatography to give compound 3-C.

3-D: To a solution of 3-C (33.7 g, 55.82 mmol) in MeOH (407 ml) at 0° C. is added NaBH₄ (9.98 g). The reaction mixture is slowly warmed to room temperature over 1 h, then heated to 45° C. for 1 h, and then cooled back to room temperature. The reaction is quenched with acetone (60 mL), and concentrated in vacuo. The residue is dissolved in ethyl acetate, washed with brine, and dried over MgSO₄. The crude material is purified by silica gel chromatography to afford product 3-D.

3-E: p-TsOH is added to a stirring solution of compound 3-D (28.2 g) in CH₂Cl₂ (300 mL) at room temperature until the solution is saturated. The reaction is stirred at room temperature for 6 h. Water is added, and the organic layer is extracted with EtOAc; washed with 1:1 mixture (V/V) of brine and 10% aqueous Na₂CO₃; dried over Na₂SO₄; and purified by silica gel chromatography to give the product 3-E.

Scheme 4

Reference compound 4

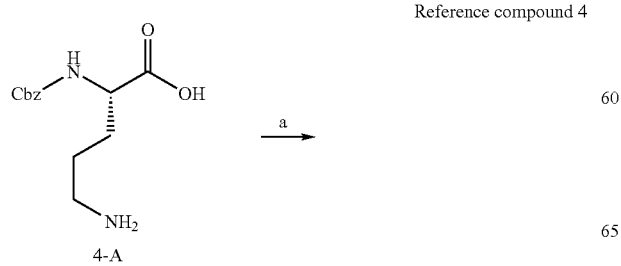

4-A

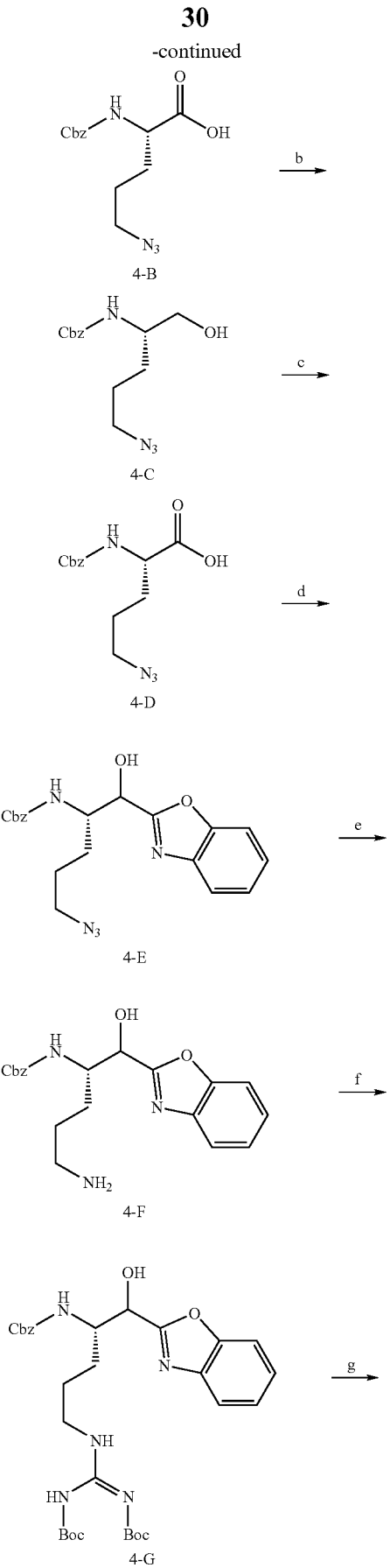

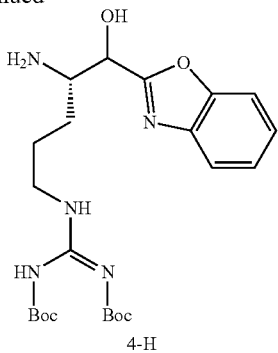

4-H

In the above Scheme 4, the reagents and conditions are: (a) i. $NaN_3$, $Tf_2O$, $H_2O$, $CH_2Cl_2$, 0° C.; ii. Cbz-Orn-OH, $K_2CO_3$, $H_2O$, $CuSO_4$, then $TfN_3$, MeOH; (b) i. iso-BuOCOCl, $Et_3N$, THF; ii. $NaBH_4$, $H_2O$; (c) Dess-Martin periodinane, $CH_2Cl_2$; (d) iso-PrMgCl, benzoxazole, THF, −20° C., 30 min, then 4-D, −20° C. to rt; (e) $PMe_3$, THF, $H_2O$ (f) N,N-Bis(tert-butoxycarbonyl)-1H-pyrazole-1-carboxamidine, MeOH; (g) $H_2$, (40 psi), 10% Pd/C, EtOH.

4-B: Preparation of the triflic azide ($TfN_3$) solution: Sodium azide (61 g, 938.8 mmol, 10 eq) is dissolved in water (150 mL), and the solution is cooled to 0° C. Dichloromethane (250 mL) is added and the biphasic system is stirred vigorously while freshly distilled trifluoromethansulfonylanhydride ($Tf_2O$) is added over a period of 30 min. The reaction mixture is stirred vigorously for an additional two hours at 0° C. The phases are separated, and the aqueous layer is extracted twice with dichloromethane (each 100 mL). The combined organic layers are washed twice with saturated aqueous $NaHCO_3$ solution (each 100 ml). This solution is kept and used as is.

Z-Orn-OH (25 g, 93.88 mmol) is dissolved in water (250 mL) followed by the addition of potassium carbonate (18.16 g, 131.4 mmol, 1.4 eq) and $CuSO_4$ (1 mol %, 250 mg). The $TfN_3$ solution is added at once to the reaction mixture at room temperature. After complete addition (biphasic mixture), methanol is added until the reaction mixture became monophasic (approximately 850 mL), and the resulting reaction solution is stirred for 24 to 48 h. The solvents are evaporated, and the blue aqueous phase is acidified with 1 M $NaHSO_4$ (color disappeared). The aqueous phase is extracted with ethyl acetate (3×400 mL), and the combined organic layers are washed with water and brine; dried on $MgSO_4$; and the solvent is removed in vacuo to give crude azide which is purified over silica gel chromatography with EtOAc/hexanes (1:9 to 1:1) as eluent to give the azide 4-B as a yellowish oil.

4-C to 4-E: Intermediates 4-C to 4-E are prepared following methods analogous to those described for preparing the intermediates of Reference compound 1.

4-F: Azide 4-E (6.275 g, 15.9 mmol) is dissolved in a mixture of THF/water (10:1, 100 mL). Trimethylphosphine (2.0 eq) is added slowly at room temperature until the complete conversion is observed by LCMS. The solvent is removed and the residue is taken up in EtOAc. The organic layer is washed with water, brine dried on $MgSO_4$, and the solvent is removed in vacuo to give the crude amine 4-F which is used in the next step without further purification.

4-G: Amine 4-F (5.608 g, 15.2 mmol) is dissolved in MeOH (100 mL) and N,N-Bis (tert-butoxycarbonyl)-1H-pyrazole-1-carboxamidine (5.189 g, 1.1 eq) is added, and the reaction mixture is stirred for two hours at room temperature. The solvent is removed in vacuo, and the residue is taken up in EtOAc. The organic layer is washed with water and brine; dried on $MgSO_4$, and the solvent is removed in vacuo to give the crude benzoxazole-derivative. Purification on silica with EtOAc/hexanes (0 to 100% EtOAc) affords the final benzoxazole derivative as an oil.

4-H: This compound is prepared from 4-G following methods analogous to those described for the preparation of intermediate 1-E for Reference compound 1.

Scheme 5

Reference compound 5

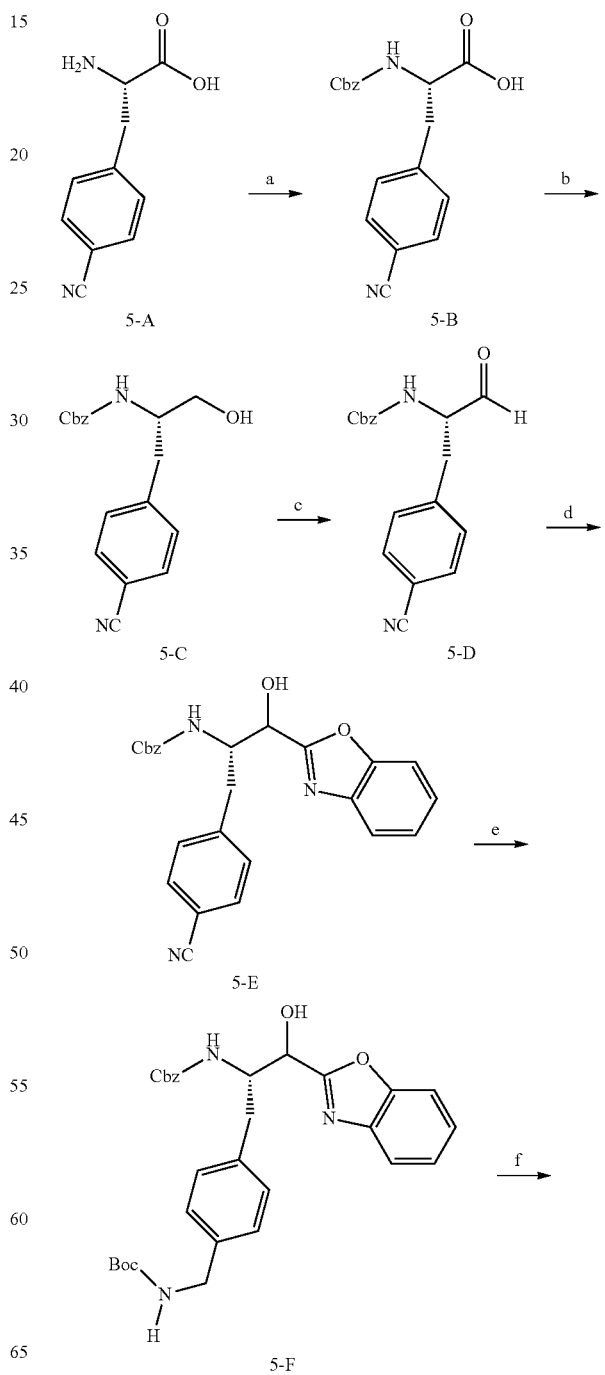

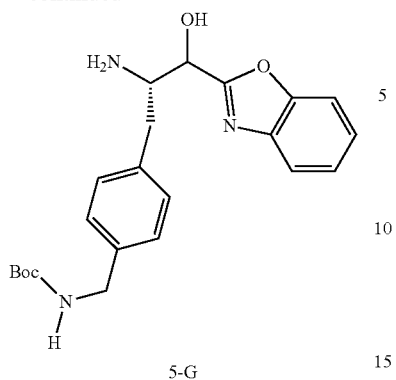

5-G

In the above Scheme 5, the reagents and conditions are: a) Cbz-OSu, Et$_3$N, THF, H$_2$O, rt, 18 h; (b) i. iso-BuOCOCl, Et$_3$N, THF; ii. NaBH$_4$, H$_2$O; (c) Dess-Martin periodinane, CH$_2$Cl$_2$; (d) iso-PrMgCl, benzoxazole, THF, −20° C., 30 min, then 5-D, −20° C. to rt; (e) NaBH$_4$, NiCl$_2$, Boc$_2$O, MeOH, 0° C., (f) H$_2$, (40 psi), 10% Pd/C, EtOH.

5-B to 5-E: This compound is prepared from L-4-cyanophenylalanine (5-A) following methods analogous to those described for intermediate 2-B for Reference compound 2. Intermediates 5-C to 5-E are prepared following methods analogous to those described for preparing intermediates 1-B to 1-D of Reference Compound 1, respectively.

5-F: Nitrile 5-E (3.68 g, 8.64 mmol) is dissolved in methanol (60 mL), and cooled to 0° C. Boc$_2$O (3.77 g, 2 eq) is added, followed by NiCl$_2$ (210 mg, 0.1 eq). The mixture is stirred, then NaBH$_4$ (2.29 g, 7.0 eq) is added slowly in small portions. The mixture is warmed to room temperature and stirred for 1 hr. Diethylene triamine (0.94 mL, 1 eq) is added. The mixture stirred for an additional 30 min, and the solvent is evaporated in vacuo. The residue is dissolved in EtOAc, washed with saturated NaHCO$_3$ (2×100 mL) twice, then dried with MgSO$_4$ and the solvent is evaporated in vacuo. The crude material is purified by silica gel flash chromatography with 0-100% gradient of EtOAc and hexanes to provide the title compound as an oil.

5-G: This compound is prepared from 5-F following methods analogous to those described for intermediate 1-E of Reference compound 1.

Scheme 6

Reference compound 6

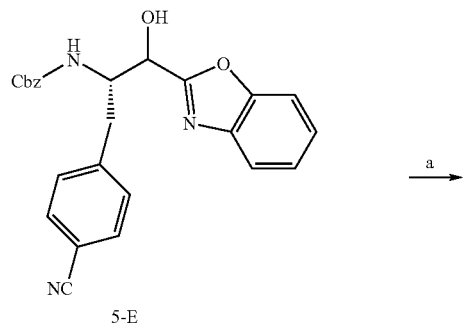

5-E

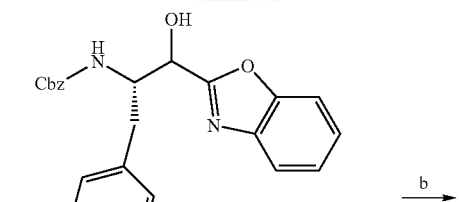

6-A

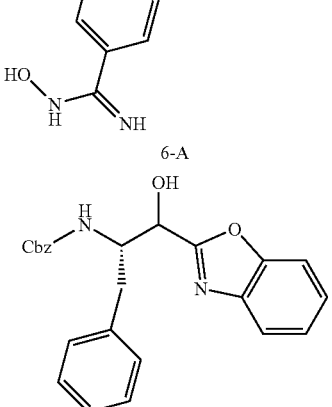

6-B

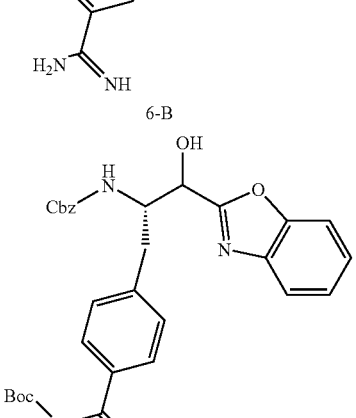

6-C

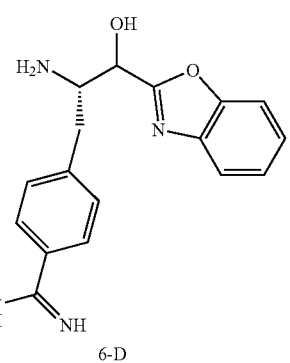

6-D

In the above Scheme 6, the reagents and conditions are: (a) HONH$_2$ 50% aq., EtOH, 40° C., 16 h; (b) SmI$_2$, THF, rt; (c) (e) H$_2$, (40 psi), 10% Pd/C, EtOH.

6-A: The nitrile intermediate 5-E from Reference compound 5 (1.92 g, 4.50 mmol) is dissolved in ethanol, and aqueous HONH$_2$ (50% aq., 1.1 mL, 18.0 mmol) is added. The reaction mixture is heated to 40° C. and stirred for 16 h. The solvent is evaporated, and the residue dissolved in EtOAc (100 mL) and washed with water (2×50 mL). The organic layer is dried (MgSO$_4$) and evaporated in vacuo to give the product as clear oil which is used in the next step without further purification.

6-B: The hydroxyamidine 6-A (2.05 g, 4.50 mmol) is dissolved in a minimum volume of THF (~2 mL), and SmI$_2$ 1M in THF (100 ml, 10 mmol) is added, and the solution is stirred for 1 h. An additional aliquot of SmI$_2$ (1M in THF solution) is added if the solution lost its blue color, and stirred for another hour. The solvent is evaporated, and the residue dissolved in EtOAc (100 mL) and washed with saturated aqueous NaHCO$_3$ (2×50 mL) and brine (50 mL). The organic layer is dried (MgSO$_4$) and evaporated in vacuo to give a clear oil which is used in the next step without further purification.

6-C: The amidine 6-B (2.10 g, 4.50 mmol) is dissolved in THF (50 mL), and Boc$_2$O (1.96 g, 9.00 mmol) and Et$_3$N (1.37 mL, 13.5 mmol) are added. The reaction is stirred at room temperature for 18 h, then the solvent is removed in vacuo. The residue is dissolved in EtOAc (100 mL), and washed with saturated aqueous NaHCO$_3$ (2×50 mL) and brine (50 mL). The organic layer is dried (MgSO$_4$) and evaporated in vacuo. The crude residue is purified by flash chromatography using a gradient of 0-100% EtOAc and hexanes to give a white foam.

6-D: This compound is prepared from 6-C following methods analogous to those described for the preparation of intermediate 1-E for Reference compound 1 in Scheme 1.

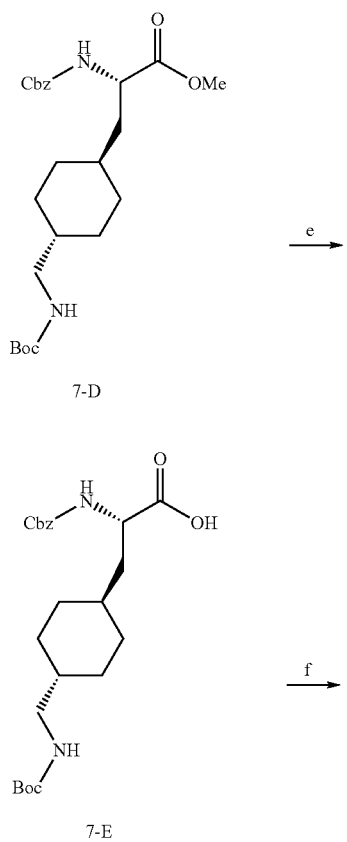

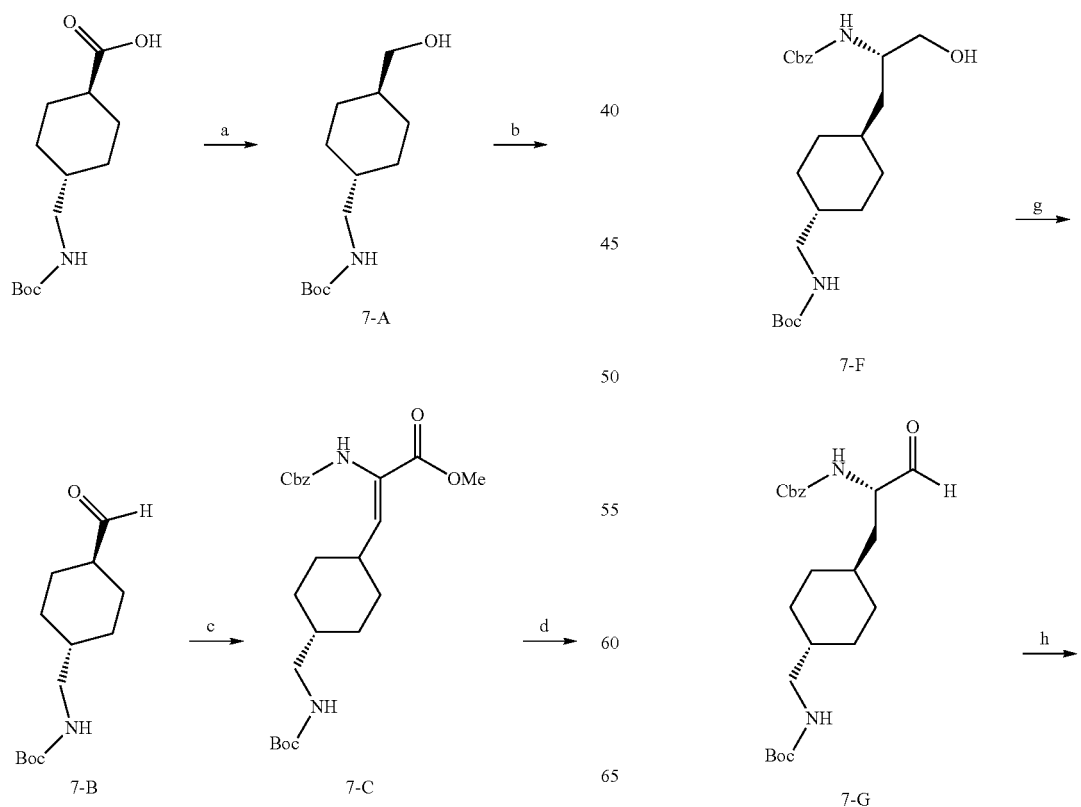

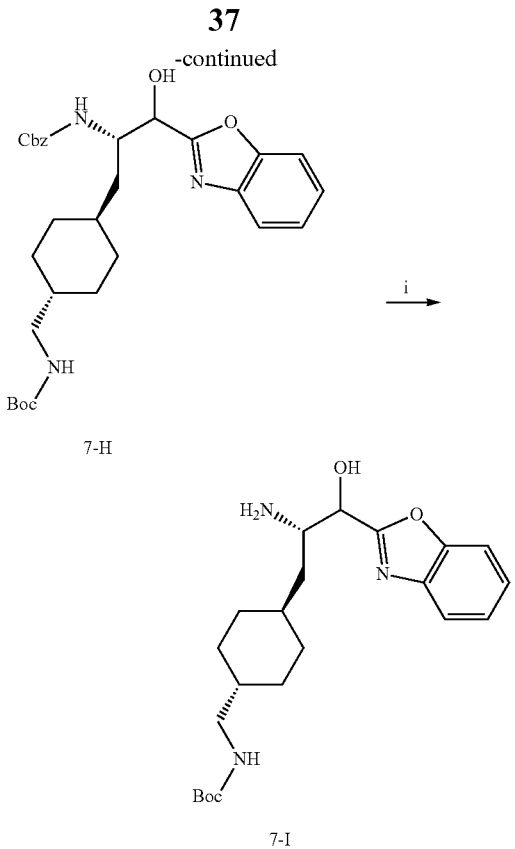

In the above Scheme 7, the reagents and conditions are: a) i. iso-BuOCOCl, Et₃N, THF; ii. NaBH₄, H₂O; (b) trichloroisocyanuric acid, TEMPO, 0° C. to rt, CH₂Cl₂, (c) Cbz-α-phosphonoglycine trimethyl ester, DBU, DCM; (d) H₂ (60 psi), (S,S)-Me-BPE-Rh(COD)⁺OTf⁻, MeOH, 96 h; (e) LiOH, Dioxane, water; (f) i. iso-BuOCOCl, Et₃N, THF; ii. NaBH₄, H₂O; (g) Dess-Martin periodinane, CH₂Cl₂; (h) iso-PrMgCl, benzoxazole, THF, −20° C., 30 min, then 7-G, −20° C. to rt; (i) H₂, (40 psi), 10% Pd/C, EtOH.

7-A: This compound is prepared from trans-4-(tert-Butoxycarbonylaminomethyl)cyclohexanecarboxylic acid (7-A) following methods analogous to those described for the preparation of intermediate 1-B for Reference compound 1 in Scheme 1.

7-B: Alcohol 7-A (4.14 g, 17.0 mmol) is dissolved in CH₂Cl₂ (35 mL), and the solution is cooled to 0° C. Trichloroisocyanuric acid (4.15 g, 17.8 mmol) is added, followed by TEMPO (28 mg, 0.17 mol). The reaction is then warmed to room temperature and stirred for a further 15 min at room temperature. A precipitate formed, and the reaction mixture is filtered through Celite and washed with CH₂Cl₂. The combined CH₂Cl₂ solution (~100 mL) is washed with saturated aqueous NaHCO₃ (2×50 mL), 1M HCl (2×50 mL), and brine (50 mL); dried (MgSO₄) and the solvent is evaporated to give the intermediate which is used without further purification.

7-C: N-Benzyloxycarbonyl-α-phosphonoglycine trimethyl ester (5.63 g, 17 mmol) is dissolved in CH₂Cl₂ (35 mL) and DBU (5.1 mL, 34 mmol) is added, and the solution is stirred for 20 min. The aldehyde 7-B (4.09 g, 17.0 mmol) is added dropwise as a solution in CH₂Cl₂ (10 mL). The reaction is stirred overnight, then the solvent is evaporated and the residue dissolved in EtOAc (100 mL) and washed with 1M NaHSO₄ (2×50 mL) and brine, then dried (MgSO₄) and evaporated in vacuo. The crude material is purified by flash chromatography using a gradient of 0-100% EtOAc/Hexanes to afford the desired product as a white solid.

7-D: The olefin 7-C (2.04 g, 4.56 mmol) is dissolved in MeOH (100 mL) and the solution is degassed prior to addition of the catalyst, (−)-1,2-Bis-((2S,3S)-2,5-dimethylphospholano)ethane(cyclooctadiene)-rhodium(I)-trifluoro-methane sulfonate (28 mg, 1 mol %). The reaction mixture is placed in a Parr shaker and shaken under 60 psi of H₂ for 4 days. The solvent is then evaporated in vacuo and the crude material purified by flash chromatography using a gradient of 0-100% EtOAc/Hexanes to afford the desired product as a white solid.

7-E: The methyl ester 7-D (1.81 g, 4.04 mmol) is dissolved in dioxane (50 mL) and stirred at 0° C. LiOH (203 mg, 4.84 mmol) dissolved in water (10 mL) is added dropwise, and the solution is then warmed to room temperature. After the starting material had disappeared (by LCMS), the solvent is evaporated, and the crude material dissolved in EtOAc (100 mL); washed with 1 N NaHSO₄ (2×50 mL) and brine (50 mL); and dried (MgSO₄). The solvent is removed in vacuo and the product is used directly in the next step without further purification.

7-F to 7-H: Intermediates 7-F to 7-H are prepared following methods analogous to those described for preparing the intermediates of Reference compound 1.

7-I: This compound is prepared from 7-H following methods analogous to those described for the preparation of intermediate 1-E for Reference compound 1. MS m/z 404.2 (M+1); 1H NMR (CDCl3, 400 MHz) d 7.66-7.64 (1H, m), 7.49-7.47 (1H, m), 7.31-7.26 (2H, m), 4.85-4.64 (1H, m), 3.44-3.16 (1H, m), 2.96-2.88 (2H, m), 1.80-1.55 (4H, m), 1.39-1.14 (13H, m), 0.89-0.72 (4H, m).

Reference compound 8

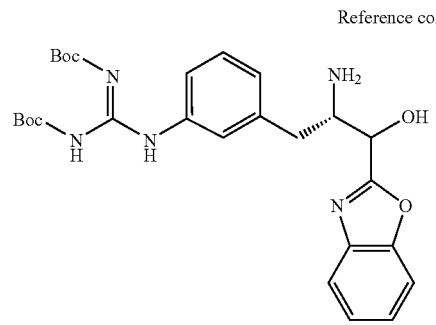

Reference compound 8 is prepared starting from 3-nitrophenylalanine following methods analogous to those described for the preparation of Reference compound 2.

Reference compound 9

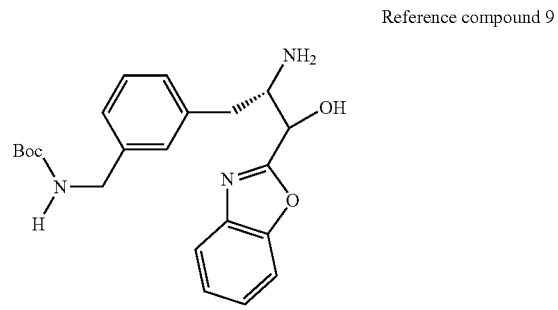

Reference compound 9 is prepared starting from 3-cyanophenylalanine following methods analogous to those described for the preparation of Reference compound 5.

Reference compound 10

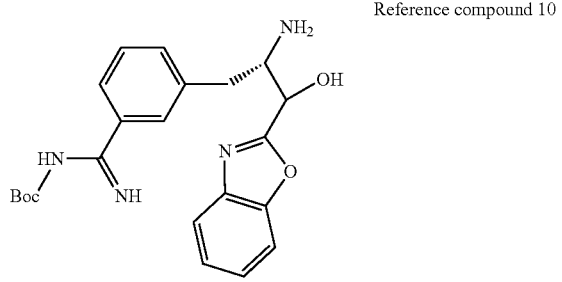

Reference compound 10 is prepared starting from 3-cyanophenylalanine following methods analogous to those described for the preparation of Reference compound 6.

Reference compound 11

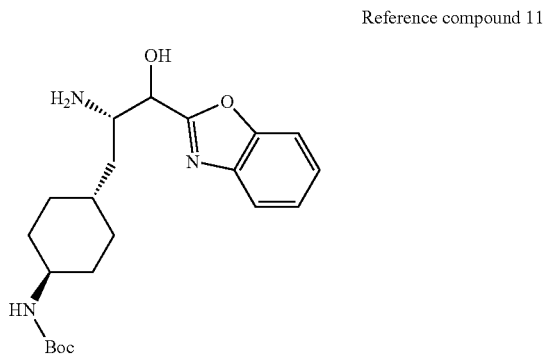

Reference compound 11 is prepared starting from trans-4-(tert-butoxycarbonylamino) cyclohexanecarboxylic acid following methods analogous to those described for the preparation of Reference compound 7.

Reference compound 12

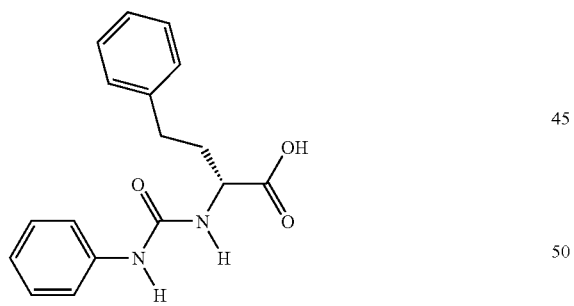

D-Homophenylalanine ethyl ester hydrochloride (2.43 g, 10.0 mmol) and Et$_3$N (1.4 mL, 20.0 mmol) are dissolved in DMF (20 mL) and stirred at room temperature. Phenyl isocyanate (1.55 g, 13.0 mmol) is added dropwise and the reaction mixture is stirred overnight. The reaction is diluted with EtOAc (200 mL), and washed with water (100 mL), 1N HCl (2×100 mL), saturated aqueous NaHCO$_3$ (2×100 mL), brine (100 mL), and dried with MgSO$_4$. The solvent is evaporated to dryness, and the residue is dissolved in dioxane (20 mL). LiOH.H$_2$O (630 mg, 15.0 mmol) dissolved in water (15 mL) is added, and the reaction mixture stirred at room temperature until the ethyl ester had disappeared (by TLC and LCMS). The solvent is removed in vacuo and the crude material is partitioned with EtOAc (100 mL) and 1N HCl (100 mL). The aqueous layer is extracted with EtOAc (2×50 mL) and the combined organic phases are washed with 1M NaHSO$_4$ (2×50 mL) and brine (100 mL), and dried with MgSO$_4$. The solvent is evaporated and the crude material purified by flash chromatography (EtOAc:Hexanes gradient) to afford Reference compound 12 as a white powder.

Reference compound 13

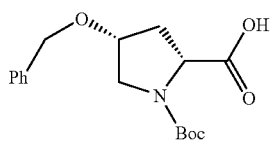

N-BOC-cis-4-hydroxy-D-proline (7.83 g, 34 mmol) is dissolved in DMF (100 mL) and cooled to 0° C. NaH 60% in mineral oil (3.0 g, 74.8 mmol) is added portionwise and stirred for 30 min. Benzyl bromide (12.8 g, 74.8 mmol) is added, and the solution is stirred for 3 h. The reaction mixture is poured into 0.1 M HCl/ice slurry and extracted with EtOAc (3×150 mL). The combined organic layer is washed with saturated aqueous NaHCO$_3$ (3×100 mL) and brine (200 mL), dried (MgSO$_4$), and solvent is evaporated in vacuo. The crude material is purified to afford the benzyl ester, which is then dissolved in dioxane (20 mL) and stirred at room temperature. LiOH.H$_2$O (1.60 mg, 38 mmol) dissolved in water (10 mL) is added and the reaction stirred until the benzyl ester had disappeared (by TLC and LCMS). The solvent is removed in vacuo, and the crude material is partitioned with EtOAc (50 mL) and 1N HCl (50 mL). The aqueous layer is extracted with EtOAc (2×50 mL), and the combined organic phases are washed with 1M NaHSO$_4$ (2×50 mL) and brine (50 mL), and dried with MgSO$_4$. The solvent is evaporated and the crude material purified by flash chromatography (EtOAc:Hexanes gradient) to afford Reference compound 13 as a white powder.

Reference compound 14

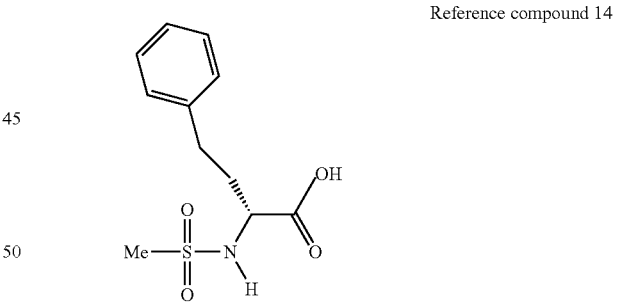

D-Homophenylalanine ethyl ester hydrochloride (5.00 g, 20.5 mmol) and DIEA (8.7 mL, 51.25 mmol) are dissolved in THF (100 mL), and stirred at room temperature. Mesyl chloride (1.67 mL, 21.52 mmol) is added dropwise, and the reaction stirred for 6 hours at room temp. The THF is evaporated and the crude dissolved in EtOAc (100 mL) and washed with water (100 mL), 1N HCl (2×100 mL) and brine (100 mL), and dried (MgSO$_4$). The solvent is removed in vacuo, and the crude material purified with flash chromatography (hexanes: EtOAc) to afford the ethyl ester. The ethyl ester is dissolved in dioxane (50 mL), and stirred at room temperature. LiOH.H$_2$O (1.00 mg, 24 mmol) dissolved in water (20 mL) is added, and the reaction stirred until the ethyl ester had disappeared (by TLC and LCMS). The solvent is removed in vacuo, and the crude material is partitioned with EtOAc (50 mL) and 1N HCl (50 mL). The aqueous layer is extracted with EtOAc (2×50 mL), and the combined organic phases are washed with 1M NaHSO₄ (2×50 mL) and brine (50 mL), and dried with MgSO₄. The solvent is evaporated, and the crude material purified by flash chromatography (EtOAc:Hexanes gradient) to afford Reference compound 14 as a white powder.

Reference compound 15

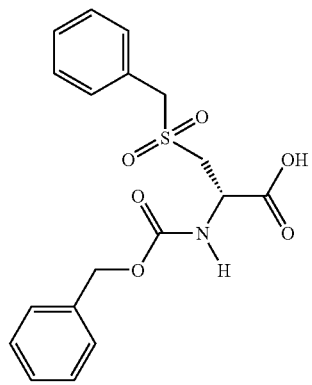

Cbz-D-Cys(Bzl)-OH is first prepared from H-D-Cys(Bzl)-OH and Cbz-OSu following methods analogous to those described for the preparation of intermediate compound 1-B. Cbz-D-Cys(Bzl)-OH (296 mg, 0.86 mmol) is then dissolved in 5 mL of MeOH:H₂O (50:50), and oxone (792 mg, 1.29 mmol) is added. The reaction mixture is stirred overnight at room temperature; diluted with water (10 mL) and extracted with dichloromethane (3×20 mL)l and the organic phase is then washed with brine (30 mL) and dried (MgSO₄). The solvent is removed in vacuo to give Reference compound 15, and used without further purification.

Reference compound 16

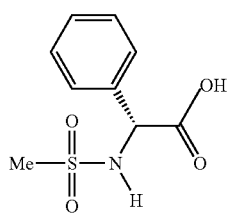

Reference compound 16 is prepared starting from D-phenylglycine ethyl ester hydrochloride following methods analogous to those described for Reference compound 14.

Reference compound 17

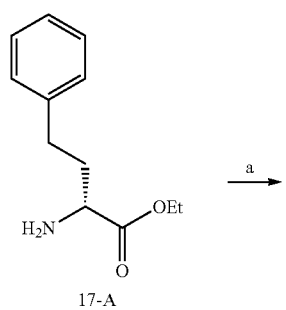

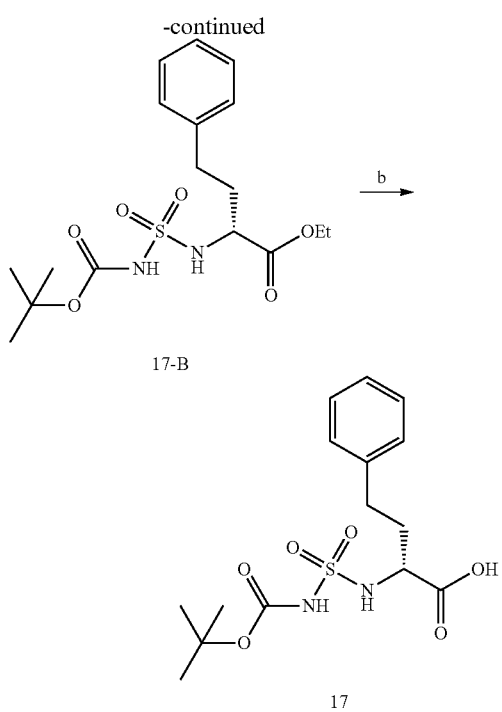

In the reaction scheme above for preparing Reference compound 17, the reagents and conditions are: (a) i. t-BuOH, ClSO₂NCO, CH₂Cl₂ 0° C. to rt ii. 17-A, CH₂Cl₂, (b) 1 N NaOH in water.

17-B: In a round bottom flask, N-chloroisocyanate (2.5 mL, 28.7 mmol) is dissolved in dichloromethane (150 mL) and cooled to 0° C. A dichloromethane solution of t-BuOH (2.7 mL, 28.7 mmol) is added drop wise. Fifteen minutes following completion of alcohol addition, commercially available 17-A is added in a dichloromethane solution. The reaction is then allowed to warm to ambient temperature and stir for 3 h. The reaction mixture is diluted with water and washed with water; and the organic layers are separated and dried over MgSO₄ to yield compound 17-B as an oil that is used directly in the next step without further purification.

17: The ethyl ester 17-B (1.46 g, 5 mmol) is dissolved in 1N NaOH (15 ml, 15 mmol). After the starting material had disappeared (by LCMS), the reaction is acidified with 1 N HCl. The product precipitated as a white solid, and used directly in the next step without further purification.

Reference compound 18

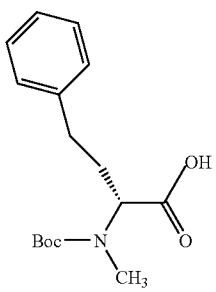

Reference compound 18 is prepared according to the method reported in Org. Lett. 5:125-128 (2003). Boc-D-homophenylalanine (1.0 g, 3.58 mmol), methylated using Me₂SO₄ and NaH in THF and catalytic water, gave a white powder.

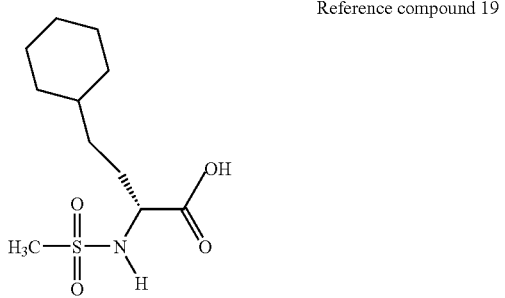

Reference compound 19

Reference compound 19 is prepared from D-homocyclohexylalanine ethyl ester hydrochloride following methods analogous to those described for Reference compound 14.

20-D: To a solution of Cbz-α-phosphonoglycine trimethyl ester, (2.8 g, 8.45 mmol) in THF at −78° C. is added 1,1,3,3-tetramethyl-guanidine (1.022 ml, 8.14 mmol). After 10 minutes, the aldehyde 20-C (1.76 g, 7.76 mmol) is added. The solution is then placed in an ice bath at 0° C. for 1 hour, and then allowed to warm to room temperature and stirred one more hour. The solution is diluted with EtOAc, washed with 1M NaHSO$_4$, dried (MgSO$_4$) and concentrated in vacuo. The residue is purified by chromatography (ISCO) with Ethyl acetate/Hexane 0 to 100% to afford 20-D as a yellow oil. MS m/z 333.2 (M+1), $^1$H NMR (CDCl3, 400 MHz) δ. 7.35-7.33 (5H, m), 6.63 (1H, t, J=8 Hz), 6.30 (1H, bs), 5.12 (2H, s), 4.10-4.04 (2H, m), 3.73 (3H, s), 2.67-2.62 (2H, m), 2.14 (2H, t, J=6.8 Hz), 1.63-1.46 (3H, m), 1.43 (9H, s), 1.14-1.06 (2H, m).

20-E: A Parr vessel is charged with 20-D (1.0 g, 2.31 mmol) and MeOH (100 mL) under nitrogen. The solution is

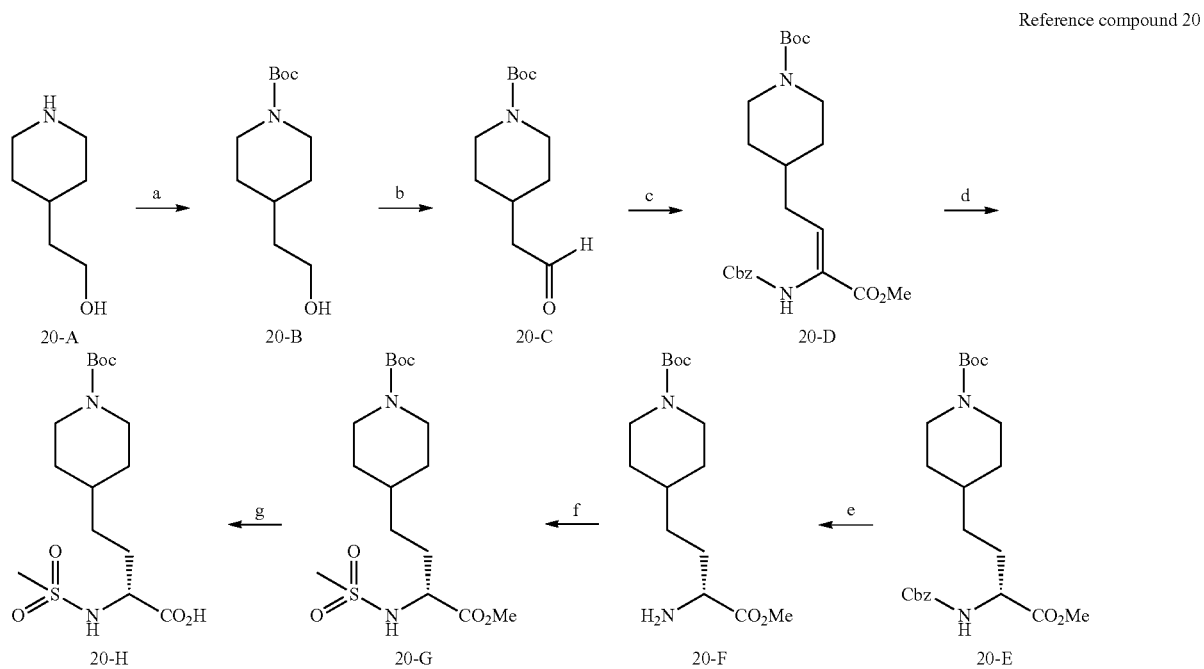

Reference compound 20

20-B: 4-piperidine ethanol (20-A) (5.0 g, 39.7 mmol) is dissolved in THF (120 mL). Triethylamine (5.6 mL, 40 mmol) is added, and the solution is cooled to 0° C. Boc$_2$O (9.59 g, 44 mmol) is added, and the reaction is stirred overnight at room temperature. Solvent is removed in-vacuo; the crude residue dissolved in ethyl acetate (120 mL) is added; the solution is washed with 0.1 N HCl (3×100 mL) and brine (1×100 mL); dried with MgSO$_4$; and filtered and solvent evaporated in vacuo to give compound 20-B as a clear oil.

20-C: Trichloroisocyanuric acid (2.66 g, 11.46 mmol) is added to a solution of the alcohol (2.39 g, 10.42 mmol) in DCM, and the solution is stirred and maintained at 0° C., followed by addition of a catalytic amount of TEMPO. After the addition, the mixture is warmed to room temperature and stirred for an hour and then filtered on Celite. The organic phase is washed with saturated aqueous Na$_2$CO$_3$, followed by 1N HCl and brine. The organic layer is dried (MgSO$_4$), and the solvent is evaporated to yield 20-C. $^1$H-NMR (CDCl$_3$, 400 MHz) δ 9.72 (1H, s), 4.07-4.01 (2H, m), 2.70-2.57 (2H, m), 2.35-2.31 (2H, m), 2.05-1.94 (1H, m), 1.64-1.46 (2H, m), 1.39 (9H, s), 1.30-1.02 (2H, m).

subjected to three cycles of vacuum and nitrogen bubbling, and the catalyst (R,R)-Ethyl-DuPHOS-Rh(COD) triflate is added (30 mg, 0.04 mmol). The mixture is placed under 60 psi of hydrogen gas at room temperature for 24 h. The conversion to 20-E is complete after 24 h with >99% e.e., the solvent is removed in vacuo, and the crude product is purified by silica gel chromatography (hexanes/EtOAc).

20-F: Intermediate 20-E is dissolved in MeOH, the solution is flushed with nitrogen, and Pd/Carbon (5% wt, Degussa) is added. The mixture is placed under 50 psi of hydrogen gas at room temperature and shaken for 24 h. The mixture is flushed with nitrogen and filtered through Celite. The cake is washed with MeOH, and the combined organic solution is concentrated under vacuum. Hexanes is added and then evaporated to azeotrope the remaining methanol to afford 20-F as an oil, which is then used in the next step without further purification.

20-G: Intermediate 20-F (0.6 g, 1.99 mmol) is dissolved in THF (10 mL), and 2,4,6-collidine (315 mg, 2.38 mmol) and methanesulfonyl chloride (0.170 ml, 2.19 mmol) are added to the solution and stirred for 2 h. The reaction is diluted with EtOAc (50 mL) solution; washed with 1M NaHSO$_4$ (2×25 mL) and brine (25 mL); and dried (MgSO$_4$). The solvent is removed in vacuo, and the crude residue purified by flash chromatography using a gradient of hexanes and EtOAc to afford the desired product 20-G.

20-H: Compound 20-G (0.70 g, 1.84 mmol) is dissolved in dioxane (7 mL), and LiOH.H$_2$O (232 mg, 5.55 mmol) dissolved in water (4 mL) is added. The reaction mixture is stirred for 1 h. The solvent is evaporated; the residue diluted with EtOAc (25 mL) and washed with 1N NaHSO$_4$ (25 mL) and brine (25 mL); and dried (MgSO$_4$). The solvent is removed in vacuo, and the crude purified by silica gel chromatography (Hexanes/EtOAc gradient) to afford the desired product, Reference compound 20, as a white solid.

Reference compound 21

Reference compound 21 is prepared starting from 3-cyanophenylalnine following methods analogous to those described for the preparation of Reference compound 14.

Reference compound 22

Reference compound 22 is prepared from D-homophenylalanine following methods analogous to those described for the preparation of Reference compound 2-B.

Reference compound 23

Reference compound 23 is prepared from D-homophenylalanine and N-(cyclopropylmethyloxycarbonyloxy)-succinimide following methods analogous to those described for the preparation of Reference compound 2-B.

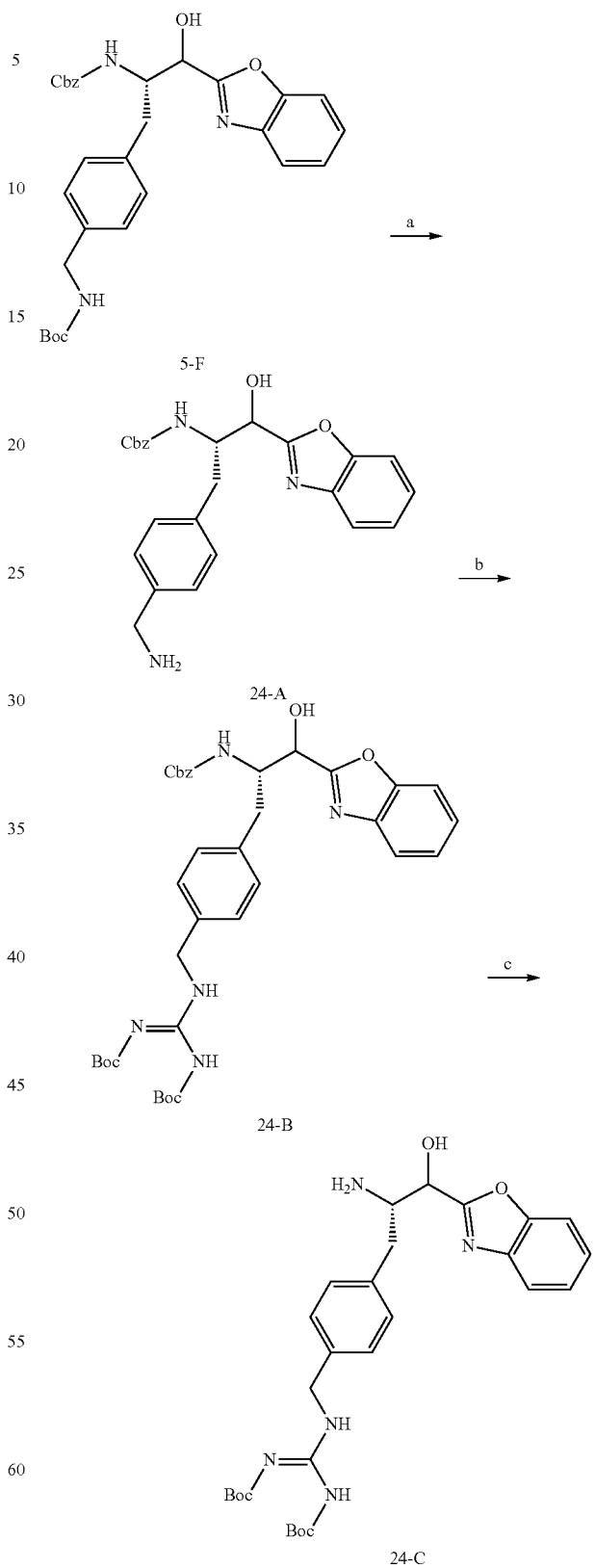

Intermediate 24-A is prepared from Reference compound 5-A by deprotection of the Boc group in 50% TFA in CH$_2$Cl$_2$, followed by evaporation of solvent in vacuo. Intermediates 24-B to 24-C are prepared following methods analogous to those described for Reference compound 2.

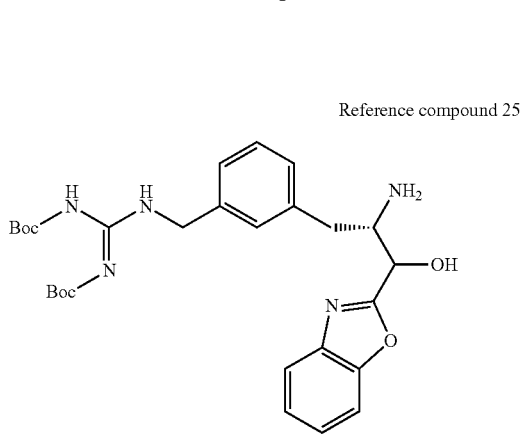

Reference compound 25

Reference compound 25 is prepared following methods analogous to those described for the preparation of Reference compound 24.

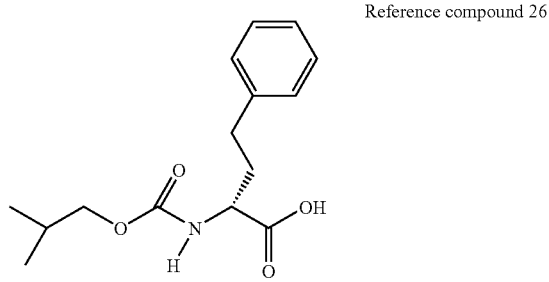

Reference compound 26

Reference compound 26 is prepared from D-homophenylalanine and N-(iso-butyloxycarbonyloxy)-succinimide following methods analogous to those described for the preparation of Reference compound 2-B.

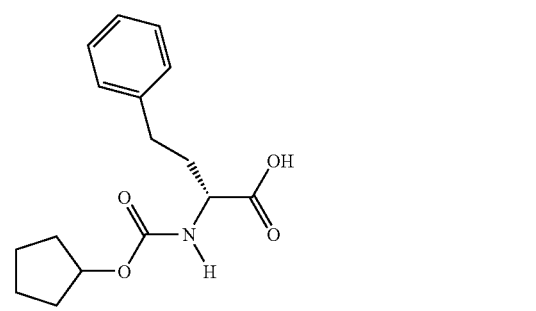

Reference compound 27

Reference compound 27 is prepared from D-homophenylalanine and N-(cyclopentyloxycarbonyloxy)-succinimide following methods analogous to those described for the preparation of Reference compound 2-B.

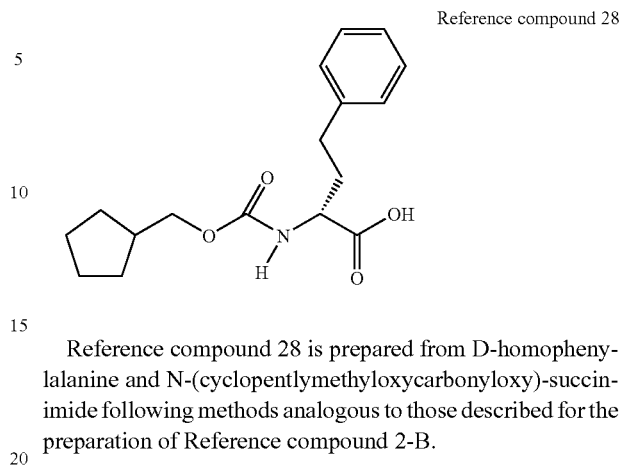

Reference compound 28

Reference compound 28 is prepared from D-homophenylalanine and N-(cyclopentlymethyloxycarbonyloxy)-succinimide following methods analogous to those described for the preparation of Reference compound 2-B.

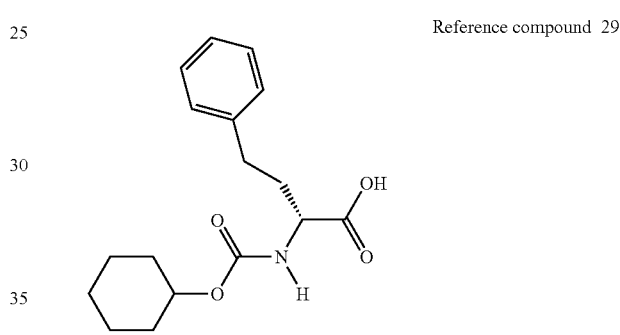

Reference compound 29

Reference compound 29 is prepared from D-homophenylalanine and N-(cyclohexyloxycarbonyloxy)-succinimide following methods analogous to those described for the preparation of Reference compound 2-B.

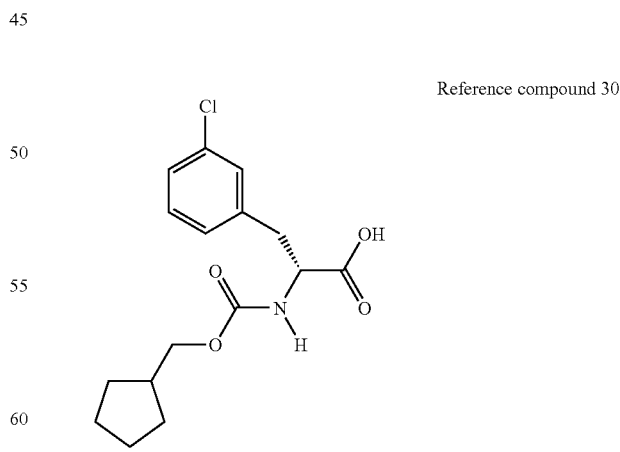

Reference compound 30

Reference compound 30 is prepared from D-3-chlorophenylalanine and N-(cyclopentylmethyloxycarbonyloxy)-succinimide following methods analogous to those described for the preparation of Reference compound 2-B.

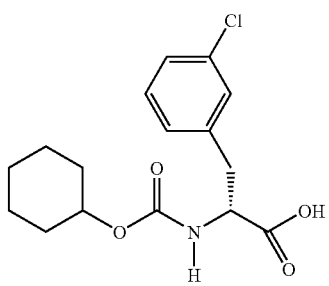

Reference compound 31

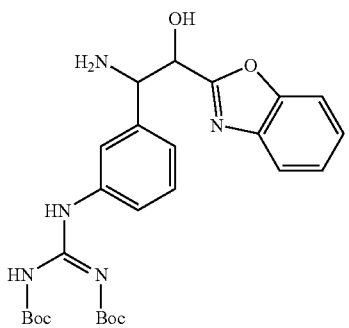

Reference compound 34

Reference compound 31 is prepared from D-3-chlorophenylalanine and N-(cyclohexyloxycarbonyloxy)-succinimide following methods analogous to those described for the preparation of Reference compound 2-B.

Reference compound 34 is prepared from 3-nitrophenylglycine following methods analogous to those described for the preparation of Reference compound 2.

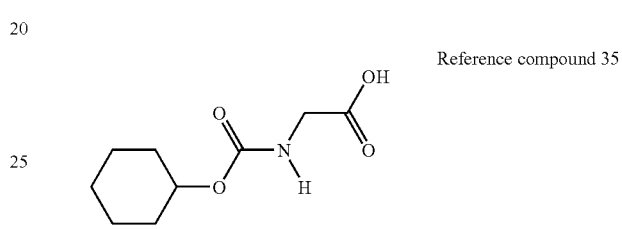

Reference compound 35

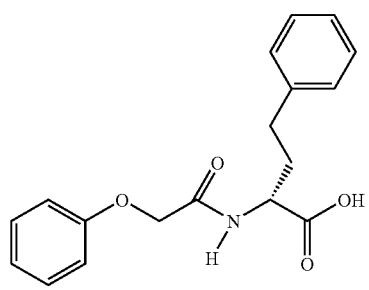

Reference compound 32

Reference compound 35 is prepared from glycine and N-(cyclohexyloxycarbonyloxy)-succinimide following methods analogous to those described for the preparation of Reference compound 2-B.

Reference compound 32 is prepared from D-Homophenylalanine ethyl ester hydrochloride and phenoxyacetyl chloride following methods analogous to those described for the preparation of Reference compound 14.

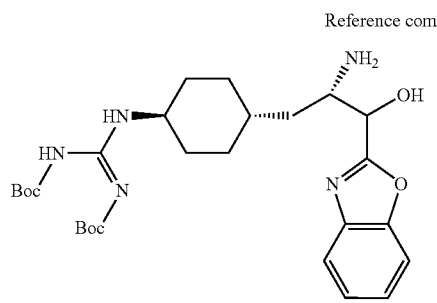

Reference compound 33

Reference compound 33 is prepared following methods analogous to those described for the preparation of Reference compound 24.

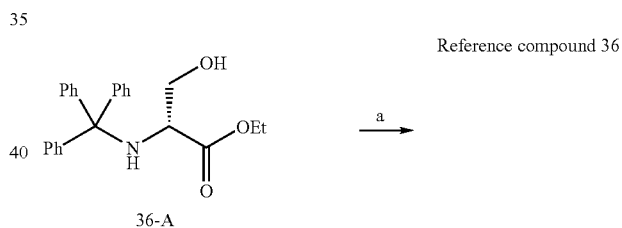

Reference compound 36

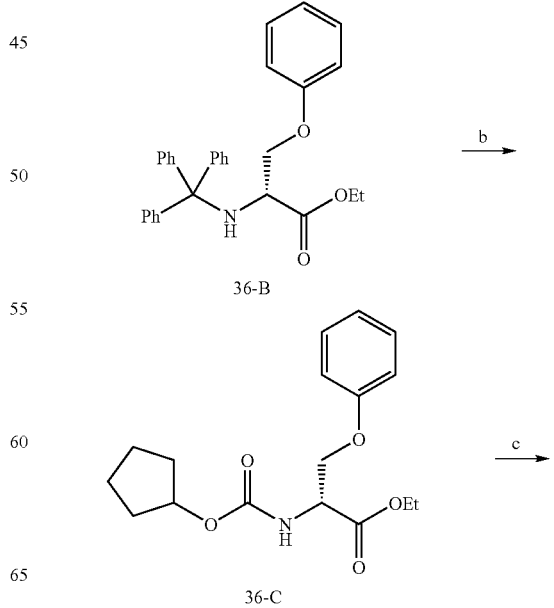

-continued

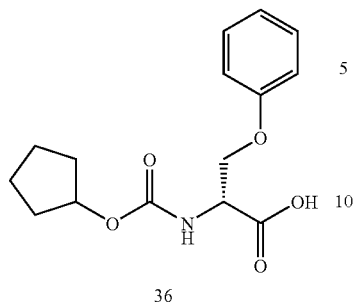

36

In the above reaction scheme above for preparing Reference compound 36, the reagents and conditions are: (a) PPh$_3$, DIAD, PhOH, toluene, rt (b) i. TFA, CH$_2$Cl$_2$, MeOH rt, 1 h. ii. CyclohexylOCOCl, Pyridine, DMAP, rt, THF.

36-B: To a round bottom flask is charged with commercially available 17-A (939 mg, 2.6 mmol), triphenylphosphine (763 mg, 2.8 mmol), phenol (346 mg, 3.8 mmol), toluene (30 mL) and diisopropyldiazodicarboxylate (542 μL, 2.8 mmol) and stirred at ambient temperature. The reaction mixture is concentrated to dryness, and the product is purified from the reaction mixture via silica gel chromatography to afford a white foam used in the preparation of 36-C.

36-C: A 40 mL vial is charged with 36-B (2.0 mmol), dichloromethane, 10 mL, methanol (1 mL) and TFA (10 mL). After 1 h at ambient temperature, all volative reagents are removed in vacuo to afford the TFA salt that is used directly in the next step. The TFA salt and N-(cyclohexylcarbonyloxy) succinimide (2.0 mmol) are added to a round bottomed flask containing THF (20 mL), pyridine (600 μL) and DMAP (~10 mg, catalytic). The mixture is stirred at room temperature overnight. The clear solution is diluted with EtOAc (200 mL); washed with 1N HCl (3×100 mL) and brine (1×100 mL); and dried with MgSO$_4$. Solvent is evaporated in vacuo to afford the desired product as a white solid with is used without further purification.

36: The ethyl ester 36-C (2 mmol) is dissolved in 1N NaOH (6 mL, 6 mmol). After the starting material had disappeared (by LCMS), the reaction is acidified with 1 N HCl and the product precipitated as a white solid that is used without further purification.

Reference compound 37

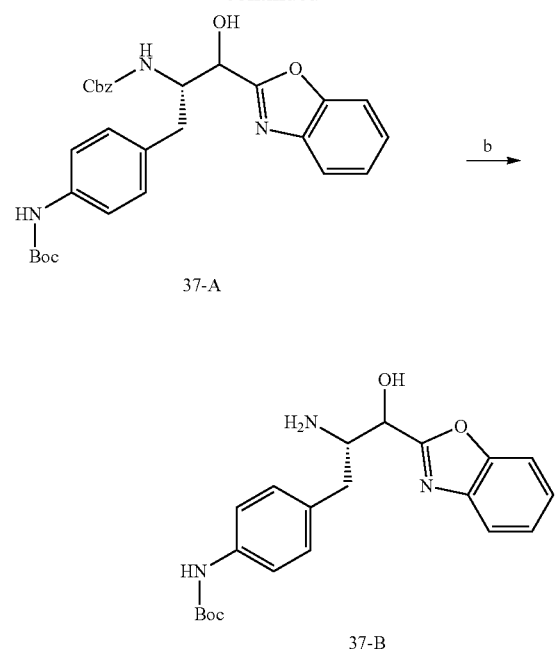

Intermediate 37-A is prepared from intermediate 2-F (Reference compound 2) following similar methods for preparing intermediate 20-B (Reference compound 20); and hydrogenolysis following analogous methods used for Reference compound 1 gives 37-B.

Reference compound 38

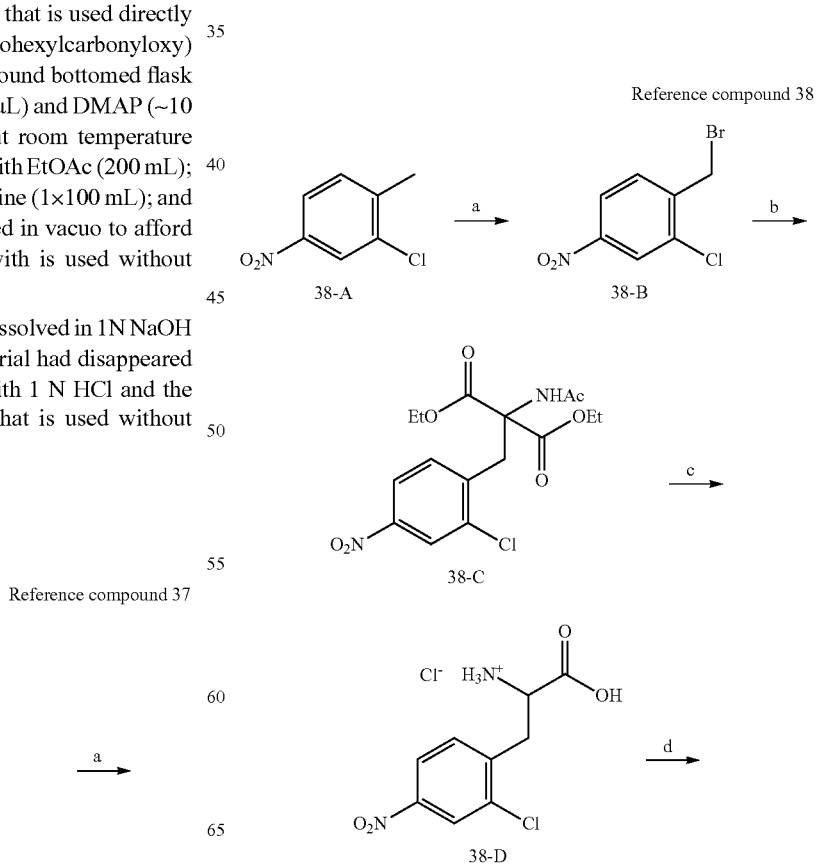

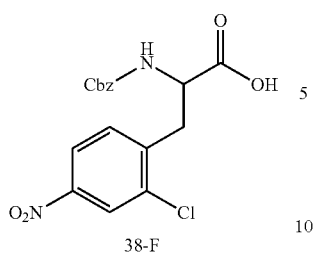

38-F

38-B: 2-Chloro-4-nitrotoluene (8.55 g, 50.0 mmol) is dissolved in 1,2-dichloroethane (120 mL). N-Bromosuccinimide (9.74 g, 55 mmol) and benzoyl peroxide (0.25 g, 1.03 mmol) are added, and the reaction mixture is stirred and heated to reflux for 16 h. The reaction is cooled to room temperature, and most of the solvent is evaporated in vacuo, leaving approximately 30 mL of dichloroethane. Hexanes (30 mL) and dichloromethane (30 mL) are added, and the precipitate that formed is filtered, and the filtrate washed with hexanes. The combined organic solution is evaporated in vacuo to afford benzyl bromide 38-B, which is used directly in the next step without further purification.

38-C: Diethyl acetamidomalonate (7.16 g, 33.0 mmol) is dissolved in EtOH (50 mL), and NaOEt (2.25 g, 33.0 mmol) is added. The solution is stirred and heated to 80° C. Bromide 38-B (9.2 g, 37.0 mmol) is dissolved in EtOH (50 mL) and added dropwise to the stirring reaction mixture. After 18 h, the solution is cooled to room temperature and a precipitate formed which is filtered. The precipitate is washed with water and recrystallized with 5% aqueous EtOH, filtered, and dried in vacuo.

38-D: Malonate 38-C is added to 12 N HCl, and the mixture is heated to reflux for 14 h. The reaction mixture is then cooled to 4° C. and a precipitate formed. The precipitate is washed with 1 N HCl and dried in vacuo.

38-F: Intermediate 38-D (4.59 g, 16.33 mmol) and Cbz-OSu (3.99 g, 16.0 mmol) are added to a solution of THF (60 mL) and water (20 mL). Et₃N (9.1 mL, 65.32 mmol) is added, and the solution is stirred for 18 h at room temperature. The solvent is evaporated in vacuo, and the residue is taken up and partitioned between EtOAc (100 mL) and 1N HCl (100 mL). The organic phase is washed with 1N HCl (2×100 mL) and brine (100 mL), and dried with MgSO₄. Solvent is removed in vacuo and the crude material is recrystallized with ethanol and water.

Reference compound 39

Reference compound 39 is prepared from 5-methyl-2-nitroanisole following methods analogous to those described for the preparation of Reference compound 38.

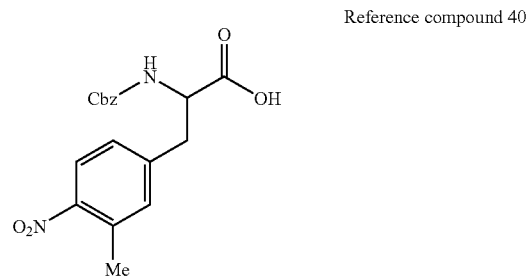

Reference compound 40

Reference compound 40 is prepared from 3-methyl-4-nitrobenzyl bromide following methods analogous to those described for Reference compound 38.

Scheme 8

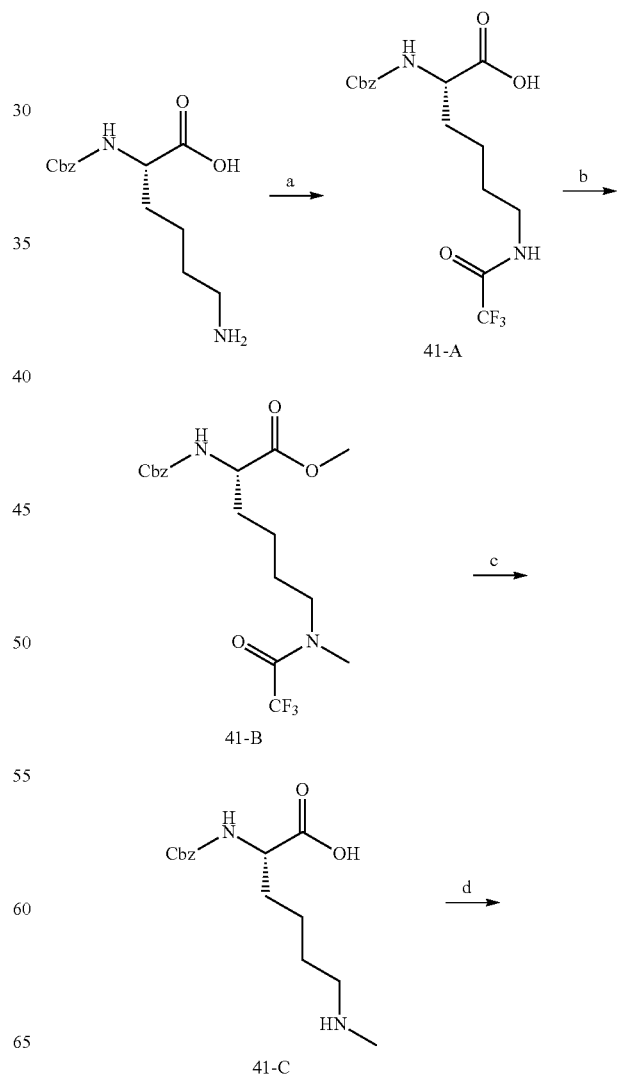

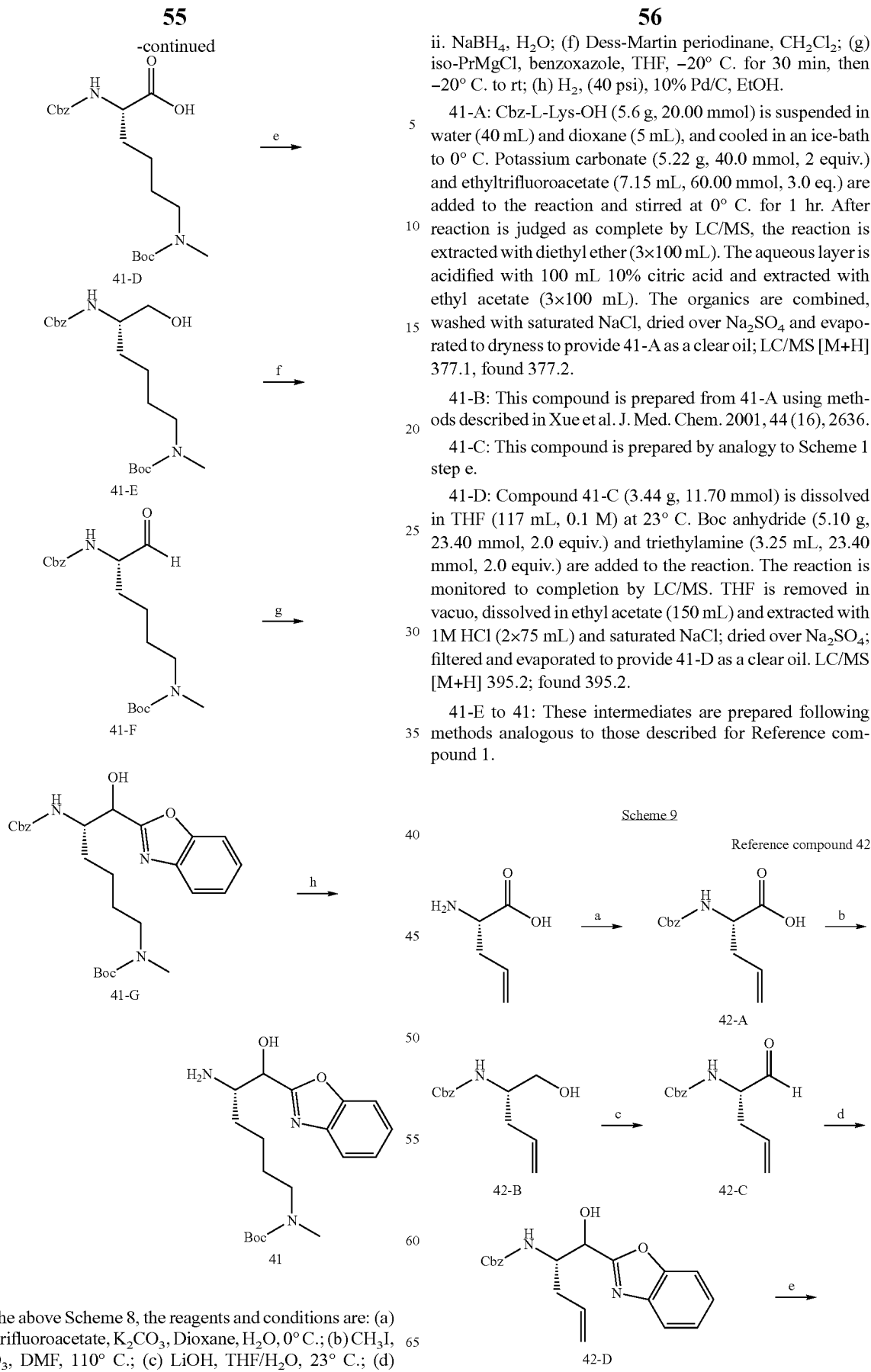

ii. NaBH$_4$, H$_2$O; (f) Dess-Martin periodinane, CH$_2$Cl$_2$; (g) iso-PrMgCl, benzoxazole, THF, −20° C. for 30 min, then −20° C. to rt; (h) H$_2$, (40 psi), 10% Pd/C, EtOH.

41-A: Cbz-L-Lys-OH (5.6 g, 20.00 mmol) is suspended in water (40 mL) and dioxane (5 mL), and cooled in an ice-bath to 0° C. Potassium carbonate (5.22 g, 40.0 mmol, 2 equiv.) and ethyltrifluoroacetate (7.15 mL, 60.00 mmol, 3.0 eq.) are added to the reaction and stirred at 0° C. for 1 hr. After reaction is judged as complete by LC/MS, the reaction is extracted with diethyl ether (3×100 mL). The aqueous layer is acidified with 100 mL 10% citric acid and extracted with ethyl acetate (3×100 mL). The organics are combined, washed with saturated NaCl, dried over Na$_2$SO$_4$ and evaporated to dryness to provide 41-A as a clear oil; LC/MS [M+H] 377.1, found 377.2.

41-B: This compound is prepared from 41-A using methods described in Xue et al. J. Med. Chem. 2001, 44 (16), 2636.

41-C: This compound is prepared by analogy to Scheme 1 step e.

41-D: Compound 41-C (3.44 g, 11.70 mmol) is dissolved in THF (117 mL, 0.1 M) at 23° C. Boc anhydride (5.10 g, 23.40 mmol, 2.0 equiv.) and triethylamine (3.25 mL, 23.40 mmol, 2.0 equiv.) are added to the reaction. The reaction is monitored to completion by LC/MS. THF is removed in vacuo, dissolved in ethyl acetate (150 mL) and extracted with 1M HCl (2×75 mL) and saturated NaCl; dried over Na$_2$SO$_4$; filtered and evaporated to provide 41-D as a clear oil. LC/MS [M+H] 395.2; found 395.2.

41-E to 41: These intermediates are prepared following methods analogous to those described for Reference compound 1.

In the above Scheme 8, the reagents and conditions are: (a) Ethyltrifluoroacetate, K$_2$CO$_3$, Dioxane, H$_2$O, 0° C.; (b) CH$_3$I, K$_2$CO$_3$, DMF, 110° C.; (c) LiOH, THF/H$_2$O, 23° C.; (d) Boc$_2$O, Et$_3$N, THF, 23° C.; (e) i. iso-BuOCOCl, Et$_3$N, THF;

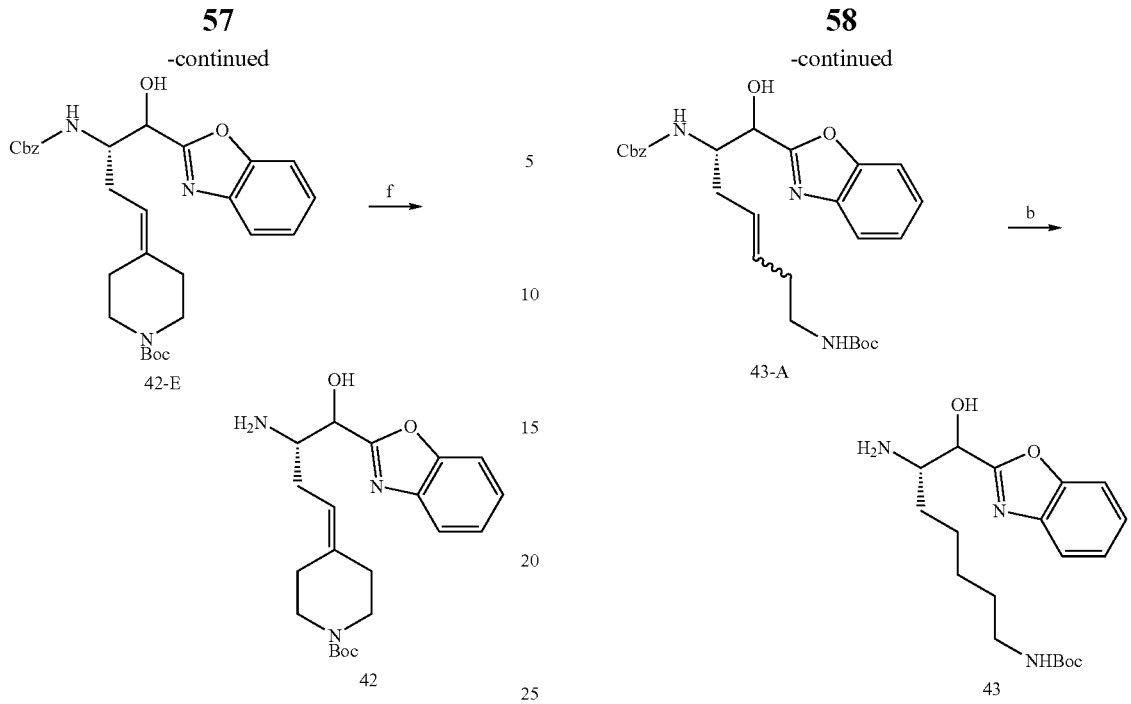

In the above Scheme 9, the reagents and conditions are: (a) Cbz-OSu, Et$_3$N, THF, H$_2$O; (b) i. iso-BuOCOCl, Et$_3$N, THF; ii. NaBH$_4$, H$_2$O; (c) Dess-Martin periodinane, CH$_2$Cl$_2$; (d) iso-PrMgCl, benzoxazole, THF, −20° C., 30 min, then, −20° C. to rt; (e) Hoveyda-Grubbs metathesis catalyst, 4-Methylene-N-Boc-piperidine, DCM, 40° C.; (f) H$_2$, (40 psi), 10% Pd/C, EtOH.

42-A: This compound is prepared by analogy to Reference compound 38 step d using L-allylglycine as the amino acid component of the reaction.

42-B-D: These compounds are prepared by analogy to Reference compound 1 step a, b and c, respectively.

42-E: Anhydrous dichloromethane (4 mL, 0.2 M) is added via syringe to 42-D (270 mg, 0.766 mmol, 1.0 eq.), Hoveyda-Grubbs 2$^{nd}$ Generation metathesis catalyst (1,3-Bis-(2,4,6-trimethylphenyl)-2-imidazolidinylidene) dichloro(o-isopropoxyphenylmethylene) ruthenium II dichloride) (98 mg, 0.115 mmol, 15 mol %) under a nitrogen atmosphere. N-Boc-4-methylenepiperidine (0.60 mL, 0.268 mmol, 4.0 eq.) is added via syringe, and the reaction is fitted with a reflux condenser and heated to 40° C. for 12 h. After the reaction is judged as complete by LC/MS, the reaction mixture is directly purified by automated silica-gel purification (0-100% ethyl acetate in hexanes) to provide 42-E as a dark green oil. MS m/z 422.3 (M-Boc+1).

42: This compound is prepared by analogy to Reference compound 1 step d.

Scheme 10

Reference compound 43

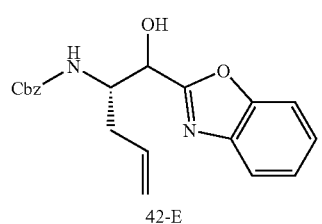

42-E

In the above Scheme 10, the reagents and conditions are: (a) Hoveyda-Grubbs metathesis catalyst, N-Boc-4-amino-1-butene, DCM, 40° C.; (f) H$_2$, (40 psi), 10% Pd/C, EtOH. Compounds 43A and 43 are prepared by analogy to Reference compound 42 step e and f, respectively.

Reference compound 44

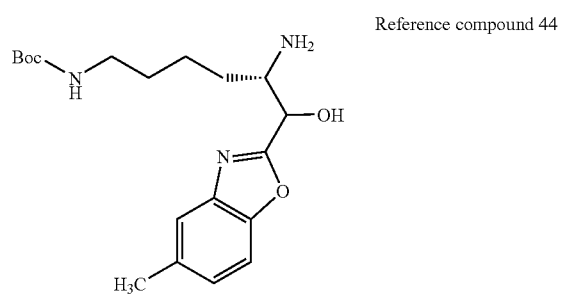

Reference compound 44 is prepared from 5-methylbenzoxazole following methods analogous to those described for the preparation of Reference compound 1.

Reference compound 45

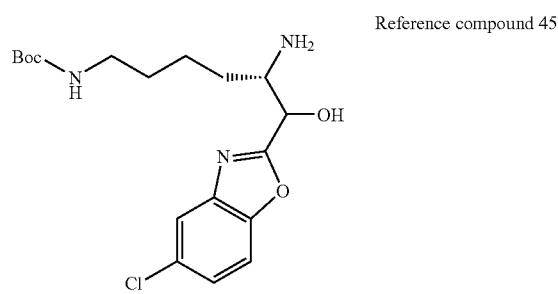

Reference compound 45 is prepared from 5-chlorobenzoxazole following methods analogous to those described for the preparation of Reference compound 1.

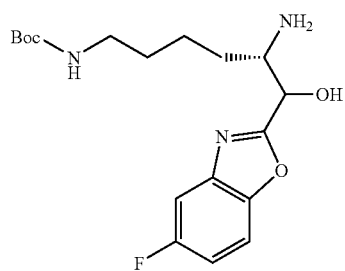

Reference compound 46

Reference compound 46 is prepared from 5-fluorobenzoxazole following methods analogous to those described for the preparation of Reference compound 1.

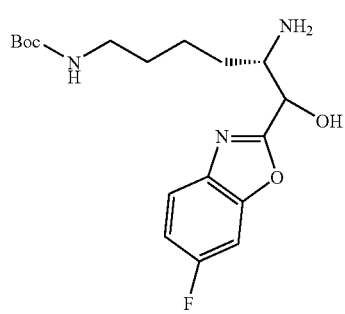

Reference compound 47

Reference compound 47 is prepared from 6-fluorobenzoxazole following methods analogous to those described for the preparation of Reference compound 1.

Scheme 11

Reference compound 48

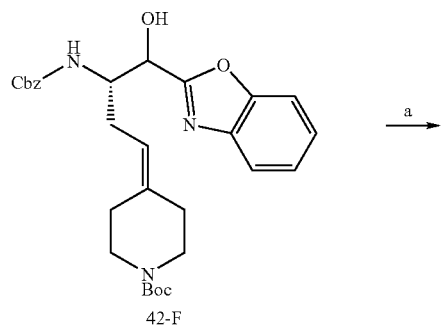

42-F

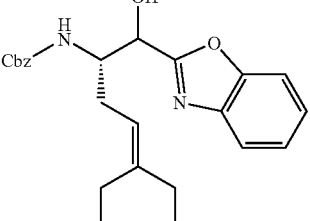

48-A

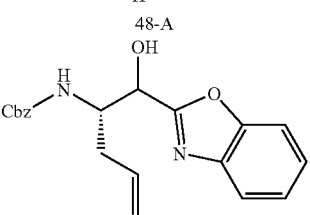

48-B

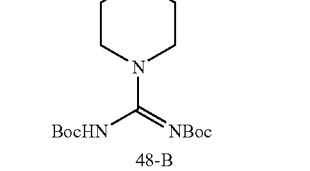

48

In the above Scheme 11, the reagents and conditions are: (a) TFA/CH$_2$Cl$_2$ 75:25, 23° C.; (b) N,N-Bis(tert-butoxycarbonyl)-1H-pyrazole-1-carboxamidine, DIEA, MeOH; (c) H$_2$, (40 psi), 10% Pd/C, EtOH. Intermediate 48-A is prepared in analogy to Scheme 1, step a using Compound 42-A. Intermediate 48-B is prepared in analogy to Reference compound 2 step f. Intermediate 48 is prepared in analogy to Reference compound 1 step d.

Reference compound 49

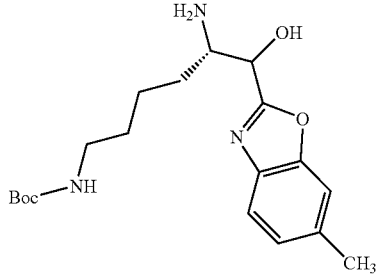

Reference compound 49 is prepared from 6-methylbenzoxazole following methods analogous to those described for the preparation of Reference compound 1.

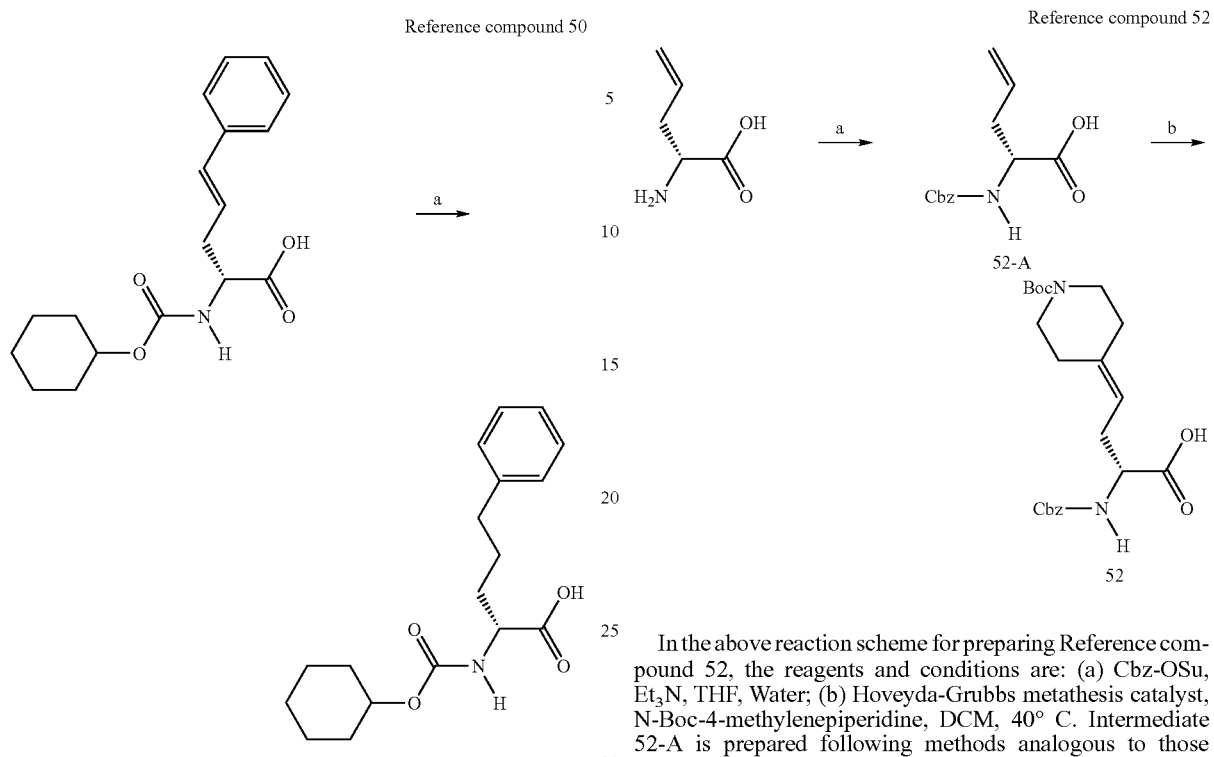

Reference compound 50 is prepared from N-(cyclohexyloxycarbonyloxy)-succinimide following methods analogous to those for Reference compound 2-B.

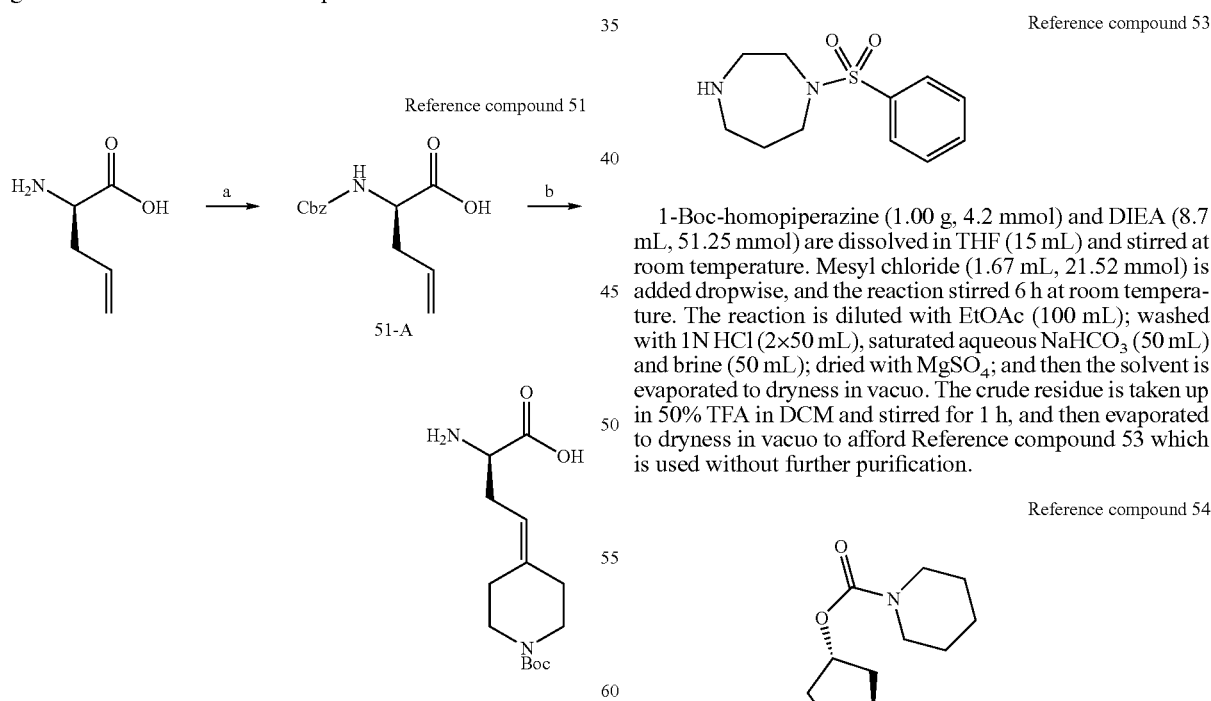

Reagents and conditions are as follows: (a) Cbz-OSu, Et₃N, THF, water; (b) Hoveyda-Grubbs metathesis catalyst, N-Boc-4-methylenepiperidine, DCM, 40° C. Compound 51-A is prepared by analogy to Scheme 2 step a for preparing Reference compound 2. Compound 51 is prepared by analogy to Scheme 9 step e for preparing Reference compound 42.

In the above reaction scheme for preparing Reference compound 52, the reagents and conditions are: (a) Cbz-OSu, Et₃N, THF, Water; (b) Hoveyda-Grubbs metathesis catalyst, N-Boc-4-methylenepiperidine, DCM, 40° C. Intermediate 52-A is prepared following methods analogous to those described for Reference compound 2 step a. Reference compound 52 is prepared following methods analogous to those described for Reference compound 42 step e.

1-Boc-homopiperazine (1.00 g, 4.2 mmol) and DIEA (8.7 mL, 51.25 mmol) are dissolved in THF (15 mL) and stirred at room temperature. Mesyl chloride (1.67 mL, 21.52 mmol) is added dropwise, and the reaction stirred 6 h at room temperature. The reaction is diluted with EtOAc (100 mL); washed with 1 N HCl (2×50 mL), saturated aqueous NaHCO₃ (50 mL) and brine (50 mL); dried with MgSO₄; and then the solvent is evaporated to dryness in vacuo. The crude residue is taken up in 50% TFA in DCM and stirred for 1 h, and then evaporated to dryness in vacuo to afford Reference compound 53 which is used without further purification.

(2S,4R)-1-((benzyloxy)carbonyl)-4-(piperidine-1-carboxyloyloxy)pyrrolidine-2-carboxylic acid is prepared starting from L-Hydroxyproline methyl ester following methods analogous to those described for the preparation of Compound 1-G.

Reference compound 55

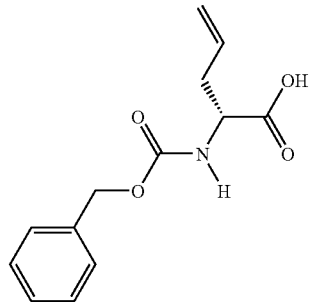

Reference compound 55 is prepared starting from D-Allylglycine following methods analogous to those described for the preparation of Reference compound 2-B.

Reference compound 56

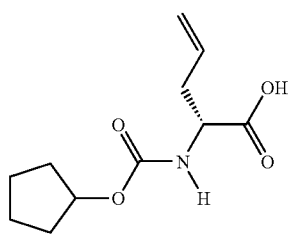

Reference compound 56 is prepared starting from D-Allylglycine following methods analogous to those described for the preparation of Reference compound 2-B.

Reference compound 57

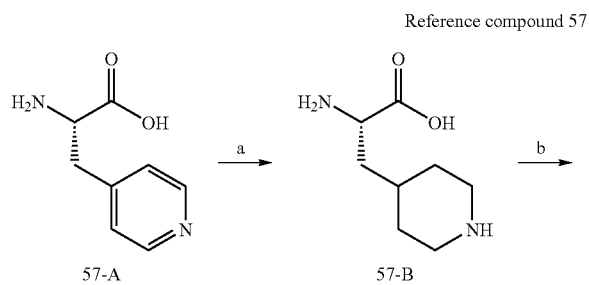

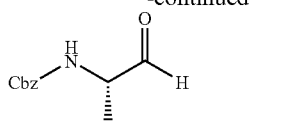

57-D

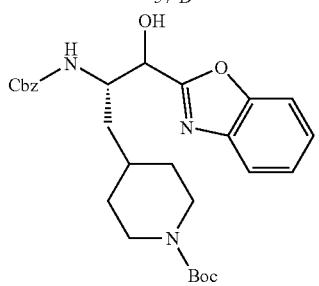

57-E

57-F

57-B: A solution of L-4-pyridylalanine 57-A (1.0 g), 10% Pd/C (300 mg) in EtOH (40 mL) and 1 N HCl aqueous solution (20 mL) is shaken on Parr Shaker for 12 hours under a hydrogen atmosphere at 50 psi. The catalyst is filtered and the filtrate is concentrated to afford the piperidine 57-B.

57-C: Piperidine 57-B (1.0 g) and copper sulfate pentahydrate (1.5 g) are dissolved in dioxane (50 mL) and water (30 mL). The pH of the solution is adjusted to pH 9 with 2 N sodium hydroxide at room temperature. Di-t-butyl-dicarbonate (2.63 g) is then added. The slurry mixture is stirred for overnight at room temperature. The precipitation is collected and washed with water, and then dissolved in dioxane. The pH of the solution is adjusted with 4N sodium hydroxide to pH 12 and Cbz-OSu (3.2 g) is added. The mixture is stirred overnight. Dioxane is removed under reduced pressure. The residue is acidified with 1N hydrochloric acid to pH 2-3, and extracted with ethyl acetate. The combined ethyl acetate solution is washed with brine, dried over sodium sulfate, and concentrated to dryness to give an oil. This crude material is taken up in DCM (50 mL) and MeOH (10 mL), and a 2 M solution of TMSCHN$_2$ in ether (3.5 mL) is added until solution is light yellow. The solvents are then removed under reduced pressure. The residue is purified on silica gel chromatography with 20% ethyl acetate in hexane to give the α-N-Cbz, ε-N-Boc methyl ester 57C.

57-D: A solution of 57-C (150 mg) in dichloromethane (20 mL) is cooled to −78° C., then 1M DiBAl-H in hexane (1.07 mL) is added over a period of 10 min. The mixture is stirred at −78° C. for 50 min, and a 5% citric acid aqueous solution (10 mL) is added to quench the reaction. The DCM layer is separated, and the aqueous layer is extracted with DCM. The combined DCM solution is washed with water, dried over sodium sulfate and filtered. The filtrate is concentrated to dryness to give the aldehyde. The aldehyde is dissolved in THF (8 mL) and used directly in the next step.

57-E: To a solution of benzoxazole (128 mg) in THF, 2.5 M BuLi in hexane is added at −30° C. The solution is stirred at −20° C. for 40 min, and a dark red solution is obtained. The aldehyde 57-E in THF (8 mL) is then added to the dark red solution at −30° C. over a period of 5 min. The mixture is stirred for 2 h at −10° C. Saturated aqueous ammonium chloride solution (10 mL) is added to the reaction mixture to quench the reaction. THF is removed under reduced pressure. The residue is extracted with ethyl acetate. The combined ethyl acetate solution is washed with 1N HCl aqueous solution, water, saturated aqueous sodium bicarbonate, and brine respectively, and then dried over anhydrous sodium sulfate and filtered. The filtrate is concentrated, and the residue is purified by silica gel chromatography with 30% to 50% ethyl acetate in hexane to give the desired product.

57-F: Intermediate 57-E is dissolved in MeOH and Pd/C (50 mg) is added. Hydrogen gas from a balloon is bubbled through the mixture for 30 min. The catalyst is then removed by filtration, and the filtrate is concentrated to give the amine.

EXAMPLE 1

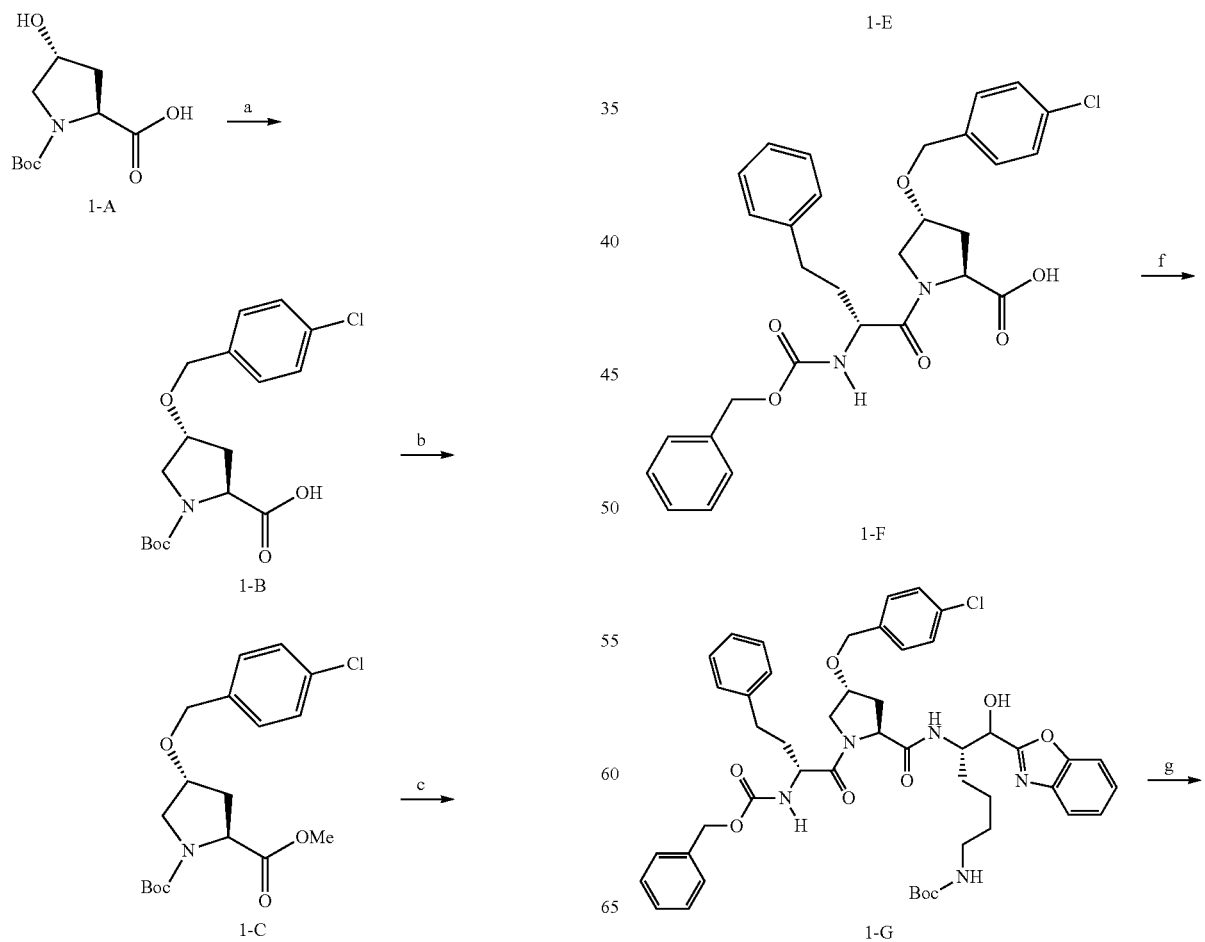

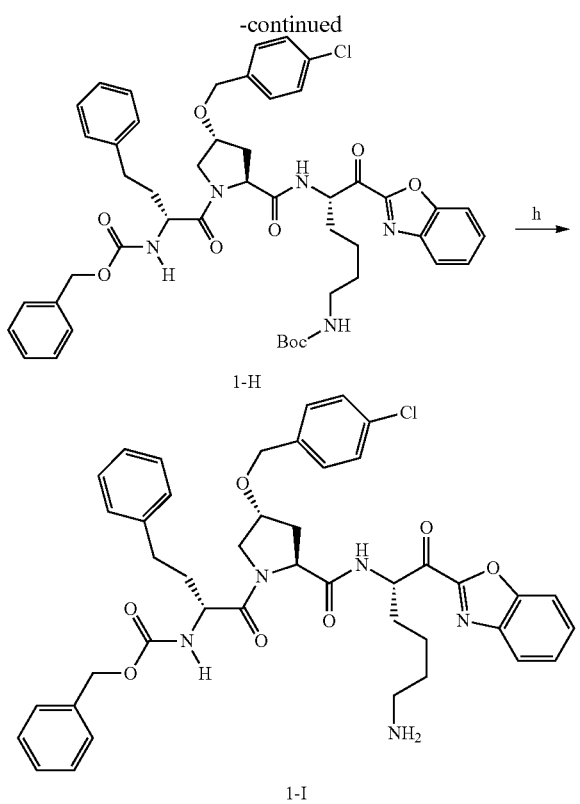

1-B: Finely powdered KOH (19.4 g, 0.346 mol) is dissolved in DMSO and stirred at room temperature for 20 min. and then cooled to 0° C. N-Boc-trans-4-hydroxy-L-proline (Boc-Hyp-OH, 1-A) (10 g, 43.3 mmol) is dissolved in DMSO (10 mL) and added, and the reaction mixture is stirred for an additional 10 min at 0° C. Next, 4-chlorobenzyl chloride (33 g, 0.204 mol) is added, and the reaction mixture is stirred at 0° C. for an additional 15 min, after which point the ice bath is removed, and the reaction mixture is allowed to warm to room temperature and stir for 4 h. The reaction mixture is poured into water (300 mL), and the reaction vessel is rinsed with an additional aliquot of water (300 mL). The combined aqueous layer is extracted with ether (2×300 mL) and discarded. The aqueous layer is acidified with 87% $H_3PO_4$ to pH 2-3, and then extracted with ether (3×300 mL). The combined ether extracts are washed with water (2×400 mL) and brine (2×400 mL); dried over $MgSO_4$; filtered and concentrated in vacuo. The residue is purified by chromatography on silica gel with EtOAc/Hexanes (gradient 0 to 100%) to yield the compound 1-B as a clear oil. MS m/z 256.1 (M+1-Boc); $^1$H-NMR (DMSO-D$_6$, 400 MHz) δ 7.39-7.31 (4H, m), 4.52-4.40 (2H, m), 4.16-4.10 (2H, m), 3.48-3.41 (2H, m), 2.40-2.30 (1H, m), 2.03-1.94 (1H, m), 1.39-1.34 (9H, m).

1-C: A solution of (trimethylsilyl)diazomethane (2M in diethylether) (4.7 ml, 9.45 mmol) is added to carboxylic acid 1-B (2.4 g, 8.6 mmol) dissolved in DCM/MeOH 5:1 (25 mL). When the starting material is consumed as determined by LCMS, the reaction mixture is concentrated in vacuo, and the crude residue is purified by flash chromatography (gradient EtOAc:Hexanes) to afford methyl ester as a clear oil.

1-D: A round bottomed flask is charged with a stirbar and 1-C (510 mg, 1.38 mmol). TFA (50%) in DCM (6 mL) is added, and the solution is stirred for 1 h at room temperature. The solvent is removed in vacuo, hexanes are added and then evaporated again in vacuo to dryness, and repeated if necessary to azeotrope remaining TFA. The crude material is used directly in the next step without further purification.

1-E: The crude material is dissolved in DCM (10 mL) followed by addition of Cbz-D-homoPhe-OH (Reference compound 22) (432 mg, 1.38 mmol) and HATU (577 mg, 1.52 mg), and the solution is stirred at room temperature for 10 min. DIEA (0.72 mL, 4.14 mmol) is added to the solution, and the reaction mixture is allowed to stir overnight at room temperature. The solvent is removed in vacuo, and the crude material is directly purified by flash chromatography (40 g silica, hexanes/EtOAc gradient). The solvent is removed in vacuo to afford the desired compound as an oily semisolid.

1-F: Methyl ester 1-E (756 mg, 1.34 mmol) is dissolved in dioxane (10 mL). Lithium hydroxide monohydrate (84 mg, 2.00 mmol) is dissolved in water (5 mL) and added dropwise to the solution of methyl ester 1-E, and allowed to stir overnight. The reaction mixture is concentrated in vacuo to remove dioxane and then acidified with 1M $NaHSO_4$. This is extracted with EtOAc, and the combined organic layer is washed with brine and dried with $MgSO_4$. The solvent is removed in-vacuo to afford carboxylic acid 1-F as a waxy solid.

1-G: Carboxylic acid 1-F (534 mg, 0.97 mmol) is dissolved in DCM (18 mL). Reference compound 1 (3.38 mg, 0.97 mmol) and HATU (405 mg, 1.07 mmol) are added, and the mixture is stirred for 10 min at room temperature. Next, DIEA (0.51 mL, 2.91 mmol) is added, and the reaction mixture is left to stir overnight at room temperature. The solvent is removed in vacuo, the crude is redissolved in EtOAc (50 mL) and washed with 1M HCl (2×25 mL), followed by saturated aqueous $NaHCO_3$ (2×25 mL) and brine (25 mL), and dried with anhydrous $Na_2SO_4$. Solvent is removed to afford the 1-G as a white foam, which is purified by flash chromatography (Hexanes/EtOAc) to afford the desired product.

1-H. Alcohol 1-G (727 mg, 0.82 mmol) is dissolved in DCM (10 mL) and Dess-Martin periodinane (524 mg, 1.24 mmol) is added. The reaction mixture is stirred overnight at room temperature. The solvent is removed in vacuo, and the crude is purified by flash chromatography (40 g silica column) using a gradient of EtOAc:Hexanes to afford the ketone 1-H as a white foam.

1-I: 1-H (579 mg, 0.66 mmol) is dissolved in DCM (1 mL), and TFA 50% in DCM (5 mL) is added. The reaction is stirred at room temp for 2 h, and the solvent is removed in vacuo. The crude material is purified by reverse-phase HPLC, and the solvent is lyophilized to afford as the product as a white powder.

EXAMPLES 2-46

Examples 2-46 are obtained by repeating the procedures described in Example 1, using appropriate Reference compounds and reagents which would be apparent to those skilled in the art, for example:
Example 2, using Reference compound 3;
Example 3, using Reference compound 14;
Example 4, using Reference compound 3 and Reference compound 14;
Example 5, using Reference compound 16;
Example 6, using Reference compound 21;
Example 7, using N-p-tosylglycine;
Example 8, using N-mesyl-L-alanine;
Example 9, using N-mesylglycine;
Example 10, using Reference compound 19;
Example 11, using D-homocyclohexylalanine (D-homo-Cha);
Example 12, using trans-3-hydroxy-L-proline;

Example 13, using trans-3-hydroxy-L-proline and Reference compound 4;
Example 14, using Reference compound 4;
Example 15, using Reference compound 4;
Example 16, using trans-3-hydroxy-L-proline and Reference compound 4;
Example 17, using Reference compound 23;
Example 18, using trans-3-hydroxy-L-proline and Reference compound 23;
Example 25, using Reference compound 14;
Example 26, using trans-3-hydroxy-L-proline;
Example 27, using trans-3-hydroxy-L-proline and Cbz-D-cyclohexylalanine;
Example 28, using trans-3-hydroxy-L-proline and Cbz-D-3-trifluoromethylphenylalanine;
Example 30, using trans-3-hydroxy-L-proline and Reference compound 14;
Example 31, using Reference compound 14;
Example 32, using Reference compound 12;
Example 34, using O-benzyl-D-tyrosine;
Example 35, using O-benzyl-D-serine;
Example 36, using D-homocyclohexylalanine (D-homo-Cha);
Example 38, using D-phenylglycine;
Example 39, using Reference compound 2;
Example 40, using Reference compound 8;
Example 41, using Reference compound 9;
Example 42, using Reference compound 2;
Example 43, using Reference compound 24;
Example 44, using Reference compound 2;
Example 45, using Reference compound 5; and
Example 46, using Reference compound 25.

EXAMPLE 47

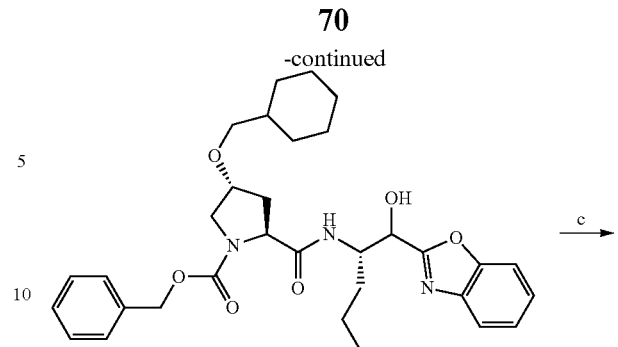
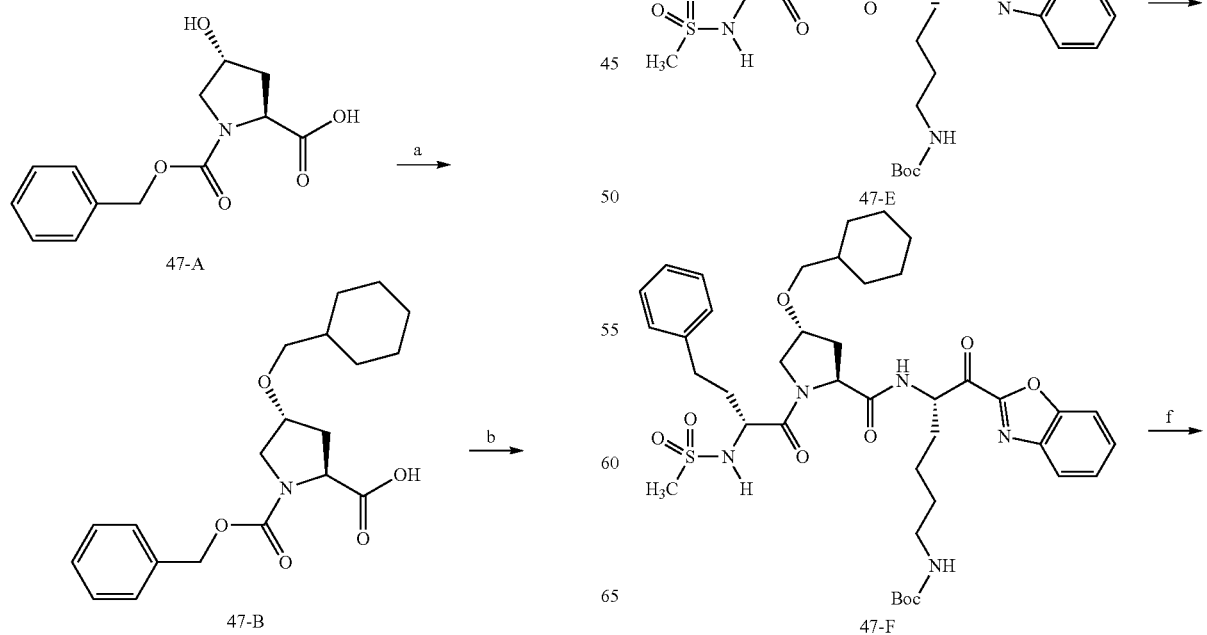

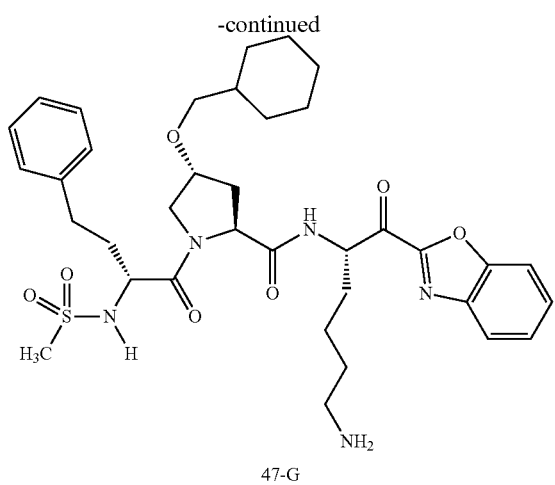

47-G

47-B: This compound is prepared from Cbz-Hyp-OH and cyclohexylbromide following methods analogous to those described for the preparation of intermediate 1-B in Example 1.

47-C: This compound is prepared from 47-B and Reference compound 1 following methods analogous to those described for the preparation of intermediate 1-G in Example 1.

47-D: A Parr reaction vessel is charged with 47-C (2.5 g, 3.6 mmol), Pd/C (3.6 g, 0.36 mmol, 1 eq), t-BuOH (20 mL) and water (5 mL). The vessel is placed into a Parr apparatus and shaken for 18 h under a pressure of 50 psi of $H_2$ gas. The reaction mixture is filtered through a pad of Celite, and the volatile solvents are removed under reduced pressure to afford compound 47-D which is used directly in the next step without further purification.

47-E: A 40 mL vial is charged with 47-D (75 mg, 0.13 mmol), N-Mesyl (D)-homophenylalanine (56 mg, 0.15 mmol, 1.1 eq), HATU (75 mg, 0.13 mmol, 1.1 eq), $iPr_2NEt$ (0.03 ml, 0.16 mmol, 1.2 eq) and $CH_2Cl_2$ (2 mL). The reaction is stirred at room temperature for 1 h. The volatile reagents are removed under reduced pressure, and the reaction mixture is dissolved in EtOAc. The organic layers are washed with $NaHSO_4$, water saturated $NaHCO_3$, and brine. The organic layers are then dried with $MgSO_4$, and the product purified from the reaction mixture via silica gel chromatography using a gradient of 3-9% MeOH in $CH_2Cl_2$ over gradient to afford compound 47-D.

47-F: This compound is prepared by oxidation of 47-E following methods analogous to those described for the preparation of intermediate 1-H in Example 1.

47-G: This compound is prepared by deprotection of 47-F following methods analogous to those described for the preparation Example 1.

EXAMPLES 48-115

Examples 48-57, 83-84 and 86-87 are obtained by repeating the procedures described in Example 47, using appropriate Reference compounds and reagents which would be apparent to those skilled in the art, for example:
Example 48, using D-cyclohexylglycine;
Example 49, using 4-(trifluoromethoxy)-DL-phenylalanine;
Example 50, using Reference compound 23;
Example 51, using Reference compound 27;
Example 52, using Reference compound 28;
Example 53, using D-3-chlorophenylalanine;
Example 54, using 3-(trifluoromethyl)-D-phenylalanine;
Example 55, using Reference compound 29;
Example 56, using Reference compound 30;
Example 57, using Reference compound 31;
Example 83, using Reference compound 36;
Example 84, using Reference compound 17;
Example 86, using Reference compound 26; and
Example 87, using Reference compound 22.

Examples 58-82, 85 and 88-115 are obtained by repeating the procedures described in Example 1, using appropriate Reference compounds and reagents which would be apparent to those skilled in the art, for example:
Example 58, using Reference compound 32;
Example 59, using Reference compound 2 and Reference compound 28;
Example 60, using Reference compound 11 and Reference compound 28;
Example 61, using Reference compound 33 and Reference compound 28;
Example 62, using Reference compound 29;
Example 63, using D-pyroglutamic acid;
Example 64, using Reference compound 18;
Example 65, using Reference compound 18 and Reference compound 2;
Example 66, using Reference compound 18 and Reference compound 3;
Example 67, using Reference compound 18 and Reference compound 5;
Example 68, using Reference compound 18 and Reference compound 9;
Example 69, using Reference compound 14 and Reference compound 2;
Example 70, using Reference compound 18 and Reference compound 7;
Example 71, using Reference compound 18 and Reference compound 4;
Example 72, using Reference compound 14 and Reference compound 4;
Example 73, using Reference compound 18 and Reference compound 11;
Example 74, using Reference compound 14 and Reference compound 5;
Example 75, using Reference compound 14 and Reference compound 9;
Example 76, using Reference compound 18 and Reference compound 8;
Example 77, using Reference compound 18 and Reference compound 34;
Example 78, using Reference compound 18 and Reference compound 6;
Example 79, using Reference compound 18 and Reference compound 10;
Example 80, using Reference compound 27;
Example 81, using Reference compound 23;
Example 82, using Reference compound 35;
Example 85, using Boc-D-1,2,3,4-tetrahydroisoquinoline-3-carboxylic acid (Boc-D-Tic-OH);
Example 88, using Reference compound 20;
Example 89, using Reference compound 20 and Reference compound 3;
Example 90, using Reference compound 20 and Reference compound 2;
Example 91, using Reference compound 20 and Reference compound 5;
Example 92, using Reference compound 20 and Reference compound 9;

Example 93, using Reference compound 20 and Reference compound 6;

Example 94, using Reference compound 20 and Reference compound 10;

Example 95, using Reference compound 20 and Reference compound 11;

Example 96, using Reference compound 20 and Reference compound 7;

Example 97, using Reference compound 2 and Reference compound 18;

Example 98, using Reference compound 37;

Example 99, using Reference compound 38;

Example 100, using Reference compound 39 and Reference compound 14;

Example 101, using Reference compound 40 and Reference compound 18;

Example 102, using Reference compound 38 and Reference compound 18;

Example 103, using Reference compound 34;

Example 104, using Reference compound 40;

Example 105, using Reference compound 38;

Example 106, using Reference compound 41;

Example 107, using Reference compound 42;

Example 108, using Reference compound 43;

Example 109, using Reference compound 44;

Example 110, using Reference compound 45;

Example 111, using Reference compound 46;

Example 112, using Reference compound 47;

Example 113, using Reference compound 48;

Example 114, using Reference compound 48, with the final compound isolated as a mixture of diastereomers; and Example 115, using Reference compound 49 and Reference compound 18.

EXAMPLE 116

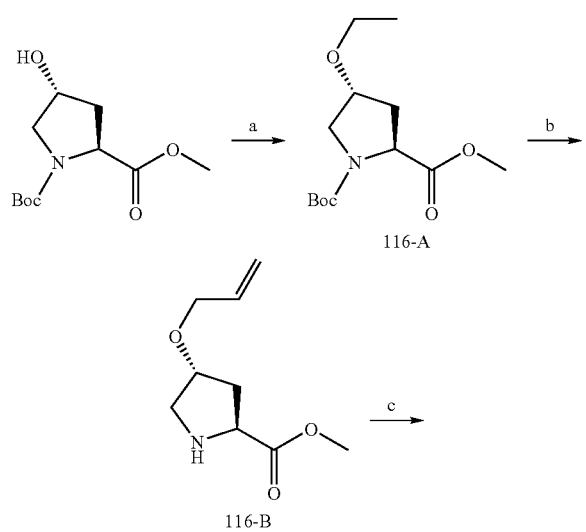

116-A

116-B

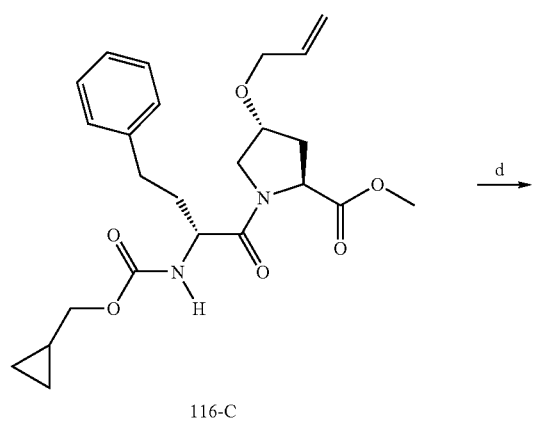

116-C

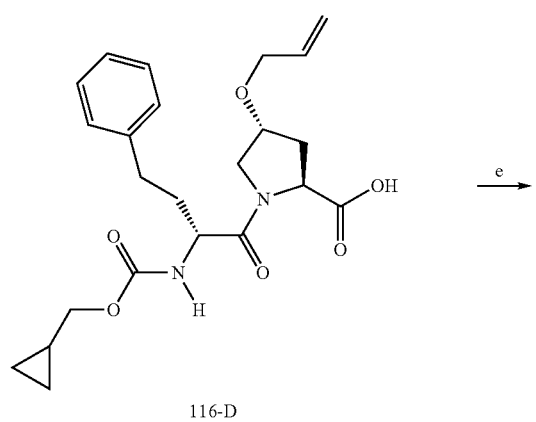

116-D

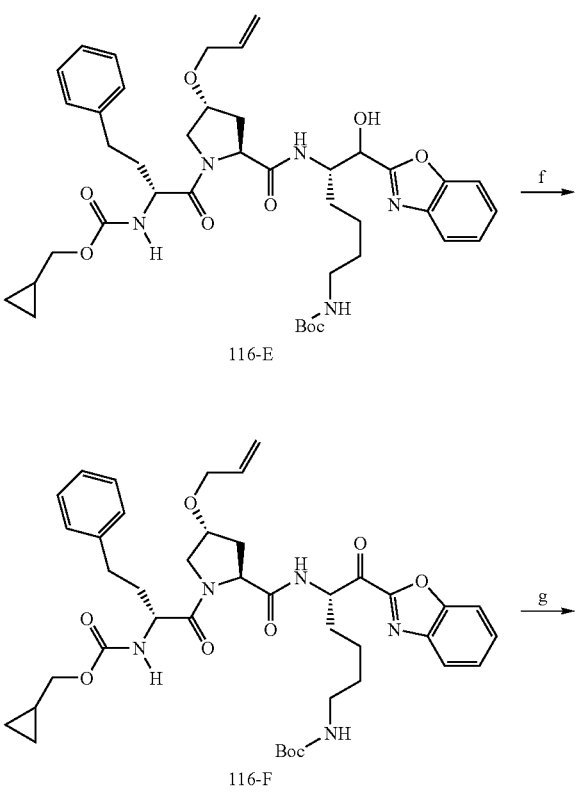

116-E

116-F

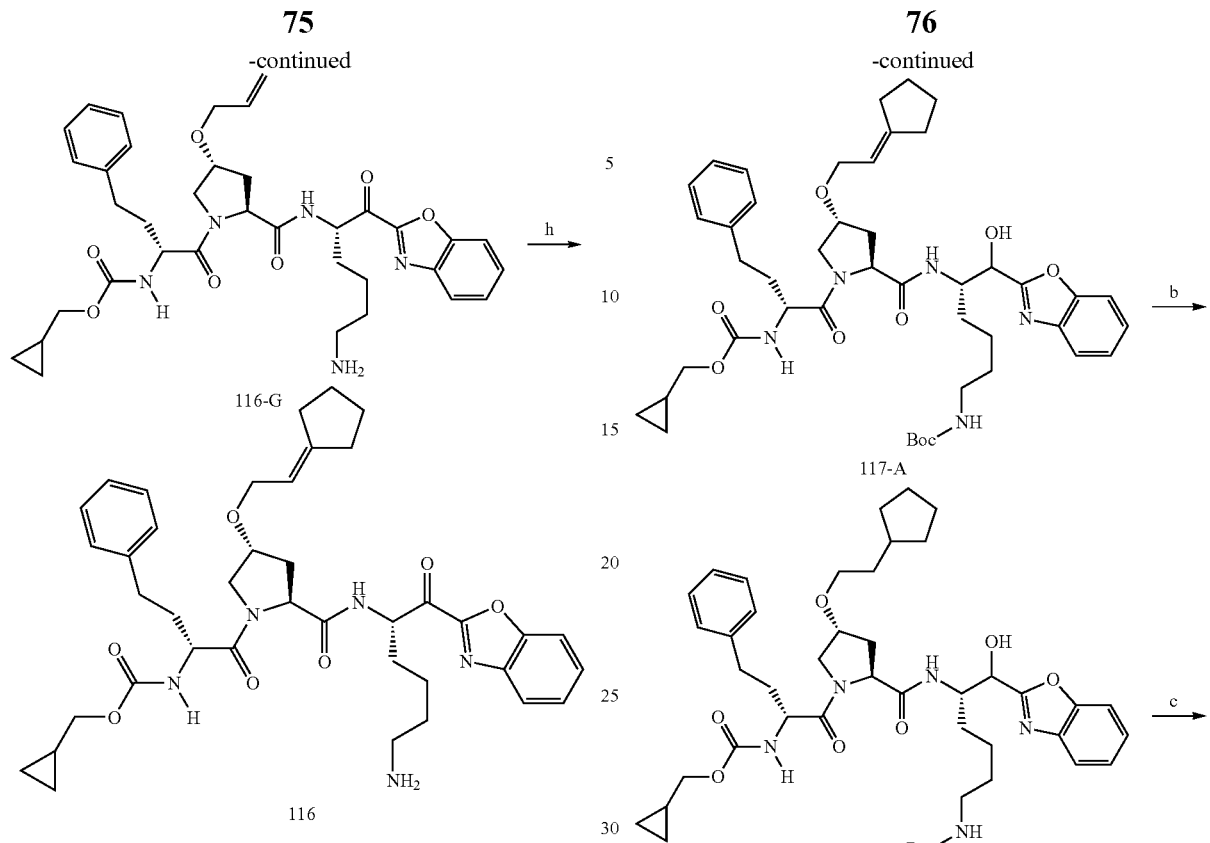

In Example 116, the reagents and conditions are: (a) Ag₂O, allylbromide, Et₃N, acetone, 23° C.; (b) TFA, DCM, 23° C. (c) HATU, DIEA, DCM, Reference compound 50, 23° C.; (d) LiOH, dioxanes, water, 23° C.; (e) HATU, DIEA, DCM, Reference compound 1, 23° C.; (f) Dess-Martin periodinane, DCM; (g) TFA, DCM, 23° C.; (h) Hoveyda-Grubbs metathesis catalyst, methylenecyclopentane, DCM, 40° C.

Compound 116-A is prepared following procedures in Park, M.-S. J. Kor. Chem. Soc. 45:549 (2001). Compound 116-B is prepared following Example 1 step h. Compound 116-C is prepared following Example 1 step d using Reference compound 23 as the acid component. Compound 116-D is prepared following Example 1 step 3. Compound 116-E is prepared following Example 1 step f using Reference compound 1 as the amine component. Compound 116-F and 116-G are prepared following Example 1 step g and step h, respectively. The compound 116 is prepared following Scheme 9 step e for preparing Reference compound 42.

EXAMPLE 117

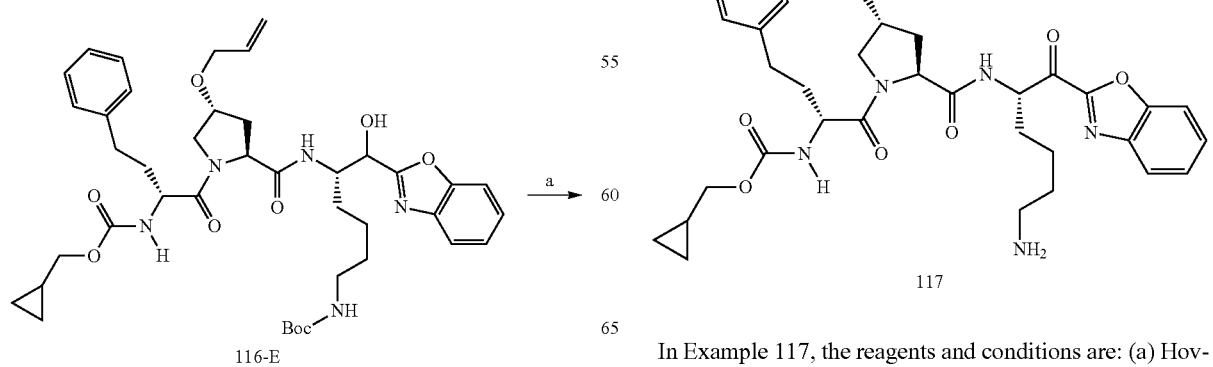

In Example 117, the reagents and conditions are: (a) Hoveyda-Grubbs metathesis catalyst, methylenecyclopentane, DCM, 40° C.; (b) H₂ (40 psi), MeOH, Pd/C (10 wt %, wet); (c) Dess-Martin periodinane, DCM; (d) TFA, DCM, 23° C.

Compound 117-A is prepared following Example 1 step f using Reference compound 1 as the amine component. Compound 117-B and 117-C are prepared following Example 1 step g and step h, respectively. Compound 117 is prepared following Scheme 9 step e for preparing Reference compound 42.

EXAMPLES 118-123

Examples 118-123 are obtained by repeating the above procedures, using appropriate Reference compounds and reagents which would be apparent to those skilled in the art, for example:

Example 118, using styrene in Example 117 step a;

Example 119, using 4-chlorostyrene in Example 116 step h;

Example 120, using N-Boc-L-3-hydroxyproline in Example 116 step a, and methylenecyclohexane in Example 116 step h;

Example 121, using N-Boc-L-3-hydroxyproline in Example 116 step a, and methylenecyclohexane in Example 117 step a;

Example 122, using N-Boc-L-3-hydroxyproline in Example 116 step a, and N-Boc-4-methylenepiperidine in Example 117 step a;

Example 123, following methods analogous to those described in Example 1, using Reference compound 50 in step d; and Example 123, following methods analogous to those described for Example 1, using Reference Compound 50 in step d.

EXAMPLE 124

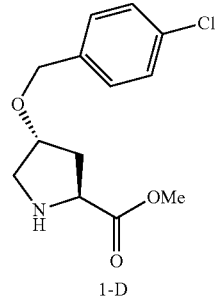
1-D

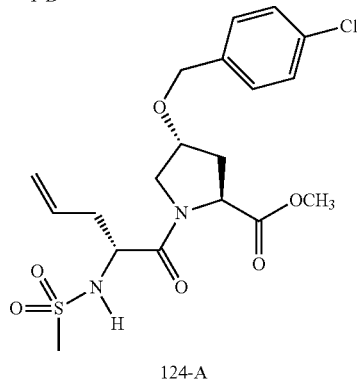
124-A

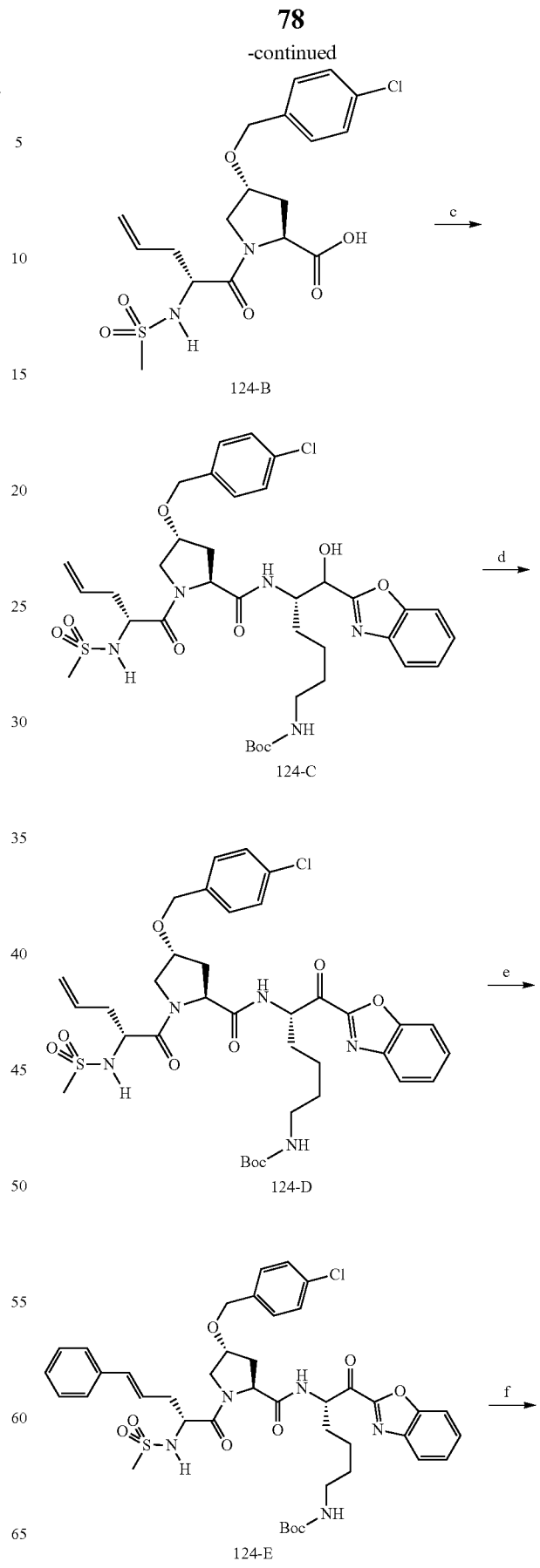

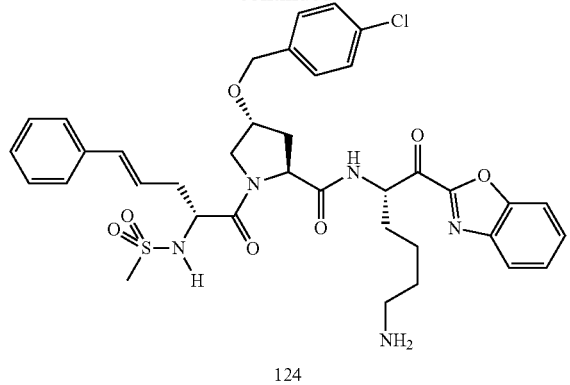

124

In Example 124, the reagents and conditions are: (a) HATU, DIEA, DCM, Reference compound 21, 23° C.; (b) LiOH, dioxanes, water, 23° C.; (c) HATU, DIEA, DCM, Reference compound 1, 23° C.; (d) Dess-Martin periodinane, DCM; (e) Hoveyda-Grubbs metathesis catalyst, methylenecyclopentane, DCM, 40° C.; (f) TFA, DCM, 23° C.

Compound 124-A is prepared following Example 1 step d using Reference compound 21 as the acid component and compound 1-A as the amine component. Compound 124-B is prepared following Example 1 step e. Compound 124-C is prepared following Example 1 step f using Reference compound 1 as the amine component. Compound 124-D is prepared following Example 1 step g. Compound 124-E is prepared following Scheme 9 step e for preparing Reference compound 42. Compound 124 is prepared following Example 1 step h.

EXAMPLES 125-134

Examples 125, 127-130 and 133-134 are obtained by repeating the procedures described in Example 124, using appropriate Reference compounds and reagents which would be apparent to those skilled in the art, for example:

Example 125, using methylenecyclohexane as a reagent;
Example 127, using 4-carboxystyrene as a reagent;
Example 128, using 4-chlorostyrene as a reagent;
Example 129, using N-Boc-4-methylenepiperidine as a reagent;
Example 130, using methylenecyclopentane as a reagent; and
Example 133, using methylenecyclohexane as a reagent.

Examples 126 and 131-132 are obtained by repeating the procedures described in Example 1, using appropriate Reference compounds and reagents which would be apparent to those skilled in the art, for example:

Example 126, using Reference Compound 51;
Example 131, using Reference Compound 52; and
Example 132, using Reference Compound 52.

EXAMPLE 135

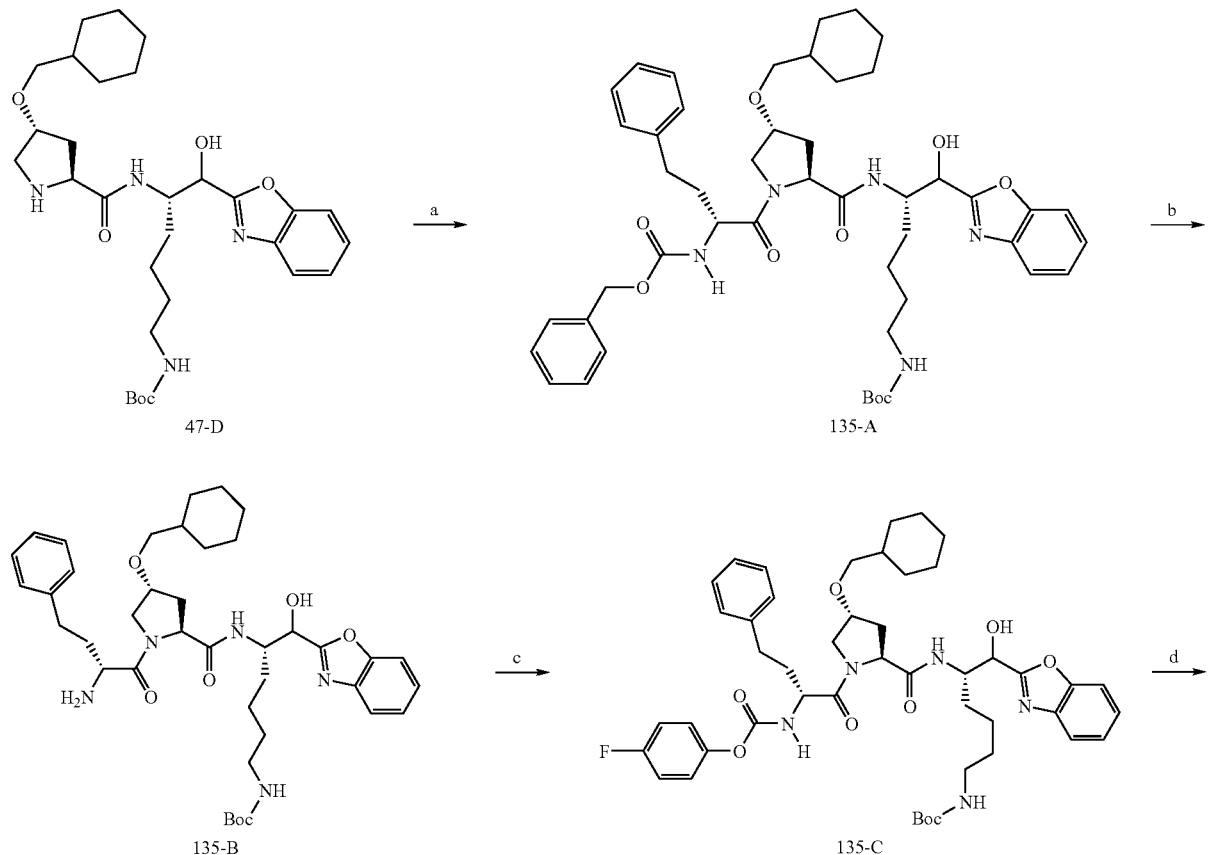

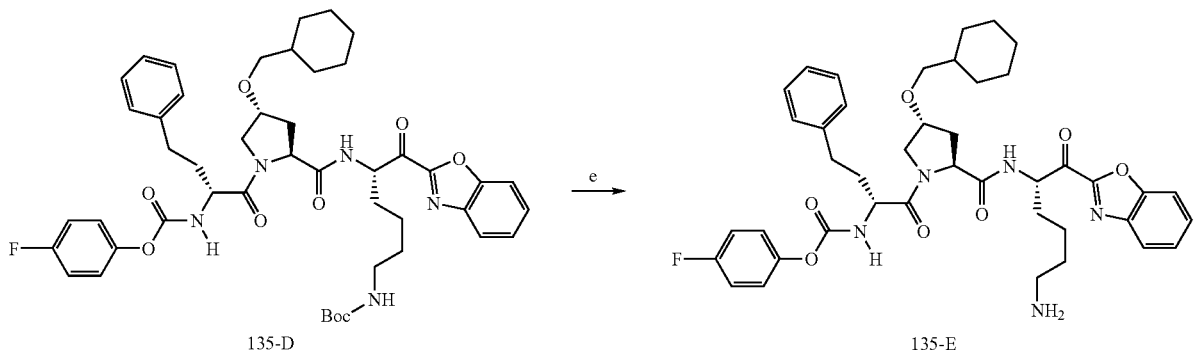

135-A: This compound is synthesized from 47-D and Cbz-D-homophenylalanine, following methods analogous to those described for the preparation of 47-E.

135-B: The Cbz protecting group is removed by hydrogenolysis, using conditions analogous to those described for the preparation of Reference compound 1-E.

135-C: Amine 135-B (79 mg, 0.11 mmol) and pyridine (0.2 mL) are dissolved in $CH_2Cl_2$ (10 mL). 4-fluorophenyl chloroformate (21 mg, 0.12 mmol) is added, and the solution is stirred at room temperature for several hours until the starting material is consumed (by LCMS). The solvent is evaporated and the residue taken up in EtOAc (30 mL). The organic phase is washed with 1M $NaHSO_4$ (2×25 mL) and brine (25 mL), and then dried with $MgSO_4$. The solvent is evaporated, and the crude material purified by silica gel chromatography (Hexanes/EtOAc gradient 0 to 100%).

135-D: This compound is prepared from 135-C, following methods analogous to those described for the preparation of 47-F.

135-E: This compound is prepared from 135-D, following methods analogous to those described for the preparation of 47-G.

EXAMPLES 136-152 AND 258

Examples 136 and 137 are prepared, following methods analogous to those described in Example 135 and Example 1, respectively. By repeating the procedures described in the above examples and, using appropriate starting materials, Examples 138-152 and 258 are obtained.

Table 1 shows compounds of Formula (1), as described in Examples 1-152 and 258.

TABLE 1

| | Structure | Physical Data<br>MS (m/z), Elemental Analysis, and<br>$^1$H NMR 400 M Hz (DMSO-$d_6$) |
|---|---|---|
| 1 | 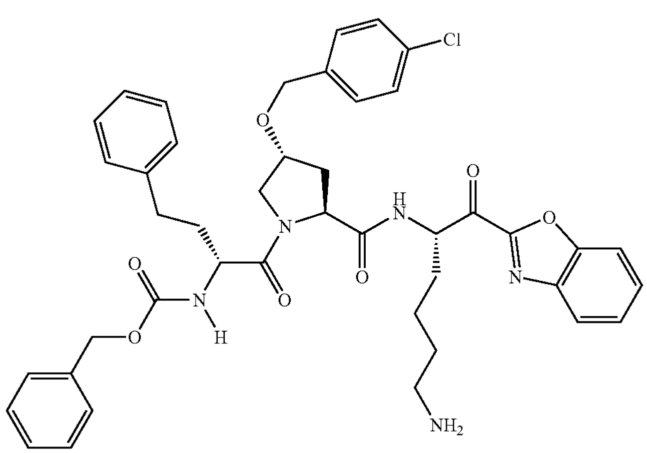 | MS m/z 780.4 (M + 1); Anal. Calcd. for $C_{45}H_{47}ClF_3N_5O_9$ (1 TFA): C, 60.43; H, 5.30; N, 7.83; Found: C, 59.92; H, 5.09; N, 7.62; $^1$H NMR ($CD_3CN$, 400 M Hz) δ 7.91(1H, d, J=8.0 Hz), 7.75 (1H, dd, J=8.0, 3.2 Hz), 7.63-7.60(1H, m), 7.54-7.50(1H, m), 7.38(2H, d, J=4.8 Hz), 7.35-7.24 (10H, m), 7.20-7.15(2H, m), 5.54-5.30(1H, m), 5.16-5.01(2H, m), 4.49-4.13(5H, m), 3.88-3.73(1H, m), 3.58-3.49(1H, m), 2.92-2.91(1H, m), 2.79-2.74 (1H, m), 2.63-2.58(1H, m), 2.26-2.19(1H, m), 2.09-1.79(1H, m), 1.91-1.84(2H, m), 1.78-1.64(3H, m), 1.61-1.35(4H, m). |

TABLE 1-continued
| Structure | Physical Data<br>MS (m/z), Elemental Analysis, and<br>¹H NMR 400 M Hz (DMSO-d₆) |
|---|---|
| 2 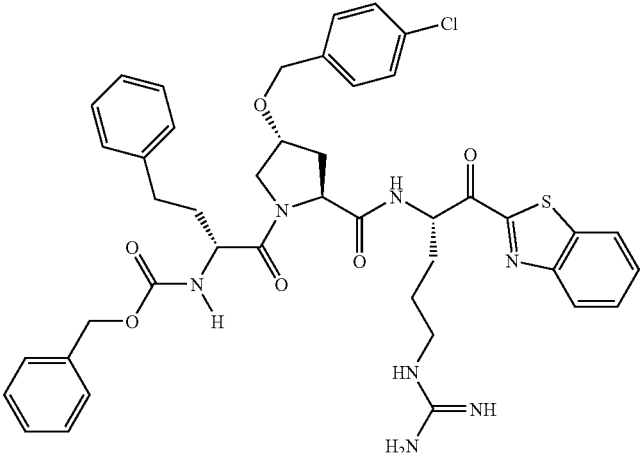 | MS m/z 824.1 (M + 1); Anal. Calcd. for C₄₃H₅₁Cl₂N₇O₈S (1 HCl, 2 H₂O): C, 57.58; H, 5.73; N, 10.93; Found: C, 57.11; H, 5.75; N, 10.27; ¹H NMR (CD₃CN, 600 M Hz) δ 8.17(1H, d, J=7.8 Hz), 8.06(1H, d, J=7.8 Hz), 8.03-8.01(1H, m), 7.66-7.55(2H, m), 7.41-7.21(10H, m), 7.20-7.12 (3H, m), 5.56-5.50(1H, m), 5.11(1H, d, J=12.6 Hz), 5.03(1H, d, J=12.6 Hz), 4.59(1H, t, J=7.8 Hz), 4.44-4.26(3H, m), 3.77-3.71(2H, m), 3.70-3.67 (2H, m), 3.57-3.53(2H, m), 3.25-3.10(2H, m), 2.78-2.58(2H, m), 2.32-2.24(1H, m), 1.93-1.86(2H, m), 1.85-1.77(1H, m), 1.76-1.68(1H, m). |
| 3 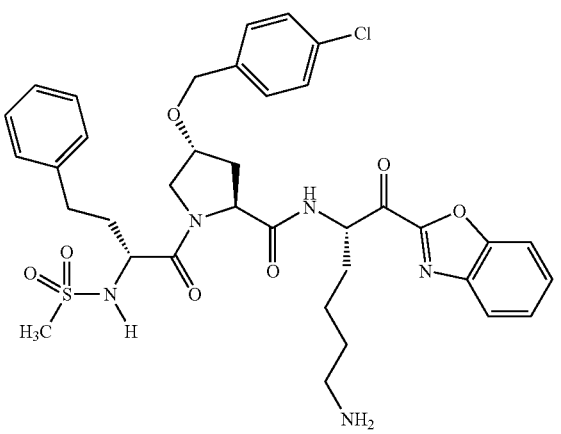 | MS m/z 724.3 (M + 1) |
| 4 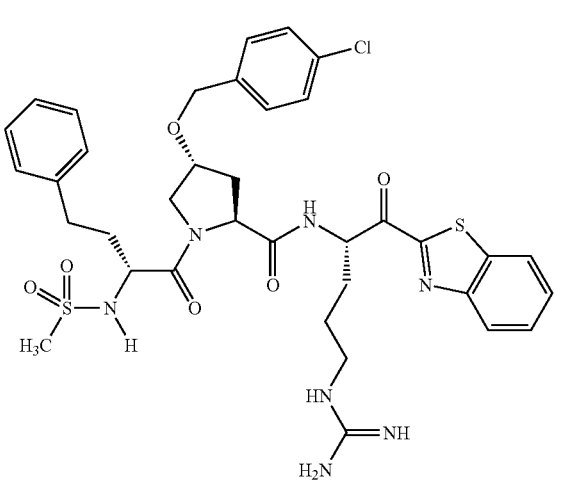 | MS m/z 768.2 (M + 1) |

TABLE 1-continued

| | Structure | Physical Data MS (m/z), Elemental Analysis, and $^1$H NMR 400 M Hz (DMSO-$d_6$) |
|---|---|---|
| 5 | 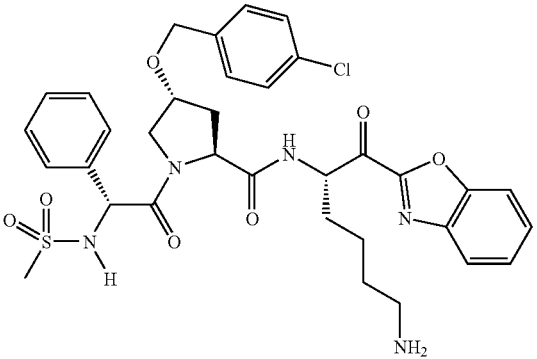 | MS m/z 696.8 (M + 1) |
| 6 | 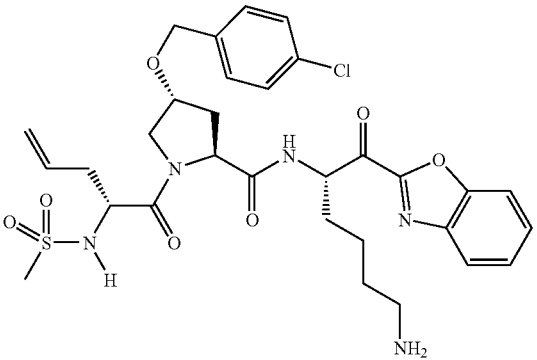 | MS m/z 660.3 (M + 1); Anal. Calcd. for $C_{33}H_{43}ClF_3N_5O_{11}S$ (2 TFA, 1 H$_2$O): C, 48.92; H, 5.35; N, 8.64; Found: C, 49.22; H, 5.06; N, 8.48; $^1$H NMR (CD$_3$CN, 400 M Hz) δ 7.91(1H, d, J=8.0 Hz), 7.76(1H, d, J=8.4 Hz), 7.65-7.39(3H, m), 7.38-7.26(3H, m), 5.87-5.73(1H, m), 5.52-5.42(1H, m), 5.22-5.02(2H, m), 4.56-4.36(3H, m), 4.34-4.22 (2H, m), 3.88-3.68(2H, m), 2.92(3H, s), 2.44-2.22 (6H, m), 2.17-1.98(2H, m), 1.81-1.54(6H, m). |
| 7 | 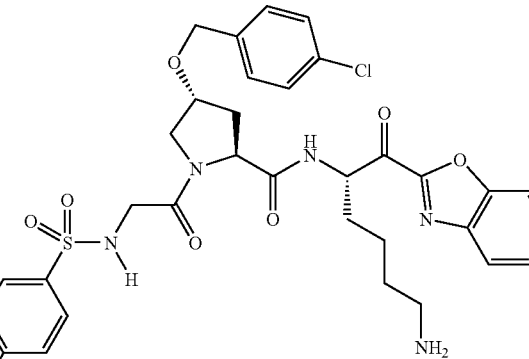 | MS m/z 696.2 (M + 1); Anal. Calcd. for $C_{36}H_{45}ClF_3N_5O_{12}S$ (1 TFA, 3 H$_2$O): C, 50.03; H, 5.25; N, 8.10; Found: C, 50.42; H, 4.71; N, 7.70; $^1$H NMR (CD$_3$CN, 400 M Hz) δ 7.93(1H, d, J=8.0 Hz), 7.78(1H, d, J=8.0 Hz), 7.76(2H, d, J=8.0 Hz), 7.66(2H, app t), 7.60-7.51(1H, m), 7.39-7.31 (4H, m), 7.15-7.08(1H, m), 5.56-5.48(1H, m), 4.54-4.38(3H, m), 4.31-4.24(1H, m), 3.79(2H, d, J=4.0 Hz), 3.66(1H, d, J=11.0, 4.4 Hz), 3.58(1H, d, J= 11.2 Hz), 3.02(2H, br s), 2.44(3H, s), 2.33-2.24 (2H, m), 2.21-2.09(2H, m), 1.84-1.59(4H, m). |
| 8 | 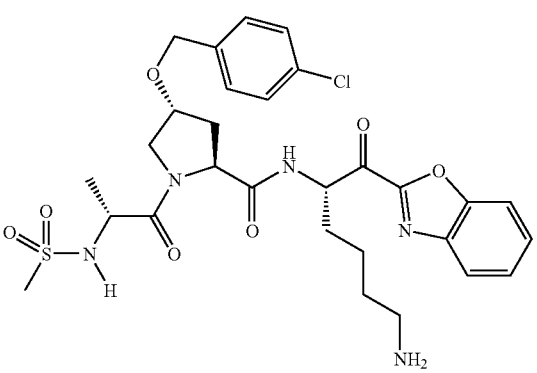 | MS m/z 634.2 (M + 1) |

TABLE 1-continued
| Structure | Physical Data<br>MS (m/z), Elemental Analysis, and<br>$^1$H NMR 400 M Hz (DMSO-$d_6$) |
|---|---|
| 9 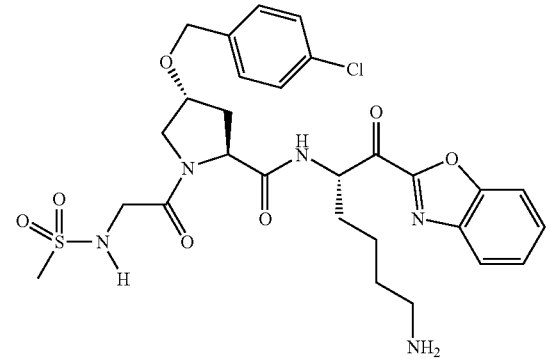 | MS m/z 620.5 (M + 1) |
| 10 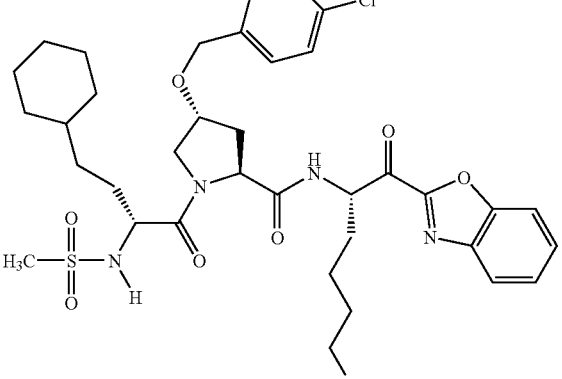 | MS m/z 730.4 (M + 1) |
| 11 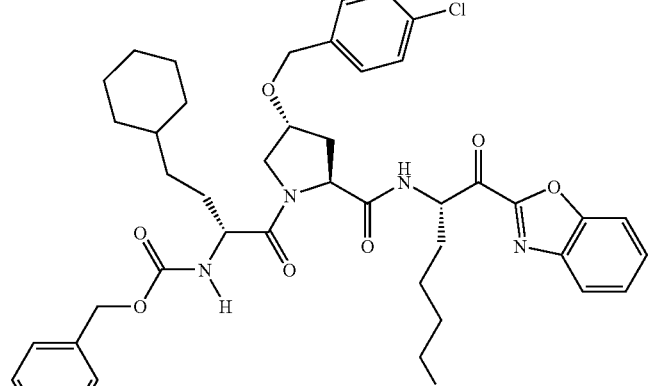 | MS m/z 786.4 (M + 1) |

TABLE 1-continued
| Structure | Physical Data MS (m/z), Elemental Analysis, and ¹H NMR 400 M Hz (DMSO-$d_6$) |
|---|---|
| 12 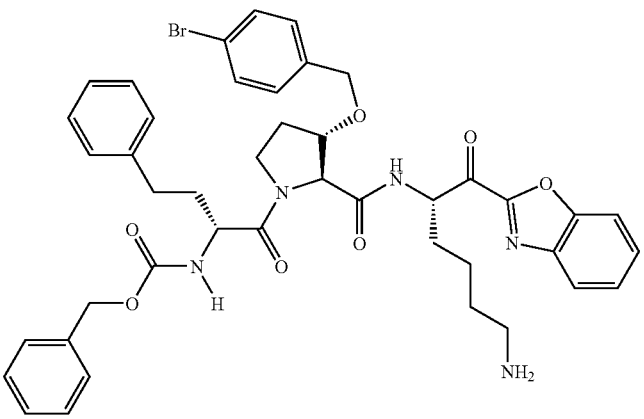 | MS m/z 824.3 (M + 1) |
| 13 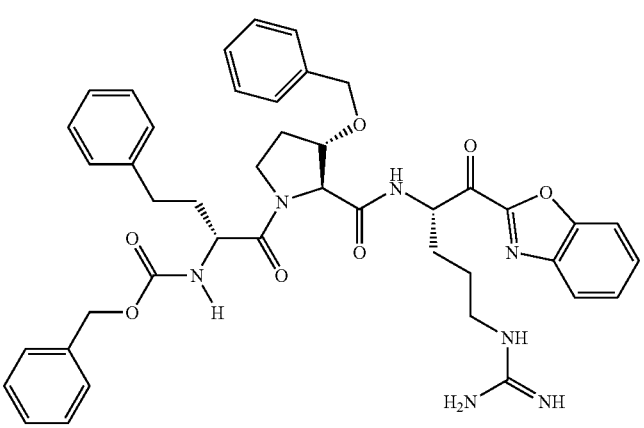 | MS m/z 774.2 (M + 1) |
| 14 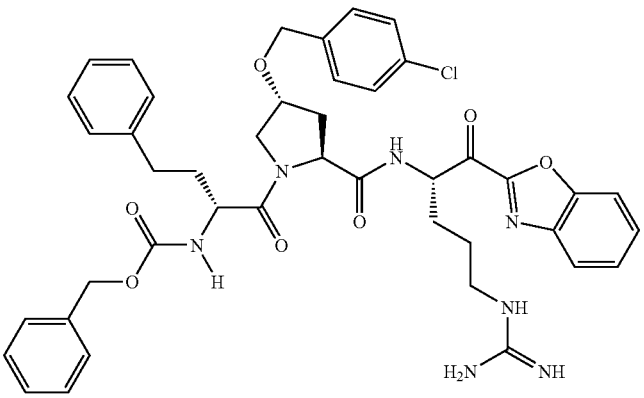 | MS m/z 808.4 (M + 1); ¹H NMR (CD$_3$CN, 400 M Hz) δ 7.85-7.79(1H, m), 7.58(1H, d, J=8.4 Hz), 7.50-7.46(1H, m), 7.42-7.38(1H, m), 7.30-7.04 (14H, m), 6.10-5.94(1H, m), 5.53-5.42(1H, m), 5.12-4.92(2H, m), 4.57-4.42(1H, m), 4.38-4.18(2H, m), 4.17-4.05(1H, m), 3.69-3.54(1H, m), 3.37-3.15 (2H, m), 3.14-2.98(2H, m), 2.77-2.48(2H, m), 2.28-2.14(1H, m), 2.13-2.00(2H, m), 1.78-1.58(4H, m). |

TABLE 1-continued

| | Structure | Physical Data MS (m/z), Elemental Analysis, and $^1$H NMR 400 M Hz (DMSO-$d_6$) |
|---|---|---|
| 15 | 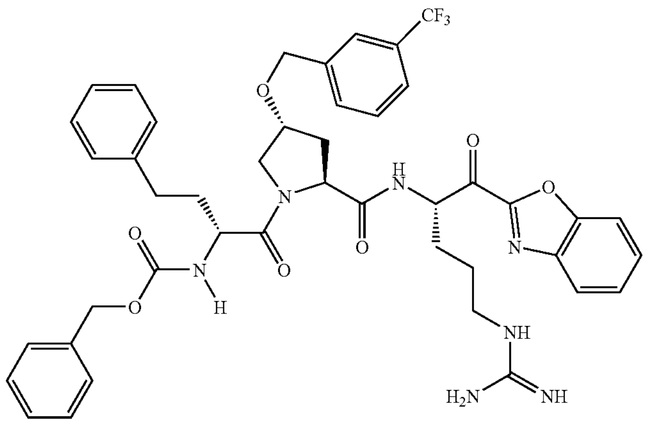 | MS m/z 842.3 (M + 1); $^1$H NMR (CD$_3$CN, 400 M Hz) δ 7.85-7.79(1H, m), 7.58(1H, d, J=8.4 Hz), 7.50-7.46(1H, m), 7.42-7.38(1H, m), 7.30-7.04 (14H, m), 6.10-5.94(1H, m), 5.53-5.42(1H, m), 5.12-4.92(2H, m), 4.57-4.42(1H, m), 4.38-4.18(2H, m), 4.17-4.05(1H, m), 3.69-3.54(1H, m), 3.37-3.15 (2H, m), 3.14-2.98(2H, m), 2.77-2.48(2H, m), 2.28-2.14(1H, m), 2.13-2.00(2H, m), 1.78-1.58(4H, m). |
| 16 | 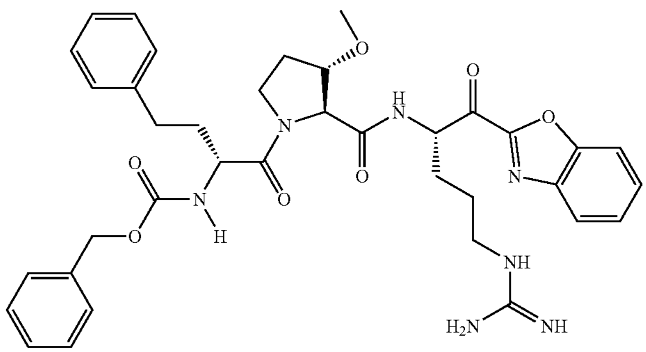 | MS m/z 698.3 (M + 1) |
| 17 | 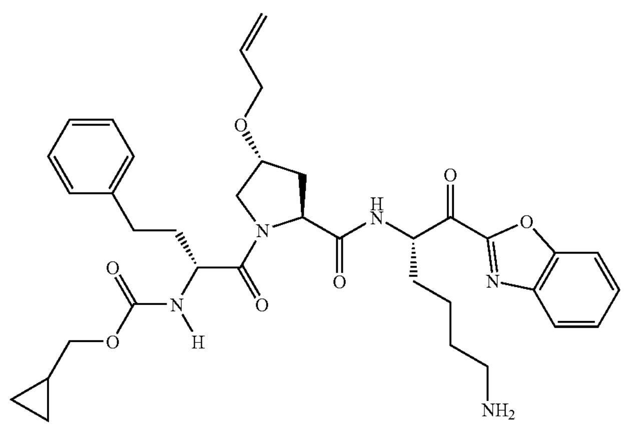 | MS m/z 660.3 (M + 1) |
| 18 | 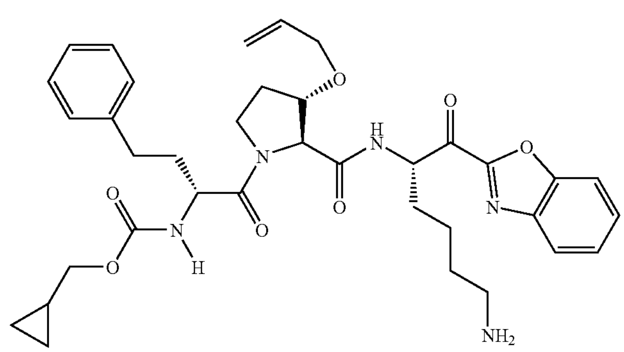 | MS m/z 660.3 (M + 1) |

TABLE 1-continued

| Structure | Physical Data MS (m/z), Elemental Analysis, and $^1$H NMR 400 M Hz (DMSO-$d_6$) |
|---|---|
| 19 | MS m/z 814.3 (M + 1); $^1$H NMR (CD$_3$CN, 400 M Hz) δ 7.91(1H, d, J=8.0 Hz), 7.75(1H, dd, J= 8.0, 3.2 Hz), 7.63-7.60(1H, m), 7.54-7.50(1H, m), 7.38(2H, d, J=4.8 Hz), 7.35-7.24(10H, m), 7.20-7.15(2H, m), 5.54-5.30(1H, m), 5.16-5.01(2H, m), 4.49-4.13(5H, m), 3.88-3.73(1H, m), 3.58-3.49(1H, m), 2.92-2.91(1H, m), 2.79-2.74(1H, m), 2.63-2.58 (1H, m), 2.26-2.19(1H, m), 2.09-1.79(1H, m), 1.91-1.84(2H, m), 1.78-1.64(3H, m), 1.61-1.35(4H, m). |
| 20 | MS m/z 760.4 (M + 1); $^1$H NMR (CD$_3$CN, 400 M Hz) δ 7.91(1H, d, J=8.0 Hz), 7.75(1H, dd, J= 8.0, 3.2 Hz), 7.63-7.60(1H, m), 7.54-7.50(1H, m), 7.38(2H, d, J=4.8 Hz), 7.35-7.24(10H, m), 7.20-7.15(2H, m), 5.54-5.30(1H, m), 5.16-5.01(2H, m), 4.49-4.13(5H, m), 3.88-3.73(1H, m), 3.58-3.49(1H, m), 2.92-2.91(1H, m), 2.79-2.74(1H, m), 2.63-2.58 (1H, m), 2.26(3H, s), 2.25-2.19(1H, m), 2.09-1.79 (1H, m), 1.91-1.84(2H, m), 1.78-1.64(3H, m), 1.61-1.35(4H, m). |
| 21 | MS m/z 764.4 (M + 1); $^1$H NMR (CD$_3$CN, 400 M Hz) δ 7.91(1H, d, J=8.0 Hz), 7.75(1H, dd, J= 8.0, 3.2 Hz), 7.63-7.60(1H, m), 7.54-7.50(1H, m), 7.38(2H, d, J=4.8 Hz), 7.35-7.24(10H, m), 7.20-7.15(2H, m), 5.54-5.30(1H, m), 5.16-5.01(2H, m), 4.49-4.13(5H, m), 3.88-3.73(1H, m), 3.58-3.49(1H, m), 2.92-2.91(1H, m), 2.79-2.74(1H, m), 2.63-2.58 (1H, m), 2.26-2.19(1H, m), 2.09-1.79(1H, m), 1.91-1.84(2H, m), 1.78-1.64(3H, m), 1.61-1.35(4H, m). |

TABLE 1-continued

| Structure | Physical Data MS (m/z), Elemental Analysis, and $^1$H NMR 400 M Hz (DMSO-$d_6$) |
|---|---|
| 22 | MS m/z 814.3 (M + 1); $^1$H NMR (CD$_3$CN, 400 M Hz) δ 7.91(1H, d, J=8.0 Hz), 7.75(1H, dd, J= 8.0, 3.2 Hz), 7.63-7.60(1H, m), 7.54-7.50(1H, m), 7.38(2H, d, J=4.8 Hz), 7.35-7.24(10H, m), 7.20-7.15(2H, m), 5.54-5.30(1H, m), 5.16-5.01(2H, m), 4.49-4.13(5H, m), 3.88-3.73(1H, m), 3.58-3.49(1H, m), 2.92-2.91(1H, m), 2.79-2.74(1H, m), 2.63-2.58(1H, m), 2.26-2.19(1H, m), 2.09-1.79(1H, m), 1.91-1.84(2H, m), 1.78-1.64(3H, m), 1.61-1.35(4H, m). |
| 23 | MS 830.6 m/z (M + 1); Anal. Calcd. for C$_{43}$H$_{45}$BrF$_3$N$_5$O$_9$S (1 TFA): C, 54.66; H, 4.80; N, 7.41; Found: C, 54.78; H, 4.57; N, 7.28; $^1$H NMR (CD$_3$CN, 600 M Hz) δ 8.05(1H, br s), 7.94(1H, d, J= 7.8 Hz), 7.78(1H, d, J=8.4 Hz), 7.65-7.61(2H, m), 7.54(1H, t, J=7.2 Hz), 7.45-6.94(9H, m), 6.89(1H, d, J=7.2 Hz), 5.32-5.30(1H, m), 5.15(1H, d, J=12.6 Hz), 5.10(1H, d, J=12.6 Hz), 4.49-4.33(3H, m), 4.22(1H, br s), 3.77(1H, dd, J=11.4, 4.8 Hz), 3.53(1H, d, J=11.4 Hz), 2.97(1H, br s), 2.81-2.73(2H, m), 2.69-2.57(5H, m), 2.29-2.20(1H, m), 2.13-1.99(2H, m), 1.95-1.89(1H, m), 1.82-1.64(2H, m), 1.63-1.46(2H, m). |
| 24 | MS m/z 830.2 (M + 1); $^1$H NMR (CD$_3$CN, 600 M Hz) δ 7.94(1H, d, J=7.8 Hz), 7.78(1H, d, J=8.4 Hz), 7.65-7.61(2H, m), 7.54(1H, t, J=7.2 Hz), 7.53-6.79(9H, m), 6.89(1H, d, J=7.2 Hz), 5.32-5.30(1H, m), 5.15(1H, d, J=12.6 Hz), 5.10(1H, d, J=12.6 Hz), 4.49-4.33(3H, m), 4.22(1H, br s), 3.77(1H, dd, J=11.4, 4.8 Hz), 3.53(1H, d, J=11.4 Hz), 2.97(1H, br s), 2.81-2.73(2H, m), 2.69-2.57(5H, m), 2.29-2.20(1H, m), 2.13-1.99(2H, m), 1.95-1.89(2H, m), 1.82-1.64(2H, m), 1.63-1.46(2H, m). |

TABLE 1-continued

| Structure | Physical Data<br>MS (m/z), Elemental Analysis, and<br>$^1$H NMR 400 M Hz (DMSO-$d_6$) |
|---|---|
| 25 | MS m/z 774.1, 776.1 (M + 1 and M + 3), 792.0, 794.0 (M + H2O + 1 and M + H2O + 3).<br>1H NMR 400 M Hz (CD3CN-d3): δ 7.91(d, 1H), 7.76(d, 1H), 7.62(dd, 1H), 7.52(dd, 1H), 7.4-7.5(m, 1H), 7.3(m, 2H), 7.2(m, 2H), 6.96(d, 1H), 6.89(d, 1H), 6.77(d, 1H), 5.47(m,1H), 4.54(dd, 2H), 4.40(t, 1H), 4.21(s, 1H), 4.15(m, 1H), 3.64(dd, 1H), 3.41(d, 1H), 2.93(s, 3H), 2.8-3.0(m, 2H), 2.6-2.8(m, 2H), 2.2-2.4(m, 1H), 2.0-2.2(m, 1H), 1.8-2.0(m, 2H), 1.5-1.8(m, 6H). |
| 26 | MS m/z 752.4 (M + 1), 770.4 (M + H2O + 1).<br>1H NMR 400 M Hz (CD3CN-d3): δ 7.71(d, 1H), 7.56(d, 1H), 7.41(t, 1H), 7.33(t, 1H), 6.8-7.2(m, 10H), 4.7-5.1(m, 3H), 4.1-4.3(m, 2H), 3.5-3.8(m, 2H), 3.2-3.4(m, 1H), 3.0-3.1(m, 1H), 2.9-3.0(m, 1H), 2.5-2.6(m, 1H), 2.3-2.5(m, 1H), 1.8-2.0(m, 2H), 1.2-1.7(m, 13H), 0.9-1.0(m, 4H), 0.6-0.8(m, 2H). |
| 27 | MS m/z 744.4 (M + 1), 762.5 (M + H2O + 1).<br>1H NMR 400 M Hz (CD3CN-d3): δ 7.92(d, 1H), 7.85(d, NH), 7.76(d, 1H), 7.62(t, 1H), 7.52(t, 1H), 7.2-7.5(m, 5H), 6.61(d, NH), 5.22(m, 1H), 5.08(dd, 2H), 4.47(m, 1H), 4.00(m, 1H), 3.60(m, 1H), 3.19(dd, 2H), 2.91(m, 2H), 1.9-2.1(m, 2H), 1.5-1.8(m, 16H), 1.3-1.5(m, 6H), 1.1-1.3(m, 6H), 0.9-1.0(m, 4H). |

TABLE 1-continued
| Structure | Physical Data MS (m/z), Elemental Analysis, and $^1$H NMR 400 M Hz (DMSO-$d_6$) |
|---|---|
| 28 | MS m/z 806.4 (M + 1), 824.4 (M + H2O + 1). |
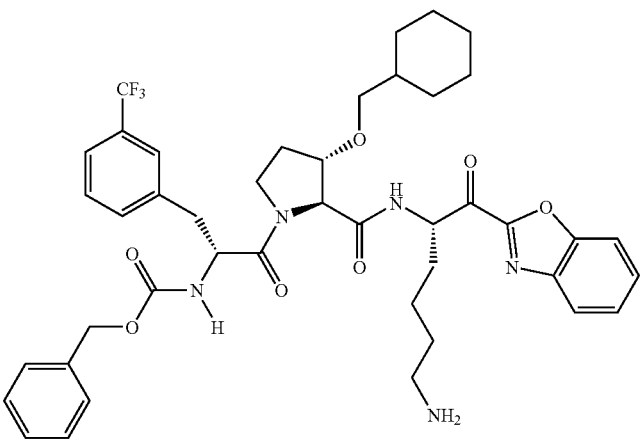
| | |
|---|---|
| 29 | MS m/z 814.3, 816.3 (M + 1 and M + 3), 832.3, 834.3 (M + H2O + 1 and M + H2O + 3). |
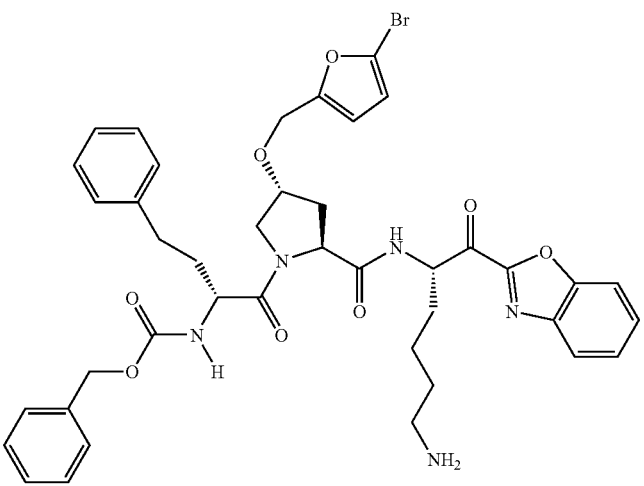
| | |
|---|---|
| 30 | MS m/z 696.3 (M + 1), 714.3 (M + H2O + 1). |
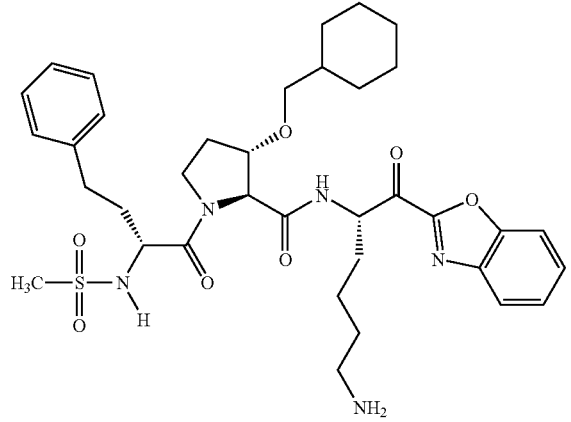

TABLE 1-continued
| Structure | Physical Data<br>MS (m/z), Elemental Analysis, and<br>$^1$H NMR 400 M Hz (DMSO-$d_6$) |
|---|---|
| 31 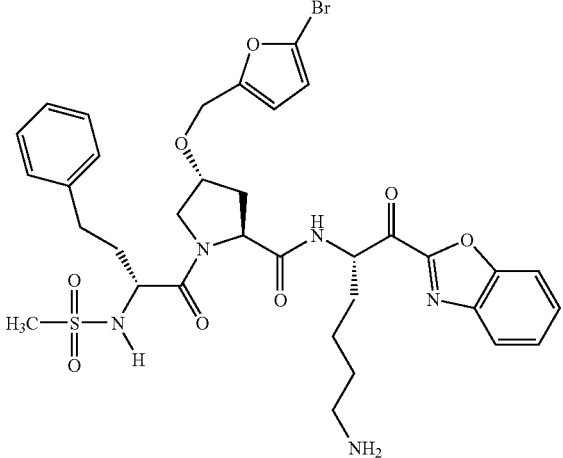 | MS m/z 758.2, 760.2 (M + 1 and M + 3), 776.2, 778.2 (M + H2O + 1 and M + H2O + 3). |
| 32 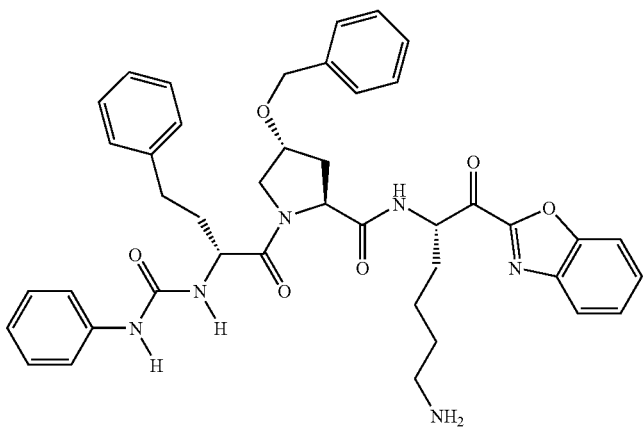 | MS m/z 731.30 (M + 1) |
| 33 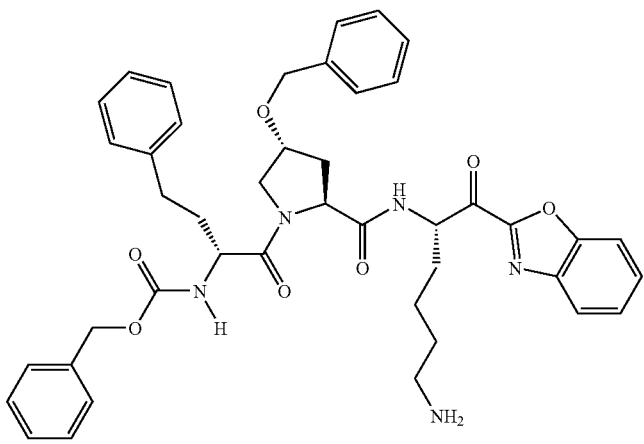 | MS m/z 746.3 (M + 1). Anal (C$_{43}$H$_{47}$N$_5$O$_7$•2TFA) |

TABLE 1-continued

| Structure | Physical Data MS (m/z), Elemental Analysis, and $^1$H NMR 400 M Hz (DMSO-$d_6$) |
|---|---|
| 34 | MS m/z 838.3 (M + 1) |
| 35 | MS m/z 762.3 (M + 1) |
| 36 | MS m/z 752.3 (M + 1) |

TABLE 1-continued
| Structure | Physical Data MS (m/z), Elemental Analysis, and $^1$H NMR 400 M Hz (DMSO-$d_6$) |
|---|---|
| 37 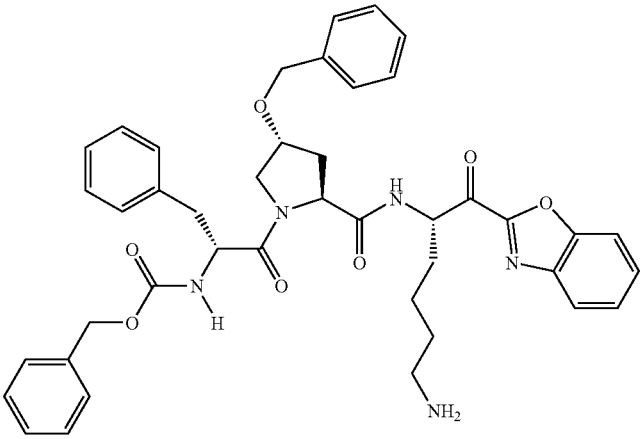 | MS m/z 732.3 (M + 1) |
| 38 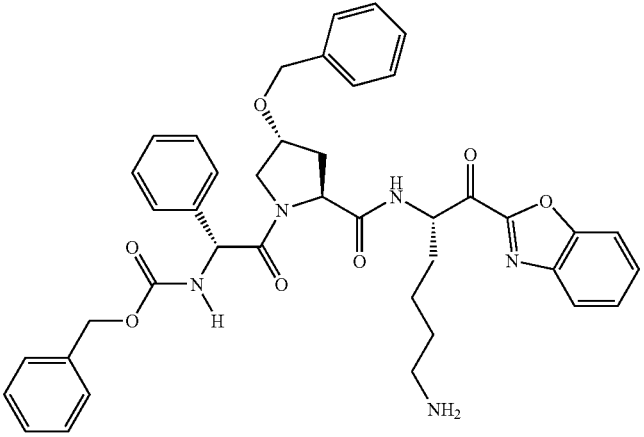 | MS m/z 718.2 (M + 1) |
| 39 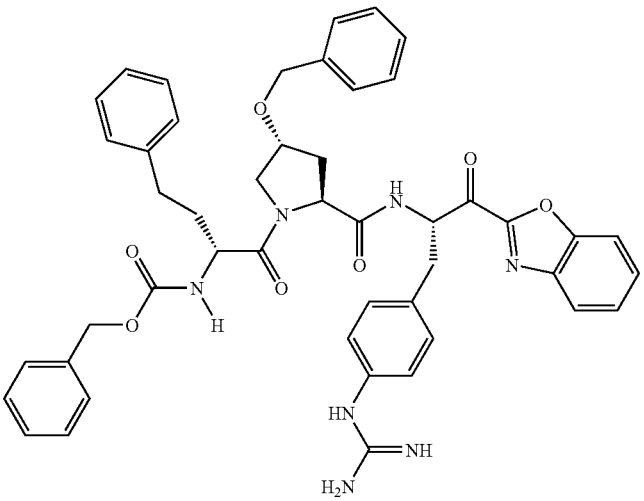 | MS m/z 822.3 (M + 1) |

TABLE 1-continued
| Structure | Physical Data MS (m/z), Elemental Analysis, and $^1$H NMR 400 M Hz (DMSO-$d_6$) |
|---|---|
| 40 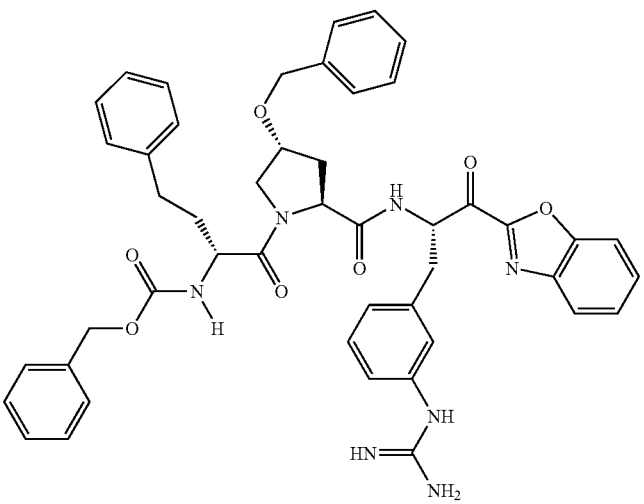 | MS m/z 822.4 (M + 1) |
| 41 | MS m/z 731.3 (M + 1) |
| 42 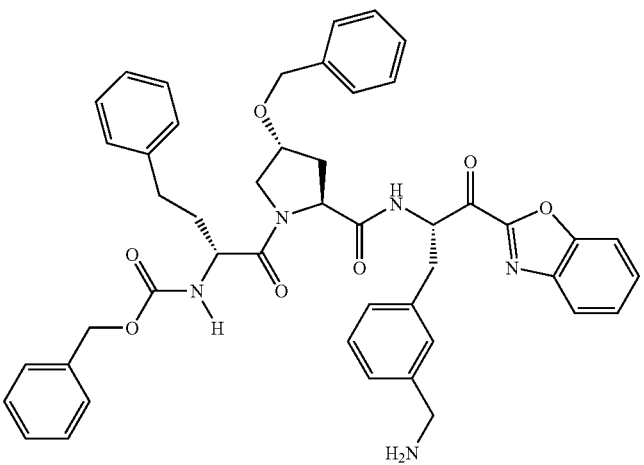 | MS m/z 857.30 (M + 1). Anal. (C$_{47}$H$_{46}$ClN$_7$O$_7$•2TFA•H2O). 400 M Hz NMR (DMSO-d6) δ 9.54(s, 1H); 7.96(d, J=5.6 Hz, 1H); 7.80(d, J=5.6 Hz, 1H); 7.65(m, 1H); 7.55(m, 1H); 7.43(m, 4H); 7.36(m, 4H); 7.32(m, 2H); 7.28(m, 2H); 7.23(m, 3H); 7.18(m, 3H); 7.12(m, 3H); 6.40(m, 1H); 5.51(m, 1H); 5.16(d, J=8.4 Hz, 1H); 5.05(d, J=8.4 Hz, 1H); 4.39(m, 1H); 4.30(m, 1H); 4.25(m, 2H); 3.91(m, 1H); 3.64(m, 1H); 3.46(m, 1H); 3.36(m, 1H); 3.13(m, 1H); 2.75(m, 1H); 2.64(m, 1H); 1.95(m, 2H); 1.87(m, 3H) |

TABLE 1-continued
| Structure | Physical Data<br>MS (m/z), Elemental Analysis, and<br>$^1$H NMR 400 M Hz (DMSO-$d_6$) |
|---|---|
| 43 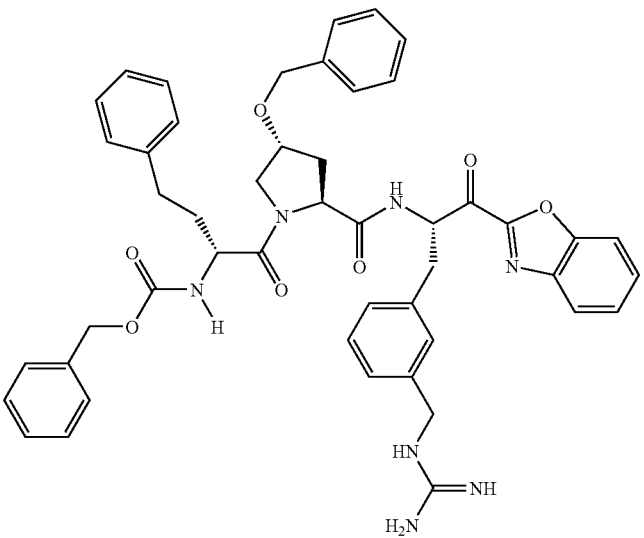 | MS m/z 836.3 (M + 1) |
| 44 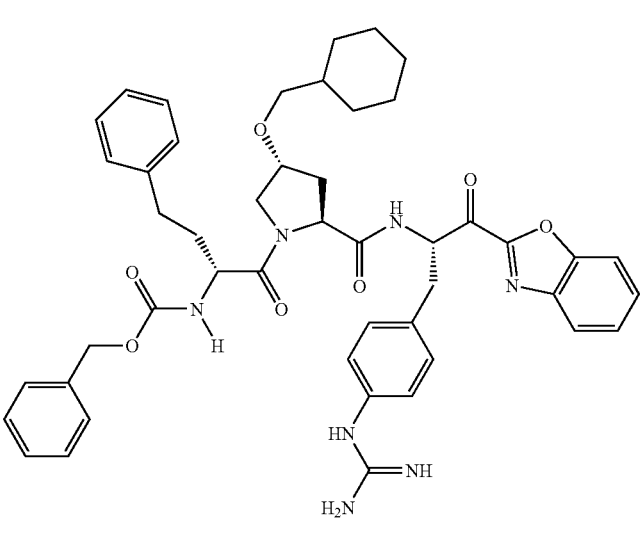 | MS m/z 828.3 (M + 1) |
| 45 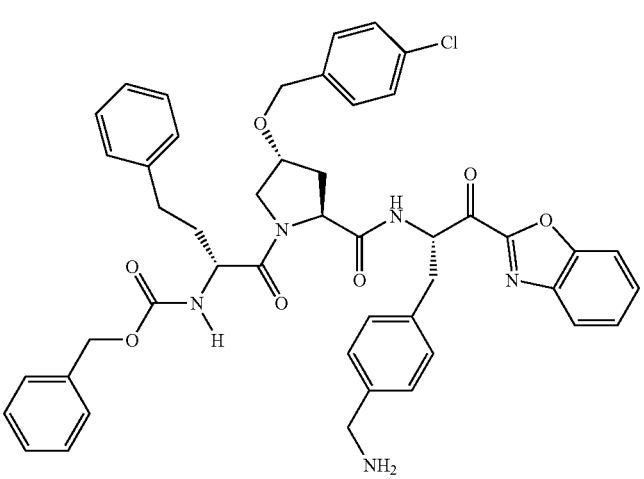 | MS m/z 828.3 (M + 1) |

TABLE 1-continued

| Structure | Physical Data MS (m/z), Elemental Analysis, and $^1$H NMR 400 M Hz (DMSO-$d_6$) |
|---|---|
| 46 | MS m/z 870.4 (M + 1) |
| 47 | MS m/z 696.9 (M + 1)<br>δ $^1$H NMR<br>7.90(d, 1H J=8.0 Hz), 7.75(d, 1H J=8.0 Hz), 7.60-7.64(m, 2H), 7.51-7.55(m, 1H), 7.36-7.43(m, 1H), 7.24-7.29(m, 6H), 5.46-5.49(m, 1H), 4.46-4.50(m, 1H), 4.15-4.18(m, 1H), 4.02(s, 1H), 3.49-3.52(m, 1H), 3.34-3.37(m, 1H), 3.10-3.20(m, 1H), 2.98-3.05(m, 2H), 2.92(s, 3H), 2.83-2.90(m, 2H), 2.70-2.77(m, 1H), 2.28-2.34(m, 1H), 2.16-2.21(m, 1H), 1.89-1.96(m, 3H), 1.67-1.70(m, 10H), 1.46-1.48(m, 2H), 1.17-1.27(m, 4H), 0.88-0.97(m, 3H). |
| 48 | MS m/z 730.5 (M + 1) |

TABLE 1-continued
| Structure | Physical Data MS (m/z), Elemental Analysis, and $^1$H NMR 400 M Hz (DMSO-$d_6$) |
|---|---|
| 49 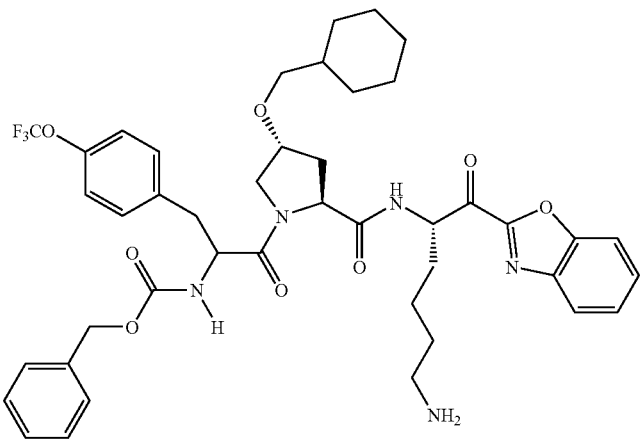 | MS m/z 822.4 (M + 1) |
| 50 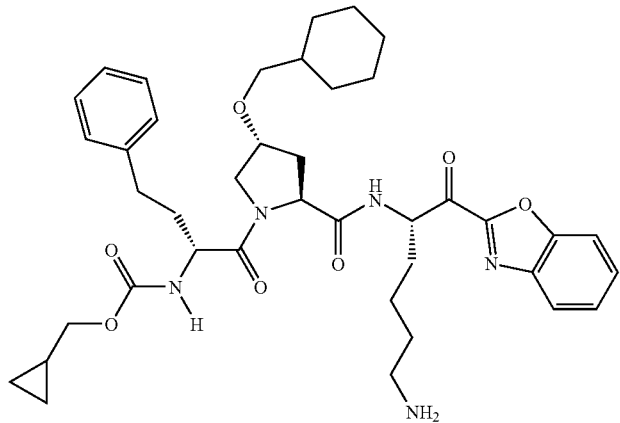 | MS m/z 716.45 (M + 1) Anal. ($C_{40}H_{53}N_5O_7 \cdot 2TFA \cdot H_2O$). |
| 51 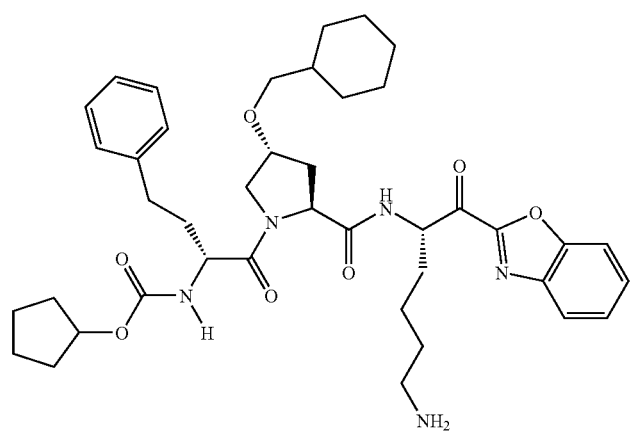 | MS m/z 730.5 (M + 1) Anal. ($C_{41}H_{55}N_5O_7 \cdot 2TFA \cdot H_2O$). |

TABLE 1-continued

| Structure | Physical Data MS (m/z), Elemental Analysis, and ¹H NMR 400 M Hz (DMSO-$d_6$) |
|---|---|
| 52 | MS m/z 744.5 (M + 1) |
| 53 | MS m/z 772.4 (M + 1) |
| 54 | MS m/z 827.3 (M + 1) |

US 7,951,823 B2
117                                                                                      118
TABLE 1-continued
| Structure | Physical Data<br>MS (m/z), Elemental Analysis, and<br>¹H NMR 400 M Hz (DMSO-$d_6$) |
|---|---|
| 55 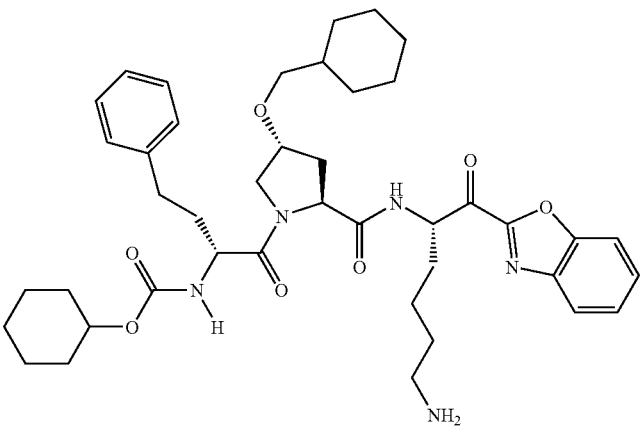 | MS m/z 744.50 (M + 1) |
| 56 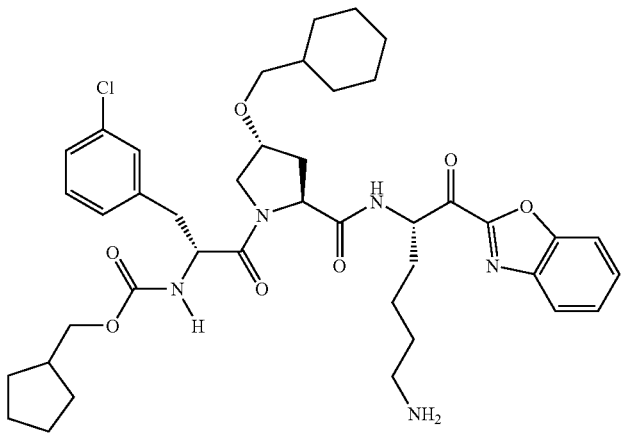 | MS m/z 764.4 (M + 1) |
| 57 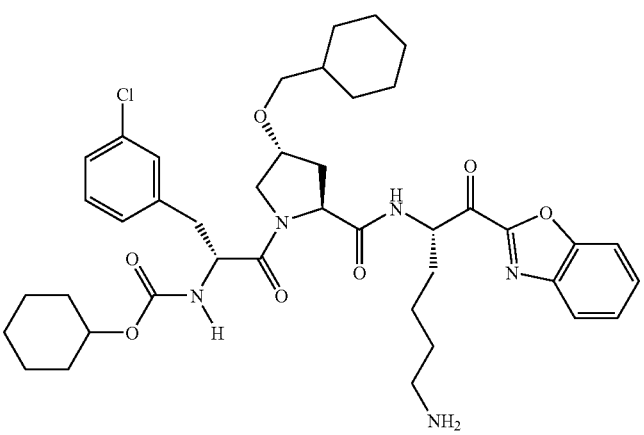 | MS m/z 764.4 (M + 1) |

TABLE 1-continued
| Structure | Physical Data MS (m/z), Elemental Analysis, and $^1$H NMR 400 M Hz (DMSO-$d_6$) |
|---|---|
| 58 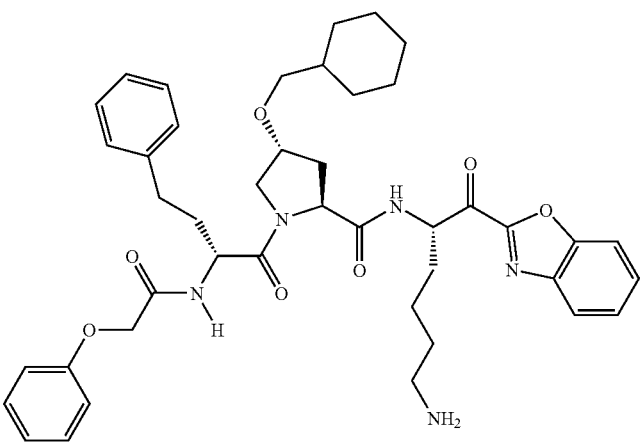 | MS m/z 752.5 (M + 1) |
| 59 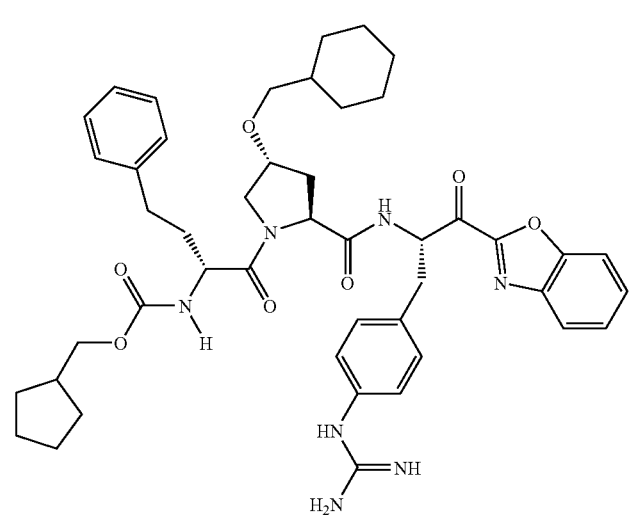 | MS m/z 820.5 (M + 1) |
| 60 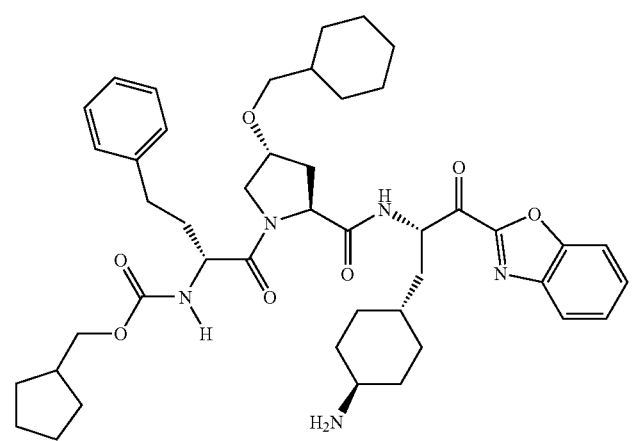 | MS m/z 784.5 (M + 1) |

TABLE 1-continued

| Structure | Physical Data MS (m/z), Elemental Analysis, and $^1$H NMR 400 M Hz (DMSO-$d_6$) |
|---|---|
| 61 | MS m/z 826.5 (M + 1). NMR ((CD$_3$)$_2$CO) δ 7.97(m, 2H); 7.81(m, 3H); 7.66(m, 4H); 7.56(m, 2H); 7.21(m, 1H); 6.55(m, 1H); 5.58(m, 1H); 4.57(m, 1H); 4.44(m, 1H); 4.07(m, 1H); 3.97(m, 2H); 3.70(m, 1H); 3.68(m, 1H); 3.56(m, 2H); 3.20(m, 2H); 2.78(m, 2H); 2.16(m, 2H); 1.71(m, 17H); 1.29(m, 7H); 0.93(m, 3H). |
| 62 | MS m/z 772.3 (M + 1) NMR ((CD$_3$)$_2$CO) δ 7.95(m, 1H); 7.81(m, 1H); 7.66(m, 1H); 7.56(m, 1H); 7.40(m, 4H); 7.24(m, 6H); 7.01(m, 1H); 5.44(m, 1H); 4.51(m, 5H); 4.29(m, 2H); 3.81(m, 4H); 2.75(m, 2H); 2.55(m, 3H); 2.31(m, 1H); 2.16(m, 1H); 1.87(m, 4H); 1.52(m, 1H); 1.36(m, 5H). |
| 63 | MS m/z 596.2 (M + 1) |

TABLE 1-continued
| Structure | Physical Data<br>MS (m/z), Elemental Analysis, and<br>$^1$H NMR 400 M Hz (DMSO-$d_6$) |
|---|---|
| 64 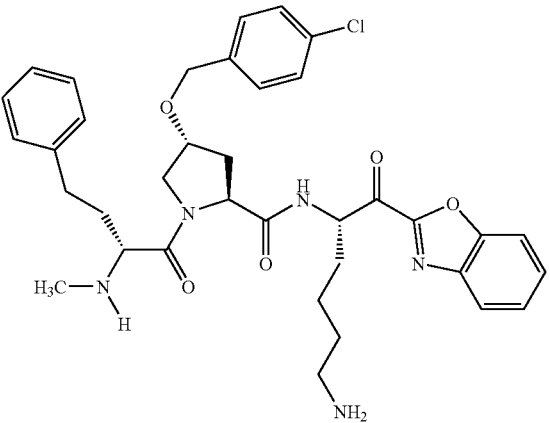 | MS m/z 660.2 (M + 1) |
| 65 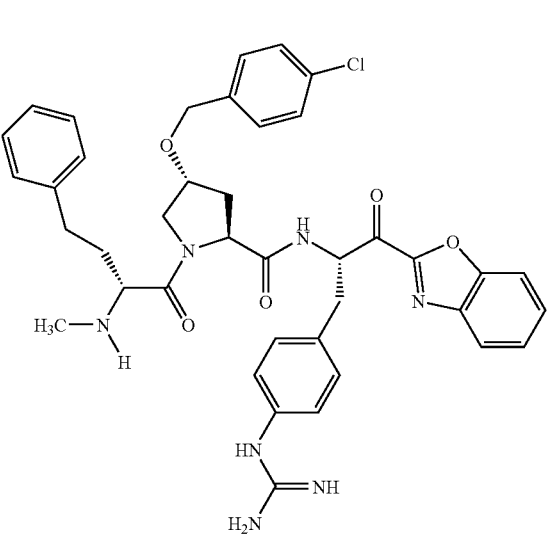 | MS m/z 736.3 (M + 1) |
| 66 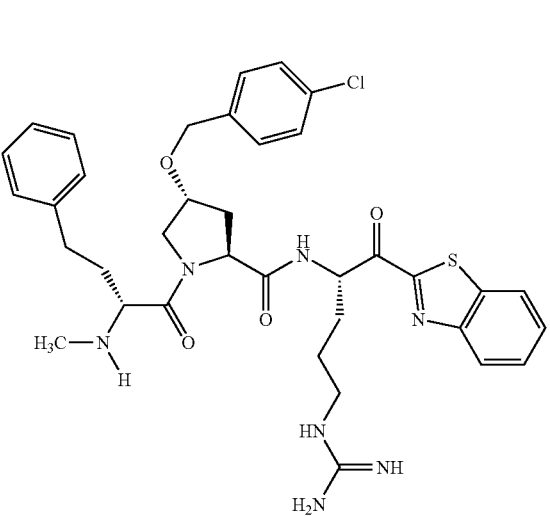 | MS m/z 704.2 (M + 1) |

TABLE 1-continued

| Structure | Physical Data MS (m/z), Elemental Analysis, and ¹H NMR 400 M Hz (DMSO-$d_6$) |
|---|---|
| 67 | MS m/z 708.3 (M + 1) |
| 68 | MS m/z 708.3 (M + 1) |
| 69 | MS m/z 800.2 (M + 1) NMR ((CD$_3$)$_2$CO) δ 10.49(m, 1H); 8.02(d, J=8.0 Hz, 1H); 7.86(m, 2H); 7.67(m, 1H); 7.61(m, 1H); 7.49(m, 1H); 7.32(m, 7H); 7.29(m, 5H); 7.21(m, 2H); 6.49(m, 1H); 5.89(m, 1H); 4.54(m, 1H); 4.43(m, 2H); 4.17(m, 2H); 3.54(m, 2H); 3.37(m, 2H); 3.08(m, 1H); 2.86(m, 1H); 2.79(s, 3H); 2.74(m, 1H); 2.31(m, 1H); 1.99(m, 1H); 1.86(m, 1H). |

TABLE 1-continued
| Structure | Physical Data MS (m/z), Elemental Analysis, and $^1$H NMR 400 M Hz (DMSO-$d_6$) |
|---|---|
| 70 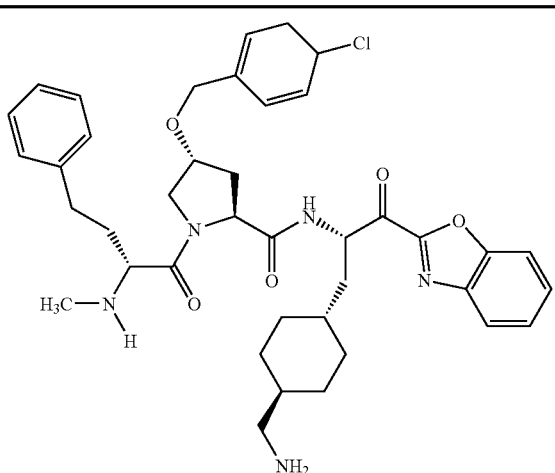 | MS m/z 714.3 (M + 1) |
| 71 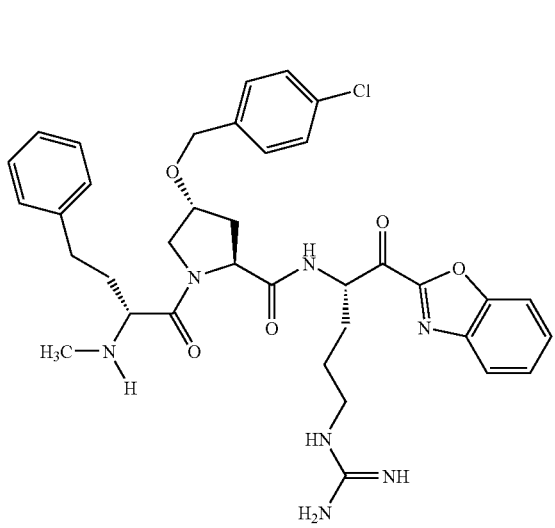 | MS m/z 688.3 (M + 1) |
| 72 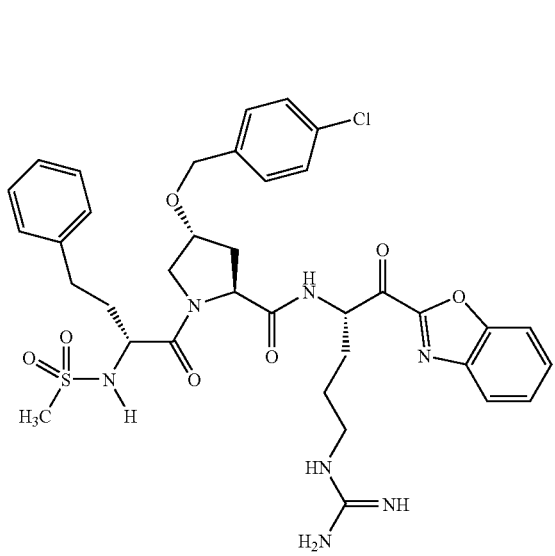 | MS m/z 752.2 (M + 1) NMR ((CD$_3$)$_2$CO) δ 8.47(m, 1H); 8.20(d, J=8.0 Hz, 1H); 7.97(d, J=8.0 Hz, 1H); 7.82(d, J=8.0 Hz, 1H); 7.67(m, 2H); 7.57(m, 2H); 7.36(m, 5H); 7.27(m, 3H) 7.01(m, 1H) 6.62(m, 1H); 5.62(m, 1H); 4.68(m, 1H); 4.52(m, 3H); 4.30(m, 1H); 3.68(m, 1H); 3.53(m, 2H); 3.38(m, 2H); 2.92(s, 3H); 2.82(m, 1H); 2.79(m, 1H); 2.39(m, 1H); 2.27(m, 1H); 1.94(m, 1H). |

| | Structure | Physical Data MS (m/z), Elemental Analysis, and $^1$H NMR 400 M Hz (DMSO-$d_6$) |
|---|---|---|
| 73 | 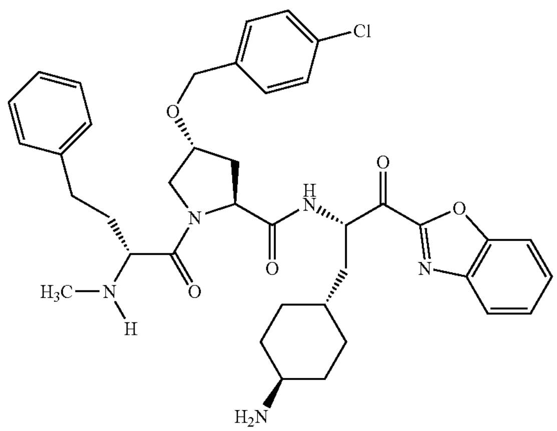 | MS m/z 700.3 (M + 1) NMR ((CD$_3$)$_2$CO) δ 8.00(m, 2H); 7.82(m, 1H); 7.68(m, 1H); 7.58(m, 1H); 7.44(m, 6H); 7.35(m, 4H); 7.22(m, 6H); 5.78(m, 1H); 4.98(m, 2H); 4.65(m, 1H); 4.47(m, 2H); 4.20(m, 2H); 3.60(m, 1H); 3.47(m, 2H); 3.21(m, 1H); 2.87(m, 1H); 2.74(s, 3H); 2.55(m, 2H); 2.32(m, 1H); 1.92(m, 2H). |
| 74 | 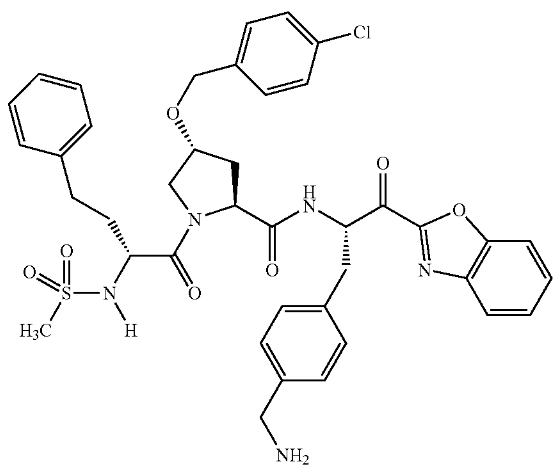 | MS m/z 772.2 (M + 1) NMR ((CD$_3$)$_2$CO) δ 8.30(m, 1H); 8.02(m, 1H); 7.85(m, 1H); 7.73(m, 2H); 7.59(m, 1H); 7.34(m, 6H); 7.27(m, 5H); 7.23(m, 3H); 5.83(m, 1H); 5.05(m, 2H); 4.81(m, 1H); 4.49(m, 2H); 4.25(m, 3H); 3.50(m, 3H); 3.27(m, 1H); 2.91(m, 1H); 2.79(s, 3H); 2.79(m, 1H); 2.75(m, 1H); 2.39(m, 1H); 1.95(m, 1H). |
| 75 | 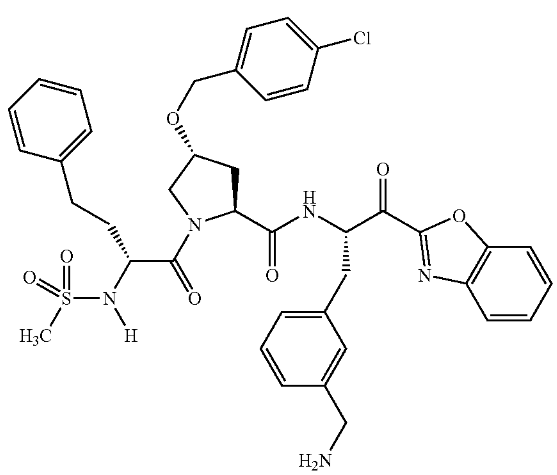 | MS m/z 772.2 (M + 1) |

TABLE 1-continued
| | Structure | Physical Data MS (m/z), Elemental Analysis, and $^1$H NMR 400 M Hz (DMSO-$d_6$) |
|---|---|---|
| 76 | 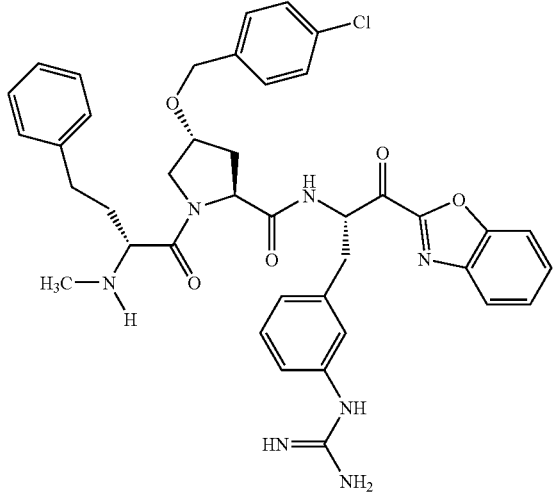 | MS m/z 736.2 (M + 1) NMR ((CD$_3$)$_2$CO) δ 11.10(m, 1H); 8.36(m, 1H); 8.20(m, 1H); 8.01(m, 1H); 7.84(m, 1H); 7.68(m, 2H); 7.54(m, 2H); 7.30(m, 5H); 7.23(m, 2H); 7.21(m, 2H); 7.15(m, 3H); 5.92(m, 1H); 4.52(m, 6H); 4.11(m, 1H); 3.78(m, 3H); 3.09(m, 1H); 2.80(m, 3H); 2.33(m, 4H). |
| 77 | 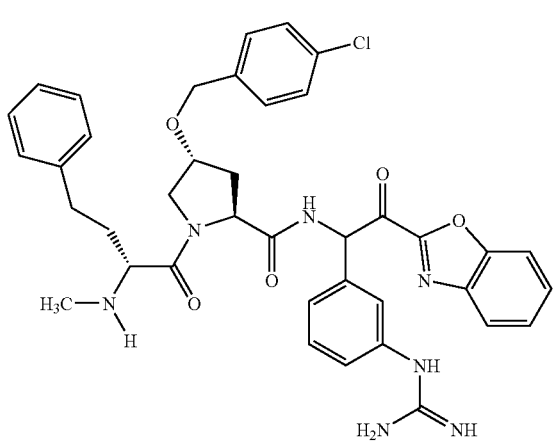 | MS m/z 722.2 (M + 1) NMR ((CD$_3$)$_2$CO) δ 11.36(m, 1H); 8.60(m, 1H); 8.31(m, 1H); 7.98(m, 1H); 7.91(m, 2H); 7.83(m, 1H); 7.68(m, 3H); 7.58(m, 1H); 7.39(m, 1H); 7.31(m, 1H); 7.23(m, 3H); 7.17(m, 3H); 5.77(m, 1H); 4.69(m, 1H); 4.52(m, 2H); 4.39(m, 2H); 3.93(m, 1H); 3.81(m, 1H); 3.65(m, 1H); 3.30(m, 1H); 2.96(m, 1H); 2.78(m, 5H); 2.41(m, 2H); 2.01(m, 1H). |
| 78 | 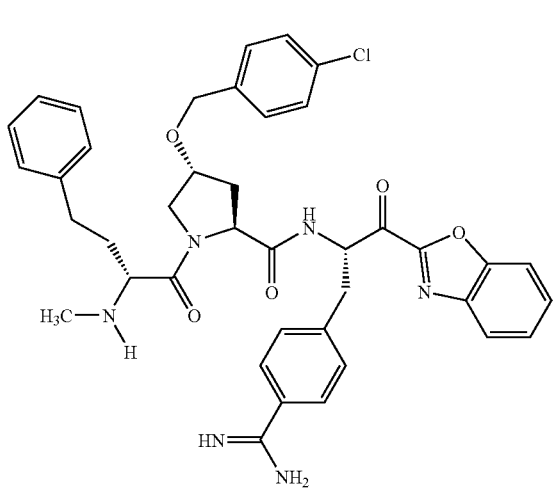 | MS m/z 721.3 (M + 1) |

TABLE 1-continued
| Structure | Physical Data MS (m/z), Elemental Analysis, and $^1$H NMR 400 M Hz (DMSO-$d_6$) |
|---|---|
| 79 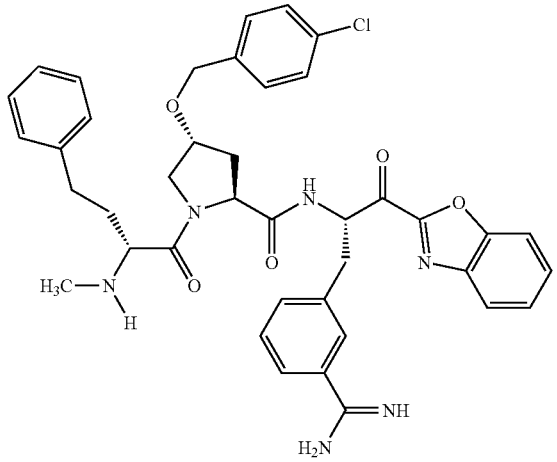 | MS m/z 721.3 (M + 1) |
| 80 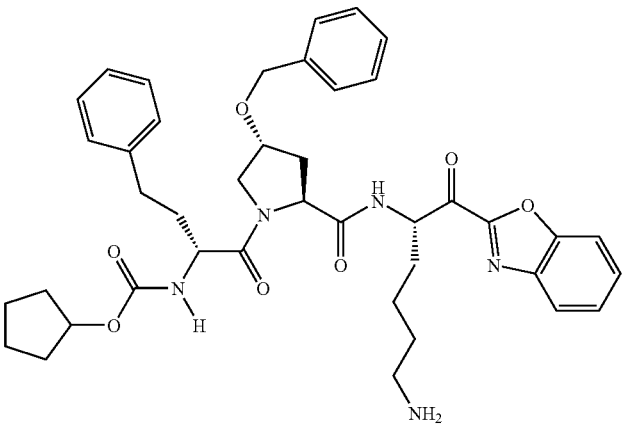 | MS m/z 724.4 (M + 1). Anal. (C$_{41}$H$_{49}$N$_5$O$_7$S•2H$_2$O•TFA). 400 M Hz NMR ((CD$_3$)$_2$CO) δ 7.95(m, 1H); 7.84(d, J=8.0 Hz, 2H); 7.67(d, J=8.0 Hz, 2H); 7.52(m, 2H); 7.41(m, 2H); 7.39(m, 3H); 7.11(m, 5H); 6.45(d, J=4.6 Hz, 1H); 5.28(m, 1H); 4.93(m, 1H); 4.49(m, 1H); 4.38(m, 2H); 4.27(m, 1H); 4.14(m, 1H); 3.67(m, 3H); 3.48(m, 1H); 2.57(m, 3H); 2.42(m, 4H); 2.15(m, 1H); 2.04(m, 2H); 1.90(m, 1H); 1.70(m, 3H); 1.55(m, 3H); 1.42(m, 3H). |
| 81 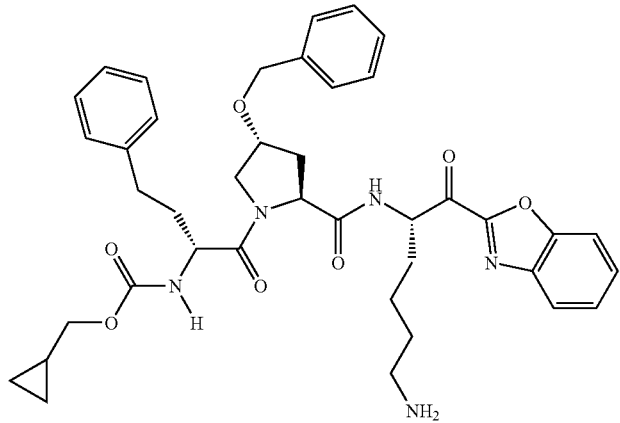 | MS m/z 710.4 (M + 1) (C$_{40}$H$_{47}$N$_5$O$_7$S•2H$_2$O•TFA). NMR ((CD$_3$)$_2$CO) δ 8.10(m, 1H); 7.96(d, J=8 Hz, 2H); 7.81(d, J=8.4 Hz, 2H); 7.65(m, 2H); 7.56(m, 2H); 7.34(m, 3H); 7.27(m, 5H); 7.20(m, 2H); 6.68(m, 1H); 5.44(m, 1H); 4.63(m, 1H); 4.51(m, 2H); 4.44(m, 1H); 4.28(m, 1H); 3.87(m, 4H); 3.64(m, 1H); 2.73(m, 2H); 2.30(m, 2H); 2.18(m, 1H); 1.85(m, 3H); 1.70(m, 1H); 1.12(m, 1H); 0.52(m, 2H); 0.29(m, 2H). |

TABLE 1-continued
| Structure | Physical Data MS (m/z), Elemental Analysis, and $^1$H NMR 400 M Hz (DMSO-$d_6$) |
|---|---|
| 82 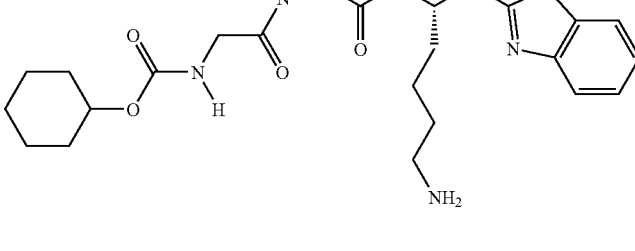 | MS m/z 634.35 (M + 1) NMR ((CD$_3$)$_2$CO) δ 8.73(m, 1H); 8.25(m, 1H); 7.95(m, 1H); 7.81(m, 1H); 7.66(m, 1H); 7.36(m, 5H); 7.29(m, 1H); 5.51(m, 1H); 4.67(m, 1H); 4.58(m, 4H); 4.36(m, 1H); 3.99(m, 1H); 3.60(m, 6H); 2.59(m, 3H); 2.32(m, 1H); 2.17(m, 1H); 1.85(m, 4H); 1.73(m, 3H); 1.52(m, 1H); 1.37(m, 4H). |
| 83 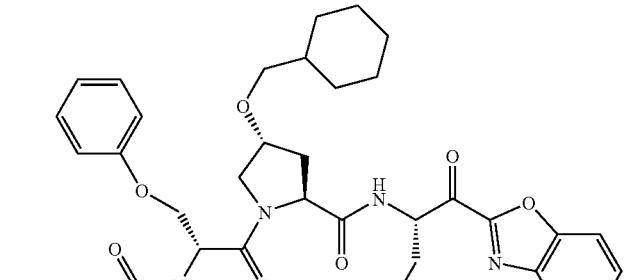 | MS m/z 732.9 (M + 1) δ $^1$H NMR 8.68(s, 1H), 7.92(d, 1H J=8.0 Hz), 7.76(d, 1H J=8.0 Hz), 7.52-7.65(m, 3H), 7.40-7.44(m, 1H), 7.36 (d, 1H J=8.0 Hz), 7.25-7.35(m, 3H), 6.93-9.95(m, 5H), 5.52-5.56(m, 1H), 5.07-5.09(m, 1H), 4.51-4.56 (m, 1H), 4.12-4.22(m, 5H), 3.89(d, 1H J=11.2 Hz), 3.77-3.81(m, 1H), 3.23-3.26(m, 2H), 2.97-3.02(m, 2H), 2.34-2.40(, 1H), 2.17-2.26(m, 1H), 1.52-1.83 (m,), 1.16-1.27(m, 4H), 0.91-0.96(m, 3H). |
| 84 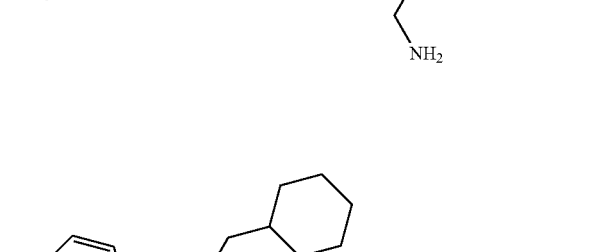 | MS m/z 697.9 (M + 1) δ $^1$H NMR 7.85(d, 1H J=8.0 Hz), 7.68(d, 1H J=8.0 Hz), 7.34-7.35(m, 3H), 7.13-7.22(m, 4H), 6.39-6.42(m, 1H), 5.62(s, 1H), 5.44-5.50(m, 1H), 4.30-4.38(m, 1H), 4.08-4.10(m, 1H), 3.94(s, 1H), 3.57-3.61(m, 1H), 3.37-3.40(m, 1H), 3.01-3.13(m, 2H), 2.69-2.76(m, 1H), 2.54-2.60(m, 1H), 2.42(s, 1H), 1.68-1.69(m, 2H), 1.55-1.60(m, 8H), 1.35-1.39(m, 2H), 1.19(s, 1H), 1.07-1.14(m, 3H), 0.78-0.87(m, 2H). |

TABLE 1-continued
| Structure | Physical Data<br>MS (m/z), Elemental Analysis, and<br>$^1$H NMR 400 M Hz (DMSO-$d_6$) |
|---|---|
| 85 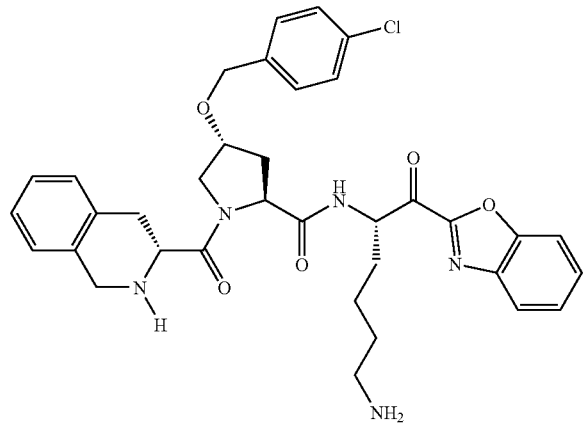 | MS m/z 645.2 (M + 1)<br>δ $^1$H NMR<br>9.16(s, 1H), 8.04(d, 1H J=8.0 Hz), 7.94(d, 1H J=<br>8.0 Hz), 7.78-7.83(m, 2H), 7.63-7.67(m, 2H), 7.47-<br>7.57(m, 3H), 7.17-7.14(m, 8H), 6.27(s, 2H), 5.48-<br>5.54(m, 1H), 4.51-4.57(m, 3H), 4.42-4.46(m, 2H),<br>4.31-4.36(m, 1H), 3.83-3.92(m, 1H), 3.73-3.789<br>(m, 1H), 2.33-2.39(m, 1H), 2.04-2.19(m, 2H), 1.68-<br>1.89(m, 3H), 1.49-1.65(m, 2H) |
| 86 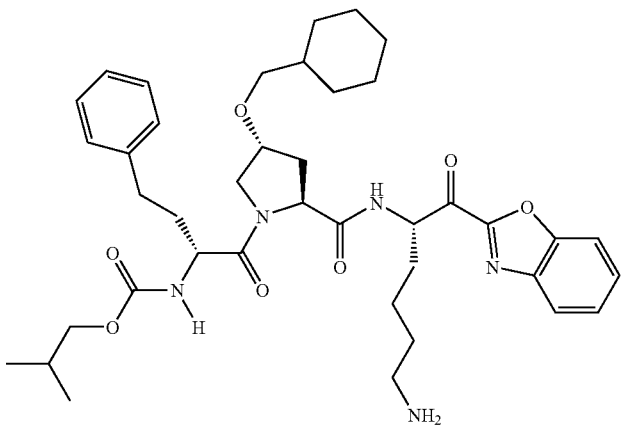 | MS m/z 718.4 (M + 1) |
| 87 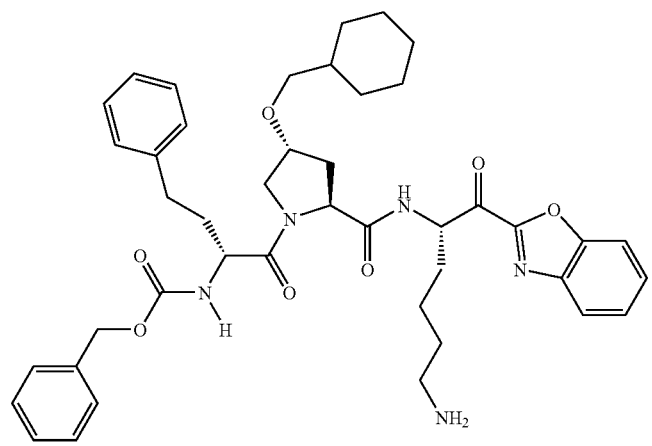 | MS m/z 752.4 (M + 1)<br>$^1$H NMR (Acetone-d6, 400 M Hz) δ 7.99-7.92(1H,<br>m), 7.83-7.79(1H, m), 7.68-7.62(1H, m), 7.58-7.52<br>(1H, m), 7.46-7.12(10H, m), 5.24-5.01(3H, m),<br>(4.54-4.35(2H, m), 4.20-4.02(1H, m), 3.87-3.51(2H,<br>m), 3.32-3.13(2H, m), 2.90-2.65(2H, m), 2.64-2.43<br>(2H, m), 2.00-1.93(1H, m), 1.90-1.42(14H, m),<br>1.32-0.85(6H, m). |

TABLE 1-continued

| Structure | Physical Data MS (m/z), Elemental Analysis, and $^1$H NMR 400 M Hz (DMSO-$d_6$) |
|---|---|
| 88 | MS m/z 731.4 (M + 1) |
| 89 | MS m/z 775.3 (M + 1) |
| 90 | MS m/z 807.4 (M + 1) |

TABLE 1-continued

| Structure | Physical Data MS (m/z), Elemental Analysis, and ¹H NMR 400 M Hz (DMSO-d$_6$) |
|---|---|
| 91 | MS m/z 779.4 (M + 1) |
| 92 | MS m/z 779.4 (M + 1) |
| 93 | MS m/z 792.4 (M + 1) |

| | Structure | Physical Data MS (m/z), Elemental Analysis, and $^1$H NMR 400 M Hz (DMSO-$d_6$) |
|---|---|---|
| 94 | 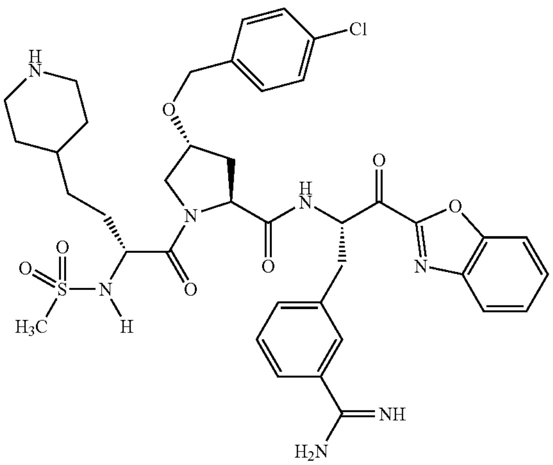 | MS m/z 792.4 (M + 1) |
| 95 | 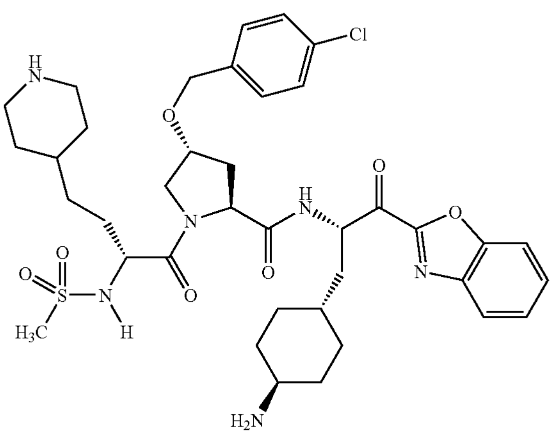 | MS m/z 771.4 (M + 1) |
| 96 | 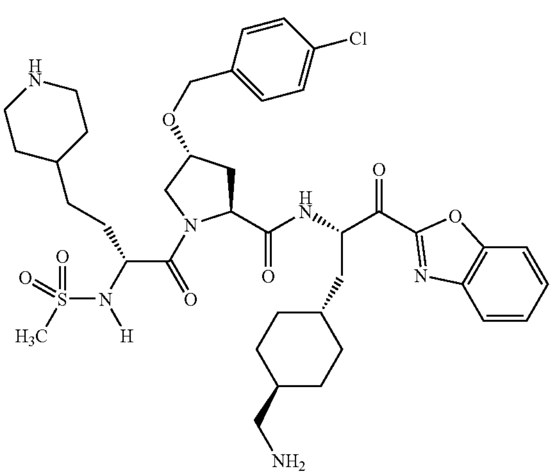 | MS m/z 785.4 (M + 1) |

TABLE 1-continued
| Structure | Physical Data MS (m/z), Elemental Analysis, and $^1$H NMR 400 M Hz (DMSO-$d_6$) |
|---|---|
| 97 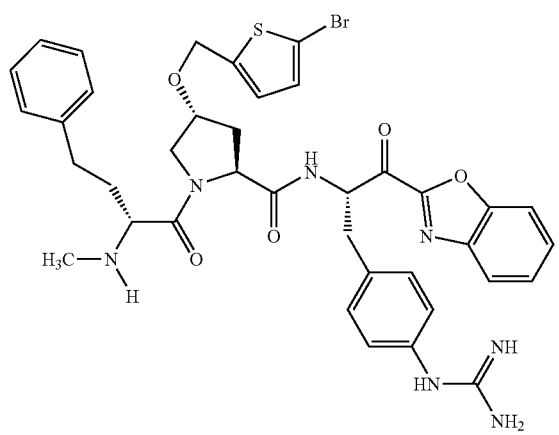 | MS m/z 786.1, 788.0 (M + 1 and M + 3), 804.1, 806.2 (M + H2O + 1 and M + H2O + 3). |
| 98 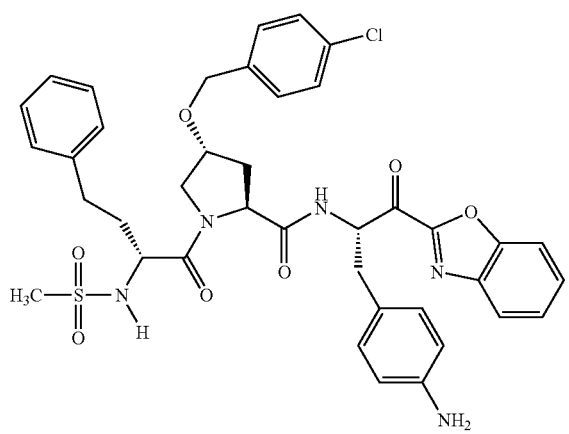 | MS m/z 758.2 (M + 1), 776.2 (M + H2O + 1). 1H NMR 400 M Hz (CD3CN-d3): δ 7.93(d, 1H), 7.76(d, 1H), 7.62(t, 1H), 7.53(t, 1H), 7.15-7.35(m, 1H), 7.05(m, 2H), 5.78(m, 1H), 5.62(m, 1H), 4.3-4.5(m, 4H), 4.0-4.1(m, 2H), 3.51(dd, 1H), 3.33(m, 2H), 3.0(dd, 1H), 2.76(s, 3H), 2.6-2.8(m, 3H), 2.15-2.25(m, 1H), 1.75-1.90(m, 3H). |
| 99 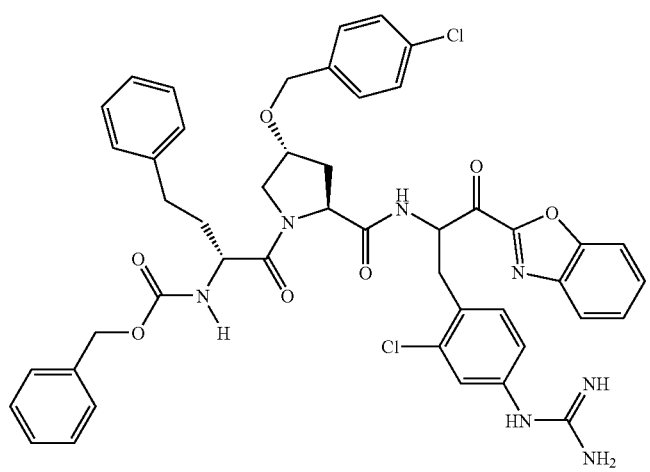 | MS m/z 890.3 Cl$^{35}$(M + 1), 892.3 Cl$^{37}$(M + 1). NMR ((CD$_3$)$_2$CO) δ 8.05(m, 1H); 7.98(m, 2H); 7.90(m, 1H); 7.82(m, 2H); 7.66(m, 2H); 7.55(m, 2H); 7.39(m, 2H); 7.34(m, 4H); 7.03(m, 2H); 6.87(m, 1H); 5.77(m, 1H); 5.60(m, 1H); 5.17(m, 2H); 5.10(m, 2H); 4.57(m, 1H); 4.50(m, 2H); 4.35(m, 2H); 4.17(m, 1H); 4.04(m, 1H); 3.72(m, 6H); 2.81(m, 2H); 2.72(m, 2H); 2.14(m, 2H); 1.99(m, 1H). |

TABLE 1-continued
| Structure | Physical Data MS (m/z), Elemental Analysis, and $^1$H NMR 400 M Hz (DMSO-$d_6$) |
|---|---|
| 100 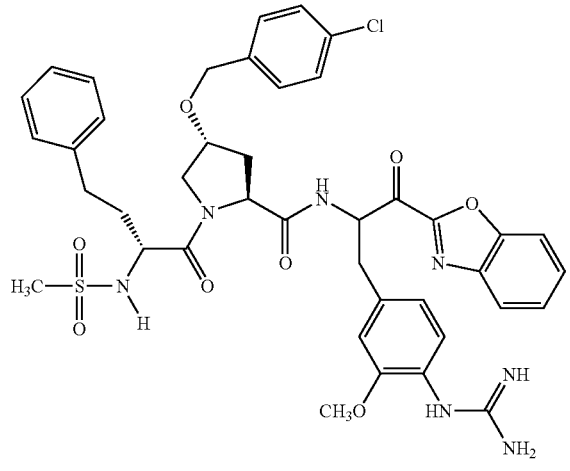 | MS m/z 830.2 (M + 1), 848.2 (M + H2O + 1). 1H NMR 400 M Hz (CD$_3$CN-d3, diasteroisomers): δ 9.03, 8.66(2s, 1H), 7.94(dd, 1H), 7.78(dd, 1H), 7.64(m, 1H), 7.61(m, 1H), 7.2-7.4(m, 1H), 6.9(ddd, 1H), 6.06, 5.71(2d, 1H), 5.7, 5.6(2m, 1H), 4.2-4.4(m, 3H), 4.0-4.1(m, 2H), 3.88, 3.86(2s, 3H), 3.4-3.6(m, 3H), 3.2-3.4(ddd, 1H), 2.9-3.1(dt, 1H), 2.7-2.9(m, 1H), 2.8, 2.7(2s, 3H), 2.6-2.7(m, 1H), 2.1-2.3(m, 1H), 1.9-2.0(m, 1H), 1.7-1.9(m, 2H). |
| 101 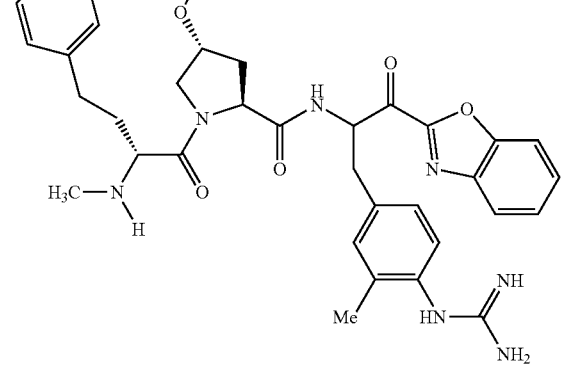 | MS m/z 750.3 (M + 1) |
| 102 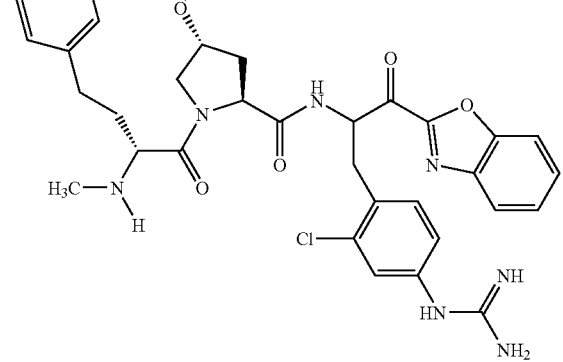 | MS m/z 770.2 (M + 1) |

TABLE 1-continued

| Structure | Physical Data MS (m/z), Elemental Analysis, and $^1$H NMR 400 M Hz (DMSO-$d_6$) |
|---|---|
| 103 | MS m/z 808.4 (M + 1) |
| 104 | MS m/z 870.4 (M + 1) |
| 105 | MS m/z 862.4 (M + 1) NMR ((CD$_3$)$_2$CO) δ 11.20(m, 1H); 8.07(m, 1H); 7.98(m, 2H); 7.80(m, 3H); 7.67(m, 2H); 7.56(m, 2H); 7.44(m, 1H); 7.40(m, 2H); 7.04(m, 2H); 6.86(m, 1H); 5.60(m, 1H); 4.51(m, 1H); 4.41(m, 1H); 4.35(m, 1H); 3.95(m, 1H); 3.66(m, 3H); 3.35(m, 3H); 3.07(m, 4H); 2.84(m, 1H); 2.74(m, 1H); 1.39(m, 2H); 1.17(m, 3H); 0.87(m, 3H). |

TABLE 1-continued

| Structure | Physical Data<br>MS (m/z), Elemental Analysis, and<br>$^1$H NMR 400 M Hz (DMSO-$d_6$) |
|---|---|
| 106 | MS m/z 794.3 (M + 1); $^1$H NMR (CD$_3$CN, 600 M Hz) δ 8.75(1H, br s), 8.46(1H, br s), 7.94(1H, d, J=7.8 Hz), 7.78(1H, d, J=8.4 Hz), 7.65-7.61(2H, m), 7.54(1H, t, J=7.2 Hz), 7.41-7.18(11H, m), 6.89(1H, d, J=7.2 Hz), 5.32-5.30(1H, m), 5.15 (1H, d, J=12.6 Hz), 5.10(1H, d, J=12.6 Hz), 4.49-4.33(3H, m), 4.22(1H, br s), 3.77(1H, dd, J=11.4, 4.8 Hz), 3.53(1H, d, J=11.4 Hz), 2.97(1H, br s), 2.81-2.73(2H, m), 2.69-2.57(5H, m), 2.29-2.20(1H, m), 2.13-1.99(2H, m), 1.95-1.89(2H, m), 1.82-1.64 (2H, m), 1.63-1.46(2H, m). |
| 107 | MS m/z 820.4 (M + 1) |
| 108 | MS m/z 794.3 (M + 1) |

TABLE 1-continued

| Structure | Physical Data<br>MS (m/z), Elemental Analysis, and<br>$^1$H NMR 400 M Hz (DMSO-d$_6$) |
|---|---|
| 109 | MS m/z 762.5 (M + 1) |
| 110 | MS m/z 794.3 (M + 1) |
| 111 | MS m/z 814.3 (M + 1) |
| 112 | MS m/z 742.2 (M + 1) |

TABLE 1-continued
| Structure | Physical Data MS (m/z), Elemental Analysis, and ¹H NMR 400 M Hz (DMSO-$d_6$) |
|---|---|
| 113 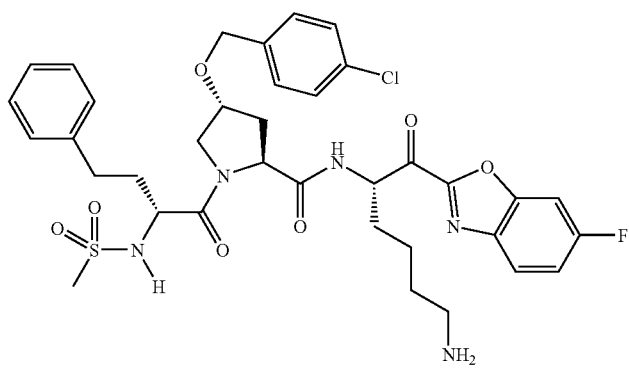 | MS m/z 742.6 (M + 1) |
| 114 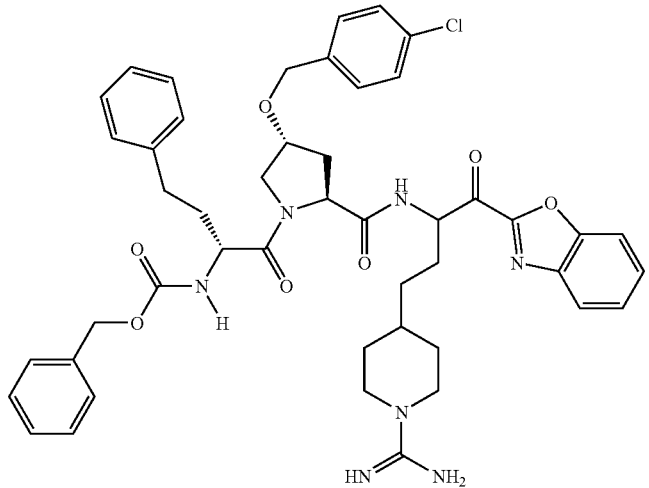 | MS m/z 862.4 (M + 1). 1H NMR 400 M Hz (CD3CN-d3, diasteroisomers): δ 7.90(t, 1H), 7.74(t, 1H), 7.61(t, 1H), 7.52(t, 1H), 7.1-7.5(m, 14H), 5.3-5.5(m, 1H), 5.0-5.2(m, 2H), 4.1-4.5(m, 5H), 3.4-3.8(m, 4H), 2.8-3.0(m, 2H), 2.6-2.8(m, 2H), 2.1-2.3(m, 1H), 2.0-2.1(m, 1H), 1.7-1.9(m, 2H), 1.5-1.7(m, 2H), 1.3-1.5(m, 1H), 0.9-1.3(m, 5H). |
| 115 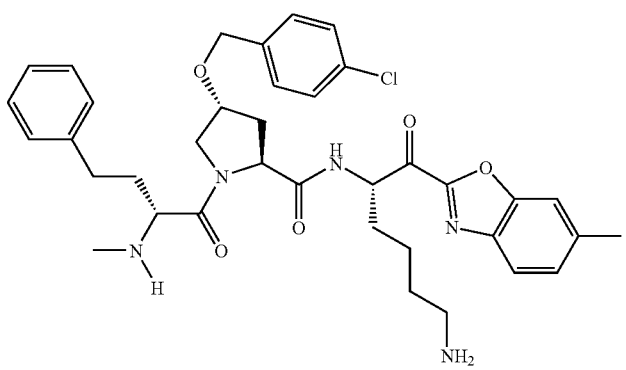 | MS m/z 674.3 (M + 1) |

TABLE 1-continued
| Structure | Physical Data MS (m/z), Elemental Analysis, and $^1$H NMR 400 M Hz (DMSO-$d_6$) |
|---|---|
| 116 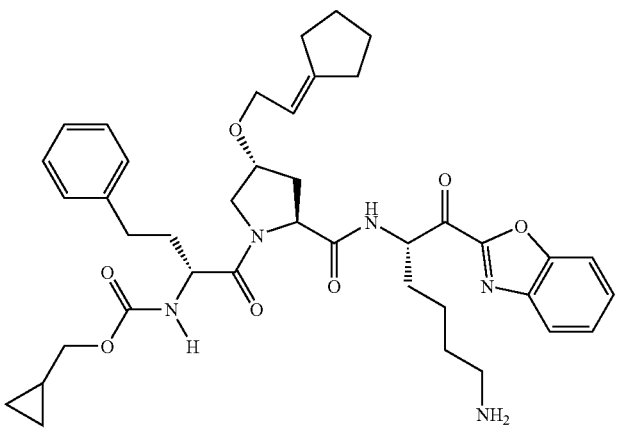 | MS m/z 714.3 (M + 1) |
| 117 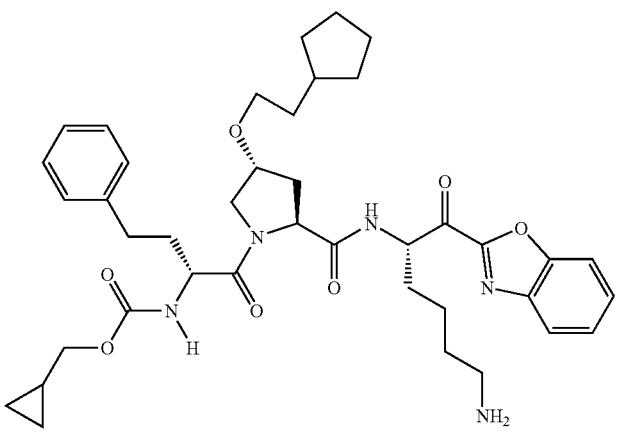 | MS m/z 716.4 (M + 1) |
| 118 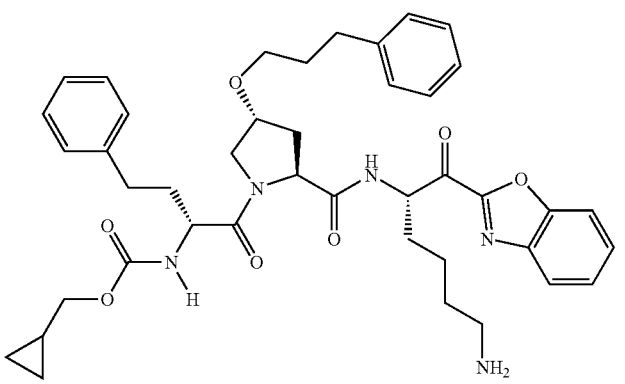 | MS m/z 738.4 (M + 1) |

TABLE 1-continued

| Structure | Physical Data<br>MS (m/z), Elemental Analysis, and<br>$^1$H NMR 400 M Hz (DMSO-$d_6$) |
|---|---|
| 119 | MS m/z 770.3 (M + 1) |
| 120 | MS m/z 728.4 (M + 1) |
| 121 | MS m/z 730.4 (M + 1) |
| 122 | MS m/z 731.4 (M + 1) |

TABLE 1-continued

| | Structure | Physical Data<br>MS (m/z), Elemental Analysis, and<br>$^1$H NMR 400 M Hz (DMSO-$d_6$) |
|---|---|---|
| 123 | 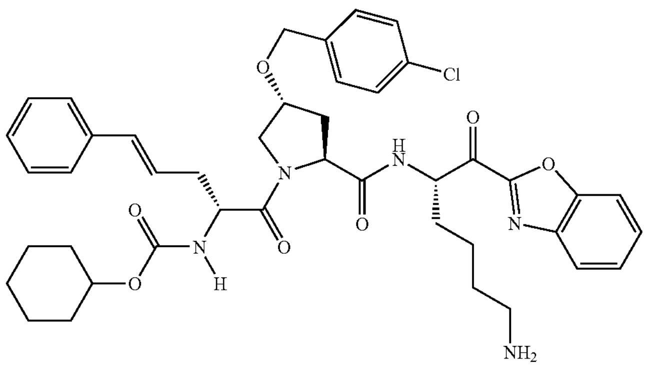 | MS m/z 784.3 (M + 1) |
| 124 | 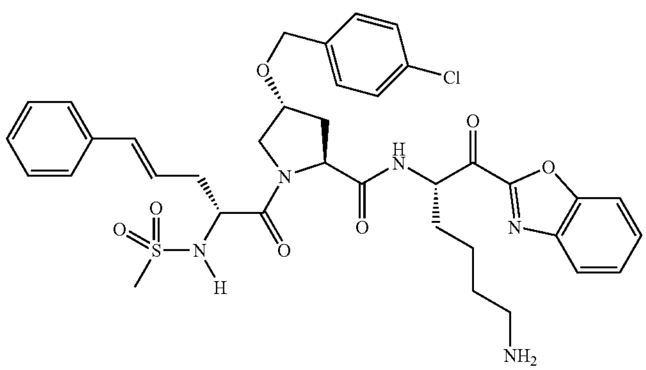 | MS m/z 736.2 (M + 1) |
| 125 | 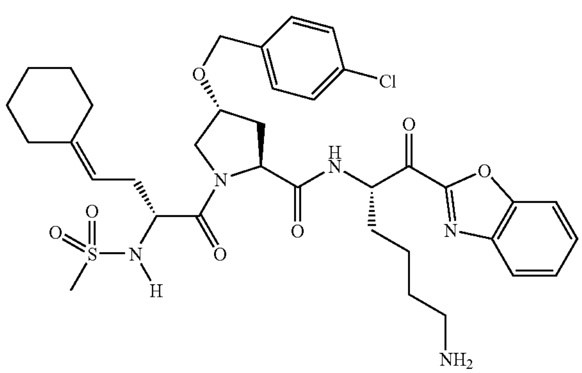 | MS m/z 728.2 (M + 1) |
| 126 | 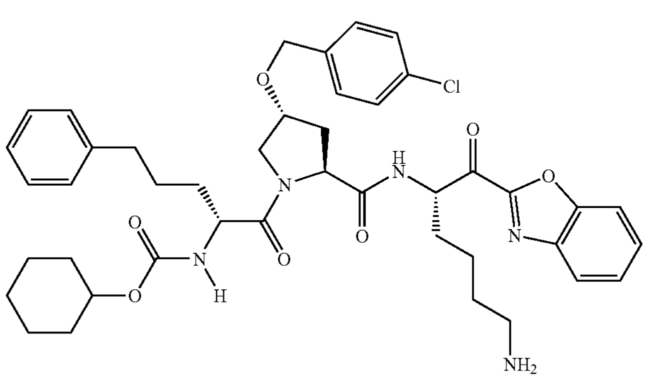 | MS m/z 786.4 (M + 1) |

TABLE 1-continued

| Structure | Physical Data MS (m/z), Elemental Analysis, and $^1$H NMR 400 M Hz (DMSO-$d_6$) |
|---|---|
| 127 | MS m/z 780.2 (M + 1) |
| 128 | MS m/z 770.2 (M + 1) |
| 129 | MS m/z 729.3 (M + 1); $^1$H NMR (CD$_3$CN, 400 M Hz) δ 9.58(1H, br s), 8.31(1H, d, J=8.8 Hz), 7.93(1H, d, J=8.0 Hz), 7.78(1H, t, J=7.2 Hz), 7.64(1H, t, J=8.0 Hz), 7.55(1H, t, J=7.6 Hz), 7.40-7.33(4H, m), 6.98(1H, d, J=8.8 Hz), 5.65-5.55(1H, m), 5.41-5.30(1H, m), 4.60(1H, t, J=8.4 Hz), 4.55-4.39(2H, m), 3.89(1H, d, J=11.6 Hz), 3.82(1H, dd, J=11.6, 4.0 Hz), 3.28-3.16(1H, m), 3.15-3.00(2H, m), 2.98(3H, s), 2.92-2.73(2H, m), 2.67-2.41(6H, m), 2.40-2.29(2H, m), 2.28-2.12(2H, m), 1.88-1.62(6H, m). |
| 130 | MS m/z 714.4 (M + 1) |

TABLE 1-continued
| Structure | Physical Data<br>MS (m/z), Elemental Analysis, and<br>$^1$H NMR 400 M Hz (DMSO-$d_6$) |
|---|---|
| 131 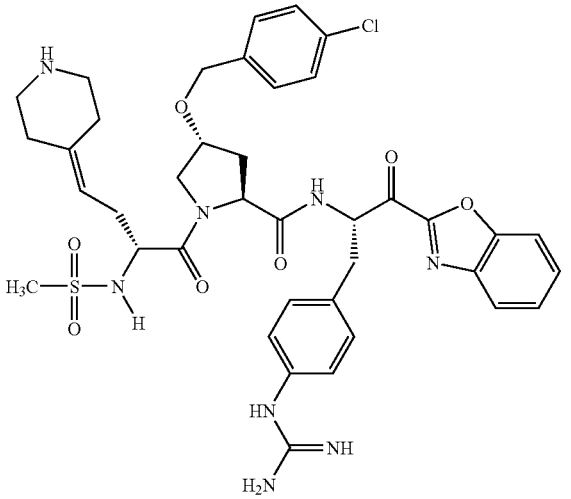 | MS m/z 805.4 (M + 1) |
| 132 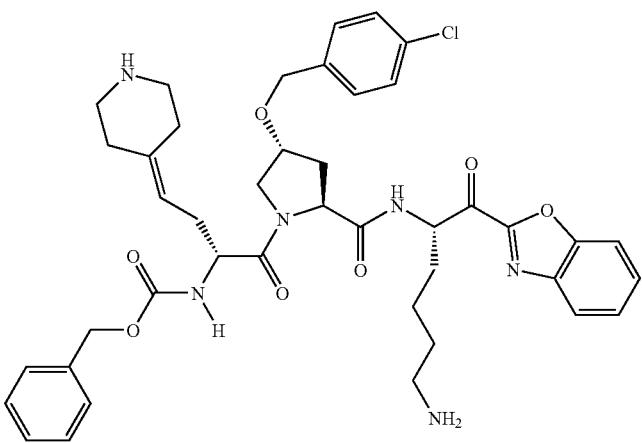 | MS m/z 785.3 (M + 1) |
| 133 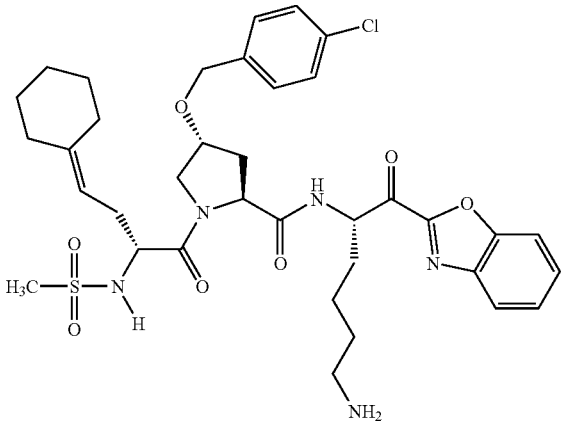 | MS m/z 728.4 (M + 1) |

TABLE 1-continued
| Structure | Physical Data MS (m/z), Elemental Analysis, and $^1$H NMR 400 M Hz (DMSO-$d_6$) |
|---|---|
| 134 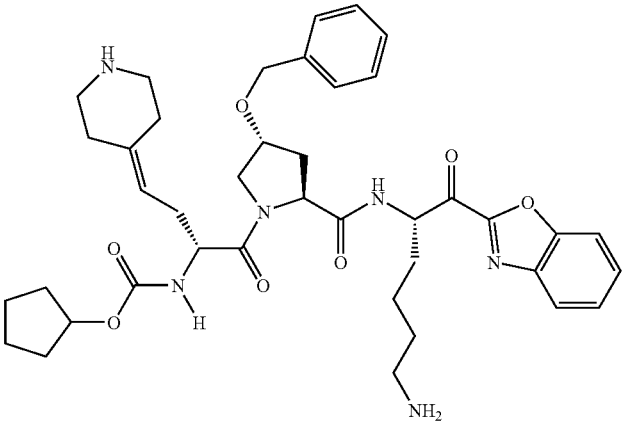 | MS m/z 729.4 (M + 1) |
| 135 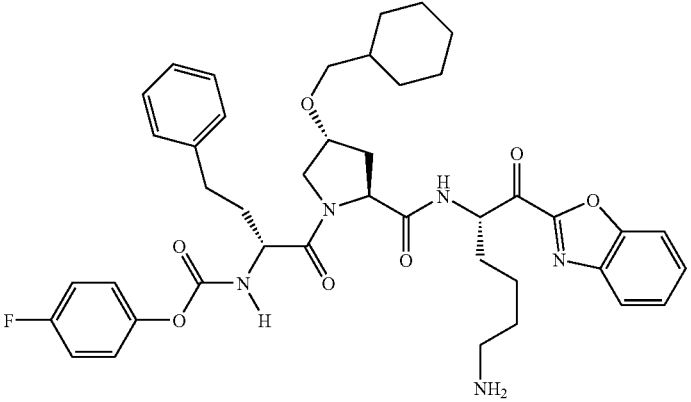 | MS m/z 756.4 (M + 1) |
| 136 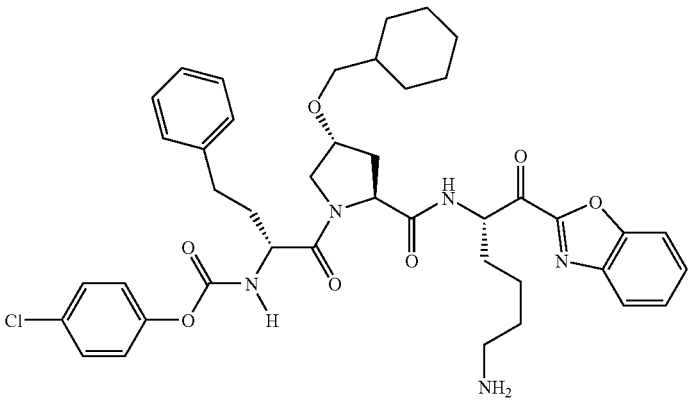 | MS m/z 756.4 (M + 1) |

TABLE 1-continued

| Structure | Physical Data MS (m/z), Elemental Analysis, and $^1$H NMR 400 M Hz (DMSO-$d_6$) |
|---|---|
| 137 | MS m/z 764.4 (M + 1) |
| 138 | MS m/z 822.2 (M + 1); $^1$H NMR (CDCl$_3$, 400 M Hz) δ 7.86(1H, dd,J=6.8 Hz), 7.62 (1H, d, J=8.0 Hz), 7.54(1H, t, J=8.0 Hz), 7.45 (1H, t, J=7.2 Hz), 7.36-7.08(12H, m), 6.84(3H, br s), 6.11-6.09(1H, m), 5.55-5.46(1H, m), 5.16-4.93 (2H, m), 4.66-4.61(1H, m), 4.21-4.06(3H, m), 3.76-3.60(2H, m), 3.25-2.96(2H, m), 2.82-2.54(6H, m), 2.52-2.49(2H, m), 2.07-1.88(2H, m). |
| 139 | MS m/z 824.4 (M + 1); $^1$H NMR (CDCl$_3$, 400 M Hz) δ 7.84(1H, dd, J=7.2 Hz), 7.73-7.71(1H, m), 7.60-7.59(1H, m), 7.50(1H, t, J=7.8 Hz), 7.46-7.41 (1H, m), 7.31-7.05(12H, m), 6.87-6.73(2H, m), 5.56-5.53(1H, m), 5.11-4.98(1H, m), 5.01-4.98(1H, m), 4.66-4.53(1H, m), 4.20-3.97(2H, m), 3.89-3.80 (1H, m), 3.76-3.50(6H, m), 2.71-2.56(2H, m), 2.31-2.12(2H, m), 2.11-1.73(4H, m), 1.70-1.31(6H, m). |

TABLE 1-continued

| Structure | Physical Data MS (m/z), Elemental Analysis, and $^1$H NMR 400 M Hz (DMSO-d$_6$) |
|---|---|
| 140 | MS m/z 828.3 (M + 1); Anal. Calcd. for C$_{43}$H$_{49}$Cl$_2$N$_5$O$_9$S (1 HCl + 1 H$_2$O): C, 58.50; H, 5.59; N, 7.93; Found: C, 58.08; H, 5.10; N, 7.79; $^1$H NMR (CD$_3$CN, 600 M Hz) δ 8.06(1H, d, J=7.2 Hz), 7.90 (1H, d, J=8.4 Hz), 7.74(3H, d, J=8.4 Hz), 7.60 (1H, t, J=7.8 Hz), 7.50(1H, t, J=7.2 Hz), 7.40-7.33(6H, m), 7.29-7.24(3H, m), 7.21-7.16(2H, m), 6.99 (1H, d, J=7.2 Hz), 5.38-5.34(1H, m), 5.10-5.08 (3H, m), 4.69-4.67(2H, m), 4.35-4.29(4H, m), 4.22 (1H, br s), 4.09-4.06(1H, t, J=8.4 Hz), 3.97-3.93 (1H, m), 3.82(2H, m), 2.91-2.90(2H, m), 2.76-2.72 (1H, m), 2.64-2.59(1H, m), 2.56-2.50(1H, m), 2.30-2.28(2H, m), 1.79-1.73(2H, m), 1.61-1.57(2H, m), 1.53-1.50(1H, m). |
| 141 | MS m/z 833.3 (M + 1) |
| 142 | MS m/z 777.2 (M + 1) |
| 143 | MS m/z 779.3 (M + 1) |

TABLE 1-continued
| Structure | Physical Data MS (m/z), Elemental Analysis, and $^1$H NMR 400 M Hz (DMSO-$d_6$) |
|---|---|
| 144 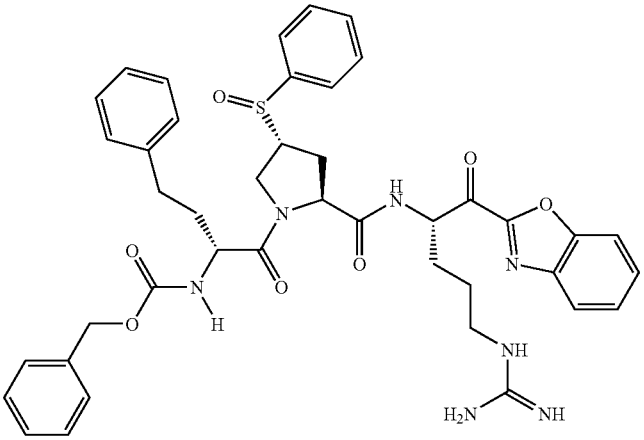 | MS m/z 792.3 (M + 1) |
| 145 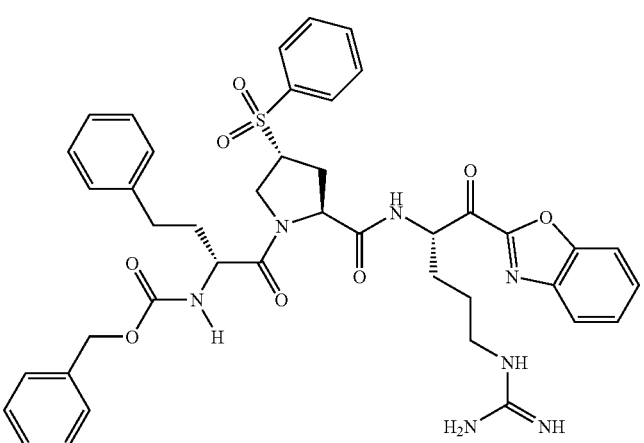 | MS m/z 808.2 (M + 1) |
| 146 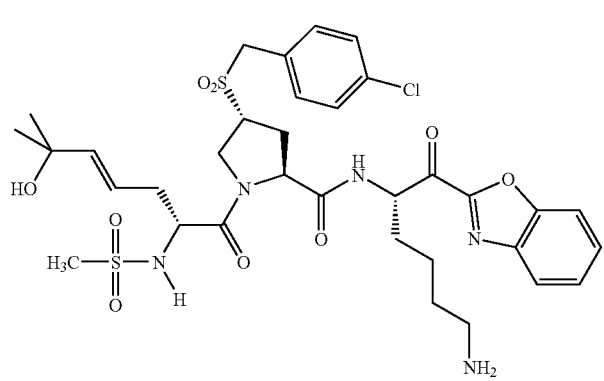 | MS m/z 822.3 (M + 1) |

TABLE 1-continued

| Structure | Physical Data MS (m/z), Elemental Analysis, and $^1$H NMR 400 M Hz (DMSO-$d_6$) |
|---|---|
| 147 | MS m/z 844.4 (M − H$_2$O + 1) |
| 148 | MS m/z 794.3 (M + 1) |
| 149 | MS m/z 793.3 (M + 1) |
| 150 | MS m/z 918.3 (M + 1) |

TABLE 1-continued
| Structure | Physical Data MS (m/z), Elemental Analysis, and $^1$H NMR 400 M Hz (DMSO-$d_6$) |
|---|---|
| 151 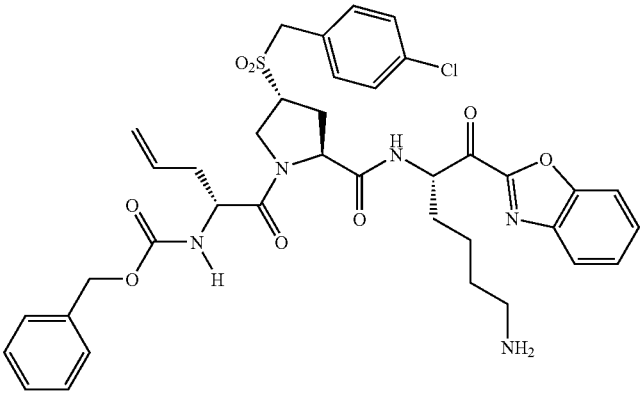 | MS m/z 764.3 (M + 1) |
| 152 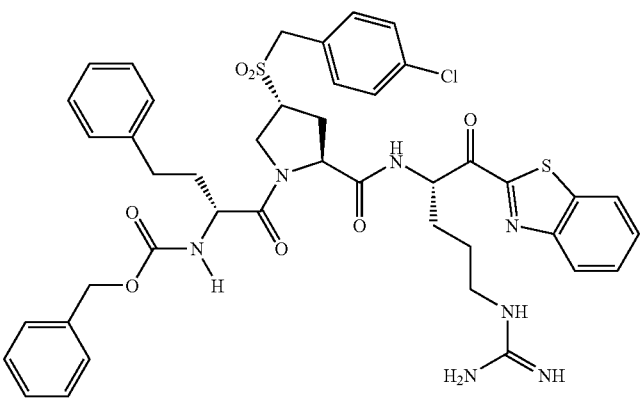 | MS m/z 872.3 (M + 1) |
| 258 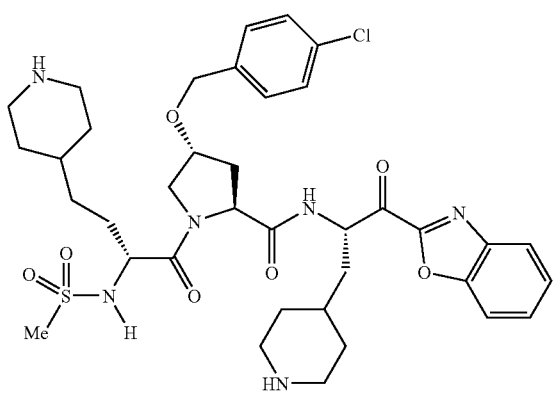 | MS m/z 767.4 (M + 1) |

EXAMPLE 153

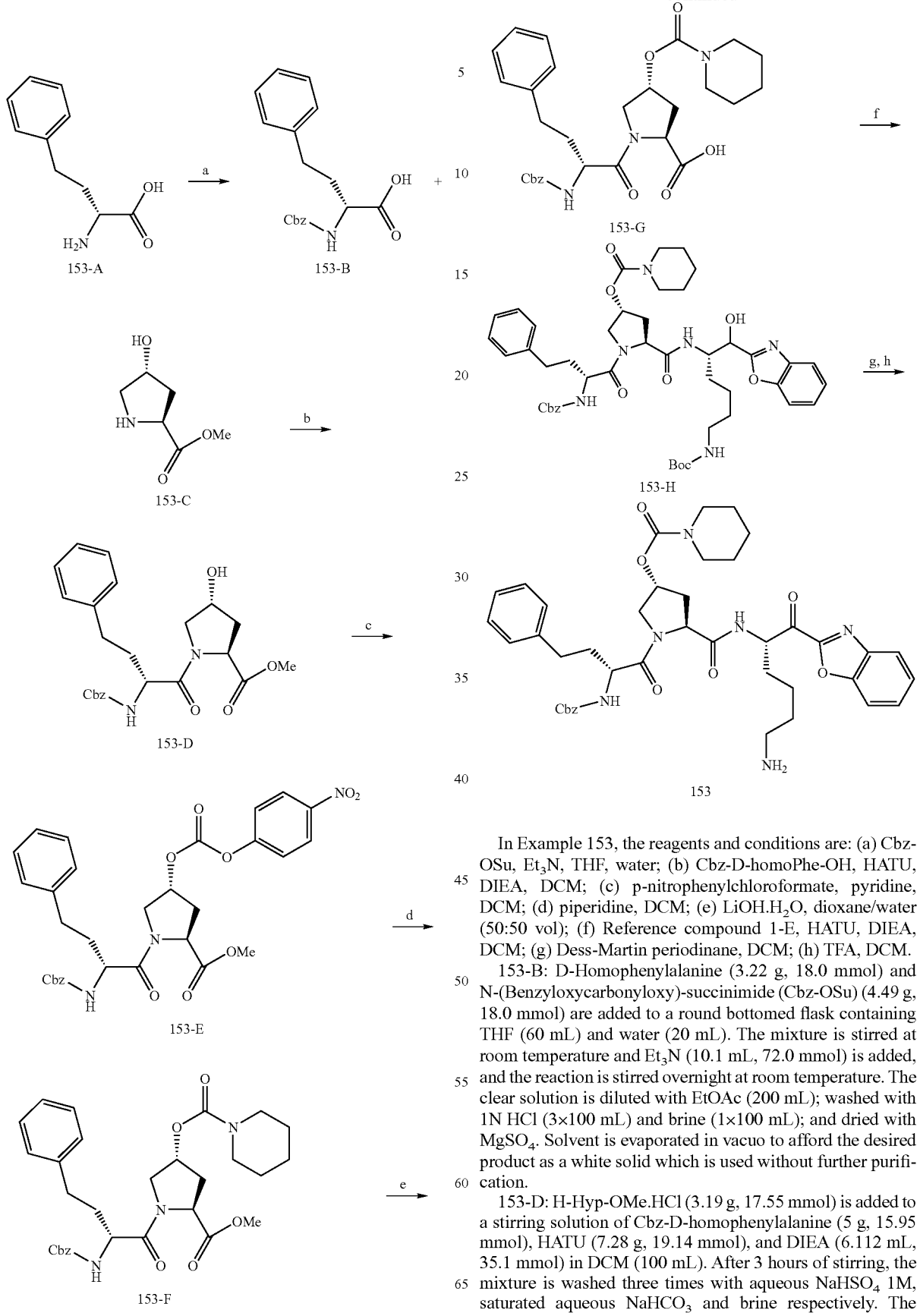

In Example 153, the reagents and conditions are: (a) Cbz-OSu, Et$_3$N, THF, water; (b) Cbz-D-homoPhe-OH, HATU, DIEA, DCM; (c) p-nitrophenylchloroformate, pyridine, DCM; (d) piperidine, DCM; (e) LiOH.H$_2$O, dioxane/water (50:50 vol); (f) Reference compound 1-E, HATU, DIEA, DCM; (g) Dess-Martin periodinane, DCM; (h) TFA, DCM.

153-B: D-Homophenylalanine (3.22 g, 18.0 mmol) and N-(Benzyloxycarbonyloxy)-succinimide (Cbz-OSu) (4.49 g, 18.0 mmol) are added to a round bottomed flask containing THF (60 mL) and water (20 mL). The mixture is stirred at room temperature and Et$_3$N (10.1 mL, 72.0 mmol) is added, and the reaction is stirred overnight at room temperature. The clear solution is diluted with EtOAc (200 mL); washed with 1N HCl (3×100 mL) and brine (1×100 mL); and dried with MgSO$_4$. Solvent is evaporated in vacuo to afford the desired product as a white solid which is used without further purification.

153-D: H-Hyp-OMe.HCl (3.19 g, 17.55 mmol) is added to a stirring solution of Cbz-D-homophenylalanine (5 g, 15.95 mmol), HATU (7.28 g, 19.14 mmol), and DIEA (6.112 mL, 35.1 mmol) in DCM (100 mL). After 3 hours of stirring, the mixture is washed three times with aqueous NaHSO$_4$ 1M, saturated aqueous NaHCO$_3$ and brine respectively. The organic phase is dried (MgSO$_4$), concentrated in vacuo, and the residue is purified by chromatography on silica gel with a gradient of Ethyl Acetate/Hexanes (0 to 100%) to give 1-C as a brown solid. MS m/z 441.2 (M+1), $^1$H NMR (Acetone-$d_6$, 400 MHz) δ. 7.43-7.17 (10H, m), 6.75 (1H, d, J=8.8 Hz), 5.24-5.11 (2H, m), 4.60-4.46 (1H, m), 3.81-3.55 (5H, m), 2.81-2.64 (2H, m), 2.32-2.25 (1H, m), 2.14-1.98 (3H, m).

153-E: 4-Nitrophenylchloroformate (1.514 g, 7.51 mmol) is added to a solution of 2-C (3 g, 6.83 mmol) and pyridine (663 µl, 8.19 mmol) in DCM (100 mL). The reaction mixture is stirred overnight. The mixture is washed with three portions of NaHSO$_4$ 1M and two portions of brine, dried (MgSO$_4$) and concentrated in vacuo to give the compound 1-D as a yellow oil. MS m/z 606.2 (M+1), $^1$H NMR (Acetone-$d_6$, 400 MHz) δ 8.34 (2H, d, J=9.2 Hz), 7.55 (2H, d, J=9.2 Hz), 7.45-7.16 (10H, m), 6.63 (1H, d, J=9.2 Hz), 5.51-5.48 (1H, m), 5.27-5.05 (2H, m), 4.56-4.50 (2H, m), 4.15-3.84 (2H, m), 3.66 (3H, s), 2.80-2.55 (3H, m), 2.37-2.26 (1H, m), 2.07-1.91 (2H, m).

153-F: Piperidine (320 mg, 3.76 mmol) is added to a solution of 1-D (1.9 g, 3.14 mmol) in DCM (100 mL), and the solution mixture is stirred at room temperature for 3 hours. The mixture is then washed with three portions of aqueous 1M NaHSO$_4$, three portions of saturated aqueous NaHCO$_3$ and two portions of brine. The organic layer is dried (MgSO$_4$), concentrated in vacuo. The residue is purified by chromatography on silica gel (AcOEt/Hexane, 0 to 100:%) to give the compound 1-E as a brown solid: MS m/z 552.3 (M+1); $^1$H NMR (Acetone-$d_6$, 400 MHz) δ. 7.42-7.17 (10H, m), 6.58 (1H, d, J=8.8 Hz), 5.27-5.04 (3H, m), 4.57-4.45 (1H, m), 3.97-3.62 (5H, m), 3.35-3.34 (4H, m), 2.82-2.60 (2H, m), 2.49-2.36 (1H, m), 2.21-2.21) 1H, m), 2.03-1.88 (6H, m).

153-G: Lithium hydroxide (hydrate) (37 mg, 0.88 mmol) is added to 1-E (400 mg, 0.72 mmol) in solution of THF:H$_2$O 50:50 (20 mL) and stirred overnight. The reaction mixture is concentrated in vacuo. The residue is diluted with ethyl acetate; washed with three portions of aqueous NaHSO$_4$ 1M and two portions of brine; dried (MgSO$_4$) and concentrated in vacuo to give 1-F as a white solid. MS m/z 538.3 (M+1); $^1$H NMR (Acetone-$d_6$, 400 MHz) δ. 7.45-7.13 (10H, m), 6.82 (1H, d, J=8.4 Hz), 5.31-5.07 (3H, m), 4.64-4.55 (1H, m), 4.45-3.96 (1H, m), 3.88-3.75 (1H, m), 3.36-3.30 (4H, m), 2.79-2.65 (2H, m), 2.65-2.16 (2H, m), 2.00-1.99 (2H, m), 1.60 (6H, m).

153-G: The compound 1-F (100 mg, 0.18 mmol) is added to a stirring solution of Reference compound 1 (Scheme 1) (65 mg, 0.18 mmol). HATU (82 mg, 0.21 mmol) and DIEA (70 µl, 0.40 mmol) in DCM (5 mL). After 3 hours of stirring, the mixture is washed three times with aqueous NaHSO$_4$ 1M, saturated aqueous NaHCO$_3$ and brine respectively. The organic phase is dried (MgSO$_4$), concentrated in vacuo and the residue is purified by chromatography on silica gel with a gradient of ethyl acetate to Hexane 0 to 100% to give 2-G as a yellow oil. MS m/z 869.4 (M+1); $^1$H NMR (Acetone-$d_6$, 400 MHz) δ 7.71-7.62 (2H, m), 7.42-7.15 (12H, m), 5.22-5.00 (4H, m), 4.56-4.38 (2H, m), 3.86-3.60 (2H, m), 3.33-3.30 (4H, m), 3.06-3.00 (2H, m), 2.87-2.64 (2H, m), 2.39-2.10 (2H, m), 2.04-1.92 (2H, m), 1.79-1.50 (2H, m), 1.50-1.37 (19H, m).

153: Dess-Martin periodinane (70 mg, 0.16 mmol) is added to a stirred solution of 1-H (120 mg, 0.14 mmol) and DCM (5 mL). The reaction mixture is stirred for 1 h and treated with 20 mL quenching solution (25 g of Na$_2$S$_2$O$_3$ in 100 mL saturated aqueous NaHCO$_3$). The resulting organic layer is washed twice with brine, dried (MgSO$_4$), and added to 20 mL of a solution of TFA (10 mL) in DCM (10 mL). The reaction mixture is stirred for another hour, concentrated in vacuo, and the residue is purified by reverse phase HPLC (gradient of acetonitrile with 0.05% TFA and water: 10 to 90%). After lyophilization, compound 153 is obtained as a white solid. MS m/z 767.7 (M+1), $^1$H NMR (DMSO-$d_6$, 400 MHz) δ8.98 (1H, d, J=6 Hz), 8.54 (1H, d, J=6 Hz), 8.00 (1H, d, J=8 Hz), 7.91 (1H, d, J=8.4 Hz), 7.72-7.54 (2H, m), 7.41-7.11 (10H, m), 5.32-5.24 (1H, m), 5.13-4.98 (3H, m), 4.45 (1H, t, J=8 Hz), 4.23 (1H, dd, J=8 Hz, 14.4 Hz), 3.99-3.47 (2H, m), 3.33-3.16 (4H, m), 2.87-2.67 (2H, m), 2.58-2.47 (2H, m), 2.37-2.06 (2H, m), 2.01-1.90 (2H, m), 1.85-1.21 (12H, m). Anal (C$_{43}$H$_{47}$N$_5$O$_7$.1TFA.3H$_2$O).

EXAMPLES 154-240

Examples 154-240 are obtained by repeating the procedures described in Example 153, using appropriate Reference compounds and reagents which would be apparent to those skilled in the art, for example:

Example 154, using Reference compound 3;
Examples 155-157, using Reference Compound 4 and trans-3-hydroxy-L-proline;
Example 158, using Reference Compound 1 and trans-3-hydroxy-L-proline;
Example 159, using Cbz-OSu and D-4-methoxyphenylglycine;
Example 160, using Cbz-OSu and D-cyclohexylalanine;
Example 161, using D-Pyroglutamic acid;
Example 162, using Cbz-D-Ala-OH;
Example 163, using Cbz-L-Lys(Boc)-OH;
Example 164, using Cbz-L-His(Boc)-OH;
Example 165, using Cbz-OSu and D-4-benzyloxyphenylglycine;
Example 166, using Cbz-OSu and D-3-trifluoromethylphenylalanine;
Example 167, using Cbz-OSu and D-4-trifluoromethylphenylalanine;
Example 168, using N-(iso-butyloxycarbonyloxy)-succinimide and D-homophenylalanine;
Example 169, using N-(ethyloxycarbonyloxy)-succinimide and D-homophenylalanine;
Example 170, using Reference compound 12;
Example 171, using Reference compound 13;
Example 172, using Reference compound 8;
Example 173, using N-(cyclohexyloxycarbonyloxy)-succinimide and D-3-chlorophenylalanine;
Example 174, using Reference compound 5;
Example 175, using Reference compound 5 and Reference compound 14;
Example 176, using N-p-tosylglycine and Reference compound 5;
Example 177, using N-Boc-4-hydroxypiperidine;
Example 178, using N—,N-diethylamine;
Example 179, using (±)-3-(tert-butoxycarbonylamino)-pyrrolidine;
Example 180, using 1-Boc-piperazine;
Example 181, using morpholine;
Example 182, using pyrrolidine;
Example 183, using N—,N-methylamine;
Example 184, using 1-acetyl-piperazine;
Example 185, using Cbz-D-Phe-OH;
Example 186, using N-benzylmethylamine;
Example 187, using N-methylfurfurylamine;
Example 188, using 4-phenylpiperidine;
Example 189, using 1-methanesulfonyl-piperazine;
Example 190, using 1-(2-furoyl)piperazine;
Example 191, using 1-(2-tetrahydrofuroyl)piperazine;
Example 192 is prepared, using 1-(benzoyl)piperazine;

Example 193, using 4-(tert-butoxycarbonylamino)-piperidine;
Example 194, using 1-phenyl sulfonyl piperazine;
Example 195, using 4-(aminomethyl)-1-N-Boc-piperidine;
Example 196, using 4-N-Boc-4-N-methyl-aminopiperidine;
Example 197, using 4-(2-aminoethyl)-1-Boc-piperidine;
Example 198, using Reference compound 14;
Example 199, using 4-methylsulphonylbenzylamine hydrochloride;
Example 200, using D-4-phenylphenylalanine;
Example 201, using D-3-methylphenylalanine;
Example 202, using D-3-chlorophenylalanine;
Example 203, using D-2-methylphenylalanine;
Example 204, using D-2-chlorophenylalanine;
Example 205, using 4-(trifluoromethoxy)-DL-phenylglycine;
Example 206, using 4-phenyl-DL-phenylglycine;
Example 207, using Reference compound 15;
Example 208, using 4,4-difluoropiperidine;
Example 209, using 2-thiophenemethylamine;
Example 210, using 1-(4-fluoro-benzenesulfonyl)-piperazine;
Example 211, using D-2-thienylalanine;
Example 212, using N-(cyclopropylmethyloxycarbonyloxy)-succinimide and D-homophenylalanine;
Example 213, using Reference compound 53;
Example 214, using N-4-piperidinyl-benzenesulfonamide;
Example 215, using D-2-fluorophenylalanine;
Example 216, using D-3-fluorophenylalanine;
Example 217, using D-4-fluorophenylalanine;
Example 218, using D-2-trifluoromethylphenylalanine;
Example 219, using 4-(trifluoromethyl)-DL-phenylglycine;
Example 220, using N-(cyclopentyloxycarbonyloxy)-succinimide and D-homophenylalanine;
Example 222, using Reference compound 2;
Example 223, using Reference compound 18;
Example 224, using Reference compound 3;
Example 225, using N-(cyclohexyloxycarbonyloxy)-succinimide and D-homophenylalanine;
Example 226, using N-p-tosylglycine;
Example 227, using N-(cyclopentyloxycarbonyloxy)-succinimide and D-homophenylalanine;
Example 228, using Reference compound 19;
Example 229, using Cbz-OSu and D-homocyclohexylalanine (D-homoCha-OH);
Example 230, using Reference compound 20;
Example 231, using Reference compound 7;
Example 232, using Reference compound 11;
Example 233, using Reference compound 9;
Example 234, using Reference compound 8;
Example 235, using Reference compound 2;
Example 236, using Reference compound 5;
Example 237, using Reference compound 6;
Example 238, using Reference compound 10;
Example 239, using N-(cyclohexyloxycarbonyloxy)-succinimide and D-allylglycine; and Example 240, using Reference compound 21.

EXAMPLE 241

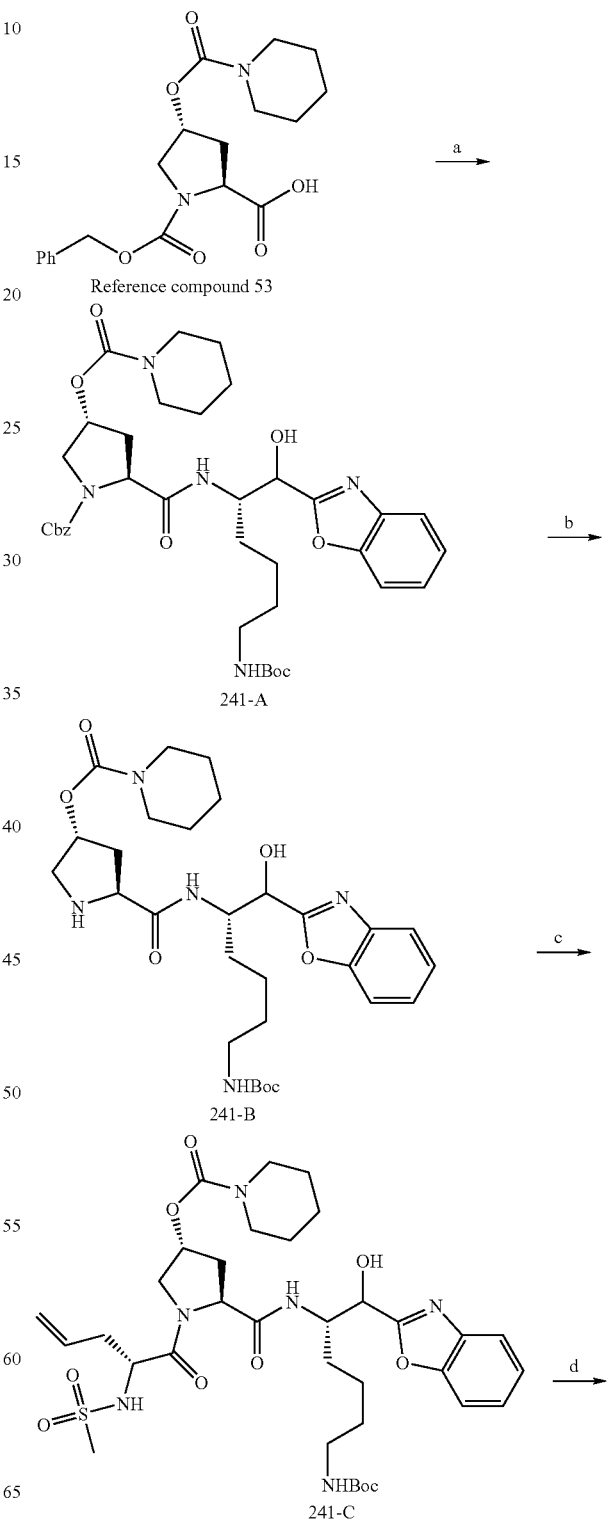

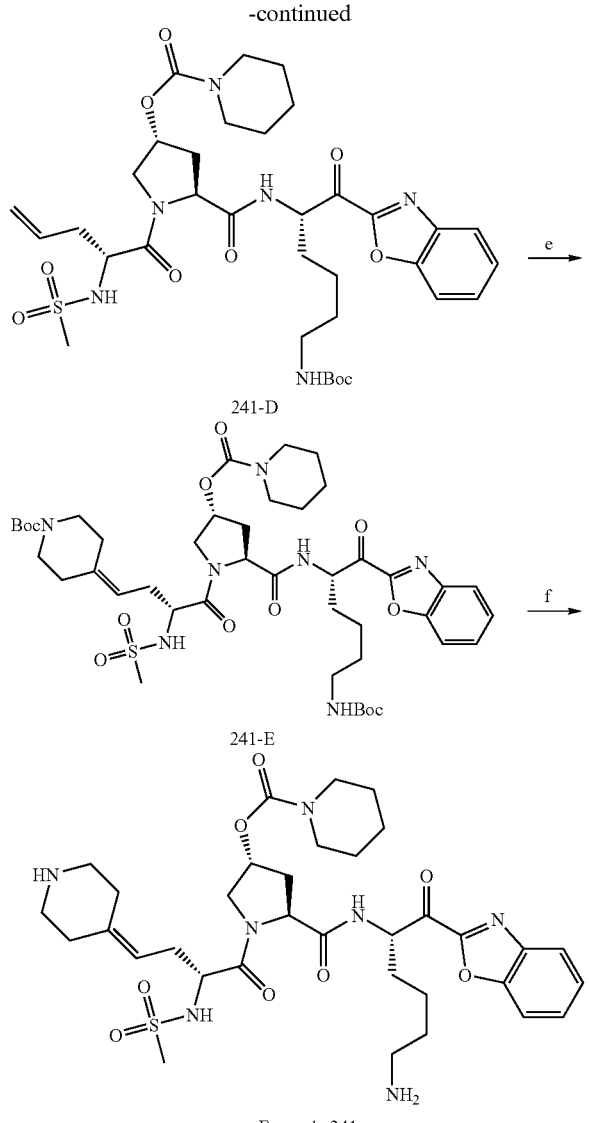

Example 241

In Example 241, the reagents and conditions are: (a) HATU, DIEA, DCM; (b) H$_2$ (40 psi), i-PrOH:H$_2$O (3:1) (c) HATU, DIEA, DCM; (d) Dess-Martin periodinane, DCM; (e) Hoveyda-Grubbs metathesis catalyst, 4-Methylene-N-Boc-piperidine, DCM, 40° C. (f) TFA, DCM.

241-A: Reference compound 54 is reacted with Reference compound 1, following methods analogous to those used in Step f of Example 153. Intermediate 241-B is obtained following hydrogenolysis conditions analogous to Step D in the synthesis of Reference compound 1. Dichloromethane (10 mL, 0.1 M) is added to intermediate 241-B (600 mg, 1.049 mmol, 1.0 eq.), Reference compound 21 (203 mg, 1.049 mmol, 1.0 eq.) and HATU (478 mg, 1.258 mmol, 1.2 eq.). DIEA (550 µL, 3.147 mmol, 3.0 eq.) is added via syringe, and the reaction is stirred at room temperature to completion, as determined by LC/MS. Solution is diluted with ethyl acetate (100 mL) and extracted with 1M HCl (3×30 mL), saturated NaHCO$_3$ (1×30 mL) and saturated NaCl (1×30 mL). The organic layer is dried over MgSO$_4$, filtered and evaporated to dryness to provide intermediate 241-C as a colorless oil. MS m/z 749.4 (M+1).

241-D: Dichloromethane (5 mL, 0.07 M) is added to 89-C (273 mg, 0.365 mmol, 1.0 eq) and Dess-Martin Periodinane (309 mg, 0.73 mmol, 2.0 eq.) at room temperature under a nitrogen atmosphere. The reaction is monitored to completion by LC/MS, diluted with ethyl acetate (50 mL), and extracted with saturated sodium thiosulfate (3×20 mL), saturated NaHCO$_3$ (1×30 mL) and saturated NaCl (1×30 mL). The organic layer is dried over MgSO$_4$, filtered and evaporated to dryness. Automated silica-gel purification (0-100% ethyl acetate in hexanes) provided 89-D as a colorless oil. MS m/z 747.4 (M+1).

241-E: Anhydrous dichloromethane (2 mL, 0.03 M) is added via syringe to 89-D (40 mg, 0.054 mmol, 1.0 eq.), Hoveyda-Grubbs 2$^{nd}$ Generation metathesis catalyst (1,3-Bis-(2,4,6-trimethylphenyl)-2-imidazolidinylidene) dichloro (o-isopropoxyphenylmethylene) ruthenium II dichloride) (10 mg, 0.016 mmol, 30 mol %) under a nitrogen atmosphere. N-Boc-4-methylenepiperidine (53 µL, 0.268 mmol, 5.0 eq.) is added via syringe, and the reaction is fitted with a reflux condenser, and heated to 40° C. for 12 h. After the reaction is judged as complete by LC/MS, the reaction mixture is directly purified by automated silica-gel purification (0-100% ethyl acetate in hexanes) to provide 241-E as a dark green oil. MS m/z 816.4 (M-Boc+1).

241: Three mL of a 25:75 mixture of trifluoroacetic acid and dichloromethane is added to 241-E (18 mg, 0.02 mmol) and stirred at room temperature until judged to completion by LC/MS. The reaction mixture is concentrated in vacuo and the residue is purified by reverse phase HPLC (gradient of Acetonitrile with 0.05% TFA and water: 10 to 90%). After lyophilization, Example 89 is obtained as a white solid. MS m/z 716.3.

EXAMPLES 242-243

Examples 242 and 243 are prepared, following methods analogous to those described for Example 241, using Reference compounds 55 and 56, respectively.

Example 244 is prepared, following methods analogous to those described in Example 241, using methylenecyclopentane in step e.

EXAMPLE 245

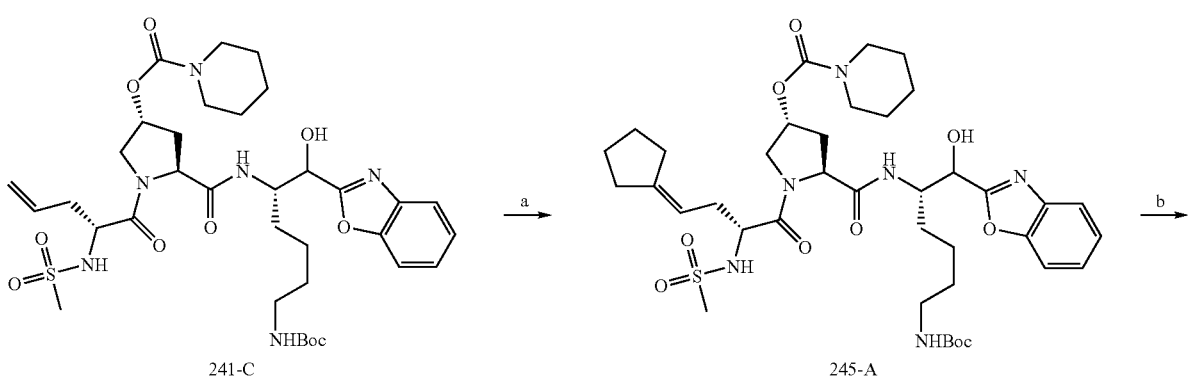

-continued

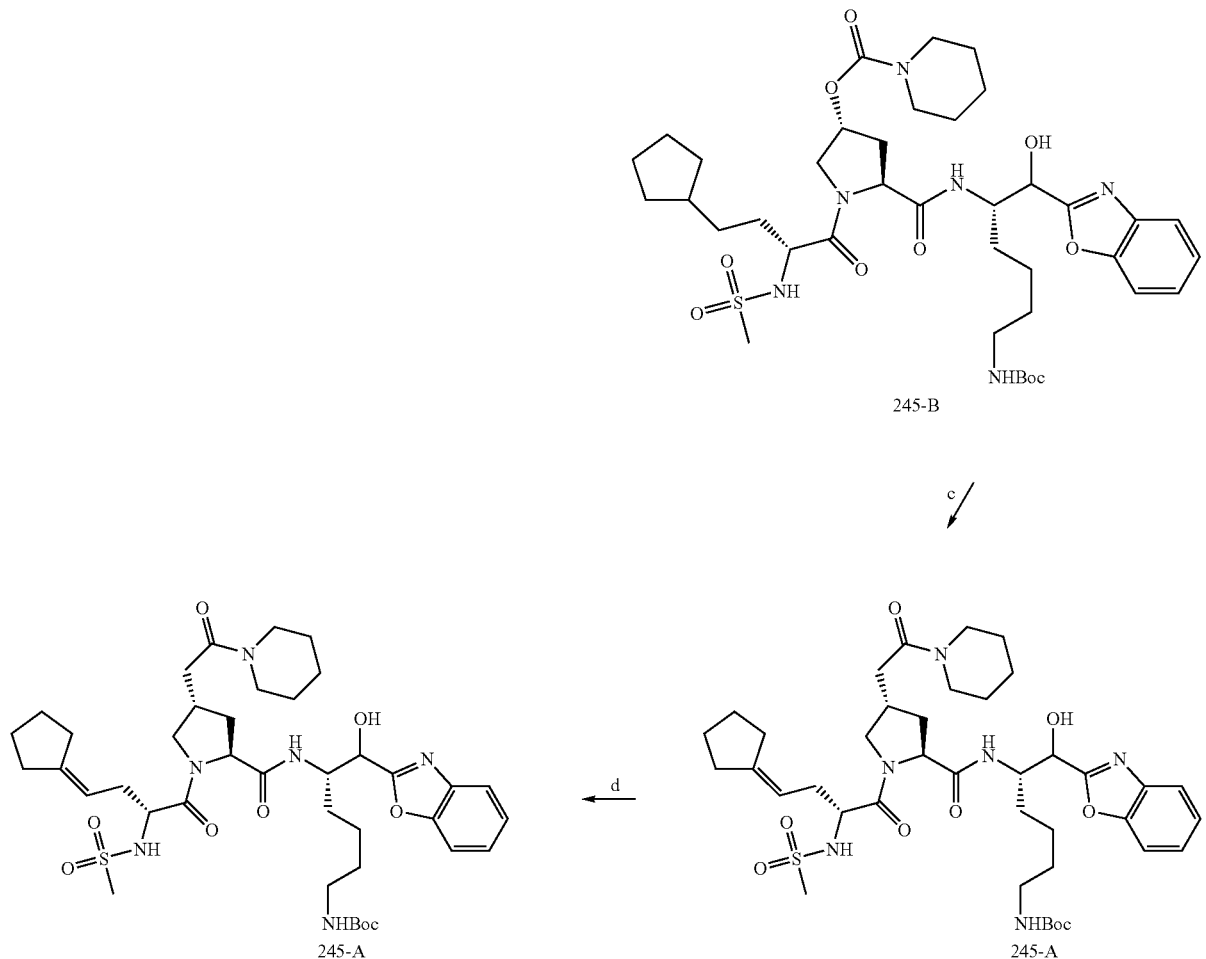

In Example 245, the reagents and conditions are: (a) Hoveyda-Grubbs metathesis catalyst, Methylenecyclopentane, DCM, 40° C. (b) $H_2$ (40 psi), i-PrOH:$H_2O$ (3:1); (c) Dess-Martin periodinane, DCM; (d) TFA, DCM.

245-A: Anhydrous dichloromethane (2 mL, 0.03 M) is added via syringe to 89-C (80 mg, 0.107 mmol, 1.0 eq.), Hoveyda-Grubbs $2^{nd}$ Generation metathesis catalyst (1,3-Bis-(2,4,6-trimethylphenyl)-2-imidazolidinylidene) dichloro (o-isopropoxyphenylmethylene) ruthenium II dichloride) (14 mg, 0.021 mmol, 20 mol %) under a nitrogen atmosphere. Methylenecyclopentane (57 μL, 0.543 mmol, 5.0 eq.) is added via syringe, and the reaction is fitted with a reflux condenser and heated to 40° C. for 12 hours. After the reaction is judged as complete by LC/MS, the reaction mixture is directly purified by automated silica-gel purification (0-100% ethyl acetate in hexanes) to provide 245-A as a dark green oil. MS m/z 803.4 (M+1).

245-B: tert-Butanol (30 mL) and water (10 mL) is added to 93-A (69 mg, 0.086 mmol, 1.0 eq.) and Pd/C (10 mg) in a Parr shaker. The Parr shaker is pressurized to 40 psi and shaken for 12 h. After the reaction is judged as complete by LC/MS, the reaction mixture is filtered over Celite, and the solvents evaporated to provide 245-B as a light green oil that is used in the next reaction without further purification. MS m/z 805.4 (M+1).

245-C: Dichloromethane (5 mL, 0.02 M) is added to 93-B (69 mg, 0.086 mmol, 1.0 eq) and Dess-Martin periodinane (70 mg, 0.17 mmol, 2.0 eq.) at room temperature under a nitrogen atmosphere. The reaction is monitored to completion by LC/MS, diluted with ethyl acetate (50 mL), and extracted with saturated sodium thiosulfate (3×20 mL), saturated $NaHCO_3$ (1×30 mL) and saturated NaCl (1×30 mL). The organic layer is dried over $MgSO_4$, filtered and evaporated to dryness. Automated silica-gel purification (0-100% ethyl acetate in hexanes) provided 245-C as a colorless oil. MS m/z 703.4 (M-Boc+1).

245: Three mL of a 25:75 mixture of trifluoroacetic acid and dichloromethane is added to 93-C (15 mg, 0.019 mmol) and stirred at room temperature until it is judged to completion by LC/MS. The reaction mixture is concentrated in vacuo, and the residue is purified by reverse phase HPLC (gradient of Acetonitrile with 0.05% TFA and water: 10 to 90%). Following lyophilization, Example 245 is obtained as a white solid. MS m/z 703.3.

EXAMPLE 246

Example 246 is prepared from Example 245-A, following methods analogous to those described for the preparation of Example 153.

Table 2 shows compounds of Formula (2), as described in Examples 153-246.

TABLE 2

| | Structure | Physical Data<br>$^1$H NMR 400 M Hz (DMSO-$d_6$) and/or MS (m/z) |
|---|---|---|
| 153 | 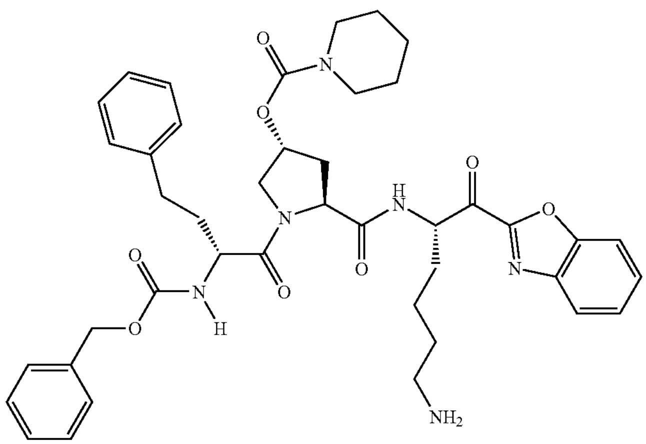 | $^1$H NMR (DMSO-d6, 400 M Hz) δ 8.98(1H, d, J=6 Hz), 8.54(1H, d, J=6 Hz), 8.00(1H, d, J= 8 Hz), 7.91(1H, d, J=8.4 Hz), 7.72-7.54 (2H, m), 7.41-7.11(10H, m), 5.32-5.24(1H, m), 5.13-4.98(3H, m), 4.45(1H, t, J=8 Hz), 4.23(1H, dd, J=8 Hz, 14.4 Hz), 3.99-3.47 (2H, m), 3.33-3.16(4H, m), 2.87-2.67(2H, m), 2.58-2.47(2H, m), 2.37-2.06(2H, m), 2.01-1.90(2H, m), 1.85-1.21(12H, m). Anal ($C_{43}H_{47}N_5O_7$•1TFA•3$H_2O$); MS m/z 767.4 (M + 1). |
| 154 | 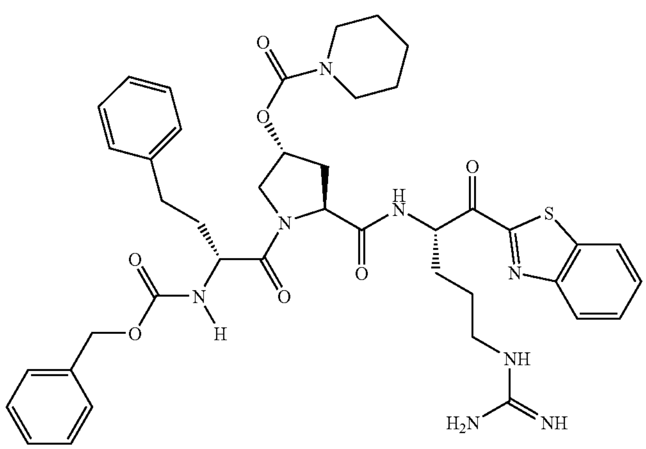 | MS m/z 811.7 (M + 1); Anal. Calcd. for $C_{44}H_{51}F_3N_8O_9S$ (1 TFA salt): C, 57.13; H, 5.56; N, 12.11; Found: C, 57.11; H, 5.38; N: 11.32; $^1$H NMR (CD$_3$CN, 400 M Hz) δ 8.21 (1H, dd, J=5.6, 2.4 Hz), 8.10(1H, dd, J= 5.2, 1.6 Hz), 7.82(1H, d, J=5.2 Hz), 7.67-7.60(2H, m), 7.37-7.34(3H, m), 7.31-7.26 (2H, m), 7.20-7.16(2H, m), 6.85(2H, br s), 6.50(1H, d, J=4.8 Hz), 5.63-5.51(1H, m), 5.33(1H, dd, J=10.8, 3.2 Hz), 5.16-5.00(3H, m), 4.57-4.51(1H, m), 4.30-4.26(1H, m), 3.89-3.70(3H, m), 3.59-3.49(1H, m), 3.30-3.12(2H, m), 2.77-2.72(1H, m), 2.65-2.59 (1H, m), 2.26-2.18(2H, m), 1.92-1.67(6H, m), 1.54-1.29(6H, m). |
| 155 | 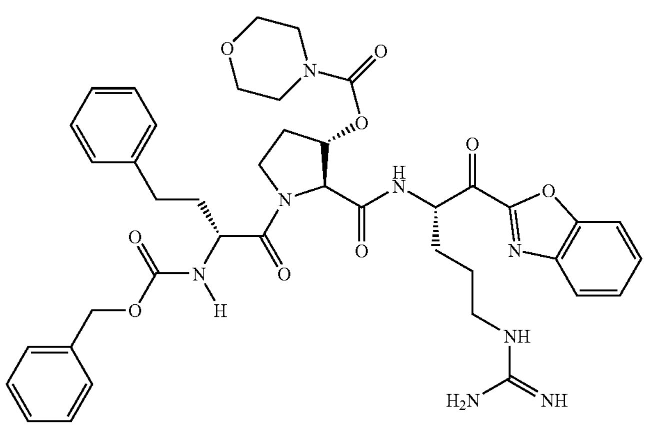 | MS m/z 797.2 (M + 1) |

TABLE 2-continued
| Structure | Physical Data<br>$^1$H NMR 400 M Hz (DMSO-$d_6$) and/or MS (m/z) |
|---|---|
| 156 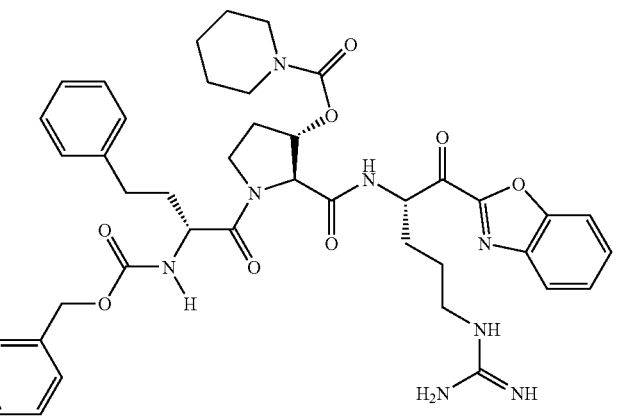 | MS m/z 795.3 (M + 1); $^1$H NMR (CDCl$_3$, 400 M Hz) δ 7.86-7.77(1H, m), 7.59-7.52(1H, m), 7.51-7.43(1H, m), 7.42-7.35(1H, m), 7.32-7.01(10H, m), 5.62-5.47(1H, m), 5.36-5.19(1H, m), 5.10-4.90(3H, m), 4.70-4.48(1H, m), 4.35-4.21(1H, m), 3.95-3.76(1H, m), 3.45-3.16(5H, m), 3.15-3.03(1H, m), 2.72-2.51(3H, m), 2.10-2.00(3H, m), 1.95-1.82(2H, m), 1.76-1.55(2H, m), 1.53-1.28(6H, m). |
| 157 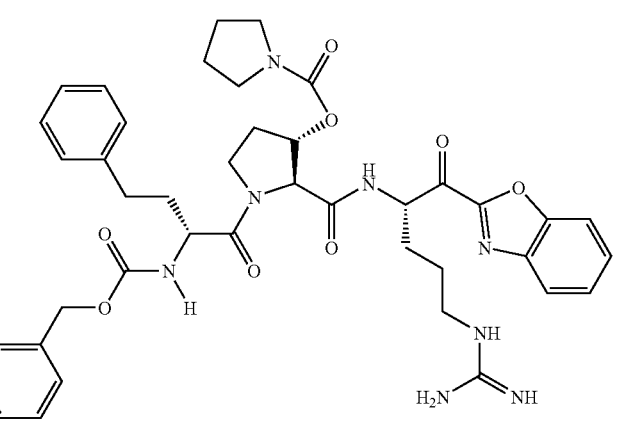 | MS m/z 781.3 (M + 1); $^1$H NMR (CDCl$_3$, 400 M Hz) δ 7.86-7.77(1H, m), 7.59-7.52(1H, m), 7.51-7.43(1H, m), 7.42-7.35(1H, m), 7.32-7.01(10H, m), 5.62-5.47(1H, m), 5.36-5.19(1H, m), 5.10-4.90(3H, m), 4.70-4.48(1H, m), 4.35-4.21(1H, m), 3.95-3.76(1H, m), 3.45-3.16(5H, m), 3.15-3.03(1H, m), 2.72-2.51(3H, m), 2.10-2.00(3H, m), 1.95-1.82(2H, m), 1.76-1.55(2H, m), 1.53-1.28(4H, m). |
| 158 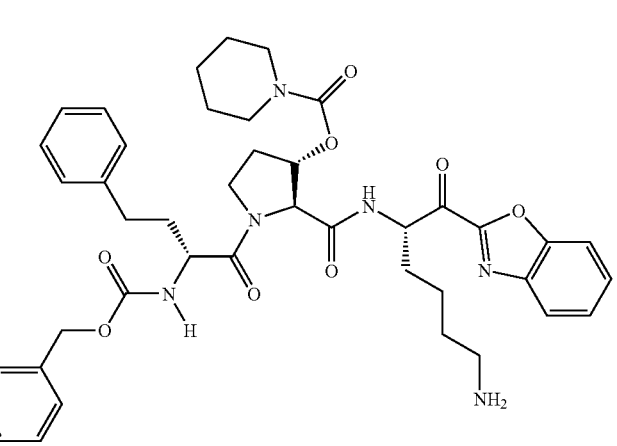 | MS m/z 767.4 (M + 1) $^1$H NMR (CD$_3$CN, 400 M Hz) δ 7.17(1H, d, J=7.6 Hz), 6.92(1H, d, J=8.4 Hz), 6.83(1H, t, J=8.0 Hz), 6.74(1H, t, J=7.6 Hz), 6.69(10H, m), 6.18-6.10(1H, m), 4.96-4.85(1H, m), 4.50-4.21(3H, m), 3.86-3.69(1H, m), 3.34-3.16(1H, m), 2.85-2.49(5H, m), 2.35-2.02(8H, m), 1.67-1.51(1H, m), 1.50-1.40(1H, m), 1.39-1.13(2H, m), 1.11-0.90(2H, m), 0.88-0.68(6H, m). |

TABLE 2-continued

| Structure | Physical Data<br>¹H NMR 400 M Hz (DMSO-d₆) and/or MS (m/z) |
| --- | --- |
| 159 | MS m/z 769.3 (M + 1) |
| 160 | MS m/z 759.4 (M + 1) |
| 161 | MS m/z 759.4 (M + 1) |

TABLE 2-continued

| Structure | Physical Data <br> ¹H NMR 400 M Hz (DMSO-d₆) and/or MS (m/z) |
| --- | --- |
| 162 | MS m/z 677.4 (M + 1) |
| 163 | MS m/z 734.4 (M + 1) |
| 164 | MS m/z 743.3 (M + 1) |

ТABLE 2-continued

| Structure | Physical Data $^1$H NMR 400 M Hz (DMSO-$d_6$) and/or MS (m/z) |
|---|---|
| 165 | MS m/z 845.4 (M + 1) |
| 166 | MS m/z 821.4 (M + 1) |
| 167 | MS m/z 821.3 (M + 1) |

TABLE 2-continued
| Structure | Physical Data<br>$^1$H NMR 400 M Hz (DMSO-$d_6$) and/or MS (m/z) |
|---|---|
| 168 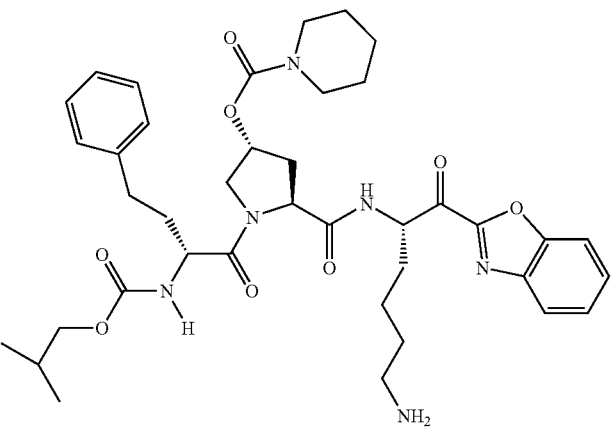 | MS m/z 733.4 (M + 1). NMR ((CD$_3$)$_2$CO) δ 7.82(m, 1H); 7.67(m, 1H); 7.52(m, 1H); 7.42(m, 1H); 7.14(m, 5H); 6.87(m, 1H); 5.10(m, 1H); 4.54(m, 1H); 4.24(m, 1H); 3.66(m 5H); 3.21(m, 4H); 2.43(m, 4H); 1.73(m, 5H); 1.58(m, 2H); 1.38(m, 7H); 0.73(m, 6H) |
| 169 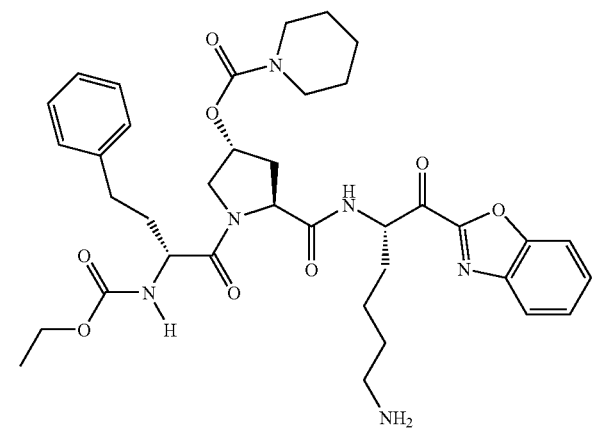 | MS m/z 705.4 (M + 1)). NMR ((CD$_3$)$_2$CO) δ 7.80(m, 1H); 7.66(m, 1H); 7.56(m, 1H); 7.44 (m, 1H); 7.38(m, 1H); 7.27(m, 4H); 7.02(m, 1H); 5.23(m, 1H); 4.05(m, 5H); 3.84(m, 5H); 3.67(m, 6H); 3.06(m, 4H); 2.71(m, 5H); 2.32 (m, 2H); 1.90(m, 2H); 1.43(m, 7H); 1.20(m, 3H). |
| 170 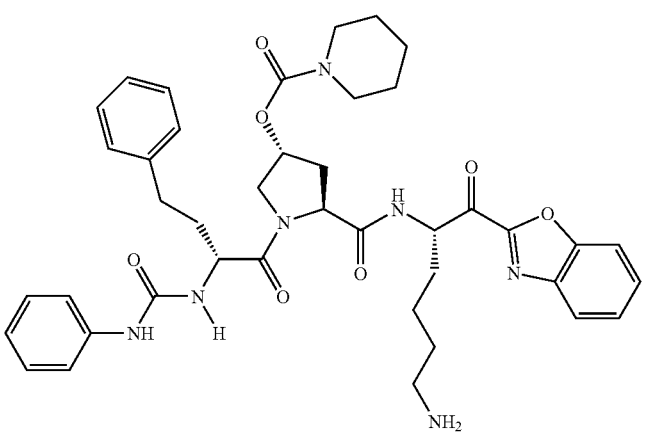 | MS m/z 752.4 (M + 1) |

TABLE 2-continued

| Structure | Physical Data $^1$H NMR 400 M Hz (DMSO-$d_6$) and/or MS (m/z) |
|---|---|
| 171 | MS m/z 675.4 (M + 1) |
| 172 | MS m/z 845.4 (M + 1) |
| 173 | MS m/z 823.35 (M + 1). Anal. ($C_{40}H_{51}ClN_8O_7S\bullet H_2O\bullet 2TFA$) NMR (($CD_3$)$_2$CO) δ 8.27(m, 3H); 8.17(m, 1H); 7.60 (m, 3H); 7.34(m, 4H); 7.04(m, 1H); 6.71(m, 1H); 5.76(m, 1H); 5.20(m, 1H); 4.69(m, 1H); 4.59(m, 1H); 4.50(m, 1H); 4.04(m, 1H); 3.56 (m, 1H); 3.07(m, 3H); 2.28(m, 3H); 1.90(m, 6H); 1.69(m, 2H); 1.60(m, 2H); 1.49(m, 7H); 1.34(m, 7H). |

TABLE 2-continued
| | Structure | Physical Data $^1$H NMR 400 M Hz (DMSO-$d_6$) and/or MS (m/z) |
|---|---|---|
| 174 | 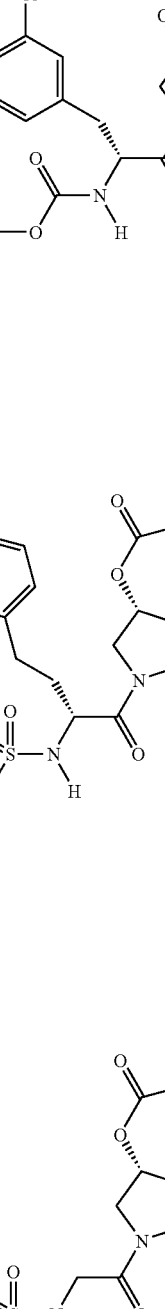 | MS m/z 827.40 (M + 1)). Anal. (C$_{44}$H$_{51}$ClN$_6$O$_8$•H$_2$O•2TFA) NMR ((CD$_3$)$_2$CO) δ 8.00(m, 1H); 7.92(m, 1H); 7.90(m, 1H); 7.68(m, 1H); 7.45(m, 6H); 7.35(m, 4H); 5.81 (m, 1H); 5.03(m, 3H); 4.75(m, 1H); 4.59(m, 2H); 4.53(m, 1H); 4.33(m, 1H); 3.88(m, 1H); 3.04(m, 4H); 2.62(m, 1H); 2.22(m, 1H); 1.87 (m, 2H); 1.68(m, 4H); 1.50(m, 6H); 1.26(m, 6H). |
| 175 | 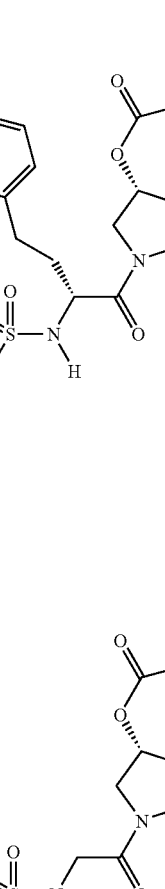 | MS m/z 759.4 (M + 1). Anal. (C$_{39}$H$_{46}$N$_6$O$_8$S•2TFA) NMR ((CD$_3$)$_2$CO) δ 8.00(m, 2H); 7.82(m, 1H); 7.68(m, 1H); 7.58 (m, 1H); 7.44(m, 5H); 7.29(m, 5H); 7.21(m, 1H); 5.81(m, 1H); 5.17(m, 1H); 4.99(m, 3H); 4.69(m, 1H); 4.15(m, 1H); 3.70(m, 1H); 3.49 (m, 2H); 3.21(m, 1H); 2.76(s, 3H); 2.74(m, 1H); 2.61(m, 1H); 2.33(m, 1H); 1.93(m, 2H); 1.53(m, 2H); 1.44(m, 4H). |
| 176 | 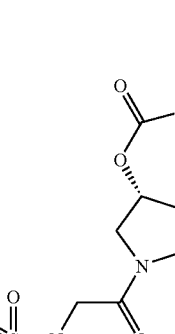 | MS m/z 731.3 (M + 1) NMR ((CD$_3$)$_2$CO) δ 7.98 (m, 2H); 7.83(m, 1H); 7.77(m, 2H); 7.68(m, 1H); 7.49(m, 2H); 7.40(m, 3H); 7.35(m, 2H); 5.72(m, 1H); 5.01(s, 2H); 4.52(m, 1H); 3.65(m, 3H); 3.49(m, 1H); 3.27(m, 1H); 3.03(m, 1H); 2.60(m, 1H); 2.47(s, 3H); 1.87(m, 1H); 1.68(m, 8H). |

TABLE 2-continued

| Structure | Physical Data<br>$^1$H NMR 400 M Hz (DMSO-$d_6$) and/or MS (m/z) |
| --- | --- |
| 177 | MS m/z 781.4 (M + 1) |
| 178 | MS m/z 755.3 (M + 1) |
| 179 | MS m/z 768.5 (M + 1) |

TABLE 2-continued
| | Physical Data |
|---|---|
| Structure | $^1$H NMR 400 M Hz (DMSO-$d_6$) and/or MS (m/z) |
180
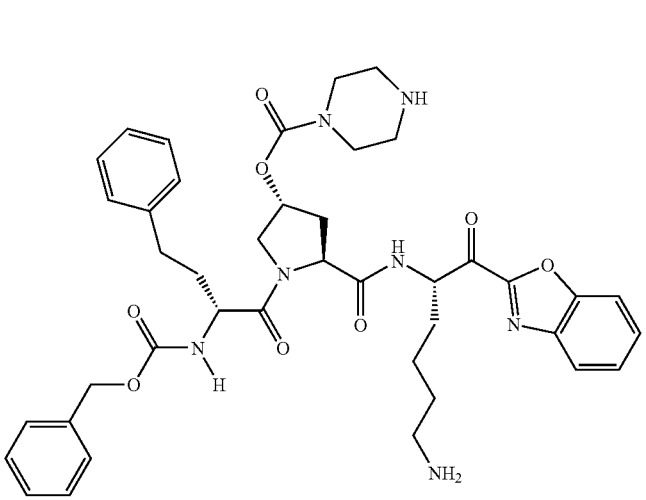
MS m/z 768.3 (M + 1), $^1$H NMR (DMSO-$d_6$, 400 M Hz) δ 7.96-7.57(4H, m), 7.43-7.05 10H, m), 5.27-4.83(4H, m), 4.60-4.35(1H, m), 4.35-4.15(1H, m), 4.05-3.26(6H, m), 3.18-2.95(6H, m), 2.82-2.54(2H, m), 2.40-2.00(4H, m), 1.85-1.45(6H, m).
181
MS m/z 769.4 (M + 1)
182
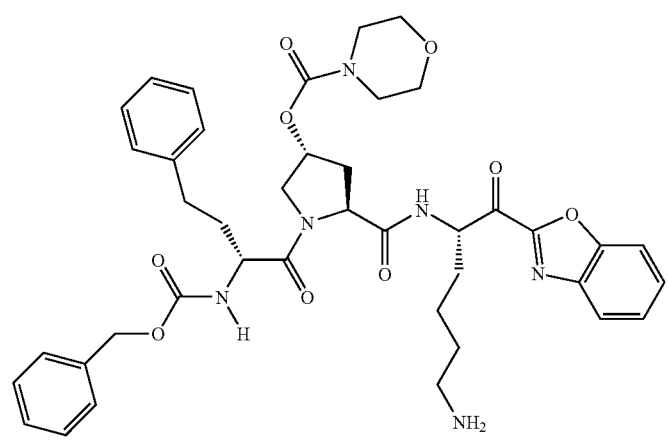
MS m/z 753.4 (M + 1), $^1$H NMR (DMSO-$d_6$, 400 M Hz) δ 8.04-7.52(4H, m), 7.42-7.01 (10H, m), 5.17-4.93(4H, m), 4.55-4.41(1H, m), 4.33-4.13(1H, m), 3.95-3.50(2H, m), 3.33-2.97(6H, m), 2.85-2.59(2H, m), 2.41-1.94(4H, m), 1.88-1.47(10H, m).

TABLE 2-continued

| Structure | Physical Data $^1$H NMR 400 M Hz (DMSO-$d_6$) and/or MS (m/z) |
| --- | --- |
| 183 | MS m/z 727.3 (M + 1) |
| 184 | MS m/z 810.4 (M + 1) |
| 185 | MS m/z 753.3 (M + 1) |

TABLE 2-continued

| Structure | Physical Data<br>$^1$H NMR 400 M Hz (DMSO-$d_6$) and/or MS (m/z) |
|---|---|
| 186 | MS m/z 803.4 (M + 1) |
| 187 | MS m/z 793.3 (M + 1) |
| 188 | MS m/z 843.4 (M + 1) |

TABLE 2-continued

| Structure | Physical Data<br>¹H NMR 400 M Hz (DMSO-d₆) and/or MS (m/z) |
| --- | --- |
| 189 | MS m/z 846.2 (M + 1) |
| 190 | MS m/z 862.4 (M + 1) |
| 191 | MS m/z 866.5 (M + 1) |

TABLE 2-continued

| Structure | Physical Data<br>¹H NMR 400 M Hz (DMSO-d₆) and/or MS (m/z) |
| --- | --- |
| 192 | MS m/z 872.5 (M + 1) |
| 193 | MS m/z 782.6 (M + 1) |
| 194 | MS m/z 908.4 (M + 1) |

TABLE 2-continued

| Structure | Physical Data $^1$H NMR 400 M Hz (DMSO-$d_6$) and/or MS (m/z) |
|---|---|
| 195 | MS m/z 796.4 (M + 1) |
| 196 | MS m/z 796.4 (M + 1) |
| 197 | MS m/z 810.4 (M + 1), 405.7 ((M + 1)/2) |

TABLE 2-continued

| Structure | Physical Data<br>$^1$H NMR 400 M Hz (DMSO-$d_6$) and/or MS (m/z) |
| --- | --- |
| 198 | MS m/z 711.6 (M + 1), Anal. (C35H46N6O8S•2H$_2$O•2TFA), $^1$H NMR (DMSO-$d_6$, 400 M Hz) δ 8.69(1H, d, J=7.2 Hz), 7.98(1H, d, J=8 Hz), 7.89(1H, d, J=8.4 Hz), 7.70-7.48(2H, m), 7.33-7.11(5H, m), 5.35-5.24(1H, m), 5.15-5.02(1H, m), 4.51-4.38(1H, m), 4.07-3.92(1H, m), 3.87-3.57 (2H, m), 3.32-3.12(2H, m), 3.12-2.60(5H, m), 2.16-1.86(2H, m), 1.86-1.67(2H, m), 1.67-1.18(12H, m). |
| 199 | MS m/z 867.3 (M + 1), $^1$H NMR (DMSO-$d_6$, 400 M Hz) δ 8.05-7.43(4H, m), 7.43-6.89 (14H, m), 5.15-4.93(4H, m), 4.53-4.00(2H, m), 3.79-3.33(2H, m), 3.16(3H, s), 2.83-2.50 (4H, m), 2.42-1.95(2H, m), 1.90-1.46(8H, m). |
| 200 | MS m/z 829.4 (M + 1) |

TABLE 2-continued

| | Structure | Physical Data<br>¹H NMR 400 M Hz (DMSO-$d_6$) and/or MS (m/z) |
|---|---|---|
| 201 | 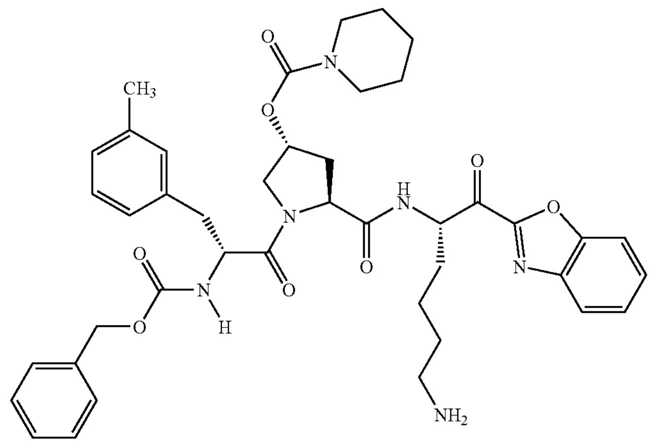 | MS m/z 757.4 (M + 1), ¹H NMR (DMSO-$d_6$, 400 M Hz) δ 7.85-7.50(4H, m), 7.37-6.85(9H, m), 5.20-4.85(4H, m), 4.50-4.20(2H, m), 3.95-3.65(2H, m), 3.30-3.20(4H, m), 2.85-2.65(4H, m), 2.25-2.20(3H, s), 2.20-1.90 (2H, m), 1.60-1.27(12H, m). |
| 202 | 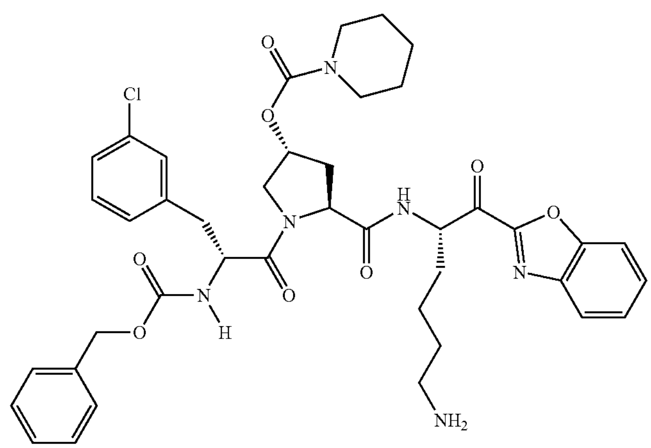 | MS m/z 787.4 (M + 1) |
| 203 | 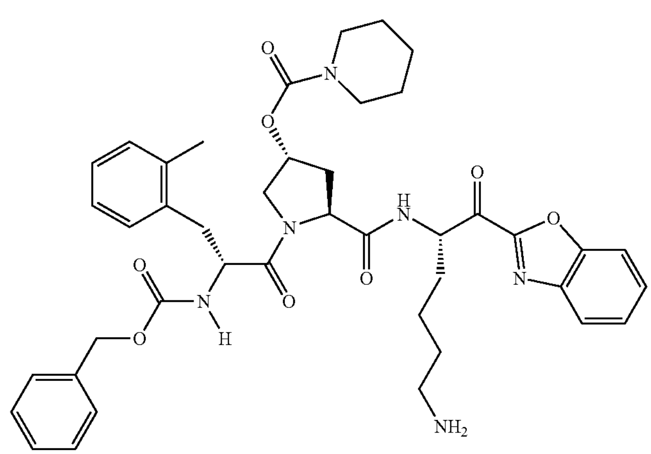 | MS m/z 767.4 (M + 1), ¹H NMR (DMSO-$d_6$, 400 M Hz) δ 8.04-7.90(2H, m), 7.80-7.56(2H, m), 7.38-7.00(9H, m), 5.12-4.82(4H, m), 4.60-4.32(2H, m), 3.97-3.60(2H, m), 3.36-3.18(4H, m), 2.97-2.83(1H, m), 2.60-2.54 (1H, m), 2.30-1.75(5H, m), 1.60-1.31(12H, m). |

TABLE 2-continued
| Structure | Physical Data<br>¹H NMR 400 M Hz (DMSO-d₆) and/or MS (m/z) |
|---|---|
| 204 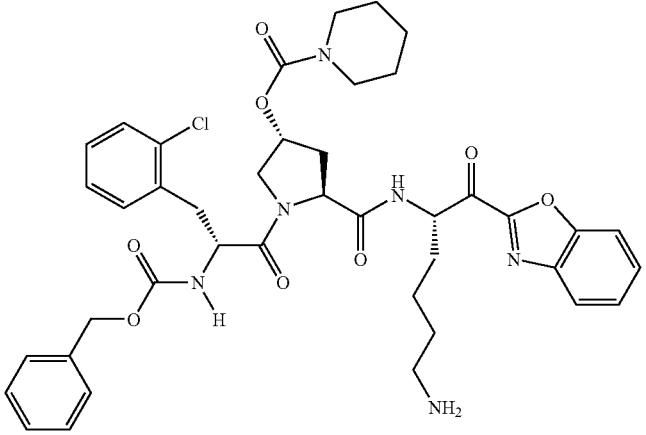 | MS m/z 787.4 (M + 1), ¹H NMR (DMSO-d₆, 400 M Hz) δ 8.04-7.90(2H, m), 7.80-7.54(2H, m), 7.43-7.12(9H, m), 5.37-5.20(1H, m), 5.15-4.83(3H, m), 4.65-4.45(2H, m), 3.85-3.65(2H, m), 3.40-3.20(4H, m), 3.15-2.70(4H, m), 2.30-1.94(2H, m), 1.75-1.30(12H, m). |
| 205 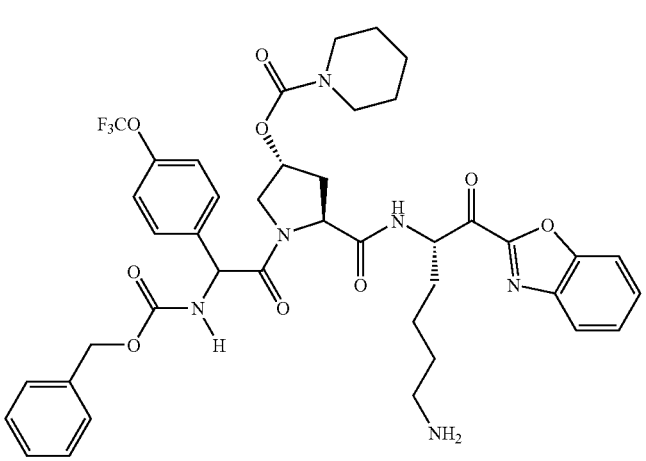 | MS m/z 823.3 (M + 1), ¹H NMR (DMSO-d₆, 400 M Hz) δ 7.70-7.54(2H, m), 7.52-7.39(2H, m), 7.39-7.23(5H, m), 7.19-7.03(2H, m), 7.02-6.89(2H, m), 5.62-5.55(1H, m), 5.20-4.93(4H, m), 4.46-4.23(1H, m), 3.90-3.68(2H, m), 3.46-3.17(4H, m), 2.87-2.67(2H, m), 2.38-1.82(2H, m), 1.67-1.34(12H, m). |
| 206 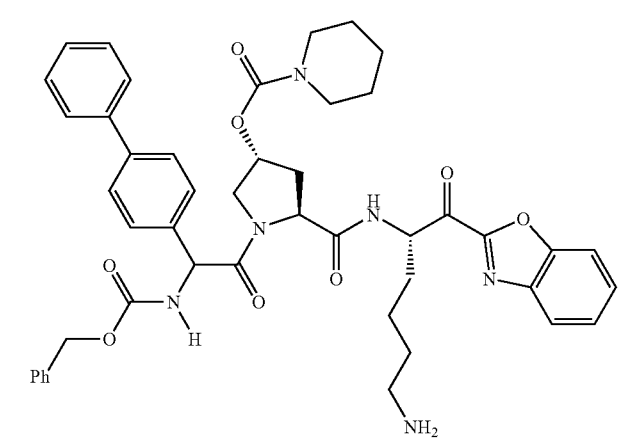 | MS m/z 815.4 (M + 1), ¹H NMR (DMSO-d₆, 400 M Hz) δ 7.77-7.58(4H, m), 7.58-7.40(4H, m), 7.40-7.24(8H, m), 5.60-5.48(1H, m), 5.28-5.13(1H, m), 5.13-4.94(3H, m), 4.50-4.30(1H, m), 3.90-3.75(2H, m), 3.44-3.20(4H, m), 2.92-2.70(2H, m), 2.36-1.90(2H, m), 1.66-1.27(12H, m). |

TABLE 2-continued

| Structure | Physical Data<br>¹H NMR 400 M Hz (DMSO-d$_6$) and/or MS (m/z) |
|---|---|
| 207 | MS m/z 831.4 (M + 1), ¹H NMR (DMSO-d$_6$, 400 M Hz) δ 7.76-7.50(4H, m), 7.42-7.25(5H, m), 5.20-4.95(4H, m), 4.87-4.72(1H, m), 4.55-4.44(1H, m), 3.85-3.45(6H, m), 3.40-3.20(4H, m), 2.85-2.70(2H, m), 2.40-1.95 (2H, m), 1.65-1.30(12H, m). |
| 208 | MS m/z 803.4 (M + 1) |
| 209 | MS m/z 795.3 (M + 1), ¹H NMR (DMSO-d$_6$, 400 M Hz) δ 7.87-7.63(2H, m), 7.56-7.30(2H, m), 7.22-6.84(13H, m), 5.01-4.70(4H, m), 4.30-4.18(1H, m), 4.18-4.07(2H, m), 4.07-3.82(1H, m), 3.50-3.16(2H, m), 2.67-2.51 (2H, m), 2.51-2.30(2H, m), 2.16-1.70(2H, m), 1.65-1.19(8H, m). |

TABLE 2-continued
| Structure | Physical Data $^1$H NMR 400 M Hz (DMSO-$d_6$) and/or MS (m/z) |
|---|---|
| 210 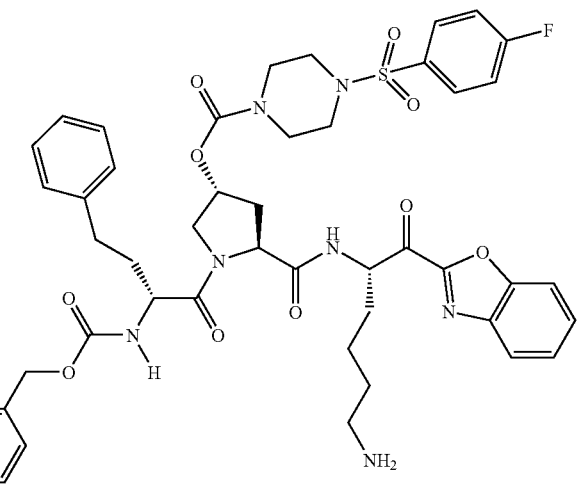 | MS m/z 926.4 (M + 1), $^1$H NMR (DMSO-$d_6$, 400 M Hz) δ 8.04-7.06(18H, m), 5.17-4.94 (4H, m), 4.50-4.33(1H, m), 4.33-4.10(1H, m), 3.91-3.54(2H, m), 3.54-3.25(8H, m), 2.97-2.50(4H, m), 2.33-1.87(2H, m), 1.84-1.40(8H, m). |
| 211 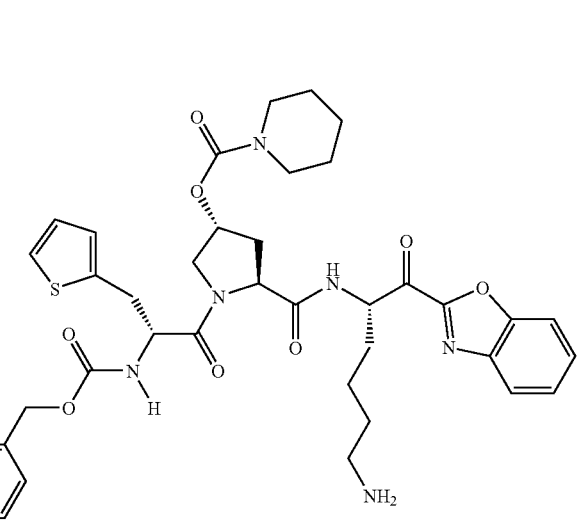 | MS m/z 759.3 (M + 1), $^1$H NMR (DMSO-$d_6$, 400 M Hz) δ 7.92-7.57(4H, m), 7.35-7.20(5H, m), 7.05-6.81(3H, m), 5.20-4.90(4H, m), 4.51-4.20(2H, m), 3.90-3.43(2H, m), 3.35-3.20(4H, m), 3.20-2.95(2H, m), 2.83-2.70 (2H, m), 2.33-2.00(2H, m), 1.70-1.28(12H, m). |
| 212 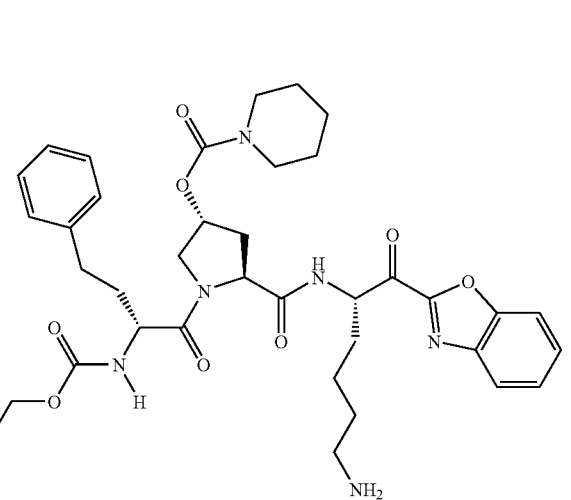 | MS m/z 731.4 (M + 1) |

TABLE 2-continued

| Structure | Physical Data<br>¹H NMR 400 M Hz (DMSO-d₆) and/or MS (m/z) |
| --- | --- |
| 213 | MS m/z 922.4 (M + 1), ¹H NMR (DMSO-d₆, 400 M Hz) δ 7.79-7.53(4H, m), 7.40-6.85 (15H, m), 5.20-4.90(4H, m), 4.50-4.33(1H, m), 4.33-4.15(1H, m), 4.04-3.55(2H, m), 3.50-3.08(8H, m), 2.86-2.60(4H, m), 2.38-1.96(2H, m), 1.88-1.34(10H, m). |
| 214 | MS m/z 922.4 (M + 1), ¹H NMR (DMSO-d₆, 400 M Hz) δ 8.01-7.45(9H, m), 7.41-7.04 (10H, m), 5.15-4.87(4H, m), 4.52-4.32(1H, m), 4.27-4.13(1H, m), 3.80-3.51(2H, m), 3.33-3.05(5H, m), 2.94-2.57(4H, m), 2.33-1.92(2H, m), 1.85-1.64(2H, m), 1.64-1.12 (10H, m). |
| 215 | MS m/z 771.4 (M + 1), ¹H NMR (DMSO-d₆, 400 M Hz) δ 8.93(1H, d, J=5.6 Hz), 8.65 (1H, d, J=6.4 Hz), 8.01(1H, d, J=8 Hz), 7.91(1H, d, J=8.4 Hz), 7.65(1H, t, J=8 Hz), 7.56(1H, t, J=7.6 Hz), 7.31-7.02(9H, m), 5.37-5.25(1H, m), 5.14-4.82(3H, m), 4.60-4.43(2H, m), 3.87-3.37(2H, m), 3.35-3.14(4H, m), 3.01-2.50(4H, m), 2.24-1.91 (2H, m), 1.75-1.18(12H, m). |

TABLE 2-continued
| Structure | Physical Data<br>$^1$H NMR 400 M Hz (DMSO-$d_6$) and/or MS (m/z) |
|---|---|
| 216 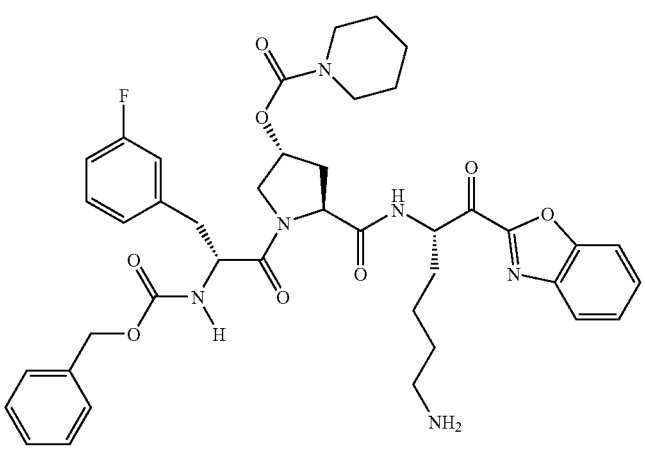 | MS m/z 771.4 (M + 1), $^1$H NMR (DMSO-$d_6$, 400 M Hz) δ 8.05-7.86(2H, m), 7.75-7.50(2H, m), 7.40-6.92(9H, m), 5.40-5.22(1H, m), 5.15-4.80(3H, m), 4.55-4.30(2H, m), 3.88-3.40(2H, m), 3.35-3.28(4H, m), 2.95-2.53(4H, m), 2.30-1.90(2H, m), 1.80-1.28(12H, m). |
| 217 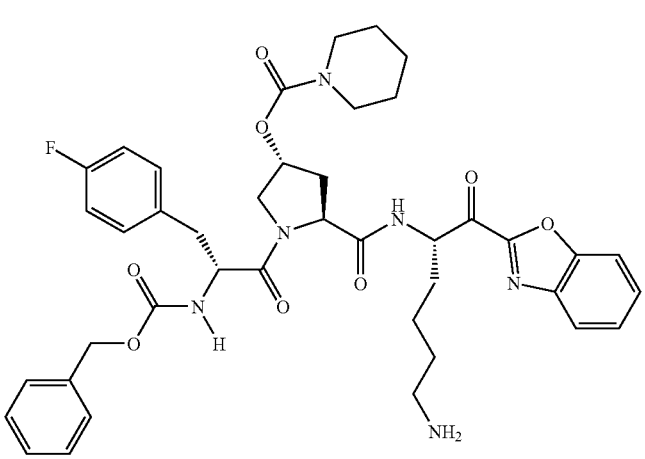 | MS m/z 771.4 (M + 1), $^1$H NMR (DMSO-$d_6$, 400 M Hz) δ 8.07-7.50(4H, m), 7.38-6.86(9H, m), 5.46-5.24(1H, m), 5.12-4.82(4H, m), 4.53-4.30(2H, m), 4.23-3.93(1H, m), 3.90-3.74(2H, m), 3.51-3.36(1H, m), 3.36-3.12(4H, m), 2.90-2.62(4H, m), 2.30-1.87(2H, m), 1.72-1.40(12H, m). |
| 218 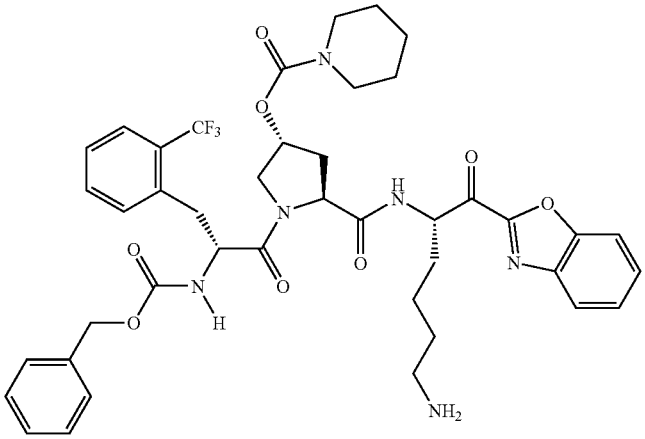 | MS m/z 821.4 (M + 1), $^1$H NMR (DMSO-$d_6$, 400 M Hz) δ 8.01-7.35(4H, m), 7.35-6.85(9H, m), 5.19-4.80(4H, m), 4.62-4.36(2H, m), 3.87-3.38(2H, m), 3.38-3.19(4H, m), 3.19-3.05(1H, m), 3.05-2.87(1H, m), 2.87-2.70(2H, m), 2.30-1.93(2H, m), 1.63-1.30(12H, m). |

TABLE 2-continued

| | Structure | Physical Data<br>¹H NMR 400 M Hz (DMSO-d₆) and/or MS (m/z) |
|---|---|---|
| 219 | 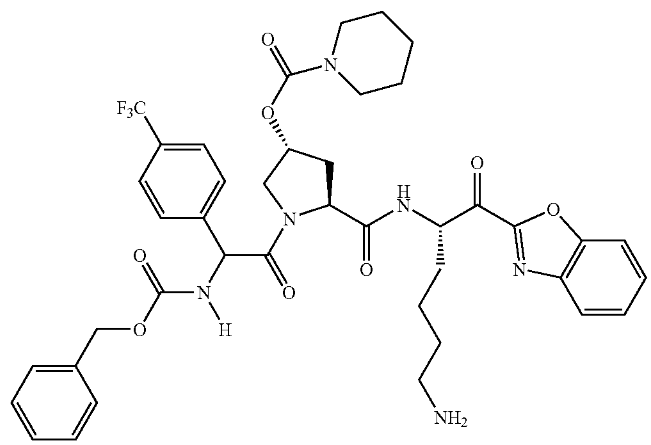 | MS m/z 807.3 (M + 1), ¹H NMR (DMSO-d₆, 400 M Hz) δ 8.06-7.85(2H, m), 7.82-7.47(2H, m), 7.42-7.19(5H, m), 5.60-5.46(1H, m), 5.13-4.85(3H, m), 4.51-4.31(1H, m), 4.31-4.17(1H, m), 3.87-3.40(2H, m), 3.35-2.85 (4H, m), 2.85-2.64(2H, m), 2.31-1.84(2H, m), 1.60-1.07(12H, m). |
| 220 | 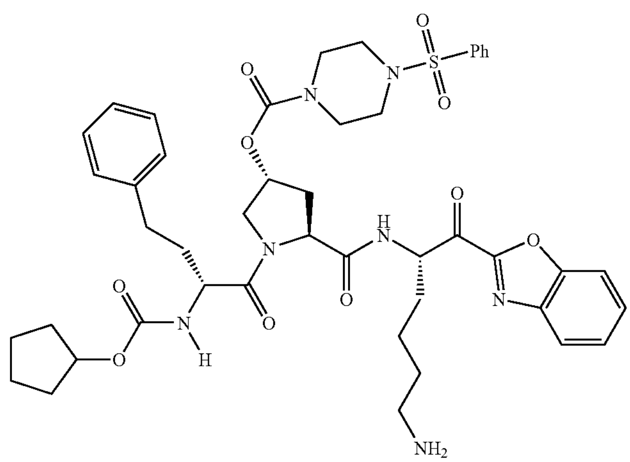 | MS m/z 886.4 (M + 1), ¹H NMR (DMSO-d₆, 400 M Hz) δ 8.03-7.41(6H, m), 7.37-7.04(8H, m), 5.14-4.83(3H, m), 4.48-4.33(1H, m), 4.23-4.08(1H, m), 4.02-3.56(2H, m), 3.44-3.23(8H, m), 2.96-2.51(4H, m), 2.30-1.92 (2H, m), 1.85-1.35(16H, m). |
| 221 | 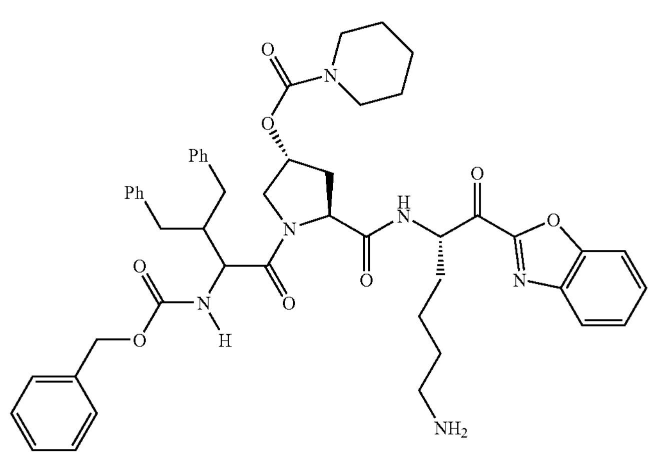 | MS m/z 857.5 (M + 1), ¹H NMR (DMSO-d₆, 400 M Hz) δ 7.77-7.48(4H, m), 7.48-7.02 (15H, m), 5.16-4.90(4H, m), 4.54-4.20(2H, m), 4.02-3.80(2H, m), 3.90-42-3.07(4H, m), 2.94-2.65(3H, m), 2.50-2.33(4H, m), 2.33-1.80(2H, m), 1.60-1.18(12H, m). |

TABLE 2-continued

| | | Physical Data |
|---|---|---|
| | Structure | $^1$H NMR 400 M Hz (DMSO-$d_6$) and/or MS (m/z) |

222

MS m/z 843.4 (M + 1)

223

MS m/z 647.4 (M + 1), Anal. (C35H46N6O6•3TFA), $^1$H NMR (acetone-$d_6$, 400 M Hz) δ 8.53(1H, d, J=6.8 Hz), 8.00-7.94(1H, m), 7.85-7.79(1H, m), 8.00-7.94 (1H, m), 7.85-7.79(1H, m), 7.70-7.62 8.00-7.94(1H, m), 7.85-7.79(1H, m), 7.59-7.53 (1H, m), 7.33-7.23(5H, m), 5.40-5.25(2H, m), 4.75(1H, t, J=4.75 Hz), 4.42(1H, dd, J= 7.92 Hz, 5.25 Hz), 4.00-3.80(2H, m), 3.45-3.16(4H, m), 2.90-2.70(2H, m), 2.47-2.33 (1H, m), 2.33-2.14(2H, m), 2.1-2.08(3H, m), 2.0-1.86(1H, m), 1.86-1.67(2H, m), 1.60-1.25(12H, m).

224

MS m/z 691.4 (M + 1), Anal. (C35H46N8O5S•4TFA)

TABLE 2-continued

| Structure | Physical Data<br>$^1$H NMR 400 M Hz (DMSO-$d_6$) and/or MS (m/z) |
|---|---|
| 225 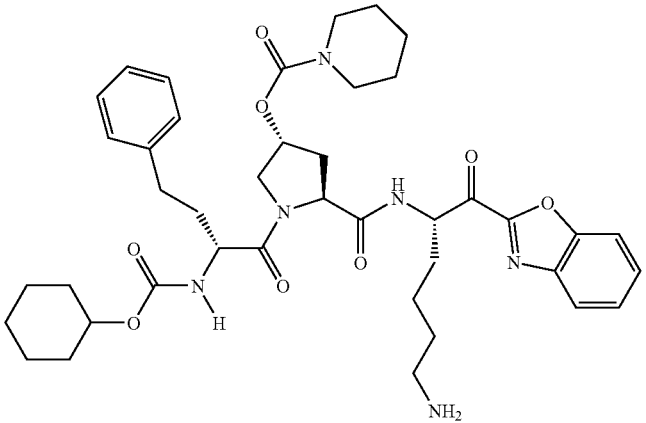 | MS m/z 759.5 (M + 1), Anal. (C41H54N6O8•2TFA), $^1$H NMR (DMSO-d6, 400 M Hz) δ 8.96(1H, d, J=4 Hz), 8.52(1H, d, J=5.6 Hz), 8.00(1H, d), 7.91(1H, d), 7.70-7.52(2H, m), 7.40-7.05(5H, m), 5.30-5.24(1H, m), 5.12-5.00(2H, m), 4.50-4.38 (2H, m), 4.27-4.13(1H, m), 3.95-3.52(2H, m), 3.40-3.06(4H, m), 2.86-2.70(2H, m), 2.70-2.53(2H, m), 2.37-1.90(4H, m), 1.84-1.11(22H, m). |
| 226 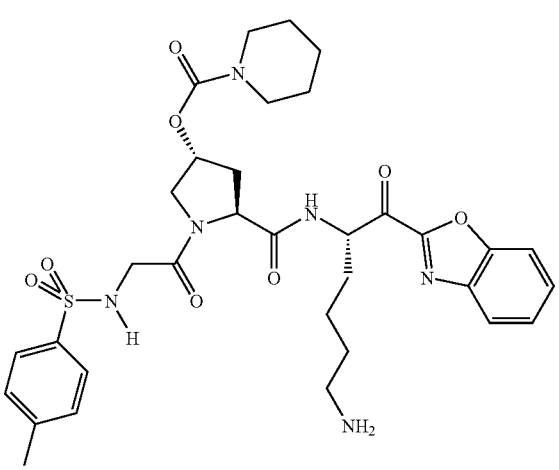 | MS m/z 683.3 (M + 1), Anal. (C33H42N6O8S•2TFA), $^1$H NMR (Acetone-$d_6$, 400 M Hz) δ 7.98-7.86(1H, m), 7.75-7.66 (1H, m), 7.62-7.54(1H, m), 7.54-7.46(1H, m), 7.40-7.27(4H, m), 5.51-5.40(1H, m), 5.21-5.13(1H, m), 4.65-4.55(1H, m), 3.89-3.41(4H, m), 3.37-3.20(4H, m), 2.60-2.43 (2H, m), 2.37(3H, s), 2.30-2.06(2H, m), 1.96-1.32(12H, m). |
| 227 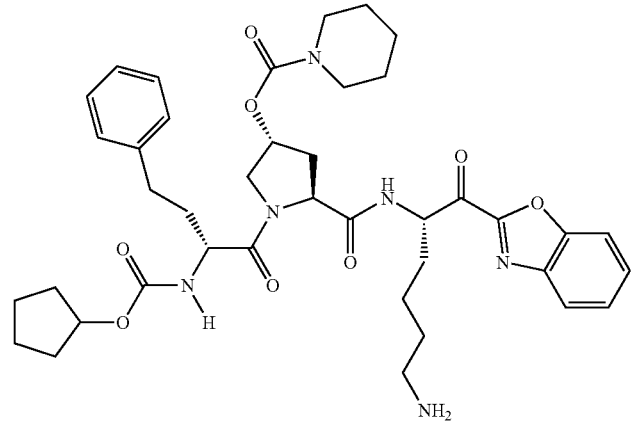 | $^1$NMR (DMSO-d6, 400 M Hz) δ 8.98(1H, d, J=6 Hz), 8.52(1H, d, J=6 Hz), 8.00(1H, d, J=7.6 Hz), 7.91(1H, d, J=8.4 Hz), 7.76-7.54(2H, m), 7.36-7.12(5H, m), 5.33-5.23 (1H, m), 5.13-4.87(3H, m), 4.44(1H, t, J=8 Hz), 4.18(1H, dd, J=7.2 Hz, 14 Hz), 3.94-3.45(2H, m), 3.38-3.16(4H, m), 2.88-2.70 (2H, m), 2.70-2.45(2H, m), 2.35-2.04(2H, m), 2.03-1.91(2H, m), 1.85-1.24(20H, m); Anal. ($C_{40}H_{52}N_6O_8$•2TFA)s |

TABLE 2-continued
| Structure | Physical Data $^1$H NMR 400 M Hz (DMSO-$d_6$) and/or MS (m/z) |
|---|---|
| 228 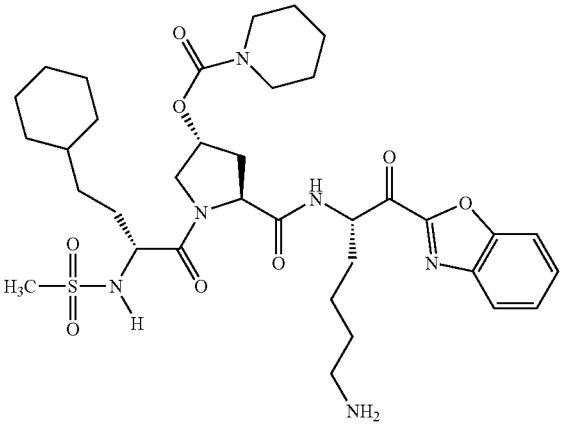 | MS m/z 717.3 (M + 1). NMR ((CD$_3$)$_2$CO) δ 8.32(m, 1H); 7.97(m, 2H); 7.82(m, 2H); 7.67(m, 2H); 7.57(m, 2H); 6.31(m, 1H); 5.52(m, 1H); 5.28(m, 1H); 4.74(m, 1H); 4.13(m, 1H); 3.95(m, 1H); 3.92-3.80(m, 4H); 2.97(m, 1H); 2.88(m, 4H); 2.62-2.52(m, 4H); 2.44(m, 1H); 2.27-2.17(m, 1H); 1.99-1.81(m, 3H); 1.76-1.59(m, 5H); 1.56-1.39(m, 6H); 1.35-1.13(m, 6H); 0.96-0.87(m, 3H) |
| 229 | MS m/z 773.4 (M + 1). NMR ((CD$_3$)$_2$CO) δ 8.01(m, 1H); 7.86(m, 2H); 7.70(m, 2H); 7.55(m, 2H)7.47-7.43(m, 5H); 7.19(m, 1H); 6.55(m, 1H); 5.37(m, 1H); 5.16(m, 1H); 4.99(m, 3H); 4.56(m, 1H); 4.28(m, 1H); 3.88(m, 1H); 3.74-3.62(m, 4H); 2.48-2.39(m, 4H); 2.25-2.11(m, 3H); 1.83-1.68(m, 3H); 1.65-1.48(m, 8H); 1.45-1.33(m, 4H); 1.28-0.99(m, 7H); 0.84-0.73(m, 2H). |
| 230 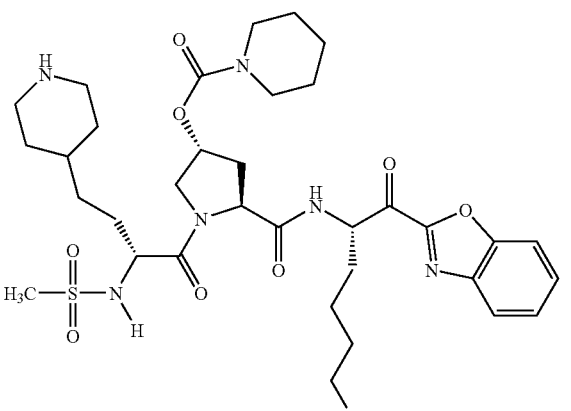 | MS m/z 718.4 (M + 1) |

TABLE 2-continued
| | Physical Data |
|---|---|
| Structure | $^1$H NMR 400 M Hz (DMSO-$d_6$) and/or MS (m/z) |
231 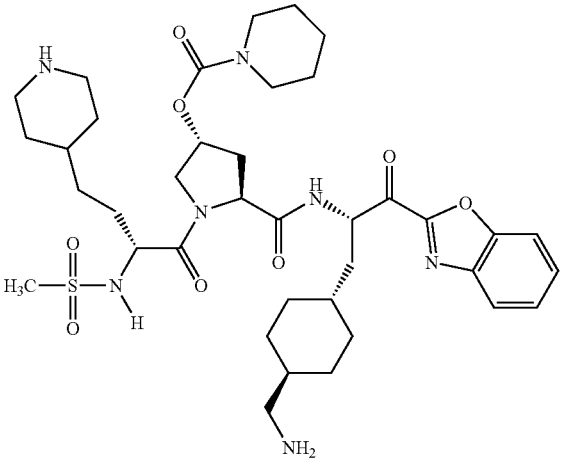
MS m/z 772.4 (M + 1)
232 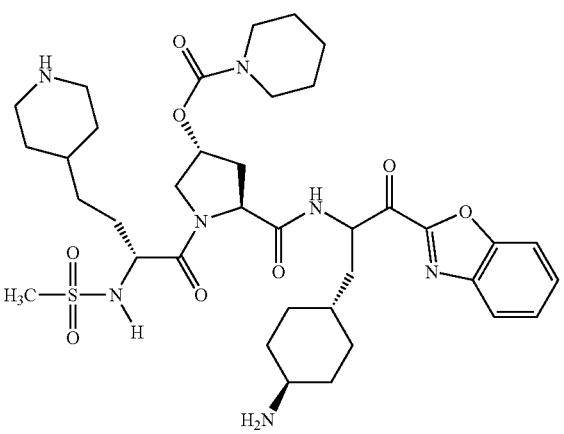
MS m/z 758.4 (M + 1)
233 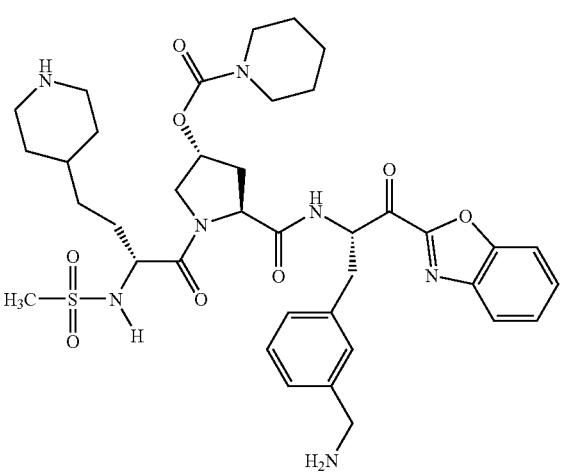
MS m/z 766.4 (M + 1)

TABLE 2-continued

| Structure | Physical Data $^1$H NMR 400 M Hz (DMSO-$d_6$) and/or MS (m/z) |
|---|---|
| 234 | MS m/z 794.4 (M + 1) |
| 235 | MS m/z 794.4 (M + 1) |
| 236 | MS m/z 766.4 (M + 1) |

TABLE 2-continued
| Structure | Physical Data<br>$^1$H NMR 400 M Hz (DMSO-$d_6$) and/or MS (m/z) |
|---|---|
| 237 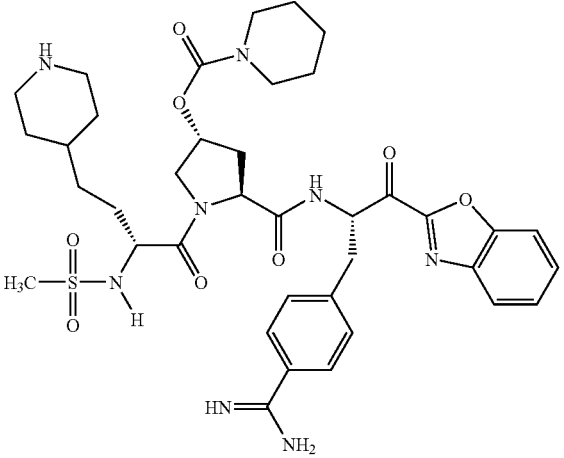 | MS m/z 779.4 (M + 1) |
| 238 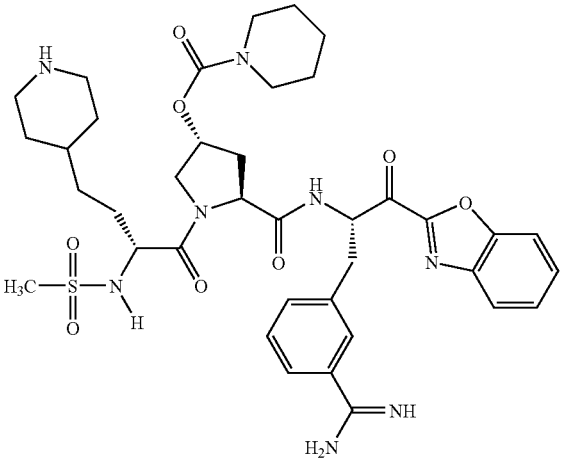 | MS m/z 779.4 (M + 1) |
| 239 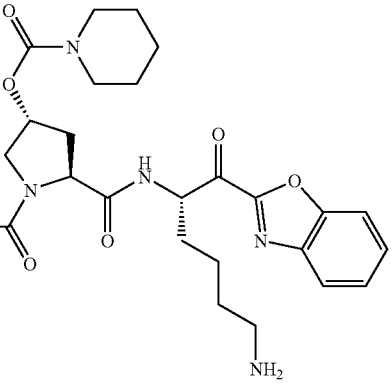 | MS m/z 695.4 (M + 1) |

TABLE 2-continued
| Structure | Physical Data<br>$^1$H NMR 400 M Hz (DMSO-$d_6$) and/or MS (m/z) |
|---|---|
| 240 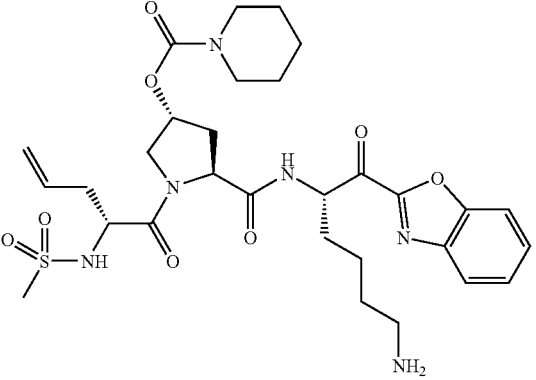 | MS m/z 647.4 (M + 1) |
| 241 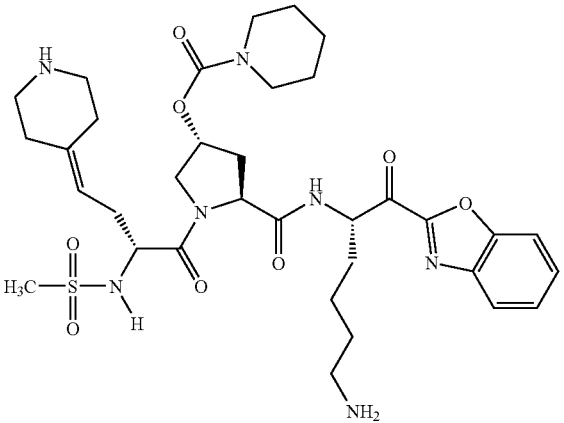 | MS m/z 716.4 (M + 1) |
| 242 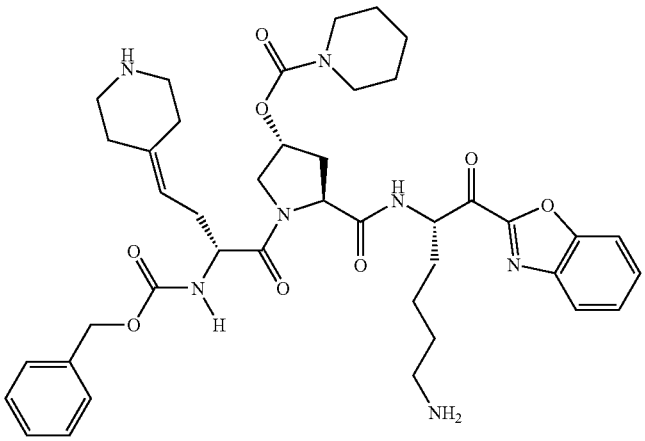 | MS m/z 772.4 (M + 1) |

TABLE 2-continued

| Structure | Physical Data<br>$^1$H NMR 400 M Hz (DMSO-$d_6$) and/or MS (m/z) |
|---|---|
| 243 | MS m/z 750.4 (M + 1) |
| 244 | MS m/z 778.4 (M + 1) |
| 245 | MS m/z 703.3 (M + 1) |

| | Physical Data |
|---|---|
| Structure | ¹H NMR 400 M Hz (DMSO-$d_6$) and/or MS (m/z) |
| 246  | MS m/z 701.4 (M + 1) |

EXAMPLE 247

Examples 247-257 are exemplary compounds of the invention having Formula (1) comprising 3-alkyl or 3-aryl substituted prolines, which may be prepared by repeating the procedures described in the above examples, using appropriate starting materials apparent to those skilled in the art.

| Structure | MS data |
|---|---|
| 247 | MS m/z 605.3 (M + 1) |
| 248 | MS m/z 667.4 (M + 1) |

| | Structure | MS data |
|---|---|---|
| 249 | 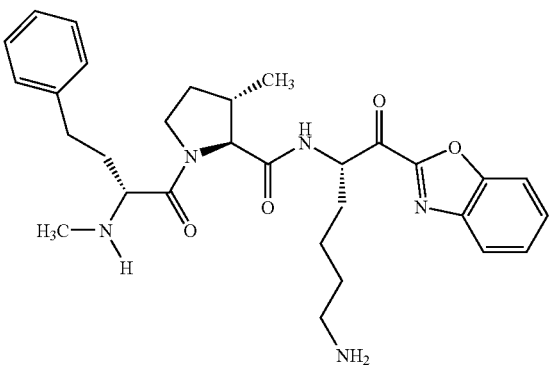 | MS m/z 534.3 (M + 1) |
| 250 | 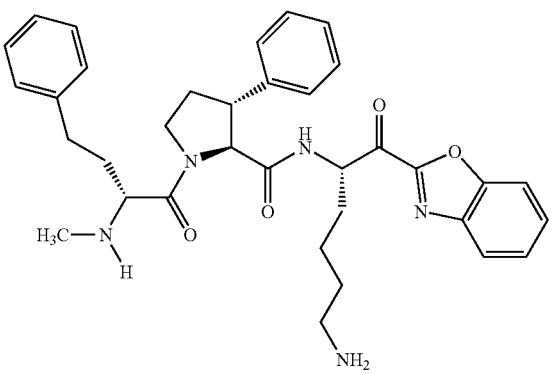 | MS m/z 596.4 (M + 1) |
| 251 | 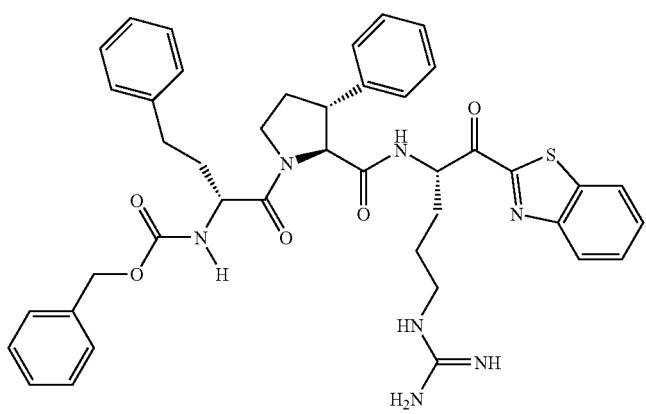 | MS m/z 746.3 (M + 1) |
| 252 | 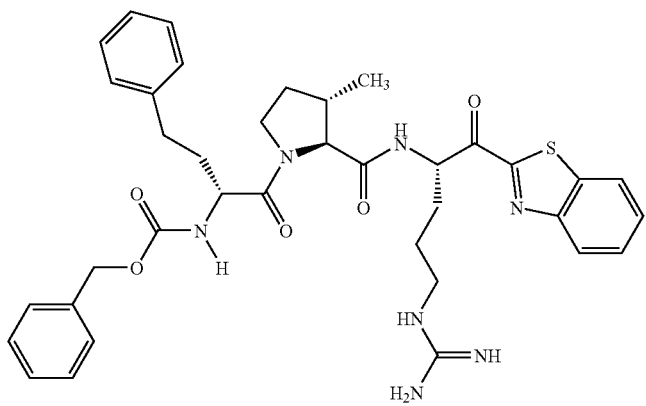 | MS m/z 698.3 (M + 1) |

| | Structure | MS data |
|---|---|---|
| 253 | 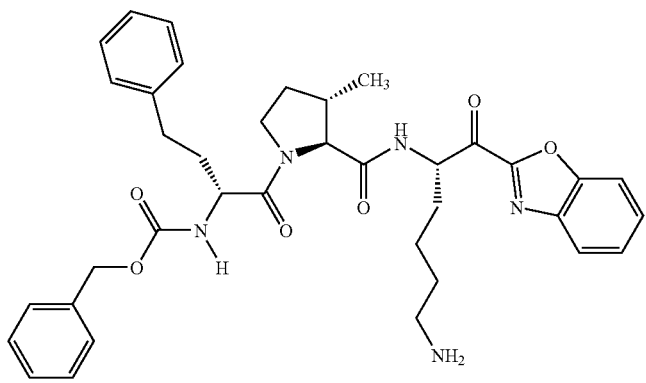 | MS m/z 654.4 (M + 1) |
| 254 | 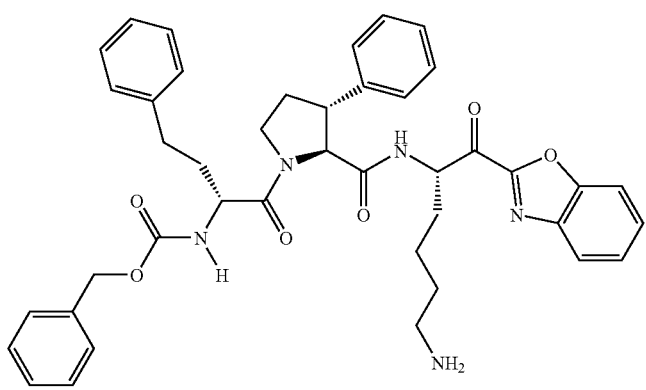 | MS m/z 716.4 (M + 1) |
| 255 | 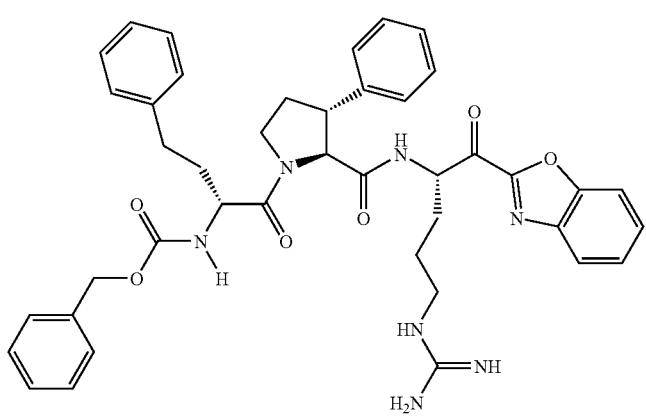 | MS m/z 744.4 (M + 1) |
| 256 | 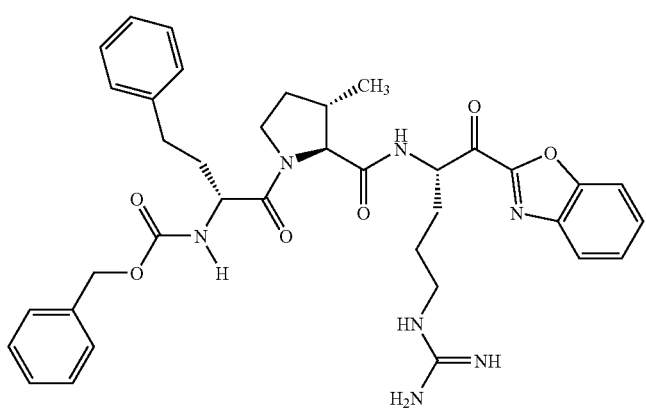 | MS m/z 682.4 (M + 1) |

| Structure | MS data |
|---|---|
| 257 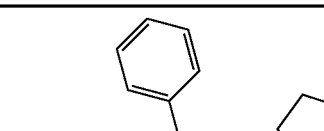 | MS m/z 708.4 (M + 1) |

Assays

The suitability of a channel activating protease inhibitor such as a prostasin inhibitor for the treatment of a disease mediated by inhibition of a channel activating protease, may be tested by determining the inhibitory effect of the channel activating protease inhibitor on: (1) the native, isolated, purified or recombinant channel activating protease, using a suitable biochemical assay format, using the method described in Shipway et al.; Biochem. Biophys. Res. Commun. 2004; 324(2):953-63); and/or (2) the ion channel/ion transport function in suitable isolated cells or confluent epithelia, using the methods described in Bridges et al.; Am. J. Physiol. Lung Cell Mol. Physiol. 2001; 281(1):L16-23; and Donaldson et al.; J. Biol. Chem. 2002; 277(10):8338-45.

Biochemical Assays

Recombinant human prostasin and matriptase and guinea pig prostasin are generated according to methods described in Shipway et al., Biochem. Biophys. Res. Commun. 2004; 324(2):953-63). The recombinant enzymes are incubated in an electrolyte buffer containing the test compounds or vehicle in a suitable multiple well assay plate such as a 96 or 384 well plate. At a defined time after the mixing of enzyme with compound or vehicle, a suitable fluorescent peptide substrate is added to the assay mixture. As substrate becomes cleaved by the active enzyme, fluorescence (measured, using a suitable fluorescence plate reader) increases and the rate of turn-over of substrate (i.e. enzyme activity) may be quantified, and thus the inhibitory effect of any test compound. The efficacy of test compounds is expressed as the concentration that induces a 50% attenuation in the enzyme activity ($K_i$).

In general, compounds of the invention may have $K_i$ values from 0.1 nM to 5 µM. In some examples, compounds of the invention may have $K_i$ values from 0.1 nM to 500 nM; from 0.1 nM to 50 nM; from 0.1 nM to 5 nM; or from 0.1 nM to 0.5 nM. In particular examples, compounds of the invention may have $K_i$ values from 0.1 nM to 0.5 nM; from 0.5 nM to 5 nM; from 5 nM to 50 nM; from 50 nM to 500 nM; or from 500 nM to 5 µM. In yet other examples, compounds may have $K_i$ values less than 0.1 nM or more than 5 µM.

Epithelial Ion Transport

Human bronchial epithelial cells are cultured according to methods described in Danahay et al., Am. J. Physiol. Lung Cell Mol. Physiol. 2002; 282(2):L226-36). When suitably differentiated (days 14-21 after establishing an apical-air interface) epithelial cells are treated with either vehicle, aprotinin (200 µg/ml) or test compound for 90 minutes. Epithelia are then placed into, using Chambers as described in Danahay et al., Am. J. Physiol. Lung Cell Mol. Physiol. 2002; 282(2): L226-36) maintaining the concentration of vehicle, aprotinin or test compound on the apical side of the epithelia. Short circuit current (ISC) is then measured by voltage clamping the epithelia to zero millivolts. The amiloride-sensitive ISC is then measured by the addition of amiloride (10 µM) to the apical surface of the epithelia. The potency of the test compound is expressed as the concentration inducing a 50% inhibition of the total aprotinin-sensitive component of the amiloride-sensitive ISC.

In general, compounds of the invention may have $IC_{50}$ values from 1 nM to 10 µM. In some examples, compounds of the invention may have $IC_{50}$ values from 1 nM to 1 µM; or more particularly from 1 nM to 100 nM. In yet other examples, compounds of the invention may have $IC_{50}$ values from 100 nM to 1 µM, or from 1 µM to 10 µM. In yet other examples, compounds may have $IC_{50}$ values less than 1 nM or more than 10 µM.

Tracheal Potential Difference (In Vivo)

Guinea pigs are anaesthetized, using a short acting inhalation anaesthesia such as halothane and $N_2O$. While under short acting anaesthesia, an oral gavage needle is inserted into the trachea via the oropharangeal route. Once inside the trachea, a small volume (50-200 µl) of vehicle or test compound, in a suitable aqueous-based diluent, is instilled into the airways. Animals then recover and become fully ambulatory. Alternatively, test compounds may be administered to animals, using aerosol or dry powder dosing. At a defined time after dosing, the animals are surgically anaesthetized, using a suitable anaesthesia such as ketamine and xylazine. The trachea is then exposed and a plastic agar bridge electrode is inserted into the tracheal lumen. A reference electrode is also inserted into the layers of muscle in the animal's neck. The tracheal potential difference is then measured, using a suitable high impedance voltmeter as described in Takahashi et al., Toxicol Appl Pharmacol. 1995; 131(1):31-6. The potency of the test compound is expressed as the dose inducing a 50% reduction in the sensitive-component of the tracheal potential difference.

It is understood that the examples and embodiments described herein are for illustrative purposes only, and that various modifications or changes in light thereof will be suggested to persons skilled in the art and are to be included within the spirit and purview of this application and scope of

The invention claimed is:
1. A compound of Formula (1):

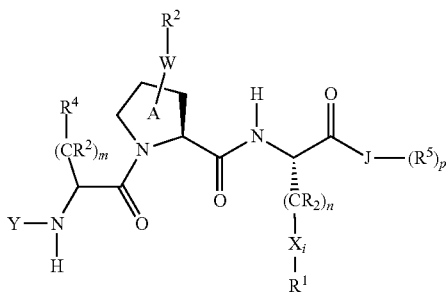

(1)

or pharmaceutically acceptable salts, or stereoisomers thereof, wherein:

J is a 5-12 membered monocyclic or fused carbocyclic ring, heteroaryl or heterocyclic ring containing N, O and/or S;

$R^1$ is $-(CR_2)_l-NR_2$, $-(CR_2)_l-NRC(=NR)-NR_2$, $-(CR_2)_l-C(=NR)-NR_2$ or a 5-7 membered nitrogen-containing non-aromatic heterocyclic ring;

W—$R^2$ is a substituent at any position on ring A;
W is $-O(CR_2)_k-$, $-S(CR_2)_k-$, $-S(O)(CR_2)_k-$, $-SO_2(CR_2)_k-$ or $-OC(O)(CR_2)_k-$;
$R^2$ is $C_{1-6}$ alkyl, $C_{2-6}$ alkenyl, $C_{2-6}$ alkynyl, $R^8$, $-CR^{10}=CR^{10}-R^8$, or

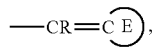

wherein ring E is an optionally substituted 5-7 membered monocyclic or fused carbocyclic or heterocyclic ring; or W—$R^2$ together form $C_{1-6}$ alkyl, aryl or $-OC(O)NR^6R^7$;

Y is $SO_2R^3$ or $SO_2NR^6R^7$;
$R^3$ is $C_{1-6}$ alkyl, $C_{2-6}$ alkenyl, $C_{2-6}$ alkynyl, $-(CR_2)_l-C_{3-7}$ cycloalkyl or $-(CR_2)_l-R^8$;
$R^4$ is $-CR^{10}=CR^{10}-R^8$, $-CR[(CR_2)_l-R^8]_2$, $C_{2-6}$ alkynyl, $-O-(CR_2)_l-R^9$, $NR^6R^7$,

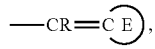

or an optionally substituted 5-7 membered carbocyclic ring, heterocyclic ring, aryl or heteroaryl; or $R^4$ together with Y form an optionally substituted 5-12 membered non-aromatic heterocyclic ring;

$R^5$ is halo, $C_{1-6}$ alkyl, $C_{1-6}$ alkoxy, $OR^9$ or $R^9$;
$R^6$ and $R^7$ are independently H, $C_{1-6}$ alkyl, $C_{2-6}$ alkenyl, $C_{2-6}$ alkynyl or $-(CR_2)_l-R^8$; or $R^6$ and $R^7$ together with N may form an optionally substituted 5-7 membered monocyclic or fused heterocyclic ring;

X, $R^8$ and $R^9$ are independently an optionally substituted 5-7 membered carbocyclic ring, heterocyclic ring, aryl or heteroaryl; or $R^9$ may be H or $C_{1-6}$ alkyl;
$R^{10}$ is H or $C_{1-6}$ alkyl;

each R is H, $C_{1-6}$ alkyl, $C_{2-6}$ alkenyl, or $C_{2-6}$ alkynyl, wherein a carbon may optionally be substituted or replaced with NR, O or S;

i is 0-1;
k, l and m are independently 0-6;
n is 1-6; and
p is 0-3.

2. The compound of claim 1, wherein $R^1$ is $-(CH_2)_l-NH_2$, $-(CH_2)_l-NHC(=NH)-NH_2$ or $-(CH_2)_l-C(=NH)-NH_2NH_2$, wherein each l is 0-1; or $R^1$ is piperidinyl.

3. The compound of claim 1, wherein W is $-O(CR_2)_k-$, $-S(CR_2)_k-$, $-S(O)(CR_2)_k-$, $-SO_2(CR_2)_k-$ or $-OC(O)(CR_2)_k-$; and k is 1.

4. The compound of claim 1, wherein $R^2$ is an optionally substituted phenyl, thienyl, $C_{5-7}$ cycloalkyl, furanyl, piperidinyl, methylenecyclohexyl,

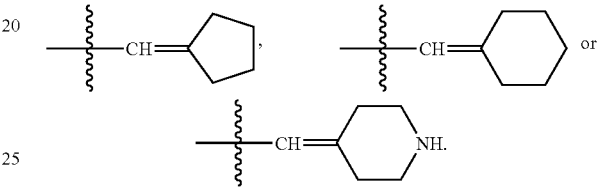

5. The compound of claim 1, wherein Y is $SO_2R^3$; $R^3$ is $C_{1-6}$ alkyl, $-(CR_2)_l$-cyclopropyl or $-(CR_2)_l-R^8$ wherein $R^8$ is an optionally substituted phenyl.

6. The compound of claim 1, wherein $R^4$ is $-NH_2$, or an optionally substituted phenyl, phenoxy, piperidinyl, $C_{5-7}$ cycloalkyl, cyclohexanol, imidazolyl, thienyl,

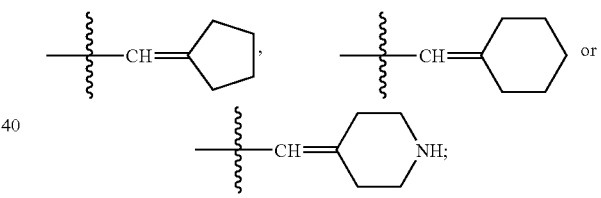

or $R^4$ together with Y form an optionally substituted pyrrolidinyl, pyrrolidinonyl, tetrahydroisoquinolinyl or tetrahydronapthalenyl.

7. The compound of claim 1, wherein -J-$(R^5)_p$ together is

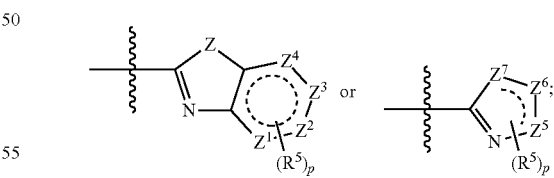

Z is O or S;
$Z^1$, $Z^2$, $Z^3$ or $Z^4$ are independently N, CH, or C when attached to $R^5$;
$Z^5$, $Z^6$ or $Z^7$ are independently N, O, S, CH, or C when attached to $R^5$;
p is 0-1; and
$R^5$ is halo or $C_{1-6}$ alkyl.

8. The compound of claim 1, wherein $R^8$ is an optionally substituted phenyl, $C_{5-7}$ cycloalkyl, piperidinyl, cyclohexanol, imidazolyl, thienyl, furanyl,

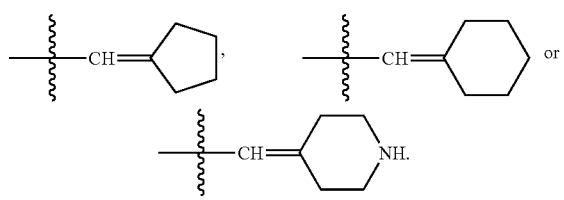

9. The compound of claim 1, wherein i is 1; and X is an optionally substituted cyclohexyl, phenyl or piperidinyl.

10. The compound of claim 1, wherein J is benzothiazolyl, benzoxazolyl, thiazolyl, or oxadiazolyl.

11. The compound of claim 1, wherein said compound has Formula (2A) or (2B):

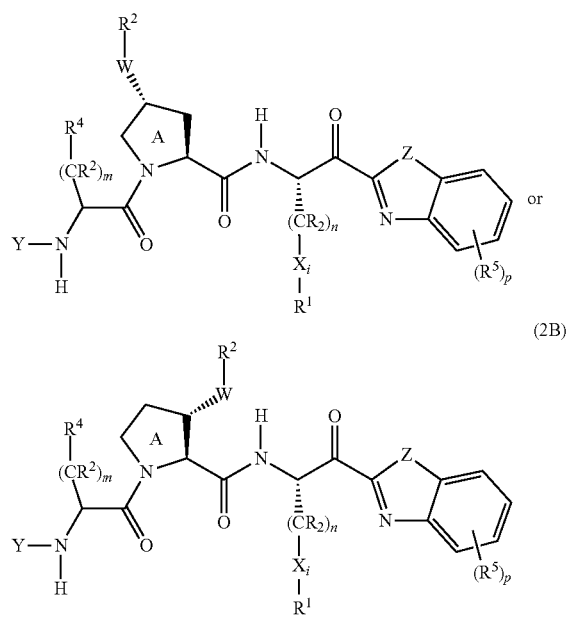

wherein Z is O or S;
$R^1$ is $NH_2$, —NHC(=NH)—$NH_2$ or —C(=NH)—$NH_2$;
W is —O($CH_2$)$_k$— or —S(O)($CH_2$)$_k$—;
$R^2$ is an optionally substituted phenyl, or W—$R^2$ together form $C_{1-6}$ alkyl or an optionally substituted phenyl;
Y is $SO_2R^3$;
$R^3$ is $C_{1-6}$ alkyl, —($CH_2$)$_l$-cyclopropyl or —($CH_2$)$_l$—$R^8$ wherein $R^8$ is an optionally substituted phenyl;
$R^4$ is an optionally substituted, phenyl, piperidinyl, $C_{5-7}$ cycloalkyl, cyclohexanol, imidazolyl, thienyl,

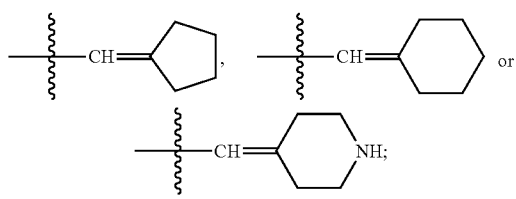

i and p are 0;
k is 1;
l is 0-1;

m and n are independently 1-4; and
R and $R^5$ are as defined in claim 1.

12. The compound of claim 11, wherein $R^4$ is piperidinyl.

13. The compound of claim 1, wherein said compound has Formula (3A) or (3B):

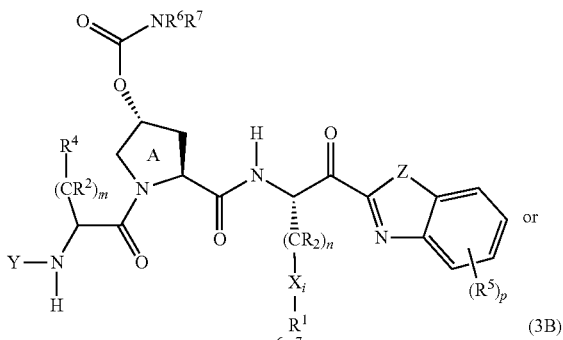

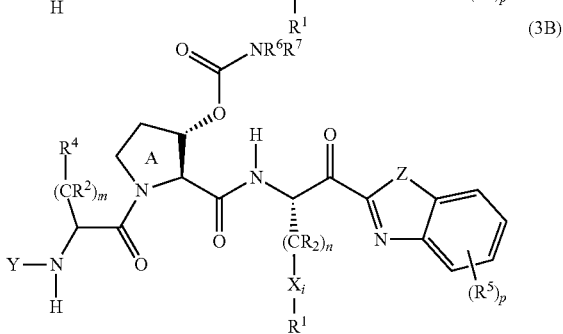

wherein $R^6$ and $R^7$ are independently H, $C_{1-6}$ alkyl or —($CR_2$)$_l$—$R^8$; or $R^6$ and $R^7$ together with N form an optionally substituted pyrrolidinyl, piperidinyl, morpholino, piperazinyl or diazepanyl;

$R^8$ is an optionally substituted phenyl, furanyl, tetrahydrofuranyl, piperidinyl or thienyl; and i and p are 0; and R, $R^1$, $R^5$, X, Y, Z, i, l, m, n and p are as defined in claim 1.

14. A pharmaceutical composition comprising a therapeutically effective amount of a compound of claim 1 and a pharmaceutically acceptable excipient.

15. The compound of claim 1, wherein said compound is selected from the group

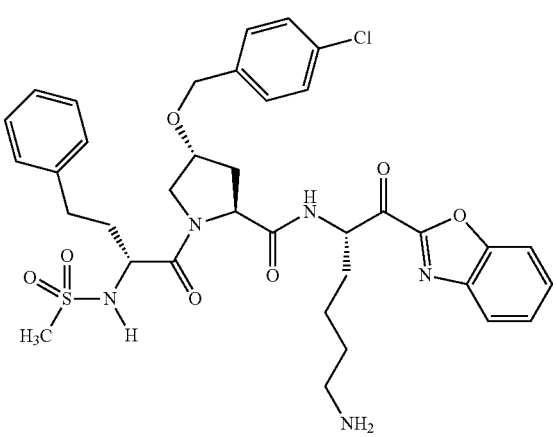

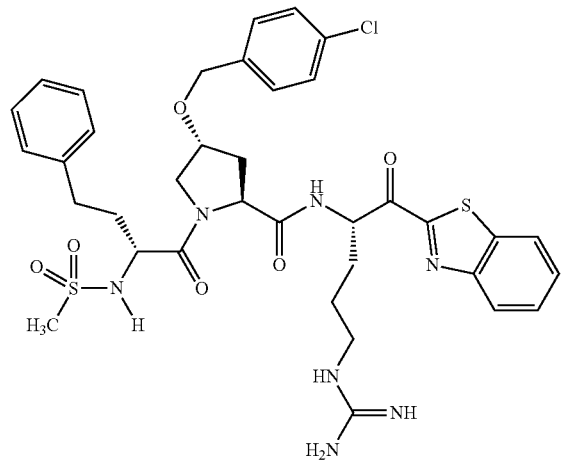
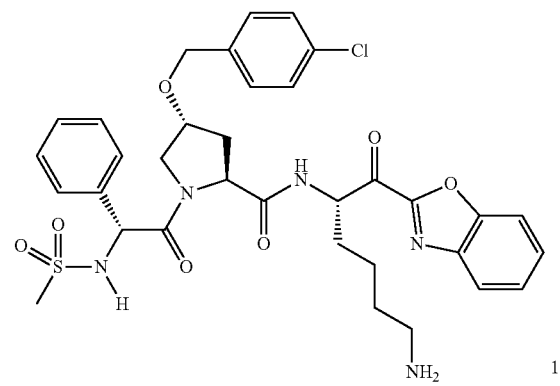
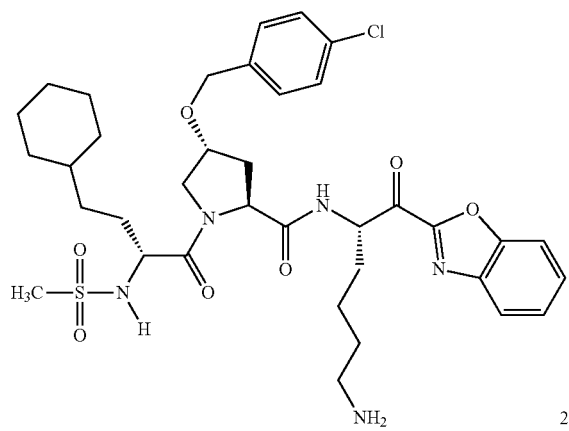
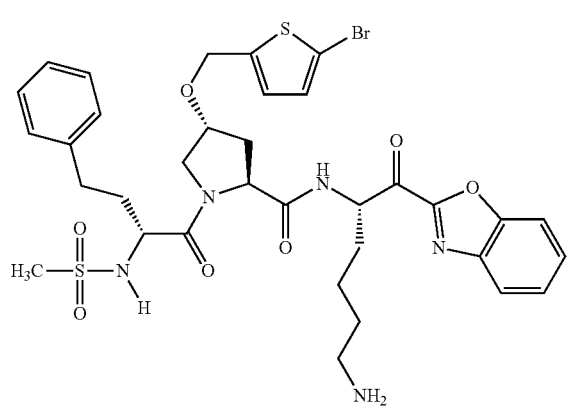
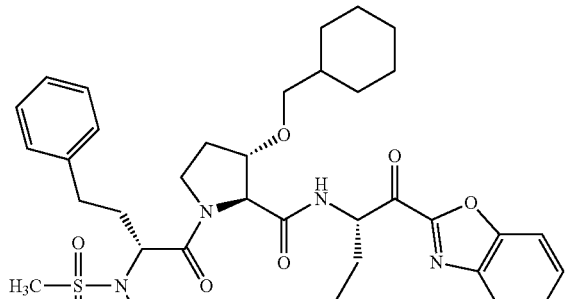
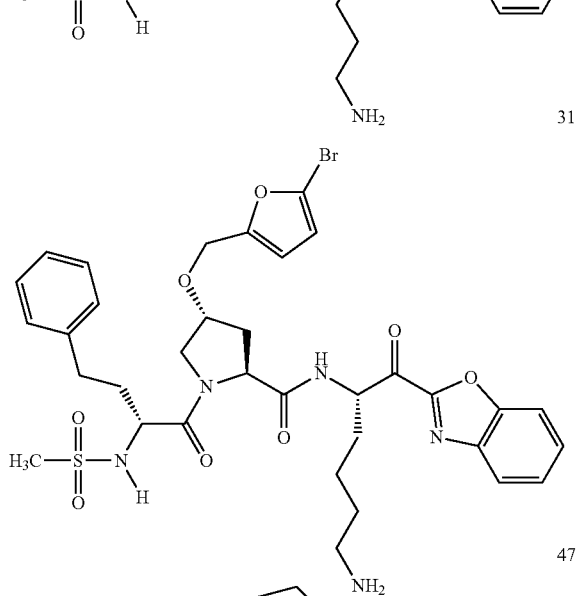
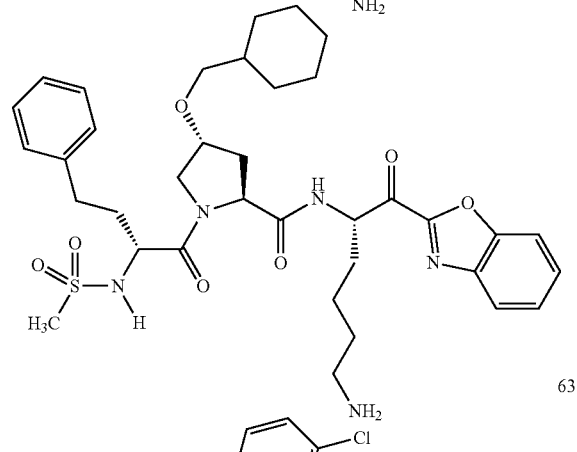
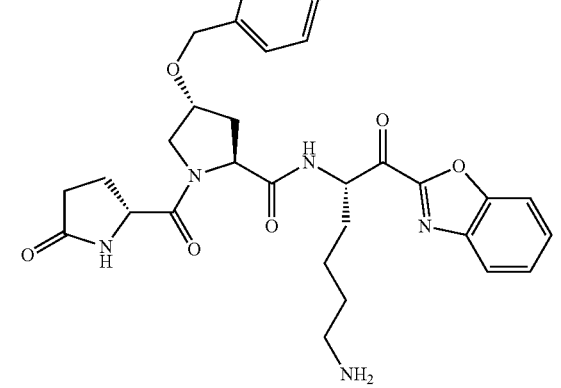

265
266
69
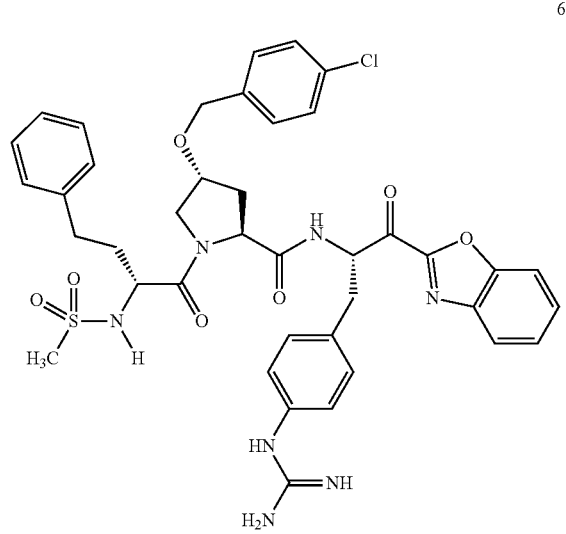
75
72
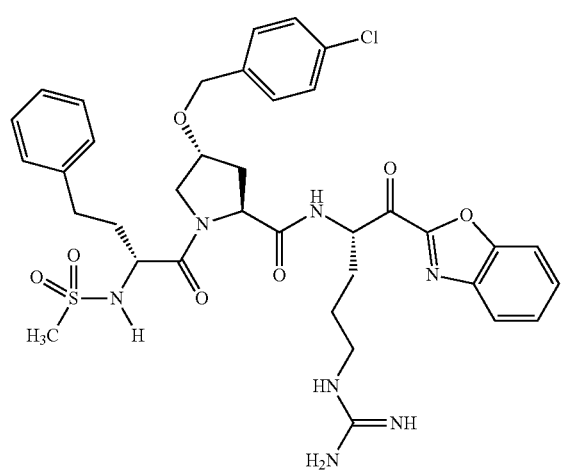
84
74
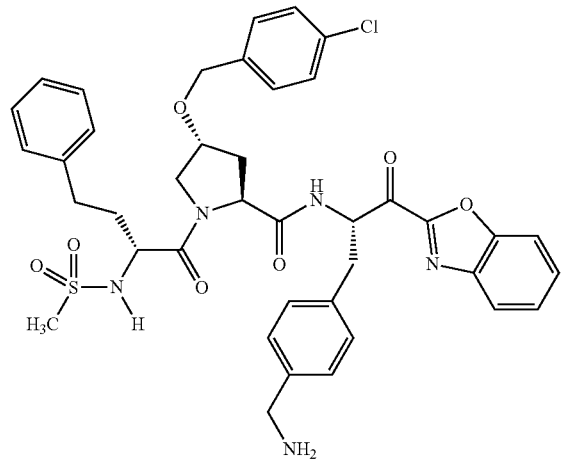
85
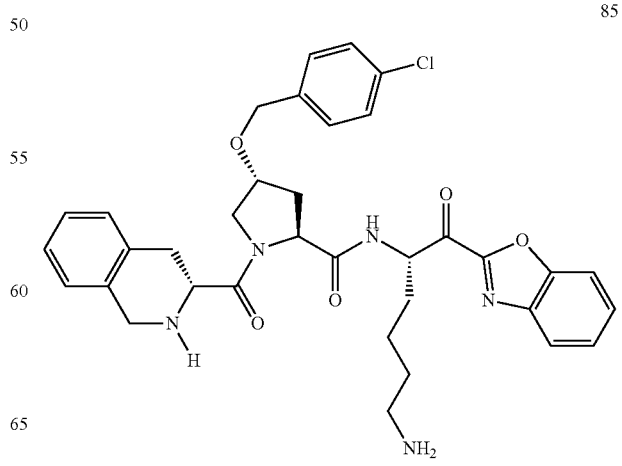

267
-continued
88
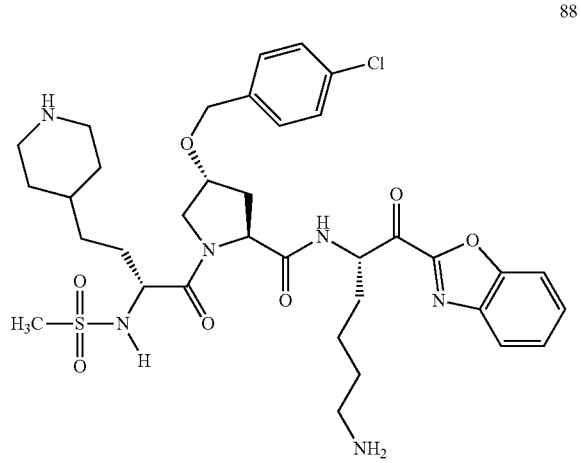
89
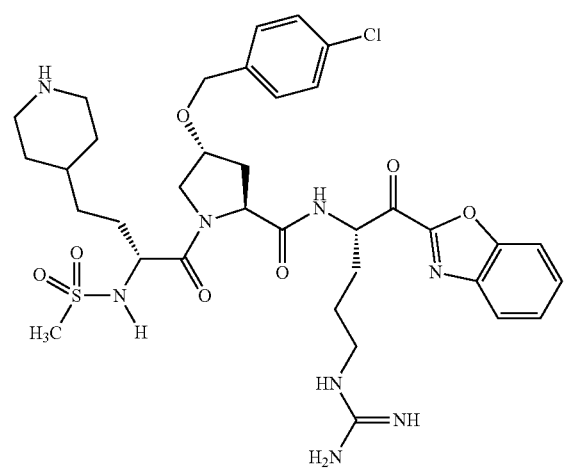
90
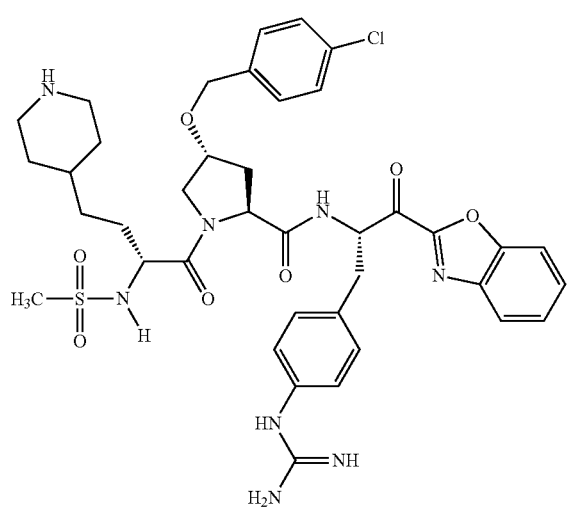
268
-continued
91
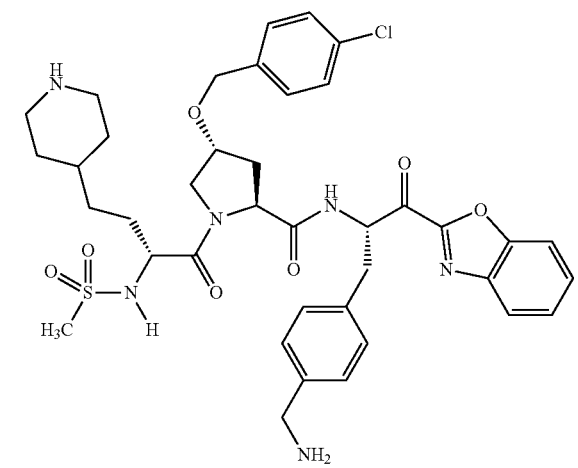
92
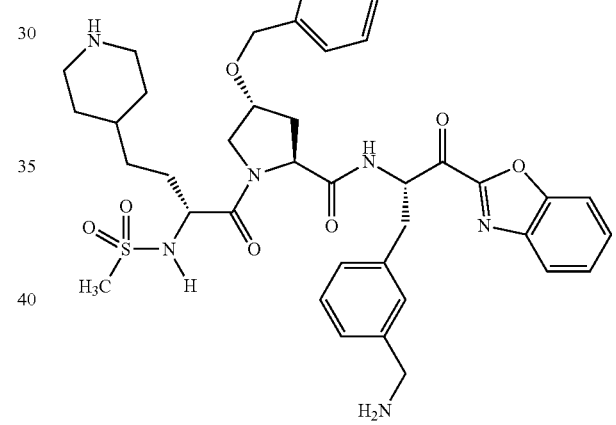
93
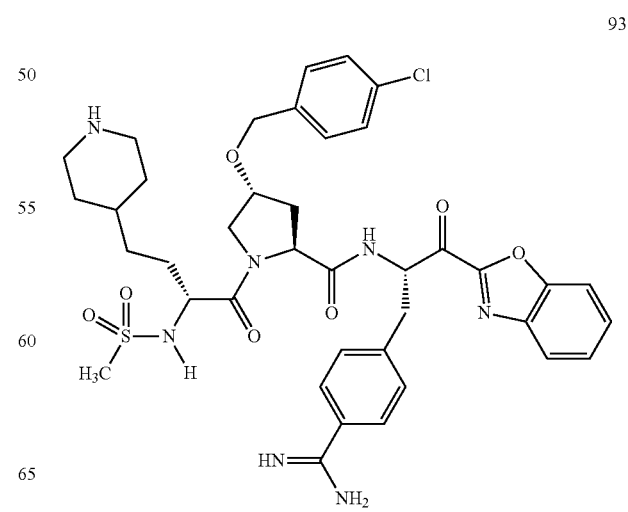

269
-continued
94
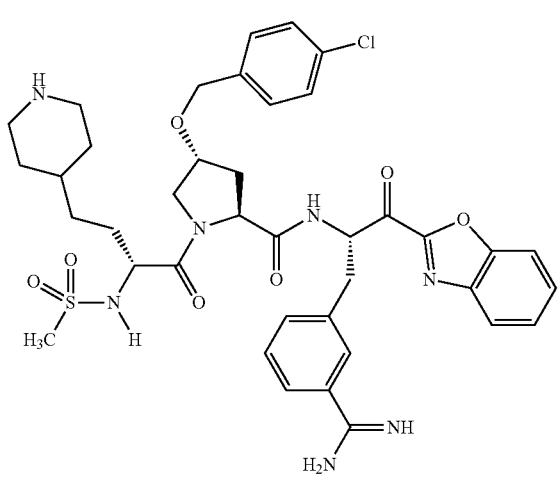
95
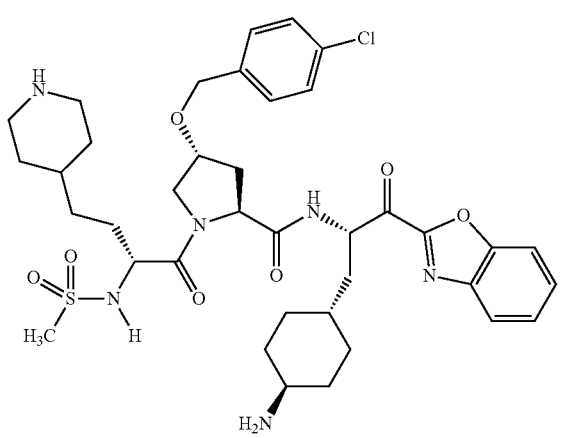
96
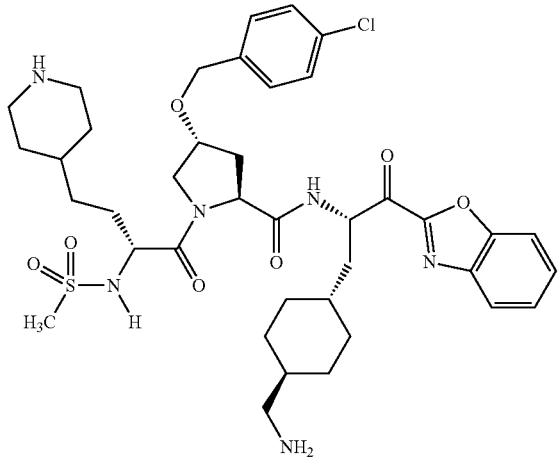
270
-continued
98
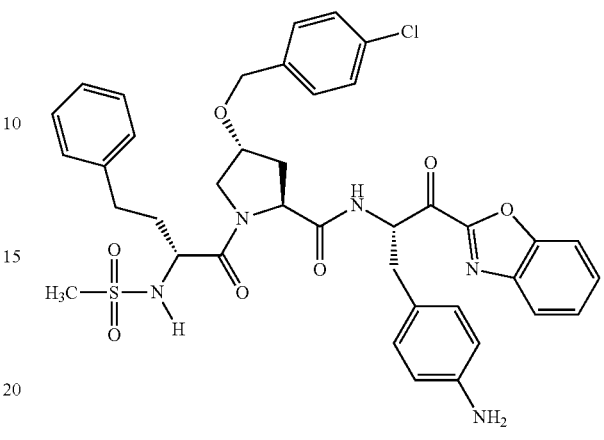
100
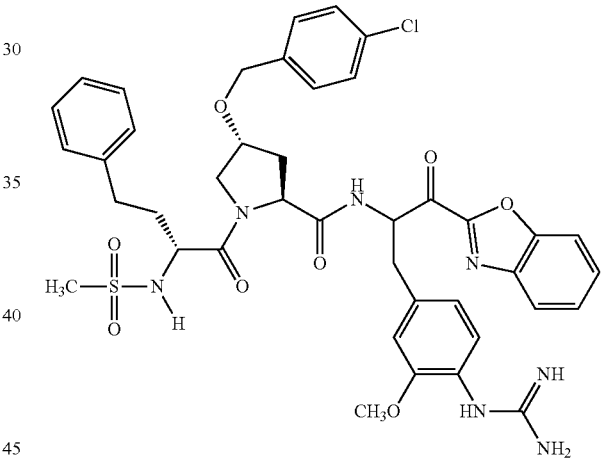
112
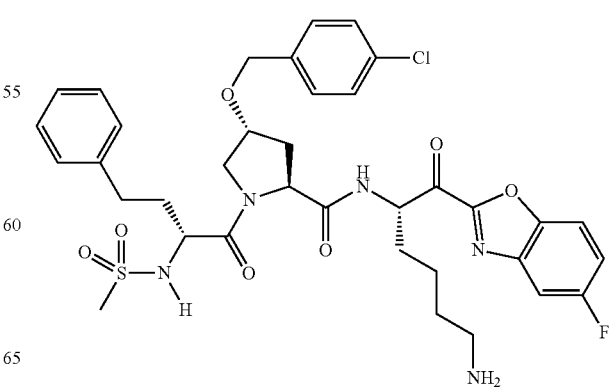

US 7,951,823 B2
271
-continued
113
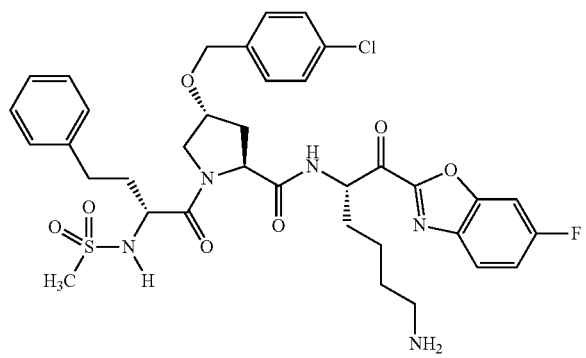
124
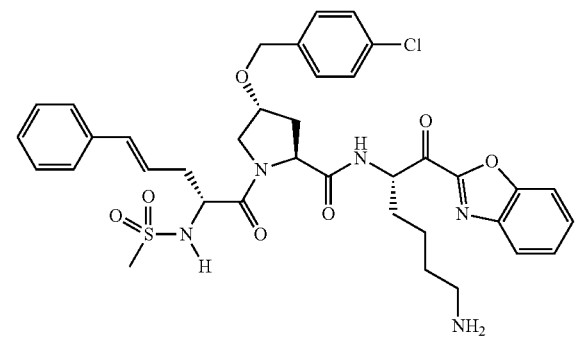
125
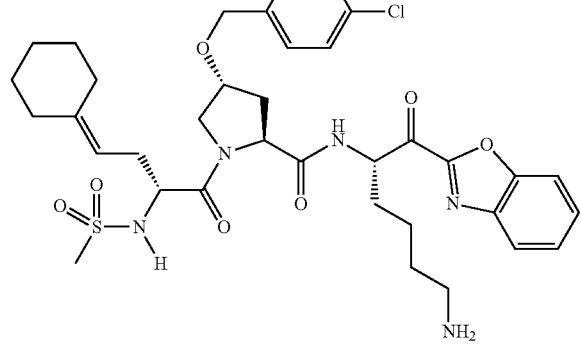
127
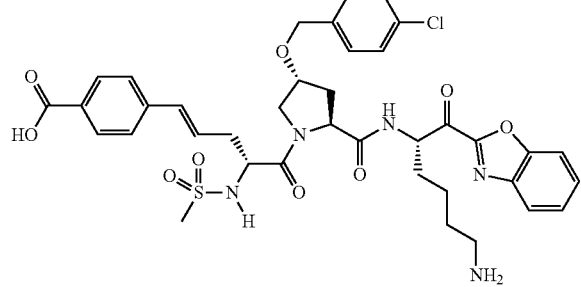
272
-continued
128
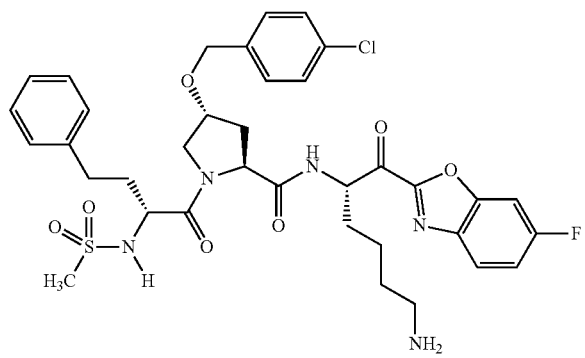
129
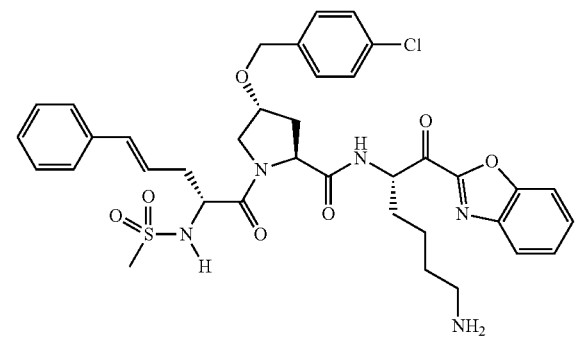
130
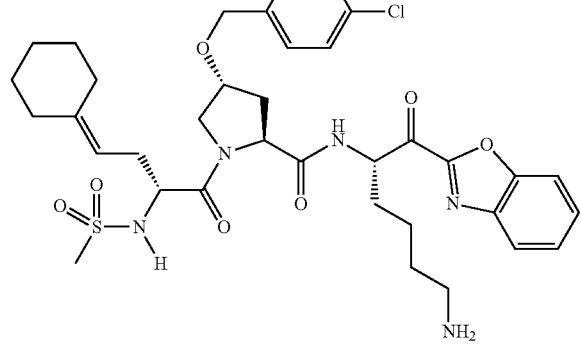
131
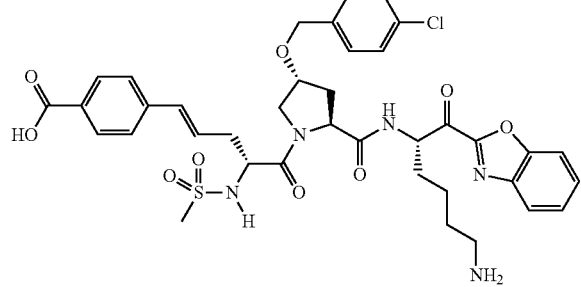

273
-continued
133
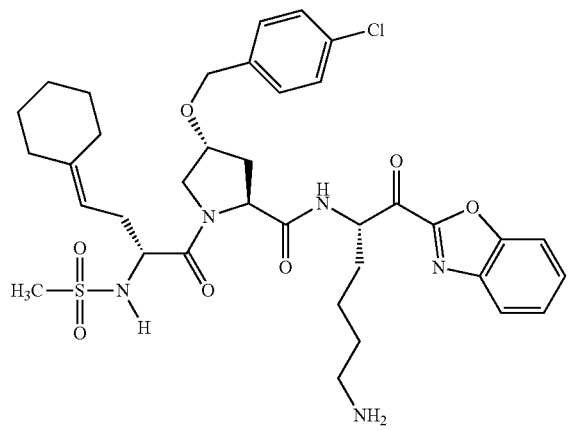
142
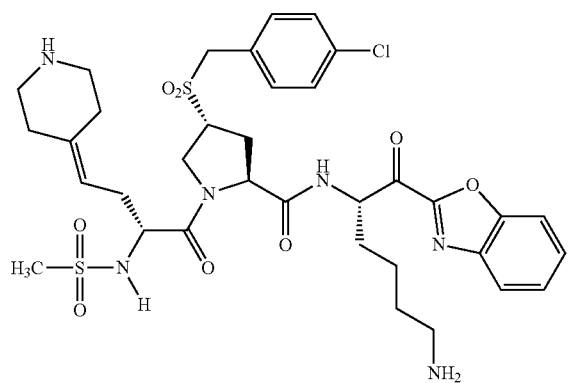
143
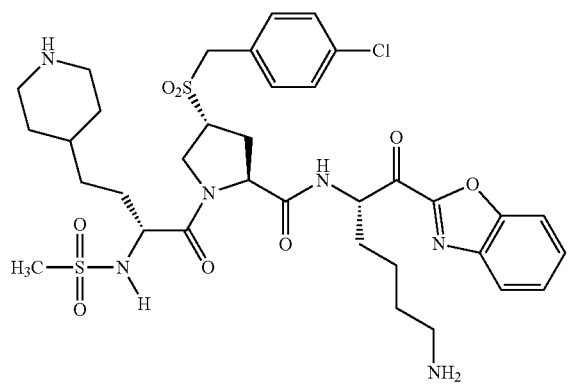
146
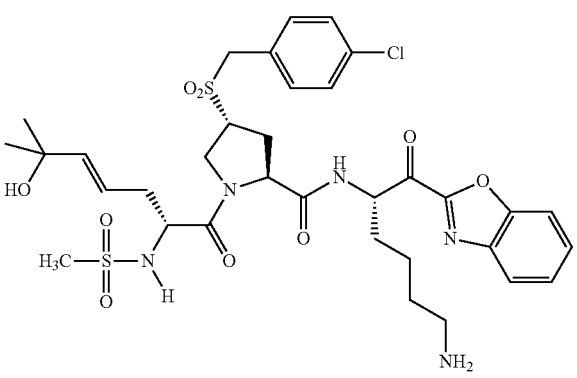
274
-continued
147
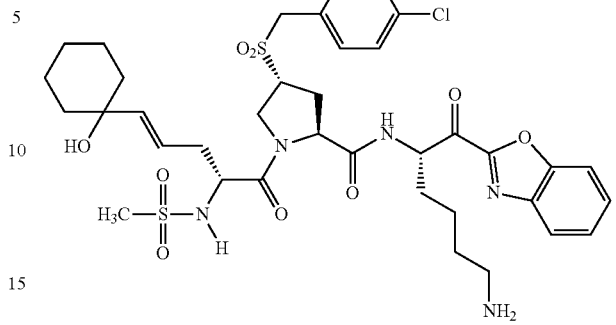
148
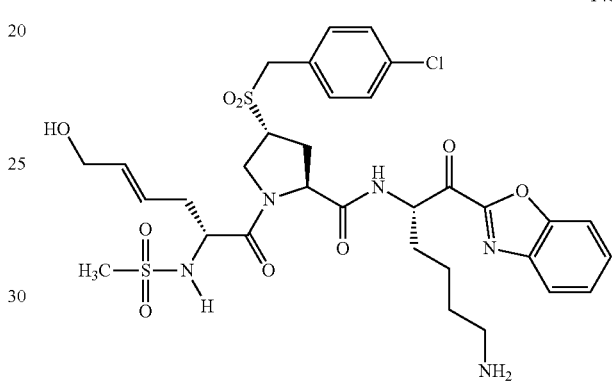
149
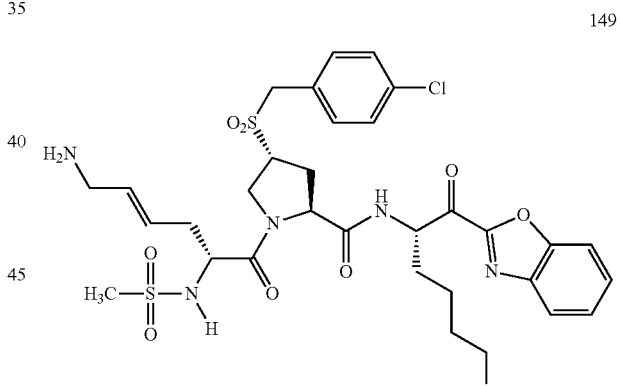
150
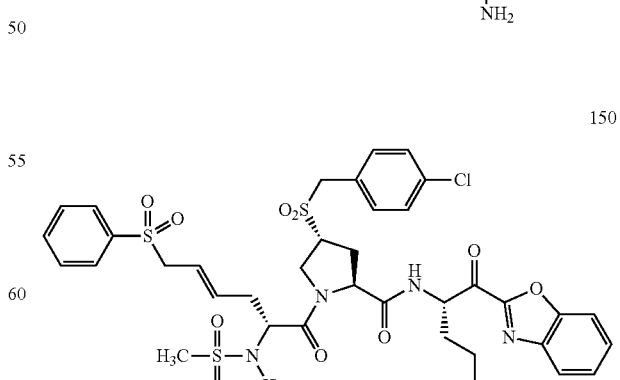

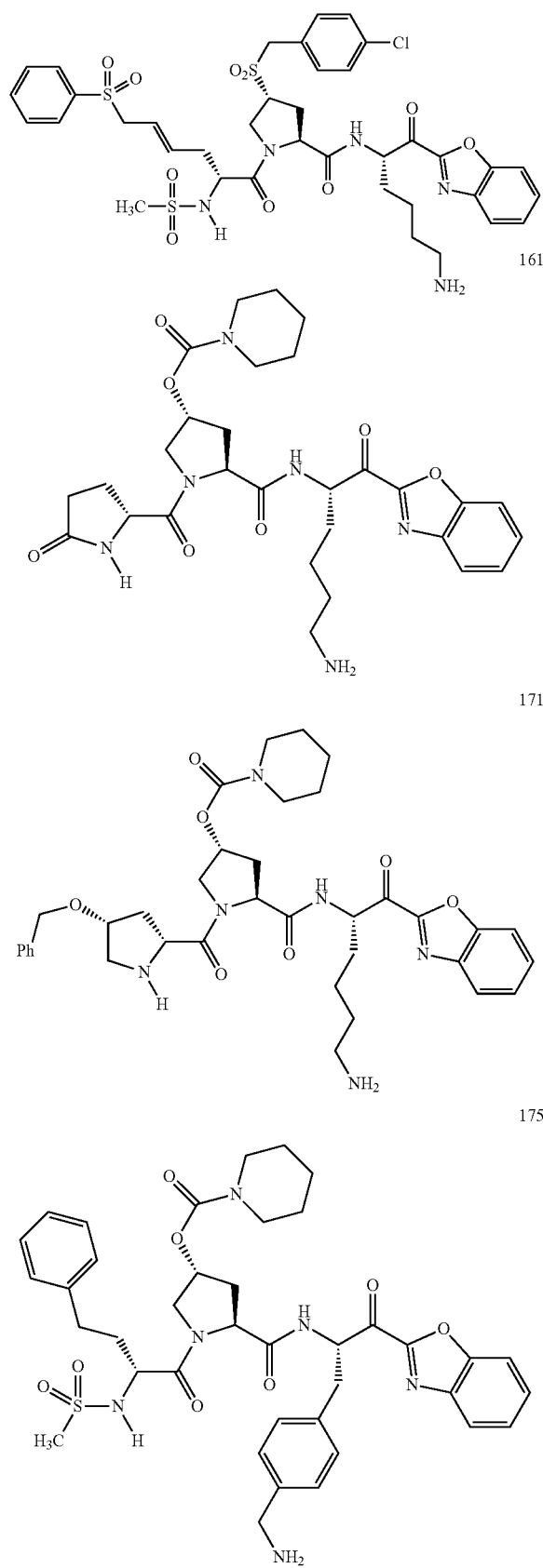
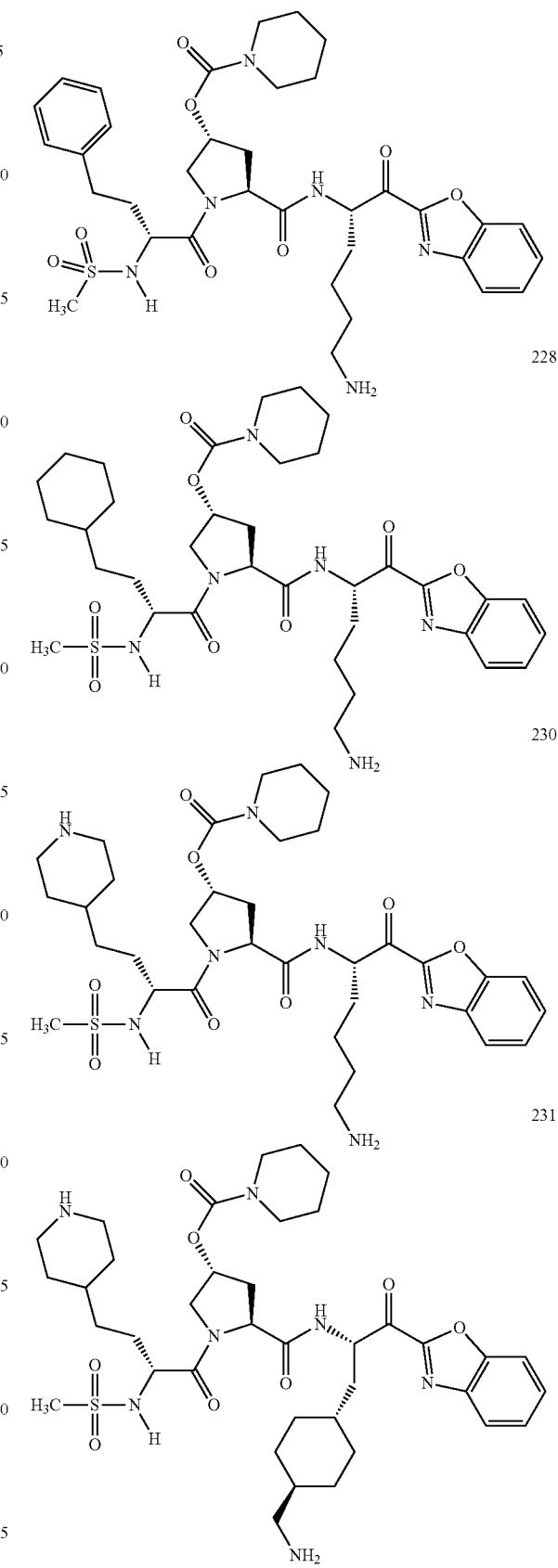

277
-continued
232
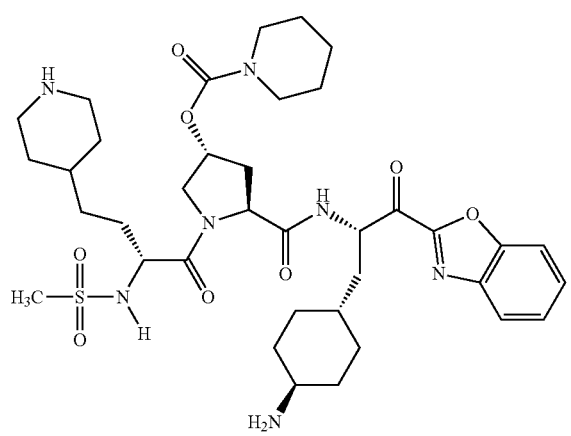
233
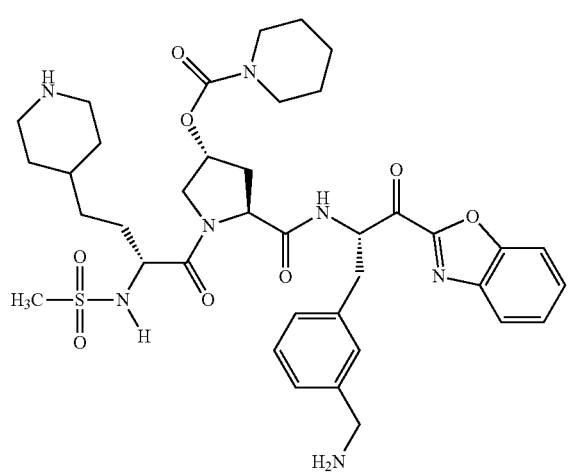
234
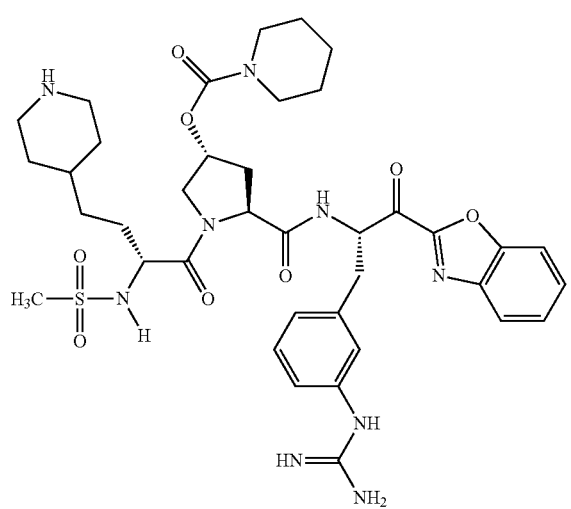
278
-continued
235
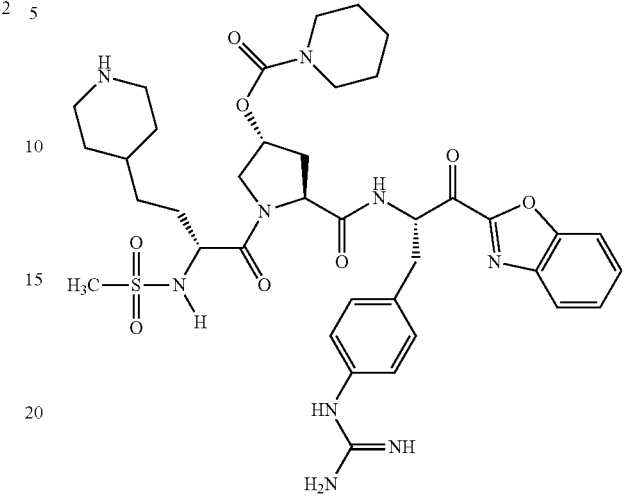
236
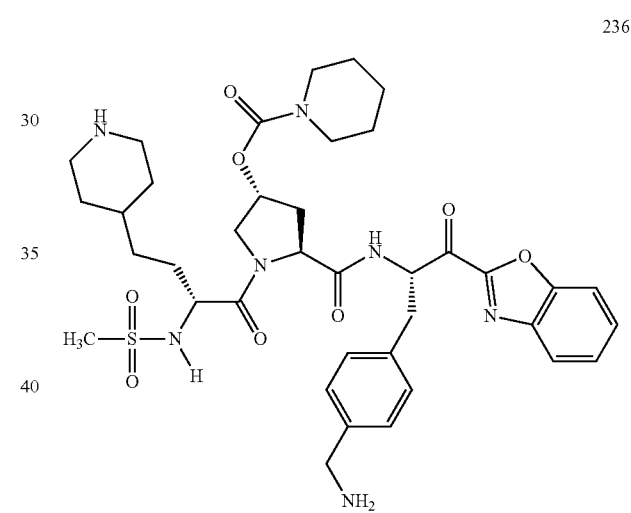
237
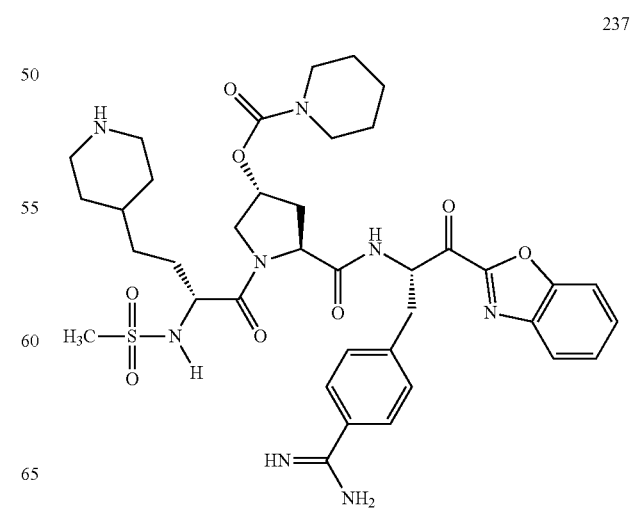

279
-continued
238
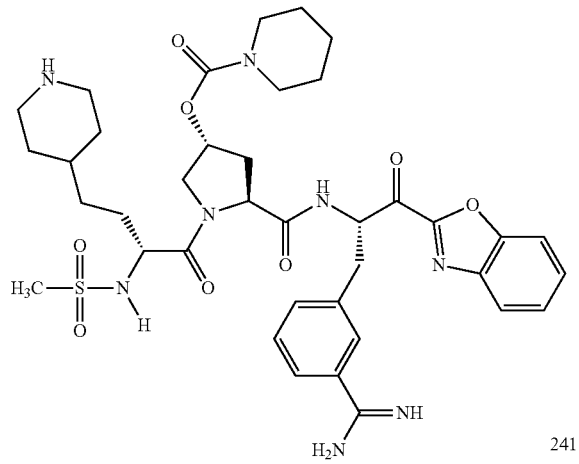
241
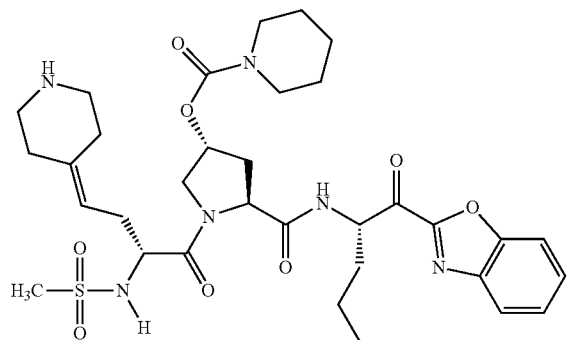
244
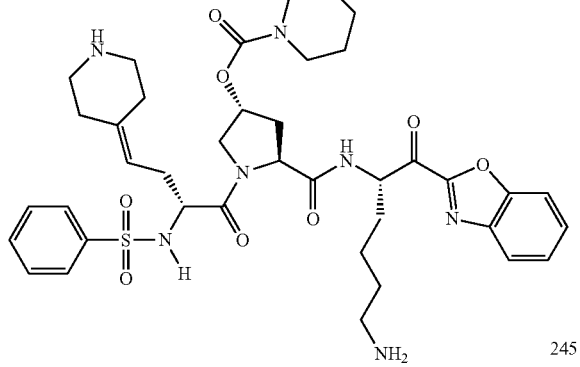
245
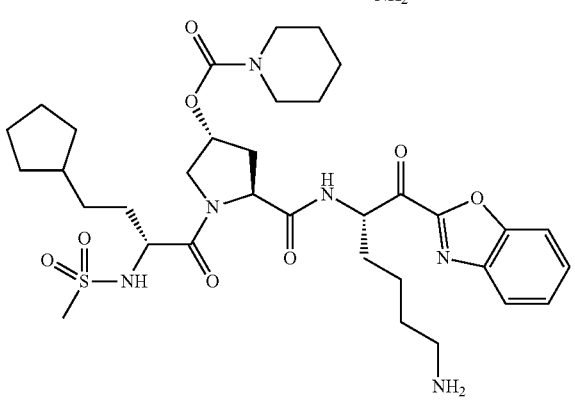
280
-continued
246
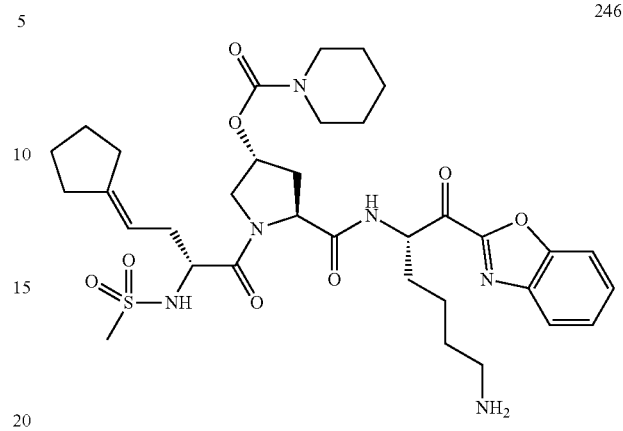
247
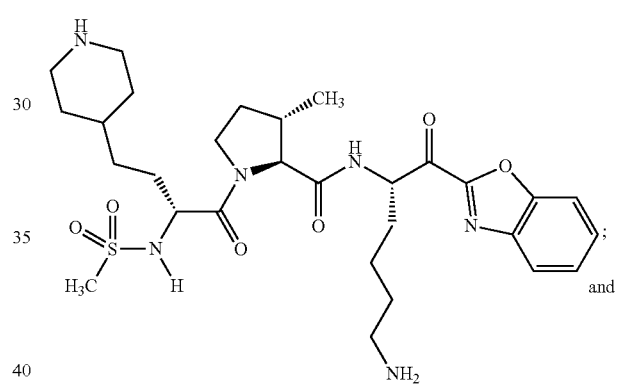
and
248
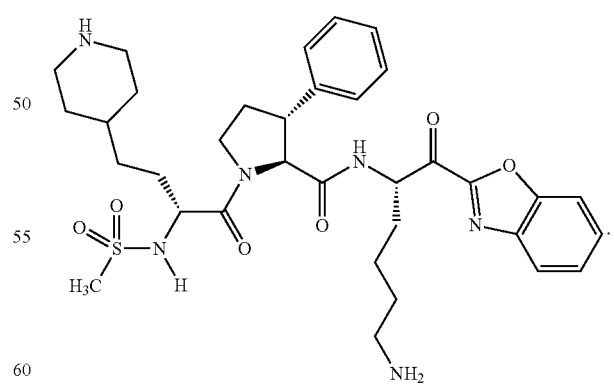
* * * * *